US011864956B2

(12) United States Patent
Shelton, IV et al.

(10) Patent No.: US 11,864,956 B2
(45) Date of Patent: Jan. 9, 2024

(54) SURGICAL SYSTEMS FOR GENERATING THREE DIMENSIONAL CONSTRUCTS OF ANATOMICAL ORGANS AND COUPLING IDENTIFIED ANATOMICAL STRUCTURES THERETO

(71) Applicant: Cilag GmbH International, Zug (CH)

(72) Inventors: Frederick E. Shelton, IV, Hillsboro, OH (US); Jason L. Harris, Lebanon, OH (US); Kevin M. Fiebig, Cincinnati, OH (US); Daniel J. Mumaw, Liberty Township, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/214,062

(22) Filed: Mar. 26, 2021

(65) Prior Publication Data

US 2021/0275252 A1   Sep. 9, 2021

Related U.S. Application Data

(63) Continuation of application No. 16/729,751, filed on Dec. 30, 2019.

(51) Int. Cl.
*A61B 34/10* (2016.01)
*G06T 17/00* (2006.01)
(Continued)

(52) U.S. Cl.
CPC ............ *A61B 90/361* (2016.02); *A61B 1/009* (2022.02); *A61B 1/000094* (2022.02);
(Continued)

(58) Field of Classification Search
CPC ... A61B 34/10; A61B 2034/105; A61B 34/30; A61B 2034/107; G06T 17/00
(Continued)

(56) References Cited

U.S. PATENT DOCUMENTS 4,753,641 A   6/1988 Vaslow
4,785,180 A   11/1988 Dietrich et al.
(Continued)

FOREIGN PATENT DOCUMENTS

CN   109011149 A   12/2018
DE   102015115903 A1   3/2017
(Continued)

OTHER PUBLICATIONS

Kurata et al. "Time-of-flight Near-infrared Spectroscopy for Nondestructive Measurement of Internal Quality in Grapefruit," J. Amer. Soc. Hort. Sci. 138(3): 225-228, 2013.
(Continued)

*Primary Examiner* — Javid A Amini

(57) ABSTRACT

A surgical visualization system includes multiple light sources, at least one optical sensor, at least one display device, and a controller. The controller is configured to control at least one light source to illuminate surgical tissue in a first manner, and control the optical sensor to receive an image from the surgical tissue illuminated in the first manner. The controller calculates a three-dimensional image from the tissue illuminated in the first manner. The controller is configured to control at the least one light source to illuminate surgical tissue in a second manner, and control the optical sensor to receive an image from the surgical tissue illuminated in the second manner. The controller calculates one or more subsurface critical anatomic structures from the tissue illuminated in the second manner and combines the display of the three-dimensional image and the anatomic structures on the at least one display device.

18 Claims, 46 Drawing Sheets

(51) Int. Cl.

| | |
|---|---|
| *A61B 90/00* | (2016.01) |
| *A61B 1/00* | (2006.01) |
| *A61B 1/005* | (2006.01) |
| *A61B 1/04* | (2006.01) |
| *A61B 1/06* | (2006.01) |

(52) U.S. Cl.
CPC .......... *A61B 1/00194* (2022.02); *A61B 1/046* (2022.02); *A61B 1/0605* (2022.02); *A61B 34/10* (2016.02); *G06T 17/00* (2013.01); *A61B 2034/105* (2016.02); *A61B 2034/107* (2016.02); *G06T 2200/04* (2013.01)

(58) Field of Classification Search
USPC ........................................................ 606/130
See application file for complete search history.

(56) References Cited

U.S. PATENT DOCUMENTS

| | | |
|---|---|---|
| 4,986,262 A | 1/1991 | Saito |
| 5,434,667 A | 7/1995 | Hutchins et al. |
| 5,460,182 A | 10/1995 | Goodman et al. |
| 5,609,562 A | 3/1997 | Kaali |
| 6,350,233 B1 | 2/2002 | Lubowski |
| 6,386,758 B2 | 5/2002 | Loser |
| 6,614,453 B1 | 9/2003 | Suri et al. |
| 6,632,183 B2 | 10/2003 | Bowman et al. |
| 6,804,012 B2 | 10/2004 | Gombert |
| 6,869,430 B2 | 3/2005 | Balbierz et al. |
| 6,951,535 B2 | 10/2005 | Ghodoussi et al. |
| 7,137,980 B2 | 11/2006 | Buysse et al. |
| 7,314,048 B2 | 1/2008 | Couture et al. |
| 7,477,931 B2 | 1/2009 | Hoyt |
| 7,516,675 B2 | 4/2009 | Kurtz et al. |
| 7,726,171 B2 | 6/2010 | Langlotz et al. |
| 7,740,623 B2 | 6/2010 | Nayak et al. |
| 7,766,210 B2 | 8/2010 | Shelton, IV et al. |
| 7,770,775 B2 | 8/2010 | Shelton, IV et al. |
| 7,798,385 B2 | 9/2010 | Boyden et al. |
| 7,810,691 B2 | 10/2010 | Boyden et al. |
| 7,901,353 B2 | 3/2011 | Vayser et al. |
| 7,905,840 B2 | 3/2011 | Pimenta et al. |
| 7,975,894 B2 | 7/2011 | Boyden et al. |
| 8,041,089 B2 | 10/2011 | Drumm et al. |
| 8,063,883 B2 | 11/2011 | Senft et al. |
| 8,073,528 B2 | 12/2011 | Zhao et al. |
| 8,079,950 B2 | 12/2011 | Stern et al. |
| 8,142,450 B2 | 3/2012 | Harris et al. |
| 8,161,977 B2 | 4/2012 | Shelton, IV et al. |
| 8,224,484 B2 | 7/2012 | Swarup et al. |
| 8,231,639 B2 | 7/2012 | Bolduc et al. |
| 8,523,043 B2 | 9/2013 | Ullrich et al. |
| 8,632,468 B2 | 1/2014 | Glossop et al. |
| 8,652,148 B2 | 2/2014 | Zuhars |
| 8,706,211 B2 | 4/2014 | Dacey, Jr. et al. |
| 8,755,576 B2 | 6/2014 | Taerum |
| 8,763,879 B2 | 7/2014 | Shelton, IV et al. |
| 8,820,603 B2 | 9/2014 | Shelton, IV et al. |
| 8,840,616 B2 | 9/2014 | Wilkinson et al. |
| 8,932,208 B2 | 1/2015 | Kendale et al. |
| 8,934,003 B2 | 1/2015 | Popovic et al. |
| 8,989,528 B2 | 3/2015 | Udd |
| 8,992,558 B2 | 3/2015 | Stone et al. |
| 9,005,118 B2 | 4/2015 | Selover et al. |
| 9,044,230 B2 | 6/2015 | Morgan et al. |
| 9,064,173 B2 | 6/2015 | Redden |
| 9,072,501 B2 | 7/2015 | Menchaca et al. |
| 9,072,535 B2 | 7/2015 | Shelton, IV et al. |
| 9,119,670 B2 | 9/2015 | Yang et al. |
| 9,141,868 B2 | 9/2015 | Xu et al. |
| 9,161,817 B2 | 10/2015 | Olson et al. |
| 9,161,820 B2 | 10/2015 | Mark et al. |
| 9,179,822 B2 | 11/2015 | Kitamura et al. |
| 9,179,890 B2 | 11/2015 | Ionasec et al. |
| 9,241,693 B2 | 1/2016 | Taylor et al. |
| 9,254,103 B2 | 2/2016 | Krishnaswamy et al. |
| 9,259,290 B2 | 2/2016 | Jenkins et al. |
| 9,265,587 B2 | 2/2016 | Vancamberg et al. |
| 9,274,047 B2 | 3/2016 | Velten et al. |
| 9,282,878 B2 | 3/2016 | Grey et al. |
| 9,295,773 B2 | 3/2016 | Prosl et al. |
| 9,326,770 B2 | 5/2016 | Shelton, IV et al. |
| 9,345,389 B2 | 5/2016 | Nie et al. |
| 9,402,726 B2 | 8/2016 | Linderman et al. |
| 9,480,534 B2 | 11/2016 | Bowling et al. |
| 9,547,940 B1 | 1/2017 | Sun et al. |
| 9,561,019 B2 | 2/2017 | Mihailescu et al. |
| 9,561,082 B2 | 2/2017 | Yen et al. |
| 9,597,054 B2 | 3/2017 | Kudavelly et al. |
| 9,649,109 B2 | 5/2017 | Ranucci et al. |
| 9,720,076 B2 | 8/2017 | Guo et al. |
| 9,730,690 B2 | 8/2017 | Shanley et al. |
| 9,775,497 B2 | 10/2017 | Igarashi et al. |
| 9,788,851 B2 | 10/2017 | Dannaher et al. |
| 9,801,685 B2 | 10/2017 | Nguyen et al. |
| 9,855,317 B2 | 1/2018 | Bright |
| 9,857,167 B2 | 1/2018 | Jovanovski et al. |
| 9,883,857 B2 | 2/2018 | Shluzas et al. |
| 9,901,409 B2 | 2/2018 | Yang et al. |
| 9,911,187 B2 | 3/2018 | Steinle et al. |
| 9,918,640 B2 | 3/2018 | Ntziachristos et al. |
| 9,987,019 B2 | 6/2018 | Sato |
| 10,010,326 B2 | 7/2018 | Sato |
| 10,022,199 B2 | 7/2018 | Gassner et al. |
| 10,042,150 B2 | 8/2018 | Brown |
| 10,045,763 B2 | 8/2018 | Sato |
| 10,068,173 B2 | 9/2018 | Vayser et al. |
| 10,070,929 B2 | 9/2018 | Tanji |
| 10,085,611 B2 | 10/2018 | Yabe et al. |
| 10,105,470 B2 | 10/2018 | Reasoner et al. |
| 10,123,706 B2 | 11/2018 | Elbaz et al. |
| 10,136,959 B2 | 11/2018 | Mintz et al. |
| 10,143,470 B2 | 12/2018 | Sato |
| 10,170,205 B2 | 1/2019 | Curd et al. |
| 10,194,981 B2 | 2/2019 | Balbas et al. |
| 10,194,990 B2 | 2/2019 | Amanatullah et al. |
| 10,219,738 B2 | 3/2019 | Monty et al. |
| 10,238,356 B2 | 3/2019 | Suzuki et al. |
| 10,255,723 B2 | 4/2019 | Thomas et al. |
| 10,314,463 B2 | 6/2019 | Agrawal et al. |
| 10,357,253 B2 | 7/2019 | Sato |
| 10,357,317 B2 | 7/2019 | Dupont et al. |
| 10,390,835 B2 | 8/2019 | Williams |
| 10,433,911 B2 | 10/2019 | Wang et al. |
| 10,467,752 B2 | 11/2019 | Tanji |
| 10,470,687 B2 | 11/2019 | Garbey et al. |
| 10,470,763 B2 | 11/2019 | Yates et al. |
| 10,506,991 B2 | 12/2019 | Govari |
| 10,510,149 B2 | 12/2019 | Cutu et al. |
| 10,512,518 B2 | 12/2019 | Vayser et al. |
| 10,531,074 B2 | 1/2020 | Wilson et al. |
| 10,546,423 B2 | 1/2020 | Jones et al. |
| 10,548,679 B2 | 2/2020 | Carlson et al. |
| 10,561,465 B2 | 2/2020 | Scholl et al. |
| 10,576,246 B2 | 3/2020 | Fischell et al. |
| 10,587,659 B2 | 3/2020 | Miller |
| 10,588,699 B2 | 3/2020 | Richmond et al. |
| 10,607,738 B2 | 3/2020 | Davidson et al. |
| 10,643,371 B2 | 5/2020 | Bharadwaj et al. |
| 10,666,928 B2 | 5/2020 | Liu |
| 10,687,797 B2 | 6/2020 | Stone et al. |
| 10,695,166 B2 | 6/2020 | Willis et al. |
| 10,702,186 B2 | 7/2020 | Amies et al. |
| 10,704,093 B2 | 7/2020 | Deng et al. |
| 10,743,868 B2 | 8/2020 | Shelton, IV et al. |
| 10,768,402 B2 | 9/2020 | Brown |
| 10,792,034 B2 | 10/2020 | Scheib et al. |
| 10,806,518 B2 | 10/2020 | Amanatullah |
| 10,813,700 B2 | 10/2020 | Amanatullah |
| 10,861,197 B2 | 12/2020 | Kobayashi |
| 10,866,783 B2 | 12/2020 | Atarot et al. |
| 10,881,458 B2 | 1/2021 | Fischell et al. |
| 10,898,064 B2 | 1/2021 | Atarot et al. |

(56) References Cited

U.S. PATENT DOCUMENTS

| | | |
|---|---|---|
| 10,925,465 B2 | 2/2021 | Tully et al. |
| 10,925,598 B2 | 2/2021 | Scheib et al. |
| 10,945,787 B2 | 3/2021 | Fischell et al. |
| 10,945,796 B2 | 3/2021 | Popovic et al. |
| 10,973,519 B2 | 4/2021 | Weir et al. |
| 10,980,420 B2 | 4/2021 | Fengler et al. |
| 10,986,999 B2 | 4/2021 | Frangioni et al. |
| 11,000,270 B2 | 5/2021 | Scheib et al. |
| 11,006,100 B1 | 5/2021 | Douglas |
| 11,013,563 B2 | 5/2021 | Shelton, IV et al. |
| 11,020,016 B2 | 6/2021 | Wallace et al. |
| 11,058,501 B2 | 7/2021 | Tokarchuk et al. |
| 11,100,631 B2 | 8/2021 | Yates et al. |
| 11,109,866 B2 | 9/2021 | Shelton, IV et al. |
| 11,213,361 B2 | 1/2022 | Denlinger et al. |
| 11,219,501 B2 | 1/2022 | Shelton, IV et al. |
| 11,257,589 B2 | 2/2022 | Shelton, IV et al. |
| 11,259,793 B2 | 3/2022 | Scheib et al. |
| 11,276,175 B2 | 3/2022 | Witte |
| 11,284,957 B2 | 3/2022 | Denlinger et al. |
| 11,284,963 B2 | 3/2022 | Shelton, IV et al. |
| 11,298,128 B2 | 4/2022 | Messerly et al. |
| 11,304,692 B2 | 4/2022 | Scheib |
| 11,304,699 B2 | 4/2022 | Shelton, IV et al. |
| 11,315,438 B1 | 4/2022 | Hannaford et al. |
| 11,369,366 B2 | 6/2022 | Scheib et al. |
| 11,389,164 B2 | 7/2022 | Yates et al. |
| 11,410,259 B2 | 8/2022 | Harris et al. |
| 11,419,604 B2 | 8/2022 | Scheib et al. |
| 11,424,027 B2 | 8/2022 | Shelton, IV |
| 11,432,885 B2 | 9/2022 | Shelton, IV et al. |
| 2001/0012327 A1 | 8/2001 | Loser |
| 2003/0069591 A1 | 4/2003 | Carson et al. |
| 2004/0082842 A1 | 4/2004 | Lumba et al. |
| 2004/0106916 A1 | 6/2004 | Quaid et al. |
| 2004/0147926 A1 | 7/2004 | Iversen |
| 2004/0176751 A1 | 9/2004 | Weitzner et al. |
| 2004/0230199 A1 | 11/2004 | Jansen et al. |
| 2005/0113846 A1 | 5/2005 | Carson |
| 2005/0124975 A1 | 6/2005 | Law |
| 2005/0167621 A1 | 8/2005 | Zeng et al. |
| 2005/0177181 A1 | 8/2005 | Kagan et al. |
| 2005/0279354 A1 | 12/2005 | Deutsch et al. |
| 2006/0013454 A1 | 1/2006 | Flewelling et al. |
| 2006/0079841 A1 | 4/2006 | Duff et al. |
| 2006/0206007 A1 | 9/2006 | Bala |
| 2006/0224045 A1 | 10/2006 | Whipple et al. |
| 2006/0227324 A1 | 10/2006 | Bloom et al. |
| 2006/0282096 A1 | 12/2006 | Papa et al. |
| 2006/0293557 A1 | 12/2006 | Chuanggui et al. |
| 2007/0014784 A1 | 1/2007 | Nayak et al. |
| 2007/0019781 A1 | 1/2007 | Haras |
| 2007/0040906 A1 | 2/2007 | Iketani |
| 2007/0066970 A1 | 3/2007 | Ineson |
| 2007/0093748 A1 | 4/2007 | Nayak et al. |
| 2007/0100210 A1 | 5/2007 | Selover et al. |
| 2007/0123912 A1 | 5/2007 | Carson |
| 2007/0156021 A1 | 7/2007 | Morse et al. |
| 2007/0172472 A1 | 7/2007 | Nayak |
| 2007/0175955 A1 | 8/2007 | Shelton et al. |
| 2007/0239149 A1 | 10/2007 | Lieponis |
| 2007/0265495 A1 | 11/2007 | Vayser |
| 2008/0001919 A1 | 1/2008 | Pascucci |
| 2008/0004633 A1 | 1/2008 | Arata et al. |
| 2008/0015664 A1 | 1/2008 | Podhajsky |
| 2008/0077158 A1 | 3/2008 | Haider et al. |
| 2008/0144906 A1 | 6/2008 | Allred et al. |
| 2008/0151233 A1 | 6/2008 | Blanke et al. |
| 2008/0194930 A1 | 8/2008 | Harris et al. |
| 2008/0205588 A1 | 8/2008 | Kim |
| 2008/0228104 A1 | 9/2008 | Uber et al. |
| 2008/0234866 A1 | 9/2008 | Kishi et al. |
| 2008/0269596 A1 | 10/2008 | Revie et al. |
| 2008/0297360 A1 | 12/2008 | Knox et al. |
| 2008/0319491 A1 | 12/2008 | Schoenefeld |
| 2009/0000627 A1 | 1/2009 | Quaid et al. |
| 2009/0234223 A1 | 9/2009 | Onoda et al. |
| 2010/0030231 A1 | 2/2010 | Revie et al. |
| 2010/0036374 A1 | 2/2010 | Ward |
| 2010/0081875 A1 | 4/2010 | Fowler et al. |
| 2010/0087755 A1 | 4/2010 | Boezaart |
| 2010/0137882 A1 | 6/2010 | Quaid, III |
| 2010/0152539 A1 | 6/2010 | Ghabrial et al. |
| 2010/0217278 A1 | 8/2010 | Tripathi |
| 2010/0280493 A1 | 11/2010 | Nayak |
| 2011/0014181 A1 | 1/2011 | Thornton |
| 2011/0071531 A1 | 3/2011 | Carson |
| 2011/0082369 A1 | 4/2011 | Mohr et al. |
| 2011/0201881 A1 | 8/2011 | Emch |
| 2011/0257611 A1 | 10/2011 | Locke et al. |
| 2011/0257661 A1 | 10/2011 | Choi et al. |
| 2011/0306985 A1 | 12/2011 | Inoue et al. |
| 2012/0004894 A1 | 1/2012 | Butler et al. |
| 2012/0046668 A1 | 2/2012 | Gantes |
| 2012/0143341 A1 | 6/2012 | Zipnick |
| 2012/0165837 A1 | 6/2012 | Belman et al. |
| 2012/0265022 A1 | 10/2012 | Menn |
| 2012/0300051 A1 | 11/2012 | Daigo et al. |
| 2013/0035583 A1 | 2/2013 | Park et al. |
| 2013/0053679 A1 | 2/2013 | Owen |
| 2013/0090554 A1 | 4/2013 | Zvuloni et al. |
| 2013/0100250 A1 | 4/2013 | Raskar et al. |
| 2013/0172902 A1 | 7/2013 | Lightcap et al. |
| 2013/0211244 A1 | 8/2013 | Nathaniel |
| 2013/0274596 A1 | 10/2013 | Azizian et al. |
| 2013/0274673 A1 | 10/2013 | Fischell et al. |
| 2013/0274674 A1 | 10/2013 | Fischell et al. |
| 2013/0296712 A1 | 11/2013 | Durvasula |
| 2014/0005685 A1 | 1/2014 | Modrow et al. |
| 2014/0024945 A1 | 1/2014 | Mung et al. |
| 2014/0035762 A1 | 2/2014 | Shelton, IV et al. |
| 2014/0039520 A1 | 2/2014 | Haider et al. |
| 2014/0114180 A1 | 4/2014 | Jain |
| 2014/0163359 A1 | 6/2014 | Sholev et al. |
| 2014/0163664 A1 | 6/2014 | Goldsmith |
| 2014/0171793 A1 | 6/2014 | Lin et al. |
| 2014/0175150 A1 | 6/2014 | Shelton, IV et al. |
| 2014/0179997 A1 | 6/2014 | von Grunberg et al. |
| 2014/0267549 A1 | 9/2014 | Pinter et al. |
| 2014/0336461 A1 | 11/2014 | Reiter et al. |
| 2014/0378843 A1 | 12/2014 | Valdes et al. |
| 2015/0018999 A1 | 1/2015 | Lee et al. |
| 2015/0025548 A1 | 1/2015 | Franklin et al. |
| 2015/0032140 A1 | 1/2015 | Khouri |
| 2015/0051460 A1 | 2/2015 | Saxena et al. |
| 2015/0066107 A1 | 3/2015 | Richter et al. |
| 2015/0133909 A1 | 5/2015 | van der Weide et al. |
| 2015/0145966 A1 | 5/2015 | Krieger et al. |
| 2015/0202005 A1 | 7/2015 | Fuflyigin et al. |
| 2015/0209035 A1 | 7/2015 | Zemlok |
| 2015/0223903 A1 | 8/2015 | Bell et al. |
| 2015/0238071 A1 | 8/2015 | Hua et al. |
| 2015/0238276 A1 | 8/2015 | Atarot et al. |
| 2015/0243056 A1 | 8/2015 | Lee et al. |
| 2015/0245878 A1 | 9/2015 | Jaramaz et al. |
| 2015/0272557 A1 | 10/2015 | Overmyer et al. |
| 2015/0297177 A1 | 10/2015 | Boctor et al. |
| 2015/0305650 A1 | 10/2015 | Hunter et al. |
| 2015/0366628 A1 | 12/2015 | Ingmanson |
| 2016/0000516 A1 | 1/2016 | Cheng et al. |
| 2016/0007827 A1 | 1/2016 | Frimer et al. |
| 2016/0014328 A1 | 1/2016 | Rokutanda |
| 2016/0022146 A1 | 1/2016 | Piron et al. |
| 2016/0038004 A1 | 2/2016 | Tanaka |
| 2016/0070436 A1 | 3/2016 | Thomas et al. |
| 2016/0086380 A1 | 3/2016 | Vayser et al. |
| 2016/0135909 A1 | 5/2016 | Ogawa et al. |
| 2016/0183841 A1 | 6/2016 | Duindam et al. |
| 2016/0206204 A1 | 7/2016 | Matsuda et al. |
| 2016/0228090 A1 | 8/2016 | Boctor et al. |
| 2016/0235304 A1 | 8/2016 | Tzoumas et al. |
| 2016/0256101 A1 | 9/2016 | Aharoni et al. |
| 2016/0270861 A1 | 9/2016 | Guru et al. |
| 2016/0331467 A1 | 11/2016 | Slamin et al. |

(56) References Cited

U.S. PATENT DOCUMENTS

| | | |
|---|---|---|
| 2016/0346034 A1 | 12/2016 | Arya et al. |
| 2017/0007350 A1 | 1/2017 | Popovic et al. |
| 2017/0020460 A1 | 1/2017 | Leblond et al. |
| 2017/0020613 A1 | 1/2017 | Kang et al. |
| 2017/0055819 A1 | 3/2017 | Hansen et al. |
| 2017/0059408 A1 | 3/2017 | Korner et al. |
| 2017/0071475 A1 | 3/2017 | Irisawa |
| 2017/0071688 A1 | 3/2017 | Cohen et al. |
| 2017/0079530 A1 | 3/2017 | DiMaio et al. |
| 2017/0099479 A1 | 4/2017 | Browd et al. |
| 2017/0165008 A1 | 6/2017 | Finley |
| 2017/0172382 A1 | 6/2017 | Nir et al. |
| 2017/0172662 A1 | 6/2017 | Panescu et al. |
| 2017/0180704 A1 | 6/2017 | Panescu et al. |
| 2017/0181808 A1 | 6/2017 | Panescu et al. |
| 2017/0181809 A1 | 6/2017 | Panescu et al. |
| 2017/0189006 A1 | 7/2017 | Shluzas et al. |
| 2017/0197028 A1 | 7/2017 | Goldsmith |
| 2017/0202624 A1 | 7/2017 | Atarot et al. |
| 2017/0238962 A1 | 8/2017 | Hansen et al. |
| 2017/0251900 A1 | 9/2017 | Hansen et al. |
| 2017/0258526 A1* | 9/2017 | Lang ................... A61B 34/74 |
| 2017/0265943 A1 | 9/2017 | Sela et al. |
| 2017/0265947 A1 | 9/2017 | Dyer et al. |
| 2017/0296213 A1 | 10/2017 | Swensgard et al. |
| 2017/0304007 A1 | 10/2017 | Piron et al. |
| 2017/0312032 A1 | 11/2017 | Amanatullah et al. |
| 2017/0319057 A1 | 11/2017 | Inglese et al. |
| 2017/0366773 A1 | 12/2017 | Kiraly et al. |
| 2017/0367580 A1 | 12/2017 | DiMaio et al. |
| 2018/0014777 A1 | 1/2018 | Amir et al. |
| 2018/0014851 A1 | 1/2018 | Hansen et al. |
| 2018/0064498 A1 | 3/2018 | Kapadia et al. |
| 2018/0082480 A1* | 3/2018 | White ................... G06T 11/00 |
| 2018/0168741 A1 | 6/2018 | Swayze et al. |
| 2018/0214016 A1 | 8/2018 | Thommen et al. |
| 2018/0228555 A1 | 8/2018 | Charron et al. |
| 2018/0228559 A1 | 8/2018 | Brierton et al. |
| 2018/0235715 A1* | 8/2018 | Amiot ................... G01B 11/25 |
| 2018/0242967 A1 | 8/2018 | Meade |
| 2018/0247128 A1 | 8/2018 | Alvi et al. |
| 2018/0247153 A1 | 8/2018 | Ganapati et al. |
| 2018/0271603 A1 | 9/2018 | Nir et al. |
| 2018/0271615 A1 | 9/2018 | Mahadik et al. |
| 2018/0333210 A1 | 11/2018 | Nijkamp et al. |
| 2018/0338806 A1 | 11/2018 | Grubbs |
| 2018/0343381 A1 | 11/2018 | Kobayashi et al. |
| 2018/0344140 A1 | 12/2018 | Aizenfeld |
| 2018/0368883 A1 | 12/2018 | Rossa et al. |
| 2019/0008579 A1 | 1/2019 | Begg et al. |
| 2019/0022418 A1 | 1/2019 | Fishman |
| 2019/0046276 A1 | 2/2019 | Inglese et al. |
| 2019/0053691 A1 | 2/2019 | Hansen et al. |
| 2019/0053872 A1 | 2/2019 | Meglan |
| 2019/0059736 A1 | 2/2019 | Maier-Hein et al. |
| 2019/0069824 A1 | 3/2019 | Darty et al. |
| 2019/0076186 A1 | 3/2019 | Fischell et al. |
| 2019/0099070 A1 | 4/2019 | Mark et al. |
| 2019/0099226 A1* | 4/2019 | Hallen ................. H04N 13/324 |
| 2019/0104919 A1 | 4/2019 | Shelton, IV et al. |
| 2019/0110924 A1 | 4/2019 | Moreno et al. |
| 2019/0117319 A1 | 4/2019 | Cima et al. |
| 2019/0125361 A1 | 5/2019 | Shelton, IV et al. |
| 2019/0125454 A1 | 5/2019 | Stokes et al. |
| 2019/0125455 A1 | 5/2019 | Shelton, IV et al. |
| 2019/0125456 A1 | 5/2019 | Shelton, IV et al. |
| 2019/0125457 A1 | 5/2019 | Parihar et al. |
| 2019/0125459 A1 | 5/2019 | Shelton, IV et al. |
| 2019/0142524 A1 | 5/2019 | Hladio et al. |
| 2019/0159848 A1 | 5/2019 | Quaid et al. |
| 2019/0175272 A1 | 6/2019 | Khan et al. |
| 2019/0180865 A1 | 6/2019 | Kashima et al. |
| 2019/0192145 A1 | 6/2019 | Shelton, IV et al. |
| 2019/0192150 A1 | 6/2019 | Widenhouse et al. |
| 2019/0192151 A1 | 6/2019 | Shelton, IV et al. |
| 2019/0200905 A1 | 7/2019 | Shelton, IV et al. |
| 2019/0200906 A1 | 7/2019 | Shelton, IV et al. |
| 2019/0200981 A1 | 7/2019 | Harris et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201102 A1 | 7/2019 | Shelton, IV et al. |
| 2019/0201116 A1 | 7/2019 | Shelton, IV et al. |
| 2019/0201136 A1* | 7/2019 | Shelton, IV ............ G16H 20/40 |
| 2019/0201137 A1 | 7/2019 | Shelton, IV et al. |
| 2019/0201142 A1 | 7/2019 | Shelton, IV et al. |
| 2019/0201594 A1 | 7/2019 | Shelton, IV et al. |
| 2019/0204201 A1 | 7/2019 | Shelton, IV et al. |
| 2019/0205567 A1 | 7/2019 | Shelton, IV et al. |
| 2019/0206562 A1 | 7/2019 | Shelton, IV et al. |
| 2019/0206564 A1 | 7/2019 | Shelton, IV et al. |
| 2019/0206569 A1 | 7/2019 | Shelton, IV et al. |
| 2019/0223961 A1 | 7/2019 | Barral et al. |
| 2019/0247050 A1 | 8/2019 | Goldsmith |
| 2019/0269476 A1 | 9/2019 | Bowling et al. |
| 2019/0279524 A1 | 9/2019 | Stoyanov et al. |
| 2019/0293554 A1 | 9/2019 | Nakao et al. |
| 2019/0307524 A1 | 10/2019 | Popovic |
| 2019/0311542 A1 | 10/2019 | Douglas et al. |
| 2019/0320117 A1 | 10/2019 | Wu et al. |
| 2019/0320878 A1 | 10/2019 | Duindam et al. |
| 2019/0321118 A1* | 10/2019 | Genova ................ A61B 90/37 |
| 2019/0374140 A1 | 12/2019 | Tucker et al. |
| 2019/0388157 A1 | 12/2019 | Shameli et al. |
| 2020/0008879 A1 | 1/2020 | Popovic et al. |
| 2020/0015898 A1 | 1/2020 | Scheib et al. |
| 2020/0015899 A1 | 1/2020 | Scheib et al. |
| 2020/0015900 A1 | 1/2020 | Scheib et al. |
| 2020/0015901 A1 | 1/2020 | Scheib et al. |
| 2020/0015902 A1 | 1/2020 | Scheib et al. |
| 2020/0015903 A1 | 1/2020 | Scheib et al. |
| 2020/0015904 A1 | 1/2020 | Scheib et al. |
| 2020/0015907 A1 | 1/2020 | Scheib |
| 2020/0015924 A1 | 1/2020 | Scheib et al. |
| 2020/0015925 A1 | 1/2020 | Scheib |
| 2020/0018844 A1 | 1/2020 | Fridman et al. |
| 2020/0030036 A1 | 1/2020 | Forstein |
| 2020/0037858 A1 | 2/2020 | Pedreira de Cerqueira Filho |
| 2020/0038112 A1 | 2/2020 | Amanatullah et al. |
| 2020/0060725 A1 | 2/2020 | Sato |
| 2020/0121245 A1 | 4/2020 | Barclay et al. |
| 2020/0188032 A1 | 6/2020 | Komp et al. |
| 2020/0222146 A1 | 7/2020 | Komp |
| 2020/0246073 A1 | 8/2020 | Rossetto et al. |
| 2020/0273577 A1 | 8/2020 | Wolf et al. |
| 2020/0281662 A1 | 9/2020 | Cong et al. |
| 2020/0289205 A1 | 9/2020 | Scheib et al. |
| 2020/0289216 A1 | 9/2020 | Denlinger et al. |
| 2020/0289217 A1 | 9/2020 | Denlinger et al. |
| 2020/0289219 A1 | 9/2020 | Denlinger et al. |
| 2020/0289221 A1 | 9/2020 | Denlinger et al. |
| 2020/0289222 A1 | 9/2020 | Denlinger et al. |
| 2020/0289223 A1 | 9/2020 | Denlinger et al. |
| 2020/0289228 A1 | 9/2020 | Denlinger et al. |
| 2020/0289229 A1 | 9/2020 | Enlinger et al. |
| 2020/0291476 A1 | 9/2020 | Deng et al. |
| 2020/0315721 A1 | 10/2020 | Rabindran et al. |
| 2020/0330166 A1 | 10/2020 | Meglan et al. |
| 2020/0345451 A1 | 11/2020 | Peine et al. |
| 2020/0367972 A1 | 11/2020 | Zhang et al. |
| 2020/0397266 A1 | 12/2020 | Hufford |
| 2020/0405395 A1 | 12/2020 | Gullotti et al. |
| 2021/0045838 A1* | 2/2021 | Bradbury ............. G06T 19/006 |
| 2021/0068908 A1 | 3/2021 | Thienphrapa et al. |
| 2021/0137634 A1 | 5/2021 | Lang |
| 2021/0196098 A1 | 7/2021 | Shelton, IV et al. |
| 2021/0196108 A1 | 7/2021 | Shelton, IV |
| 2021/0196109 A1 | 7/2021 | Shelton, IV et al. |
| 2021/0196381 A1 | 7/2021 | Eckert et al. |
| 2021/0196382 A1 | 7/2021 | Mumaw et al. |
| 2021/0196383 A1 | 7/2021 | Shelton, IV et al. |
| 2021/0196384 A1 | 7/2021 | Shelton, IV et al. |
| 2021/0196385 A1 | 7/2021 | Shelton, IV et al. |
| 2021/0196386 A1 | 7/2021 | Shelton, IV et al. |

(56) References Cited

U.S. PATENT DOCUMENTS

| | | |
|---|---|---|
| 2021/0196423 A1 | 7/2021 | Shelton, IV et al. |
| 2021/0199557 A1 | 7/2021 | Shelton, IV et al. |
| 2021/0205019 A1 | 7/2021 | Shelton, IV et al. |
| 2021/0212792 A1 | 7/2021 | Shelton, IV et al. |
| 2021/0212794 A1 | 7/2021 | Shelton, IV et al. |
| 2021/0259660 A1 | 8/2021 | Bharat et al. |
| 2021/0259789 A1 | 8/2021 | Wright et al. |
| 2021/0275251 A1 | 9/2021 | Shelton, IV et al. |
| 2021/0282861 A1 | 9/2021 | Eckert et al. |
| 2021/0307835 A1 | 10/2021 | Shelton, IV et al. |
| 2021/0307865 A1 | 10/2021 | Shelton, IV et al. |
| 2021/0307866 A1 | 10/2021 | Shelton, IV et al. |
| 2021/0307867 A1 | 10/2021 | Shelton, IV et al. |
| 2021/0307868 A1 | 10/2021 | Shelton, IV et al. |
| 2021/0307869 A1 | 10/2021 | Shelton, IV et al. |
| 2021/0307870 A1 | 10/2021 | Shelton, IV et al. |
| 2022/0000559 A1 | 1/2022 | Leonard et al. |
| 2022/0000565 A1 | 1/2022 | Gururaj et al. |
| 2022/0047259 A1 | 2/2022 | Prior et al. |
| 2022/0079675 A1 | 3/2022 | Lang |
| 2022/0133412 A1 | 5/2022 | Tolkowsky et al. |
| 2022/0273288 A1 | 9/2022 | Scheib et al. |
| 2022/0323066 A1 | 10/2022 | Scheib et al. |
| 2023/0046220 A1 | 2/2023 | Scheib et al. |

FOREIGN PATENT DOCUMENTS

| | | |
|---|---|---|
| EP | 2700365 A1 | 2/2014 |
| EP | 2754383 A2 | 7/2014 |
| EP | 3367387 A1 | 8/2018 |
| JP | 2006280591 A | 10/2006 |
| JP | 4106991 B2 | 6/2008 |
| KR | 20120068597 A | 6/2012 |
| WO | WO-2008033133 A2 | 3/2008 |
| WO | WO-2013093391 A1 | 6/2013 |
| WO | WO-2013163391 A1 | 10/2013 |
| WO | WO-2015135058 A1 | 9/2015 |
| WO | WO-2018171851 A1 | 9/2018 |
| WO | WO-2018200767 A1 | 11/2018 |
| WO | WO-2019130085 A1 | 7/2019 |
| WO | WO-2020116991 A1 | 6/2020 |

OTHER PUBLICATIONS

Thyroid Fine Needle Aspiration (FNA) Biopsy, retrieved from www.fairview.org/patient-education/90246 on Feb. 4, 2020. 3 pages.

Open Technique for Low Anterior Resection, retrieved from https://abdominalkey.com/open-technique-for-low-anterior-resection/ on Feb. 4, 2020. 6 pages.

Sukumar et al., "Robotic Partial Nephrectomy Using Robotic Bulldog Clamps," JSLS: Journal of the Society of Laparoendoscopic Surgeons, 15(4), pp. 520-526, 2011.

X12C4 Robotic Drop-In, retrieved from https://bkultrasound.com/transducers/x12c4-robotic-drop-in on Feb. 13, 2020. 2 pages.

"ATM-MPLS Networking Version 2.0, af-aic-0178.001" ATM Standard, The ATM Forum Technical Committee, published Aug. 2003.

IEEE Std 802.Mar. 2012 (Revision of IEEE Std 802.3-2008, published Dec. 28, 2012.

Lacy, Antonio, "Main Steps to Perform a Sleeve Gastrectomy," retrieved from https://aischannel.com/society/main-steps-to-perform-a-sleeve-gastrectomy/ on Feb. 14, 2020. pp. 1-7, Jun. 11, 2015.

Elhajj, et al., "Sleeve Gastrectomy Surgical Assistive Instrument for Accurate Remnant Stomach Volume," ASME, J. Med. Devices, vol. 4, pp. 1-10, Jun. 2010.

Brecht, Hans-Peter et al., "Whole-body three-dimensional optoacoustic tomography system for small animals," Journal of Biomedical Optics, vol. 14, No. 6, 064007-1-064007-7 (2009).

Ge, Jiawei et al., "Landmark-Guided Deformable Image Registration for Supervised Autonomous Robotic Tumor Resection," Advances in Intelligent Data Analysis XIX, LNCS, Springer International Publishing, pp. 320-328, Oct. 10, 2019.

Ueda et al., "Quantitative computed tomography for the prediction of pulmonary function after lung cancer surgery: a simple method using simulation software," European Journal of Cardio-thoracic Surgery, 35 (2009) 414-418.

Fuchs et al., "Three-dimensional visualization and virtual simulation of resections in pediatric solid tumors," Journal of Pediatric Surgery (2005) 40, 364-370.

Brainlab Ag: "iPLAN CRANIAL—Software user guide", Jan. 1, 2014, Retrieved from the internet: URL: https://userguides.brainlab.com/wp-content/uploads/2019/12/iPlan-Cranial-3.0-Software-User-Guide-English-60914-63EN-Rev.1.4.pdf, pp. 1-268 (Jan. 1, 2014).

* cited by examiner

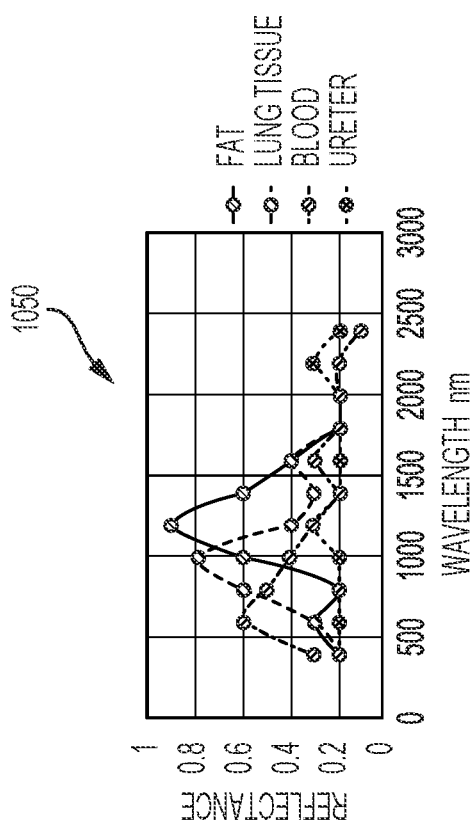
FIG. 13C
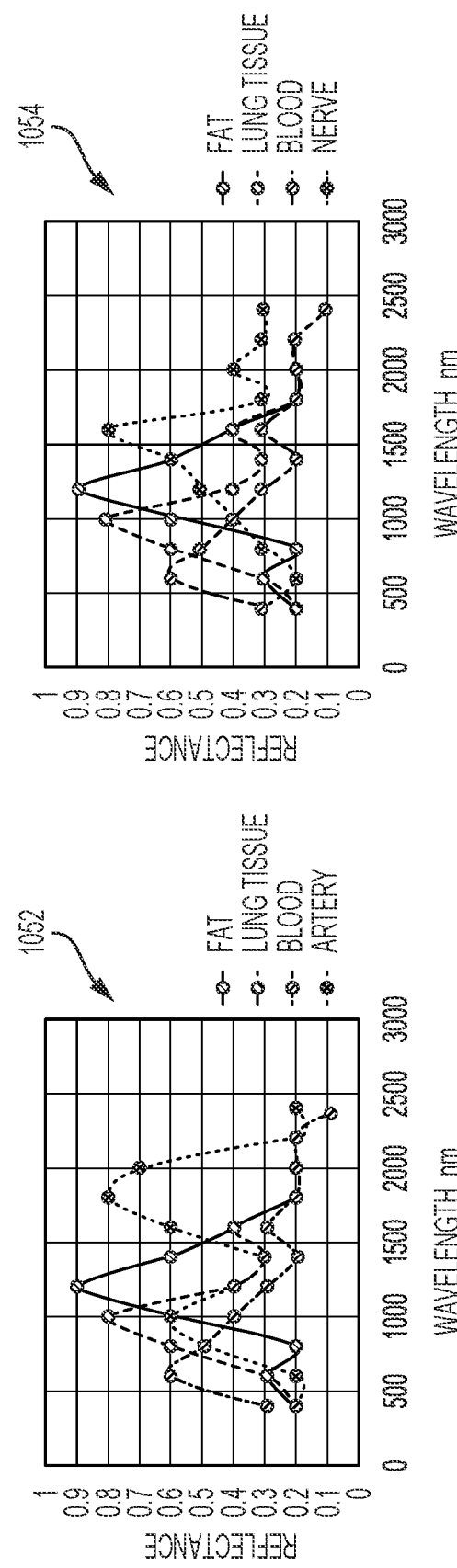
FIG. 13E
FIG. 13D

FIG. 21

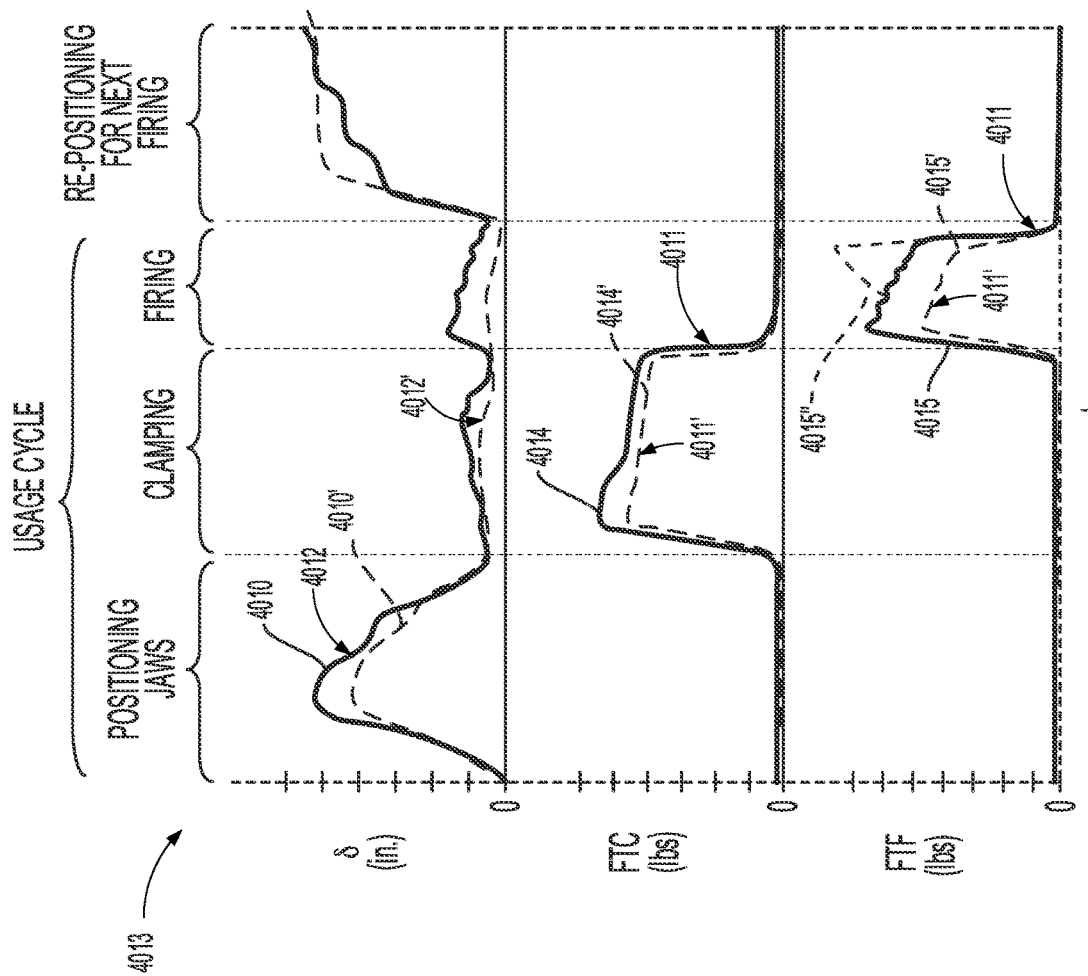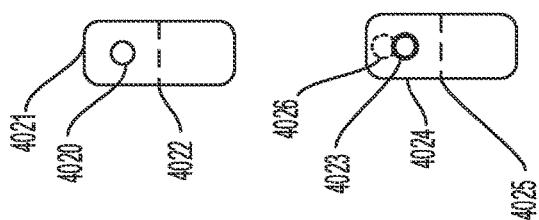
FIG. 24

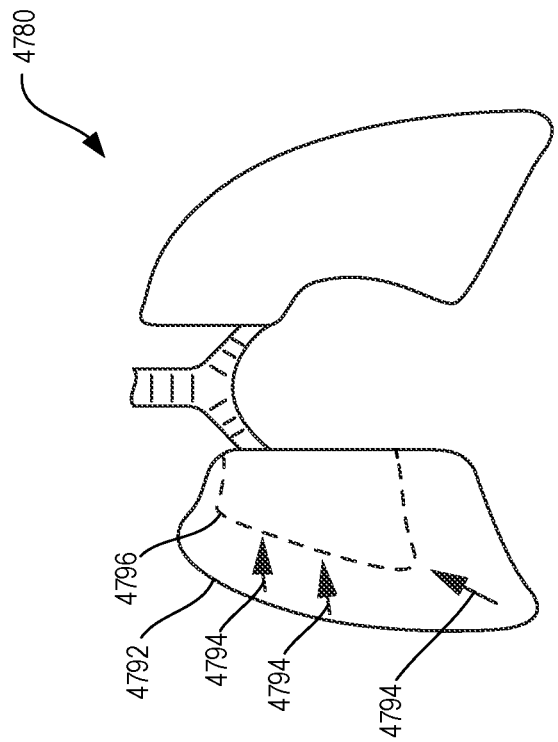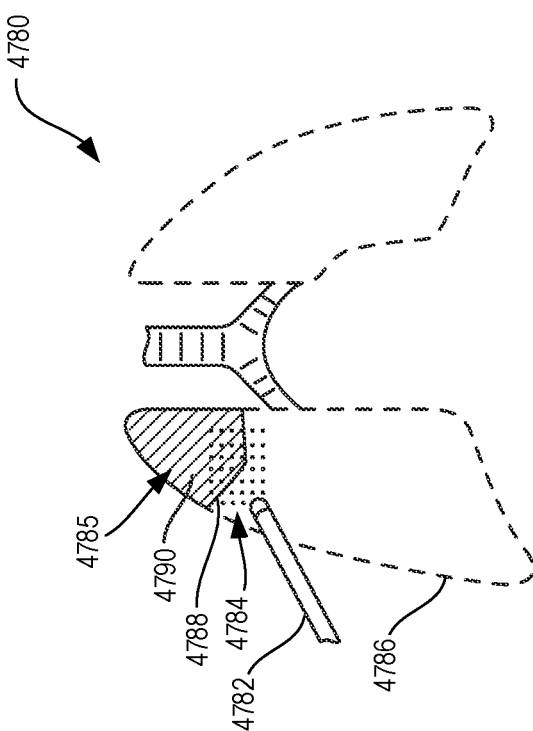
FIG. 41B
FIG. 41A

SURGICAL SYSTEMS FOR GENERATING THREE DIMENSIONAL CONSTRUCTS OF ANATOMICAL ORGANS AND COUPLING IDENTIFIED ANATOMICAL STRUCTURES THERETO

CROSS-REFERENCE TO RELATED APPLICATION

This application is a continuation patent application claiming priority under 35 U.S.C. § 120 to U.S. patent application Ser. No. 16/729,751, titled SURGICAL SYSTEMS FOR GENERATING THREE DIMENSIONAL CONSTRUCTS OF ANATOMICAL ORGANS AND COUPLING IDENTIFIED ANATOMICAL STRUCTURES THERETO, filed Dec. 30, 2019, the entire disclosure of which is hereby incorporated by reference herein.

BACKGROUND

Surgical systems often incorporate an imaging system, which can allow the clinician(s) to view the surgical site and/or one or more portions thereof on one or more displays such as a monitor, for example. The display(s) can be local and/or remote to a surgical theater. An imaging system can include a scope with a camera that views the surgical site and transmits the view to a display that is viewable by a clinician. Scopes include, but are not limited to, arthroscopes, angioscopes, bronchoscopes, choledochoscopes, colonoscopes, cytoscopes, duodenoscopes, enteroscopes, esophagogastro-duodenoscopes (gastroscopes), endoscopes, laryngoscopes, nasopharyngo-neproscopes, sigmoidoscopes, thoracoscopes, ureteroscopes, and exoscopes. Imaging systems can be limited by the information that they are able to recognize and/or convey to the clinician(s). For example, certain concealed structures, physical contours, and/or dimensions within a three-dimensional space may be unrecognizable intraoperatively by certain imaging systems. Additionally, certain imaging systems may be incapable of communicating and/or conveying certain information to the clinician(s) intraoperatively.

SUMMARY

In one general aspect, a surgical system for use in a surgical procedure is disclosed. The surgical system includes at least one imaging device and a control circuit configured to identify an anatomical organ targeted by the surgical procedure, generate a virtual three-dimensional (3D) construct of at least a portion of the anatomical organ based on visualization data from the at least one imaging device, identify anatomical structures relevant to the surgical procedure from the visualization data from the at least one imaging device, couple the anatomical structures to the virtual 3D construct, and overlay onto the virtual 3D construct a layout plan of the surgical procedure determined based on the anatomical structures.

In another general aspect, a surgical system for use with a surgical instrument in a surgical procedure is disclosed. The surgical system includes at least one imaging device and a control circuit configured to identify an anatomical organ targeted by the surgical procedure, identify anatomical structures relevant to the surgical procedure from visualization data from the at least one imaging device, and propose surgical resection paths for removing a portion of the anatomical organ by the surgical instrument. The surgical resection paths are determined based on the anatomical structures.

In yet another general aspect, a surgical system for use with a surgical instrument in a surgical procedure is disclosed. The surgical system comprises at least one imaging device and a control circuit configured to identify an anatomical organ targeted by the surgical procedure, identify anatomical structures relevant to the surgical procedure from visualization data from the at least one imaging device, propose a surgical resection path for removing a portion of the anatomical organ by the surgical instrument, and modify the surgical resection path during the surgical procedure. The surgical resection path is determined based on the anatomical structures.

FIGURES

The novel features of the various aspects are set forth with particularity in the appended claims. The described aspects, however, both as to organization and methods of operation, may be best understood by reference to the following description, taken in conjunction with the accompanying drawings in which:

FIGS. 7A and 7B are views of the critical structure taken by the three-dimensional camera of FIG. 6, in which FIG. 7A is a view from a left-side lens of the three-dimensional camera and FIG. 7B is a view from a right-side lens of the three-dimensional camera, according to at least one aspect of the present disclosure.

FIGS. 13C-13E depict illustrative hyperspectral identifying signatures to differentiate anatomy from obscurants, wherein FIG. 13C is a graphical representation of a ureter signature versus obscurants, FIG. 13D is a graphical representation of an artery signature versus obscurants, and FIG. 13E is a graphical representation of a nerve signature versus obscurants, according to at least one aspect of the present disclosure.

Figure 14:
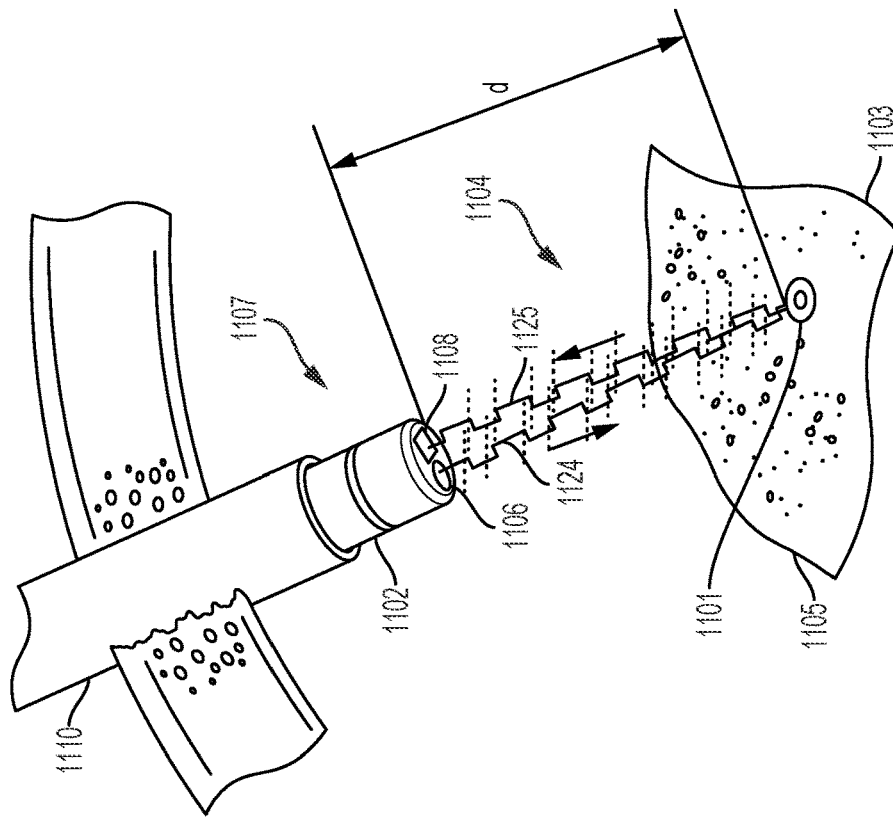

FIG. 14 is a schematic of a near infrared (NIR) time-of-flight measurement system configured to sense distance to a critical anatomical structure, the time-of-flight measurement system including a transmitter (emitter) and a receiver (sensor) positioned on a common device, according to at least one aspect of the present disclosure.

Figure 15:
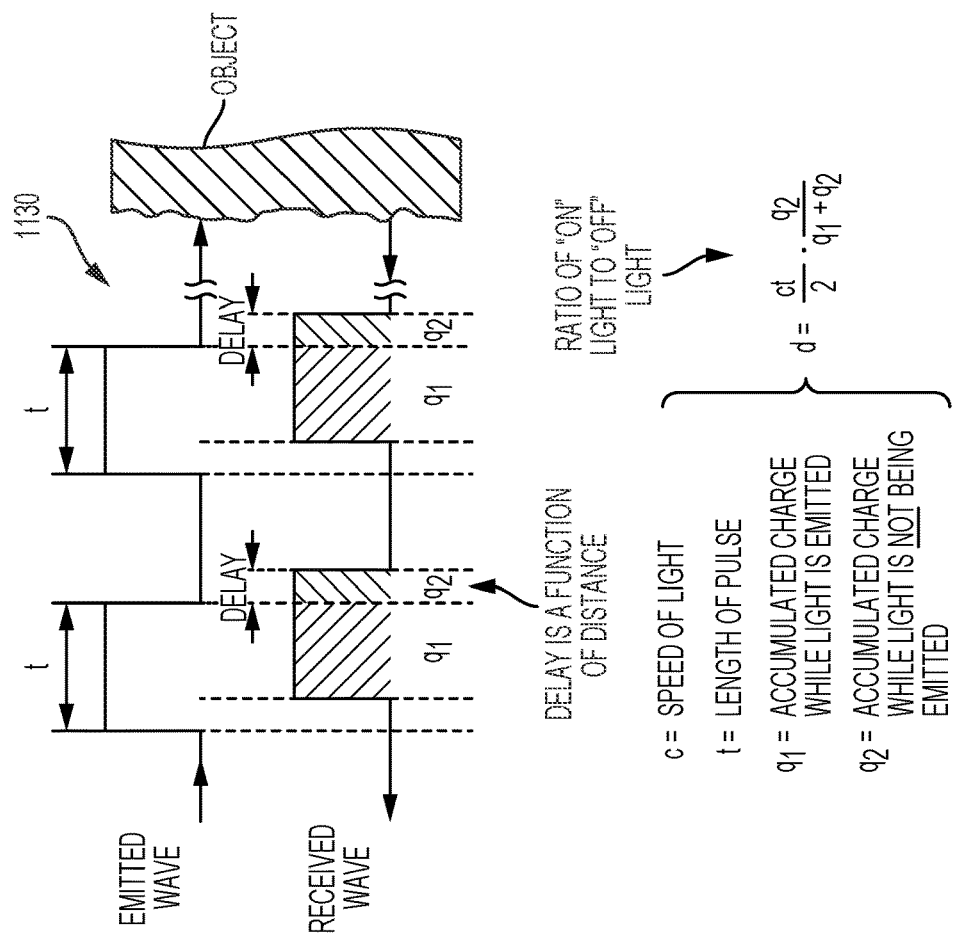

FIG. 15 is a schematic of an emitted wave, a received wave, and a delay between the emitted wave and the received wave of the NIR time-of-flight measurement system of FIG. 17A, according to at least one aspect of the present disclosure.

Figure 16:
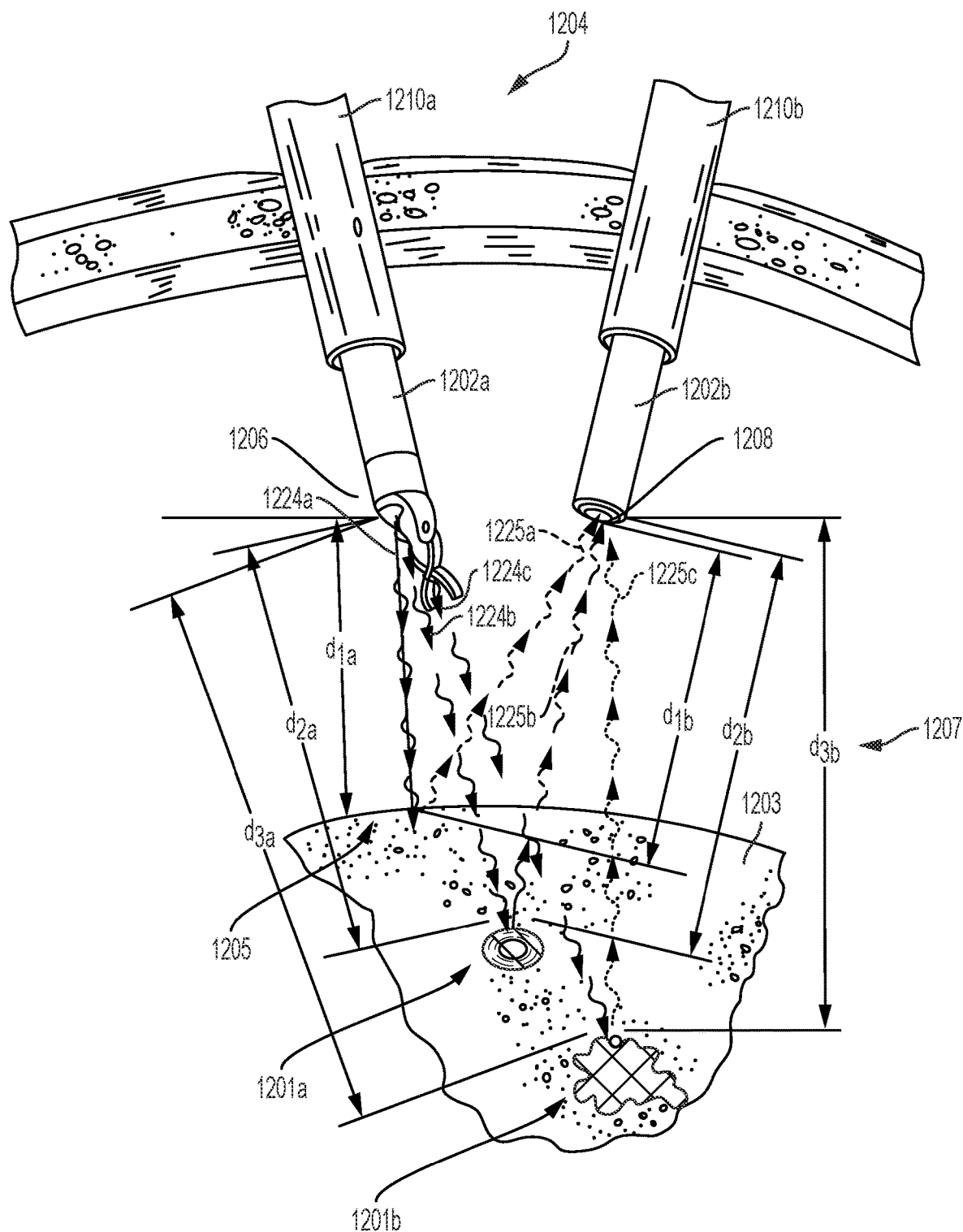

FIG. 16 illustrates a NIR time-of-flight measurement system configured to sense a distance to different structures, the time-of-flight measurement system including a transmitter (emitter) and a receiver (sensor) on separate devices, according to at least one aspect of the present disclosure.

Figure 17:
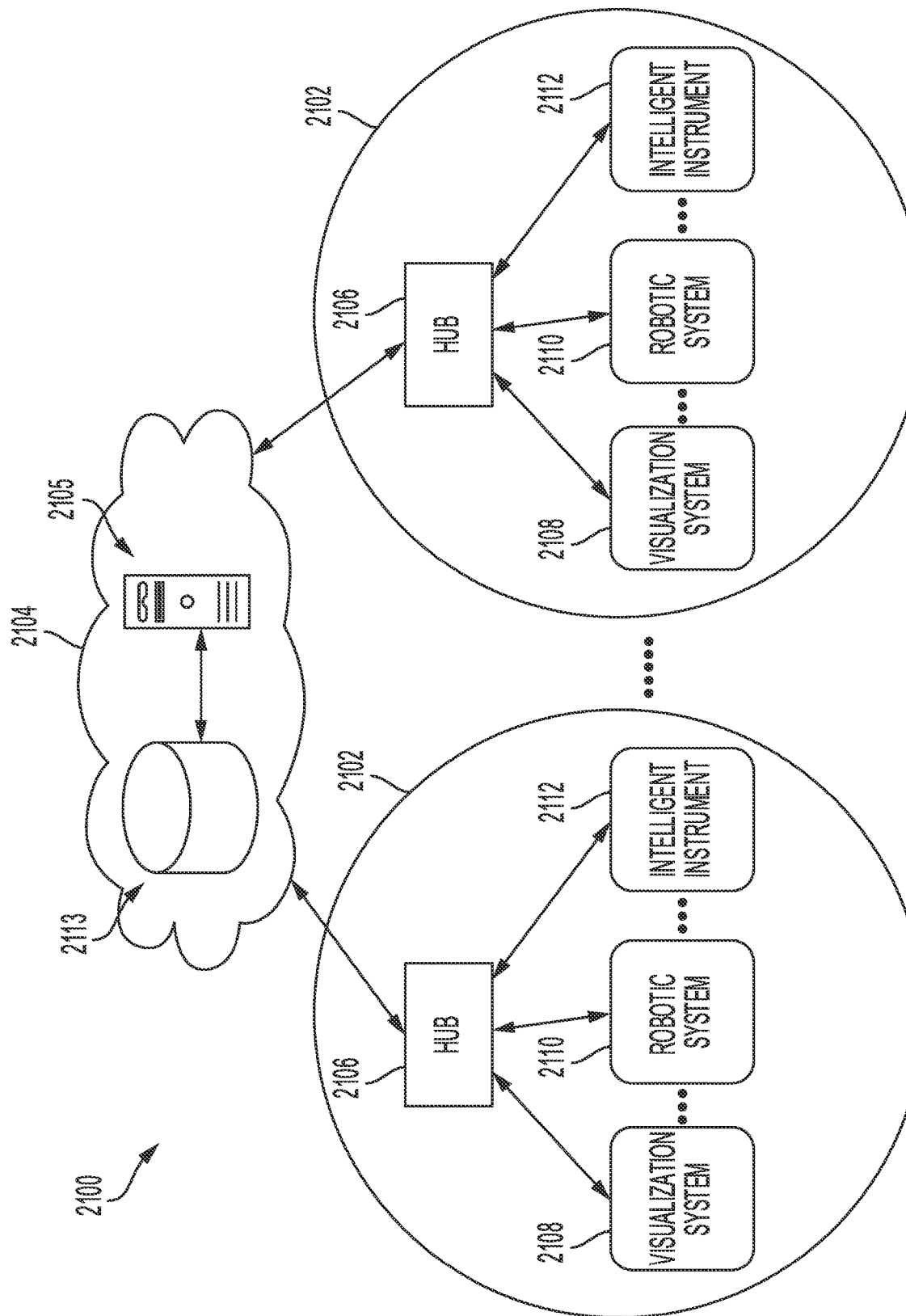

FIG. 17 is a block diagram of a computer-implemented interactive surgical system, according to at least one aspect of the present disclosure.

Figure 18:
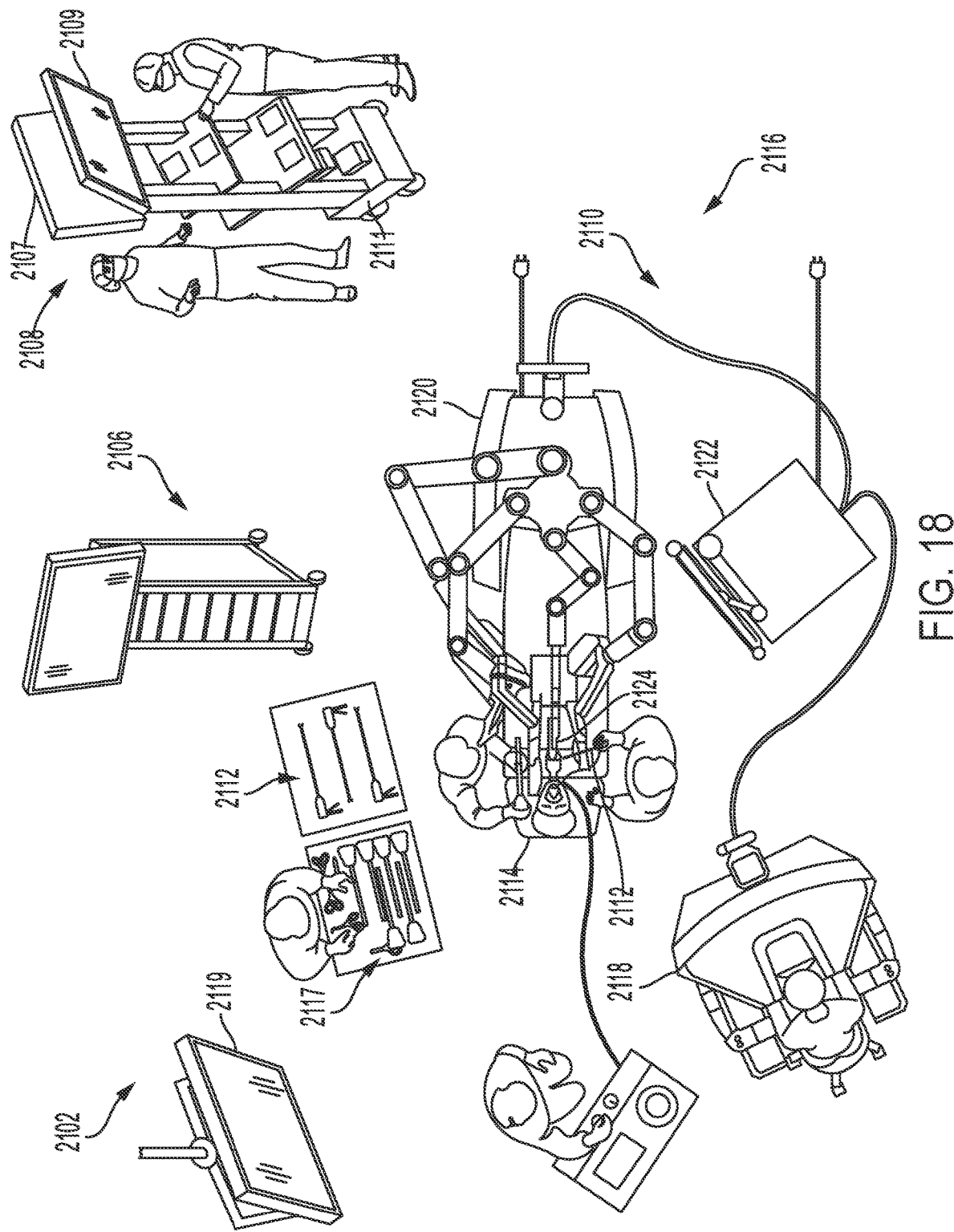

FIG. 18 is a surgical system being used to perform a surgical procedure in an operating room, according to at least one aspect of the present disclosure.

Figure 19:
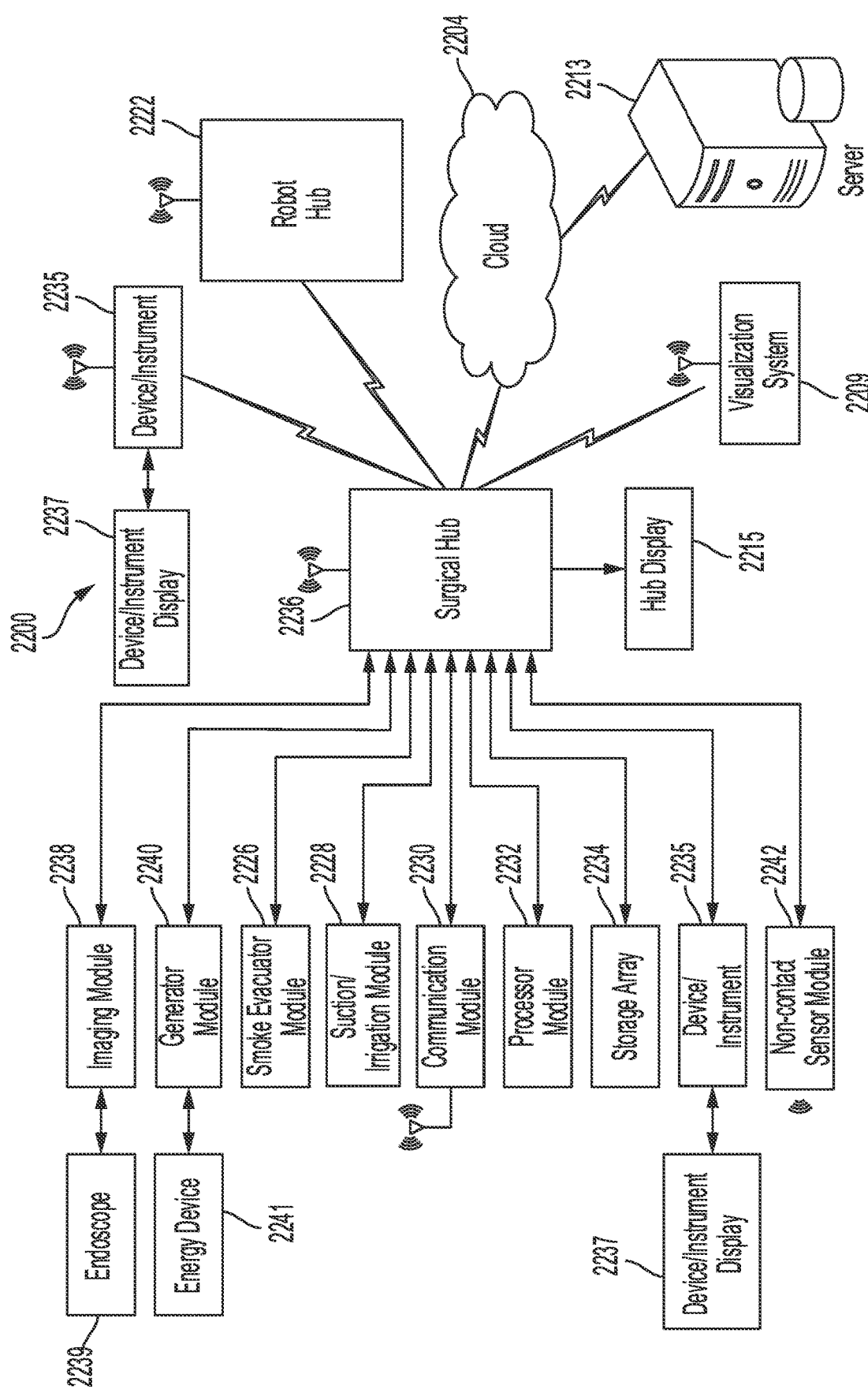

FIG. 19 illustrates a computer-implemented interactive surgical system, according to at least one aspect of the present disclosure.

Figure 20:
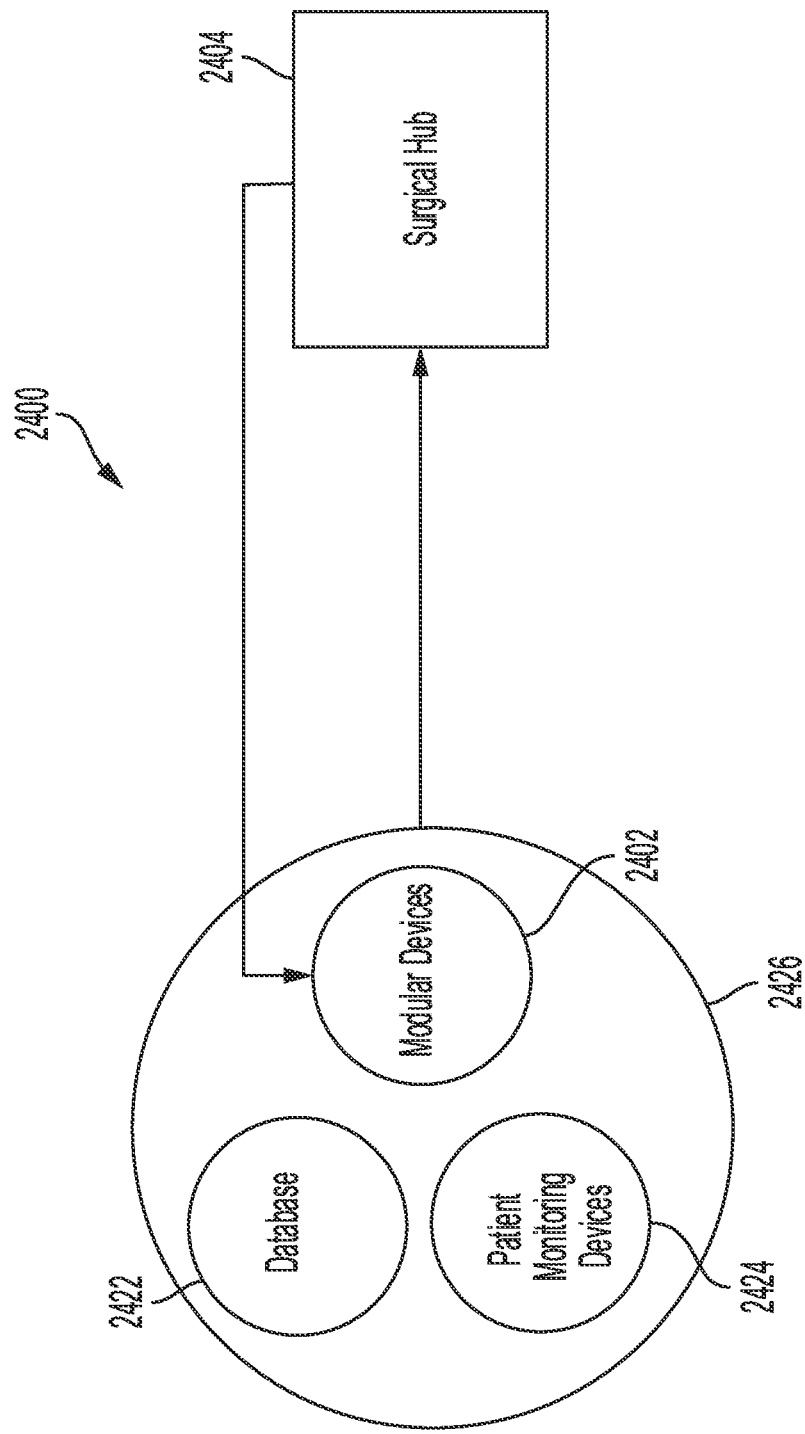

FIG. 20 illustrates a diagram of a situationally aware surgical system, according to at least one aspect of the present disclosure.

Figure 21:
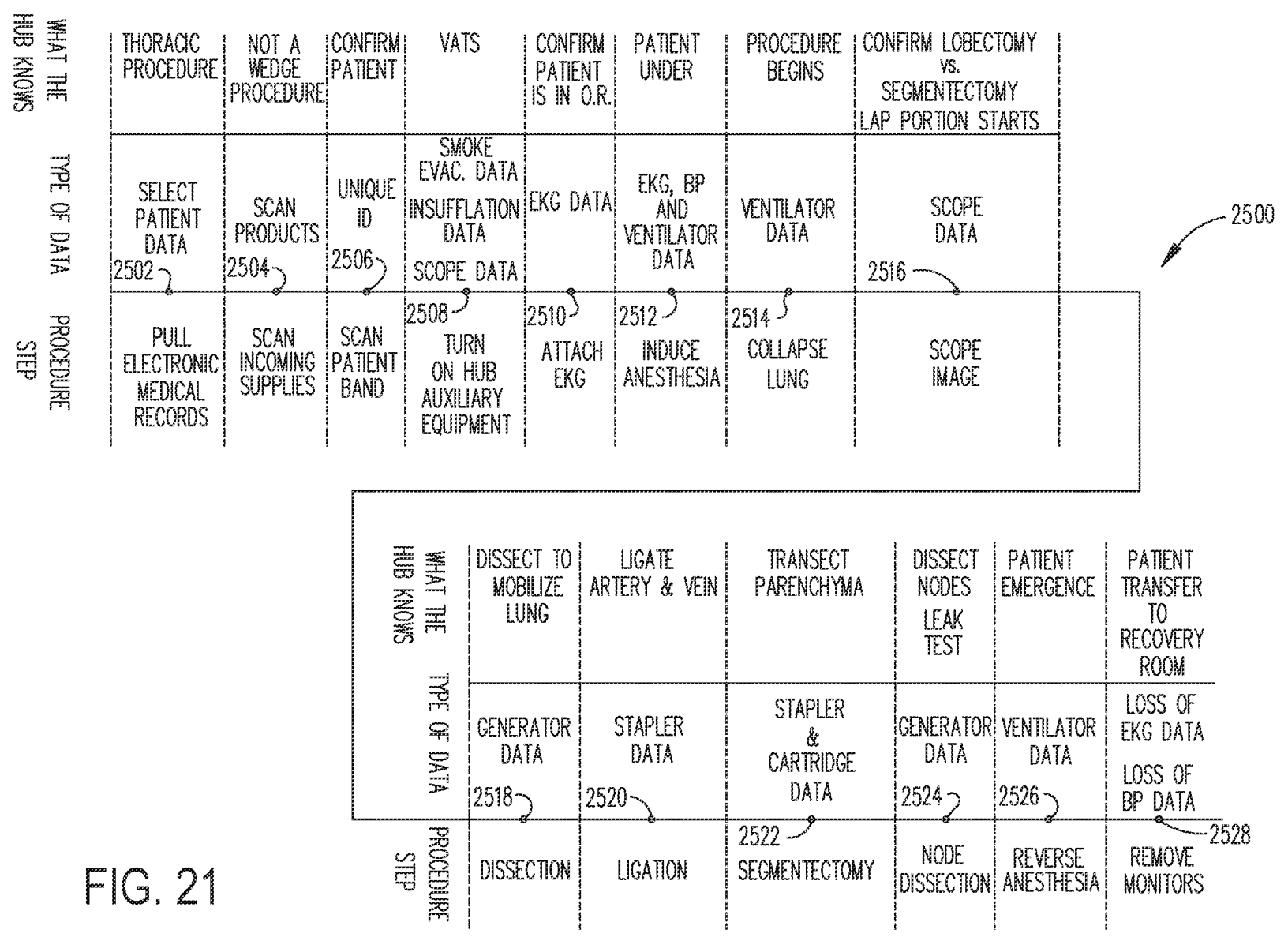

FIG. 21 illustrates a timeline depicting situational awareness of a hub, according to at least one aspect of the present disclosure.

Figure 22:

FIG. 22 is a logic flow diagram of a process depicting a control program or a logic configuration for correlating visualization data with instrument data, in accordance with at least one aspect of the present disclosure.

Figure 23:
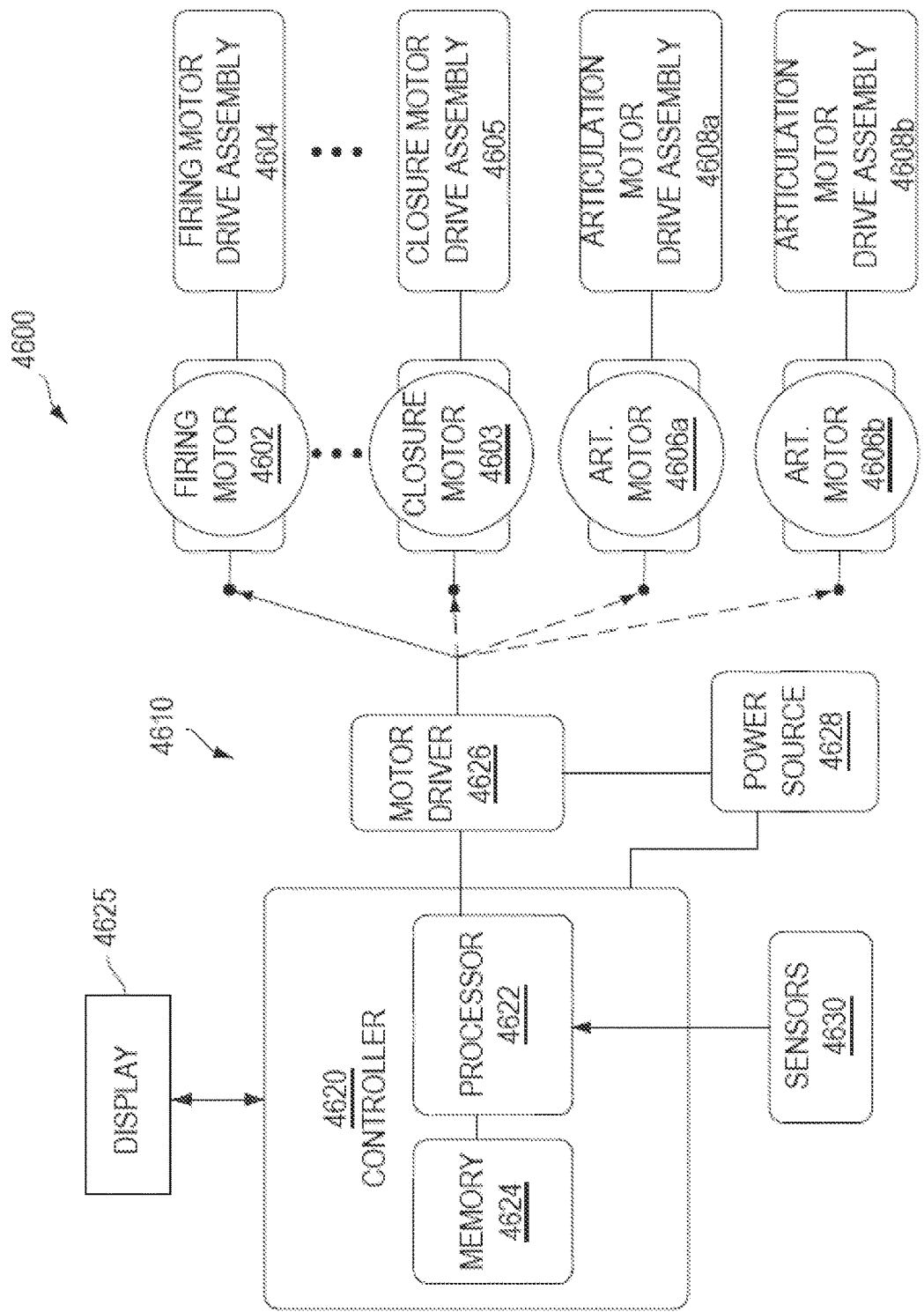

FIG. 23 is a schematic diagram of a surgical instrument, in accordance with at least one aspect of the present disclosure.

FIG. 24 is a graph depicting a composite data set and Force-to-Close ("FTC") and Force-to-Fire ("FTF") virtual gauges, in accordance with at least one aspect of the present disclosure.

Figure 25B:
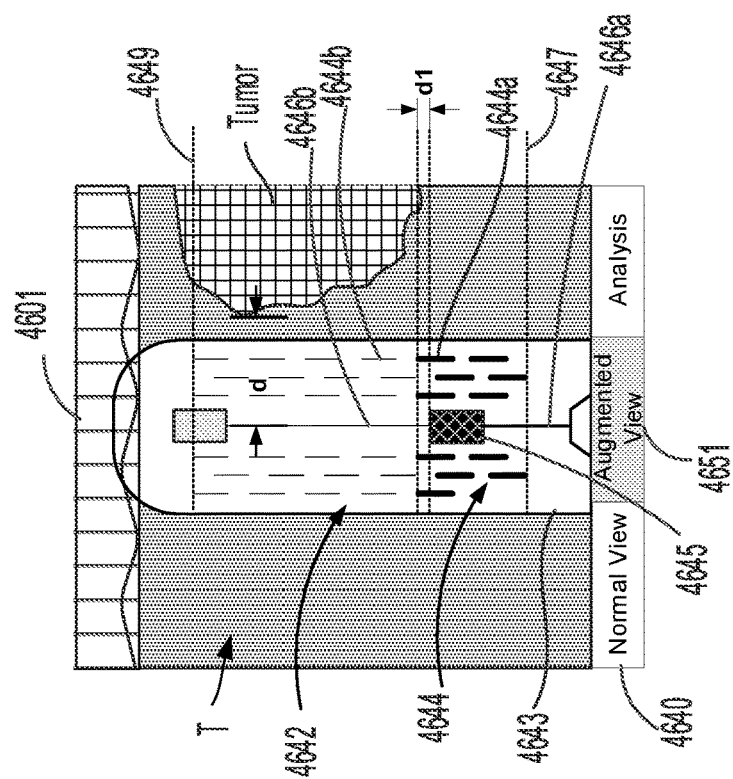
Figure 25A:
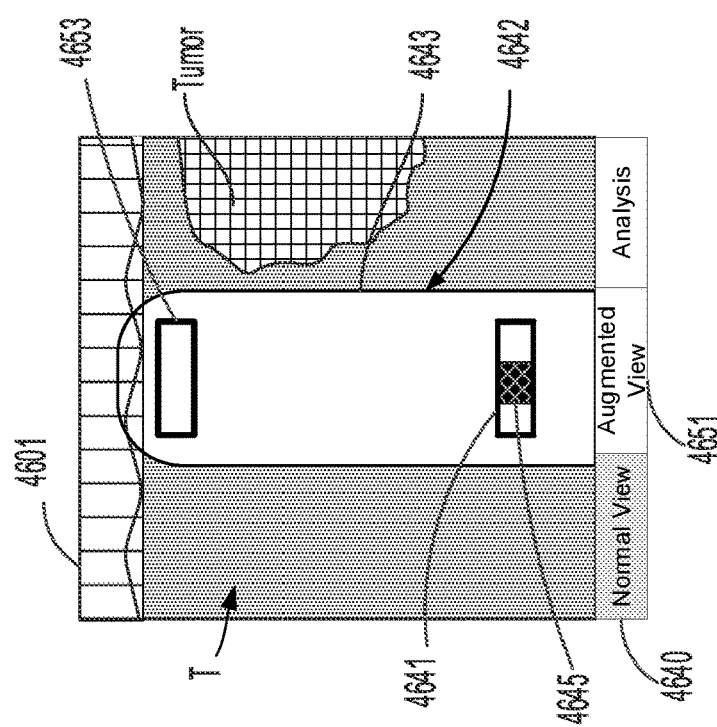

FIG. 25A illustrates a normal view of a screen of a visualization system displaying a live feed of an end effector in a surgical field of a surgical procedure, in accordance with at least one aspect of the present disclosure.

FIG. 25B illustrates an augmented view of a screen of a visualization system displaying a live feed of an end effector in a surgical field of a surgical procedure, in accordance with at least one aspect of the present disclosure.

Figure 26:
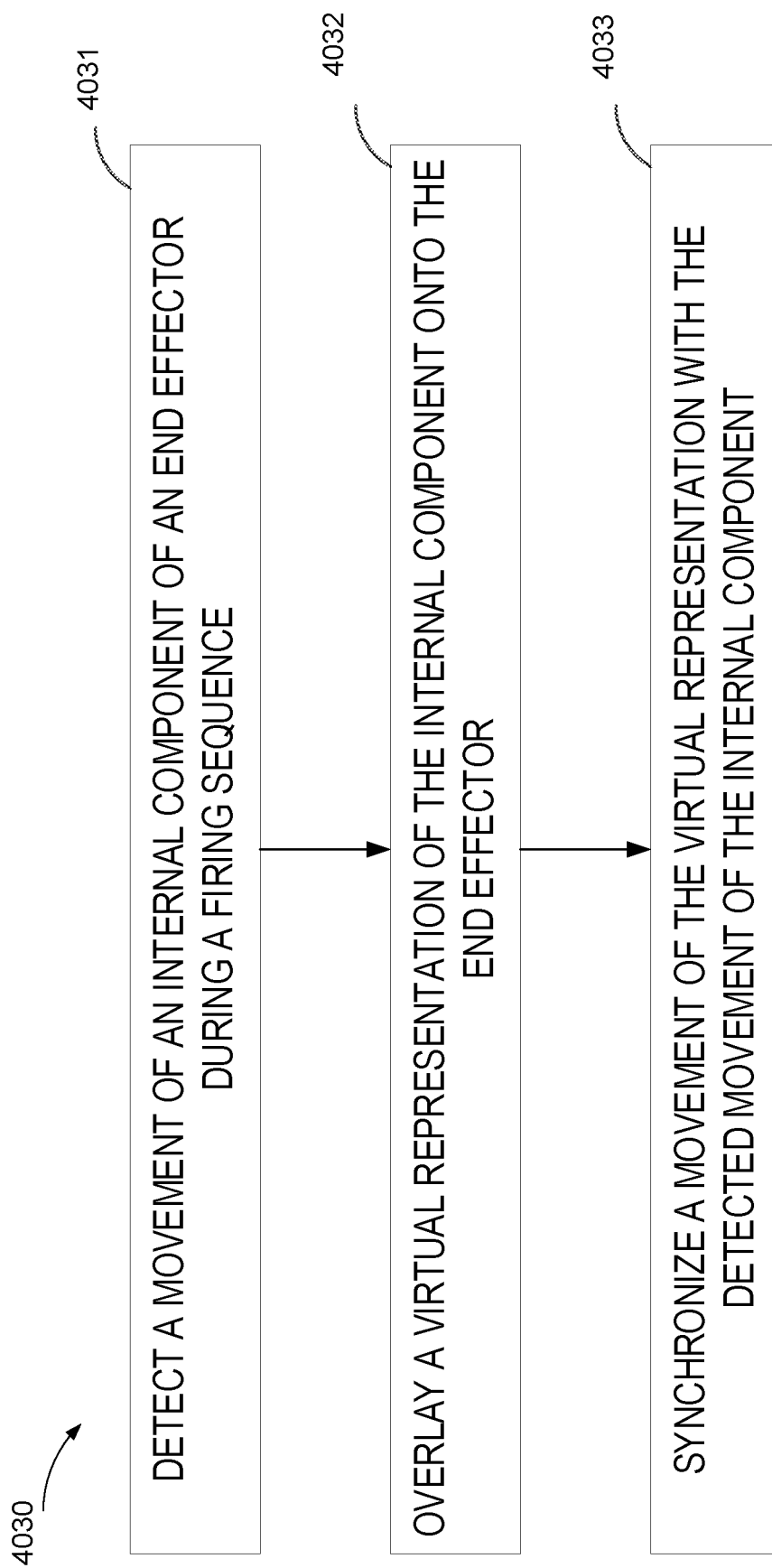

FIG. 26 is a logic flow diagram of a process depicting a control program or a logic configuration for synchronizing movement of a virtual representation of an end-effector component with actual movement of the end-effector component, in accordance with at least one aspect of the present disclosure.

Figure 27:
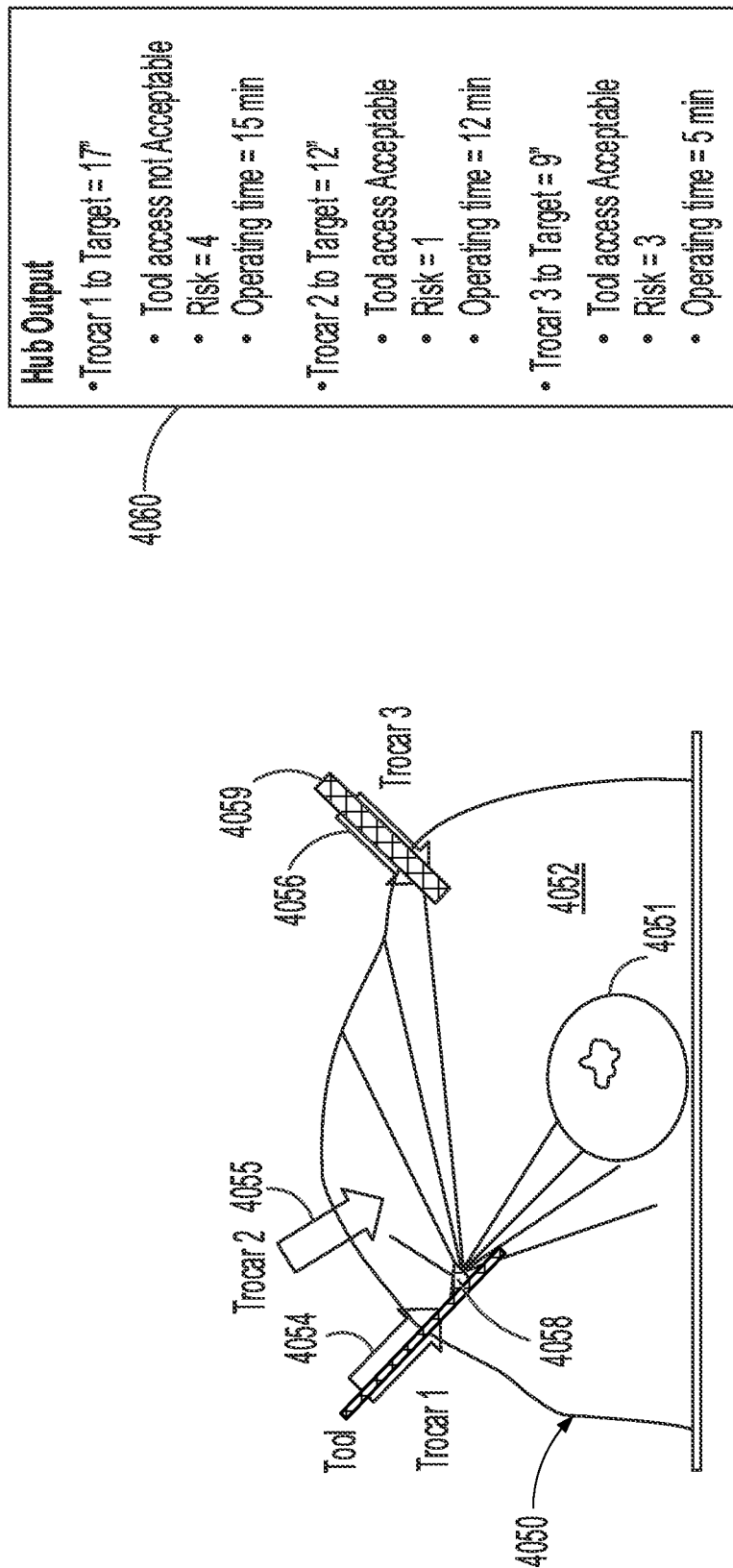

FIG. 27 illustrates a body wall and an anatomical structure in a cavity beneath the body wall, with trocars penetrating through the body wall into the cavity, and a screen displaying trocar distances from the anatomical structure, risks associated with presenting surgical instruments through the trocars, and the estimated operating times associated therewith, in accordance with at least one aspect of the present disclosure.

Figure 28:
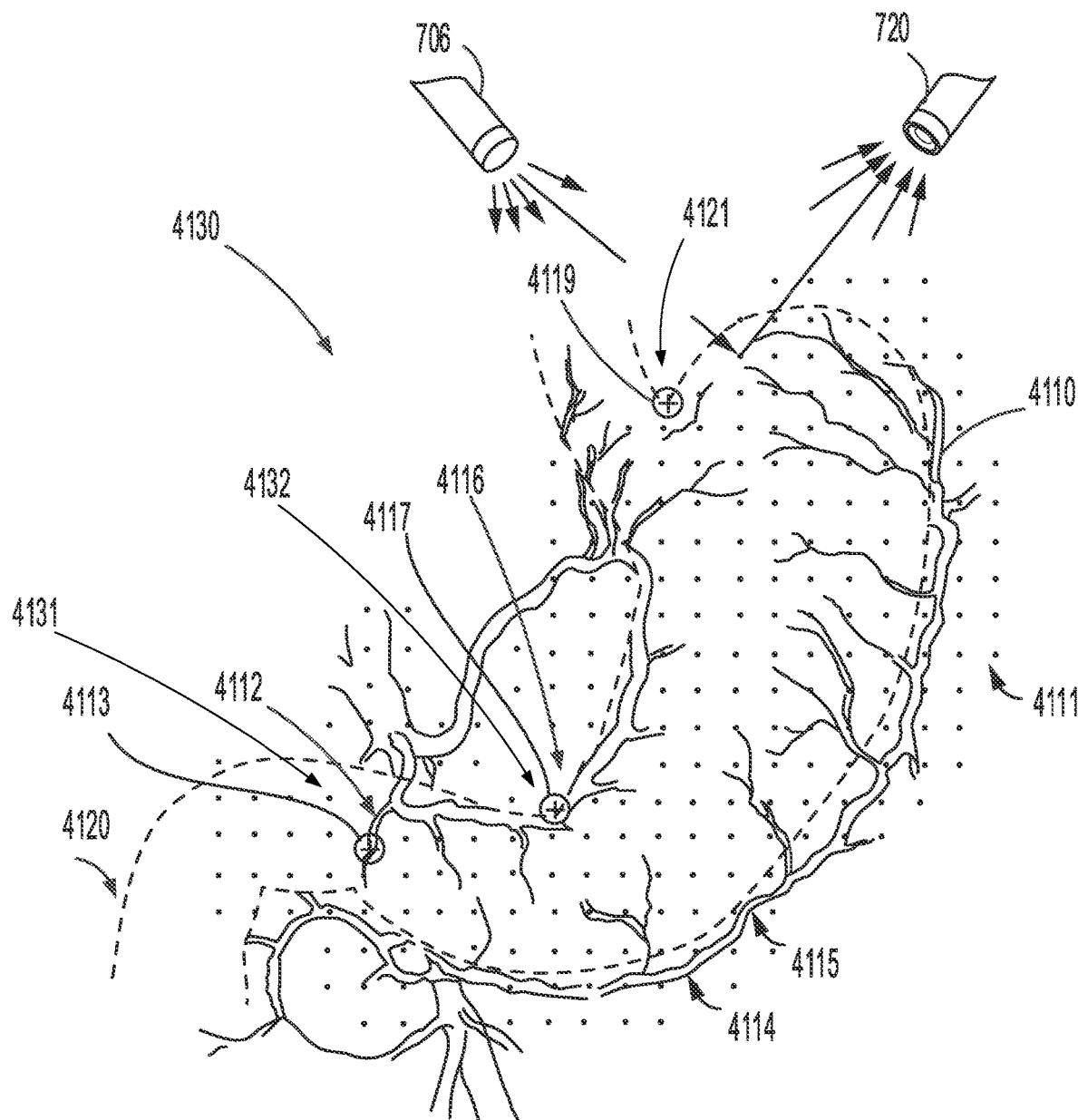

FIG. 28 illustrates a virtual three-dimensional ("3D") construct of a stomach exposed to structured light from a structured light projector, in accordance with at least aspect of the present disclosure.

Figure 29:
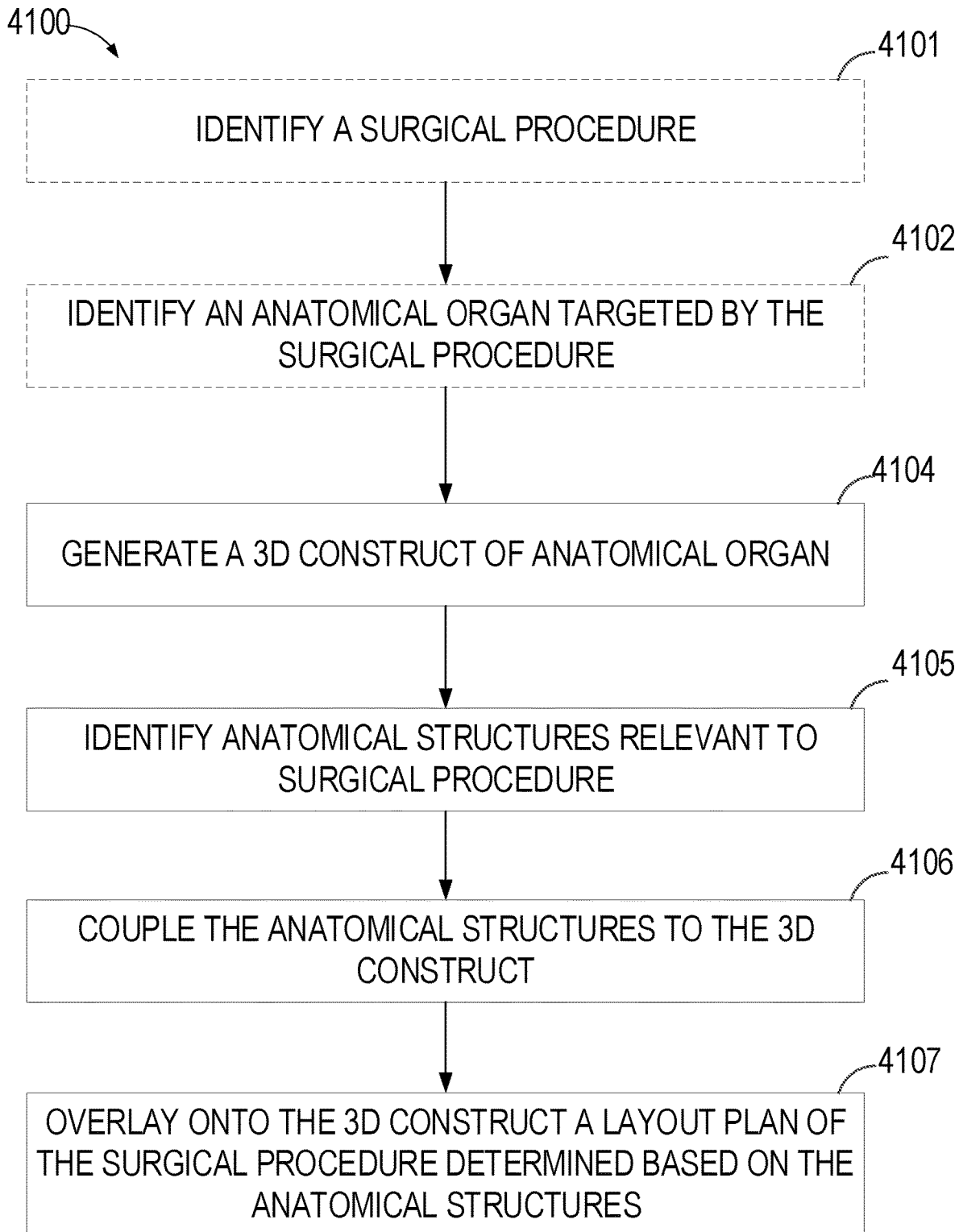

FIG. 29 is a logic flow diagram of a process depicting a control program or a logic configuration for correlating visualization data with instrument data, wherein boxes with broken lines denote alternative implementations of the process, in accordance with at least one aspect of the present disclosure.

Figure 30:
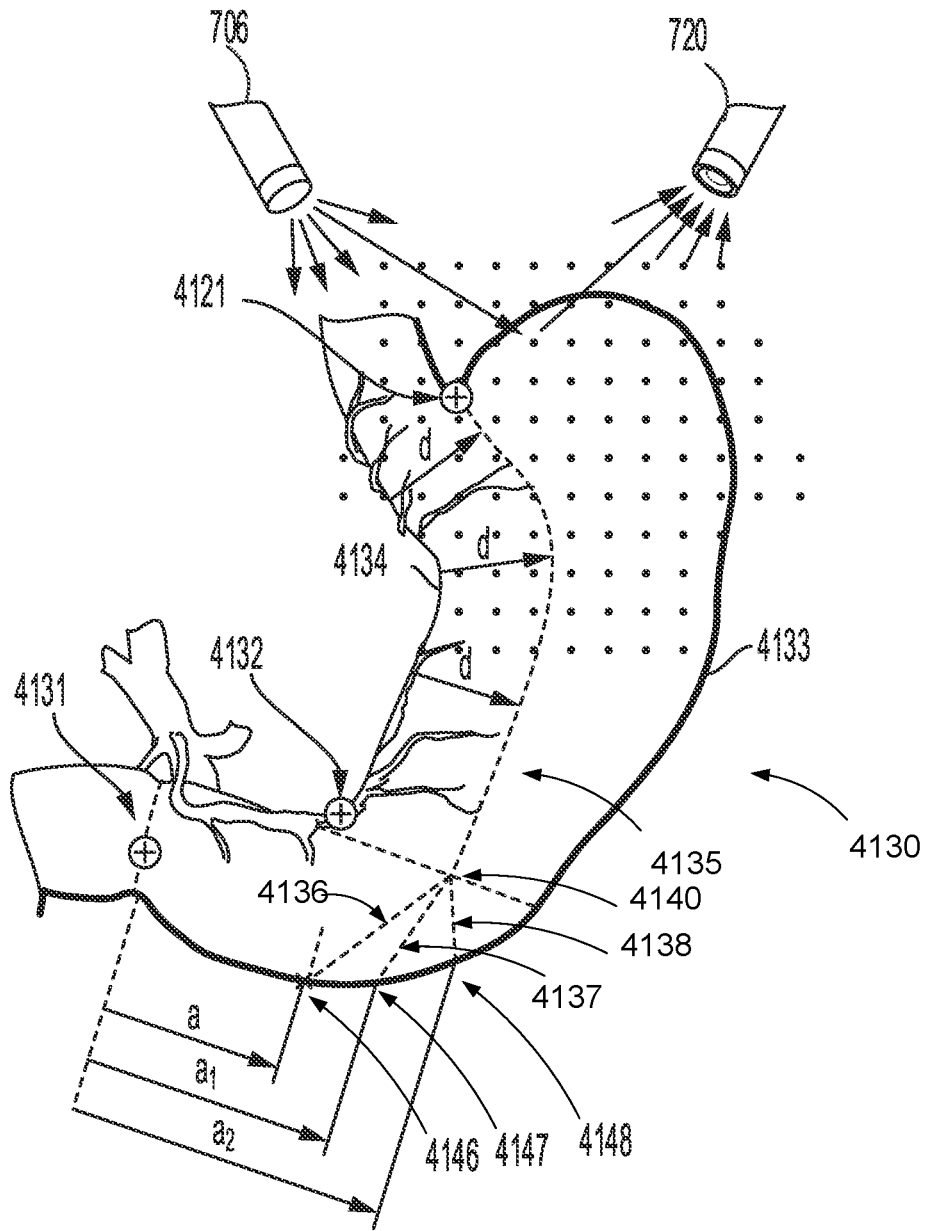

FIG. 30 illustrates a virtual 3D construct of a stomach exposed to structured light from a structured light projector, in accordance with at least aspect of the present disclosure.

Figure 31:
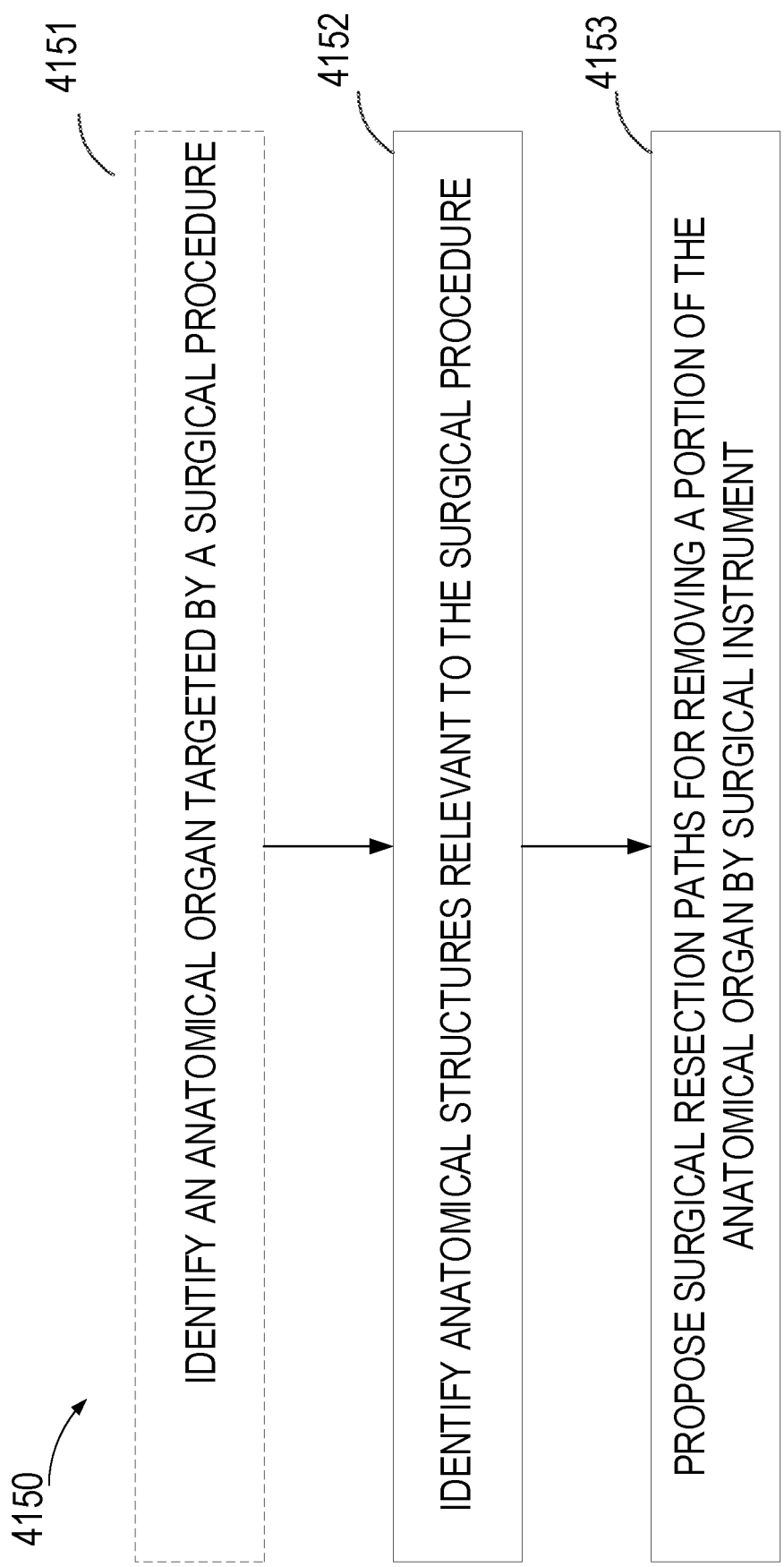

FIG. 31 is a logic flow diagram of a process depicting a control program or a logic configuration for proposing resection paths for removing a portion of an anatomical organ, wherein boxes with broken lines denote alternative implementations of the process, in accordance with at least one aspect of the present disclosure.

Figure 32A:
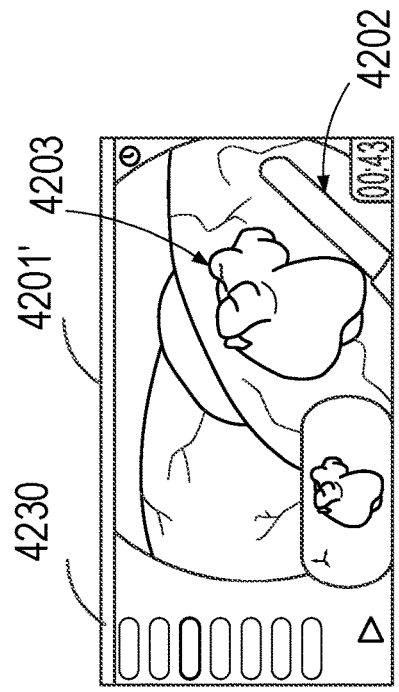

FIG. 32A illustrates a live view of a surgical field on a screen of a visualization system at the onset of a surgical procedure, in accordance with at least one aspect of the present disclosure.

Figure 32C:
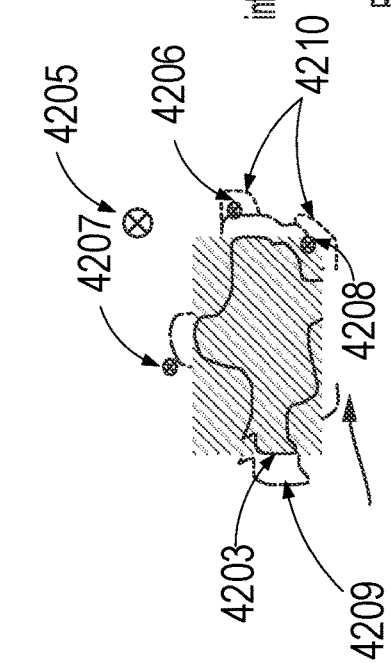
Figure 32B:
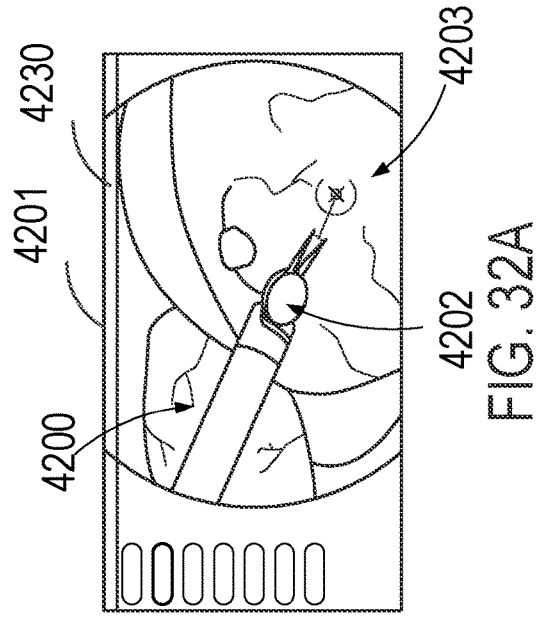

FIG. 32B is an expanded view of a portion of the surgical field of FIG. 32A outlining a proposed surgical resection path overlaid onto the surgical field, in accordance with at least one aspect of the present disclosure.

FIG. 32C illustrates the live view of the surgical field of FIG. 32B at forty-three minutes beyond the onset of the surgical procedure, in accordance with at least one aspect of the present disclosure.

Figure 32D:
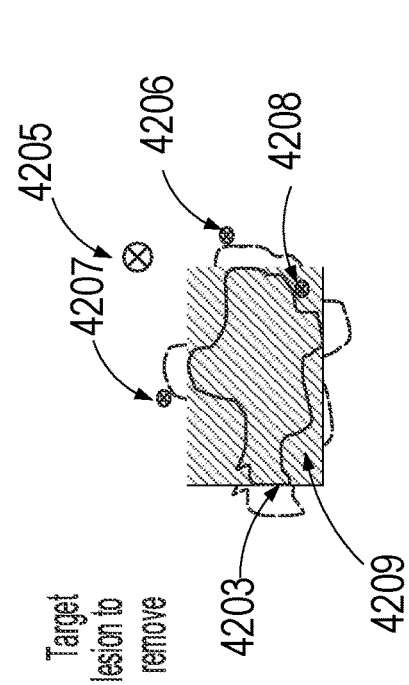

FIG. 32D illustrates an expanded view of the surgical field of FIG. 32C outlining a modification the proposed surgical resection path, in accordance with at least one aspect of the present disclosure.

Figure 33:
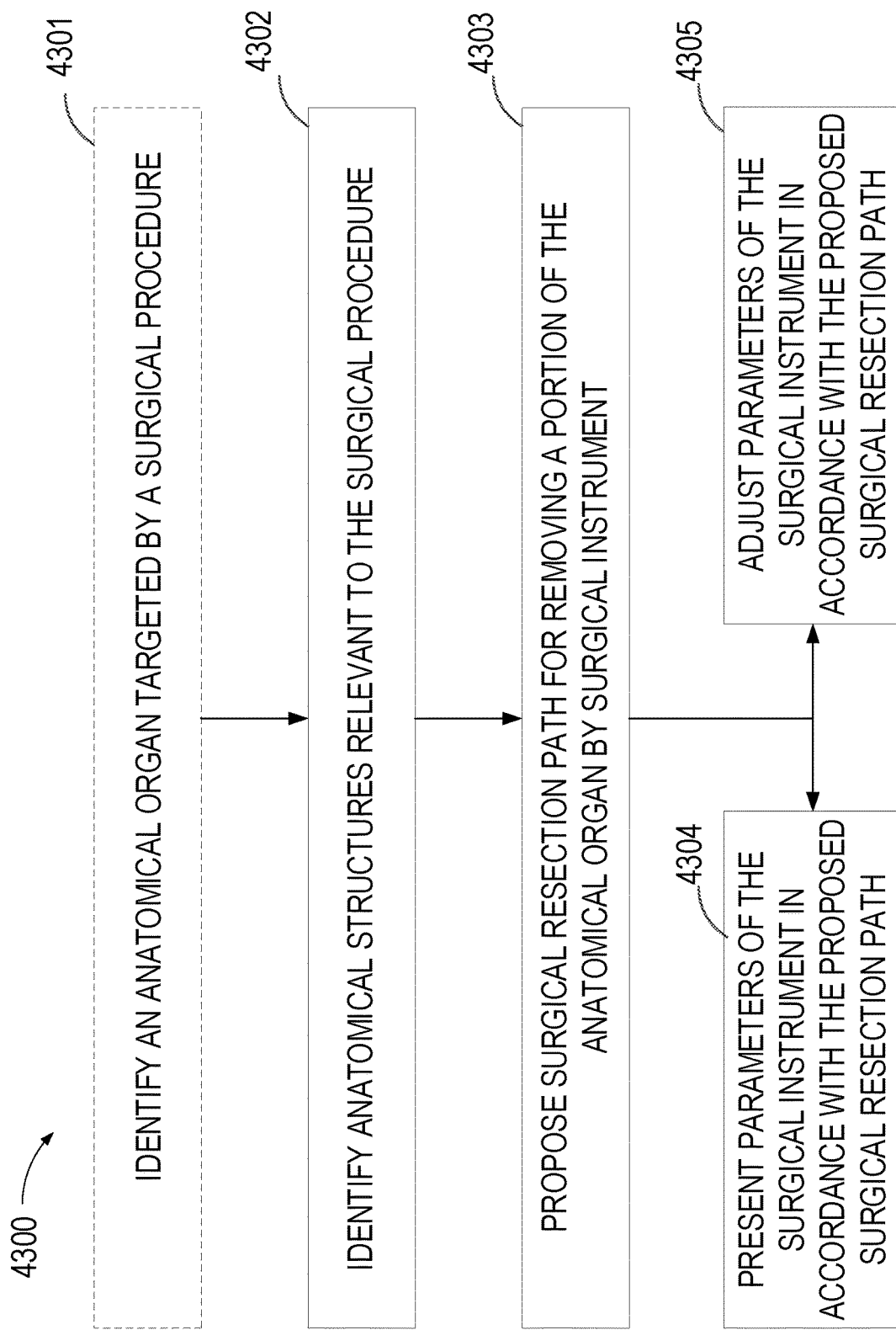

FIG. 33 is a logic flow diagram of a process depicting a control program or a logic configuration for presenting parameters of a surgical instrument onto, or near, a proposed surgical resection path, wherein boxes with broken lines denote alternative implementations of the process, in accordance with at least one aspect of the present disclosure.

Figure 34:
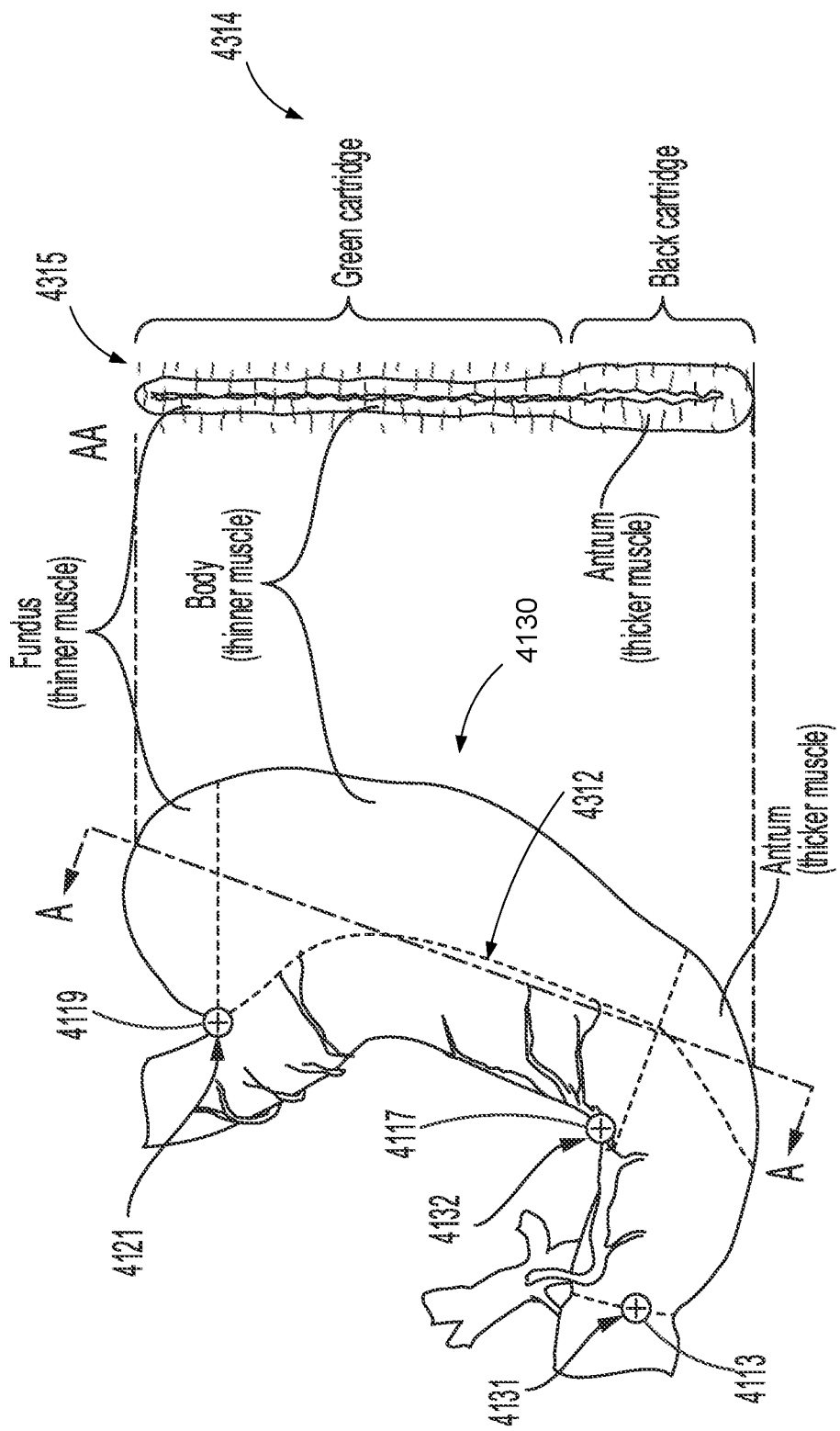

FIG. 34 illustrates a virtual 3D construct of a stomach of a patient undergoing a sleeve gastrectomy, in accordance with at least one aspect of the present disclosure.

Figure 35:
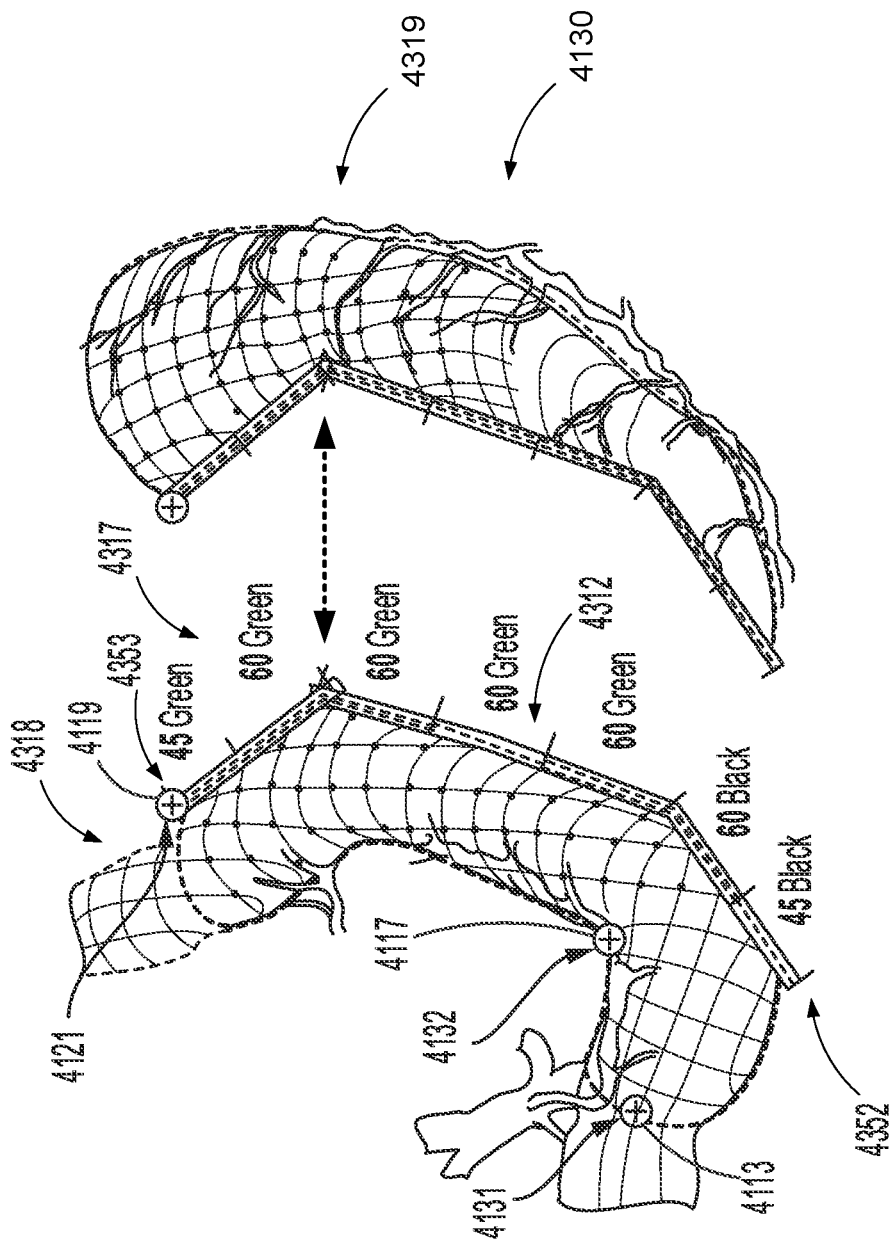

FIG. 35 illustrates a completed virtual resection of the stomach of FIG. 34.

Figure 36:
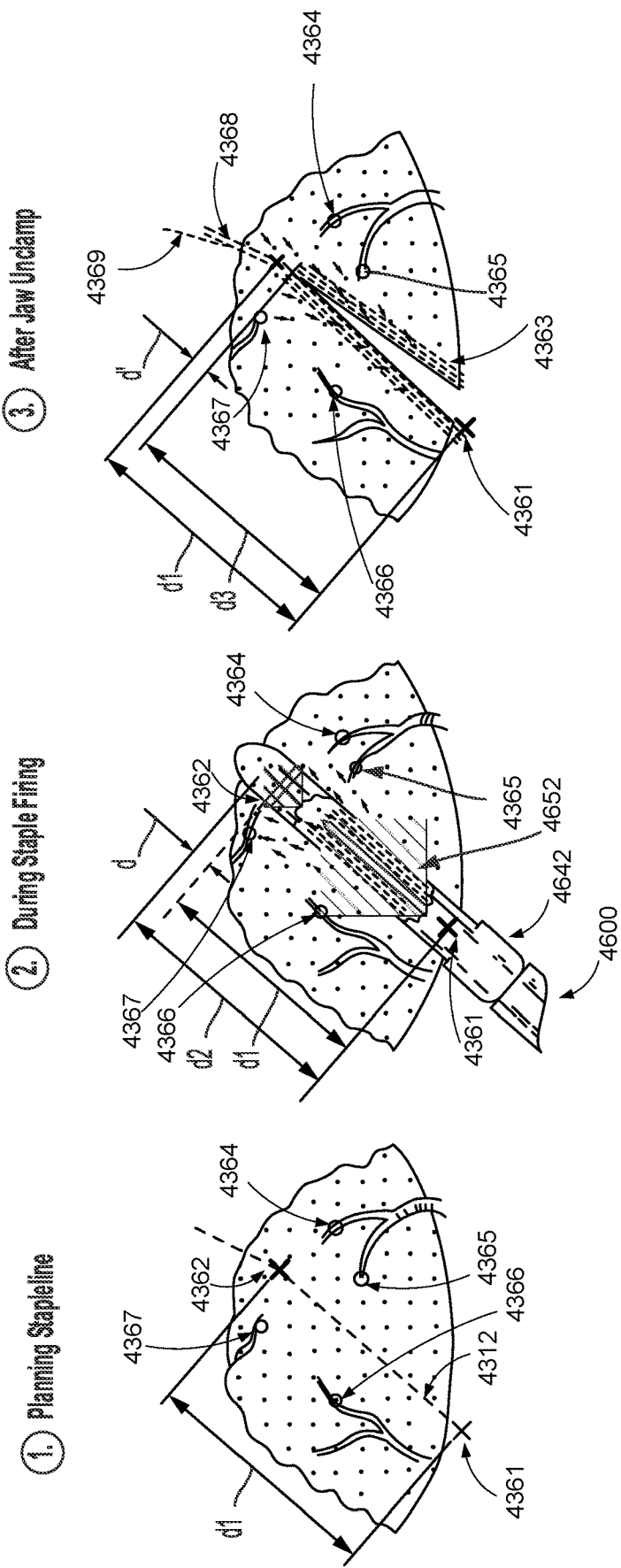

FIGS. 36A-36C illustrate firing of a surgical stapling instrument, in accordance with at least one aspect of the present disclosure.

Figure 37:
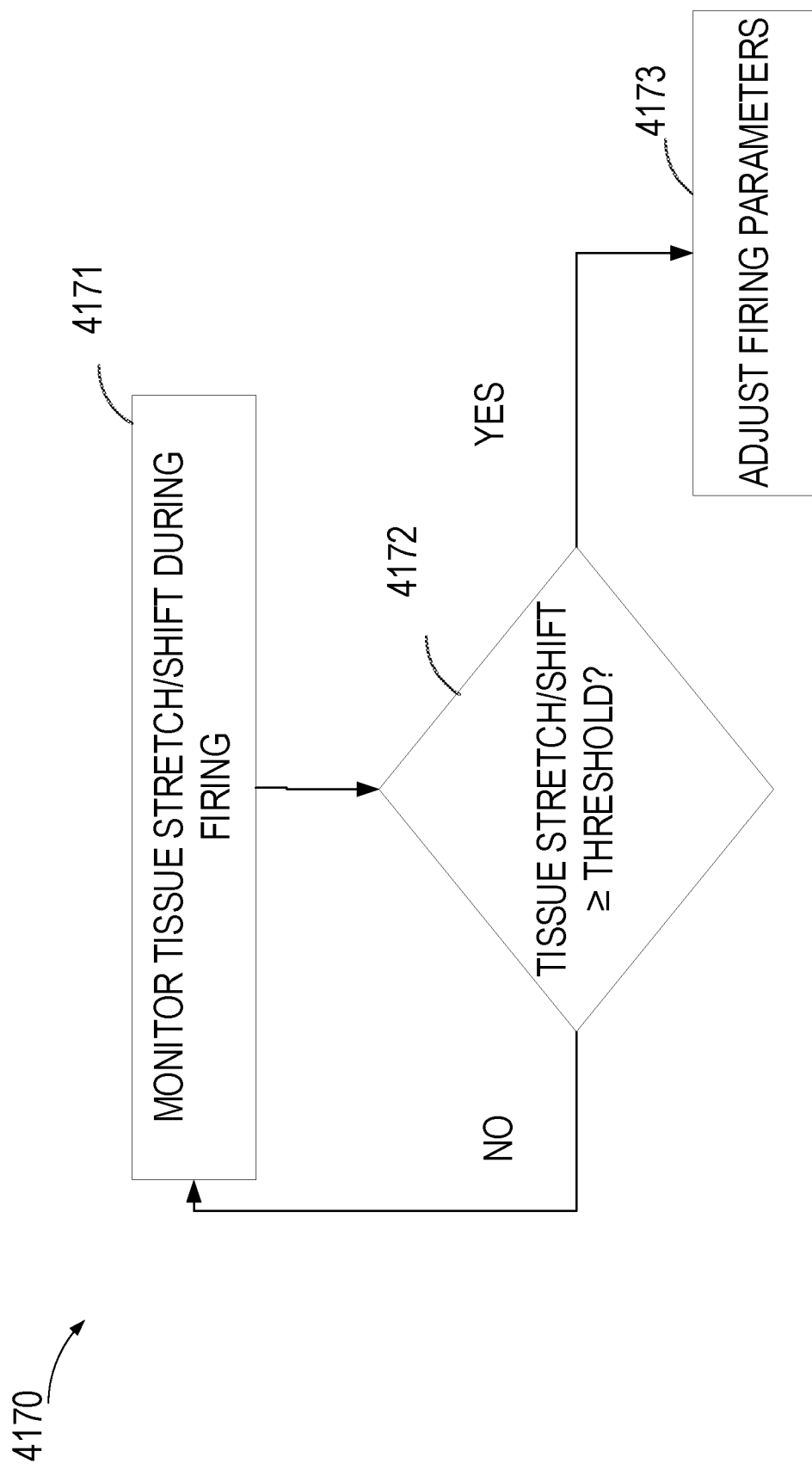

FIG. 37 is a logic flow diagram of a process depicting a control program or a logic configuration for adjusting firing speed of a surgical instrument, in accordance with at least one aspect of the present disclosure.

Figure 38:
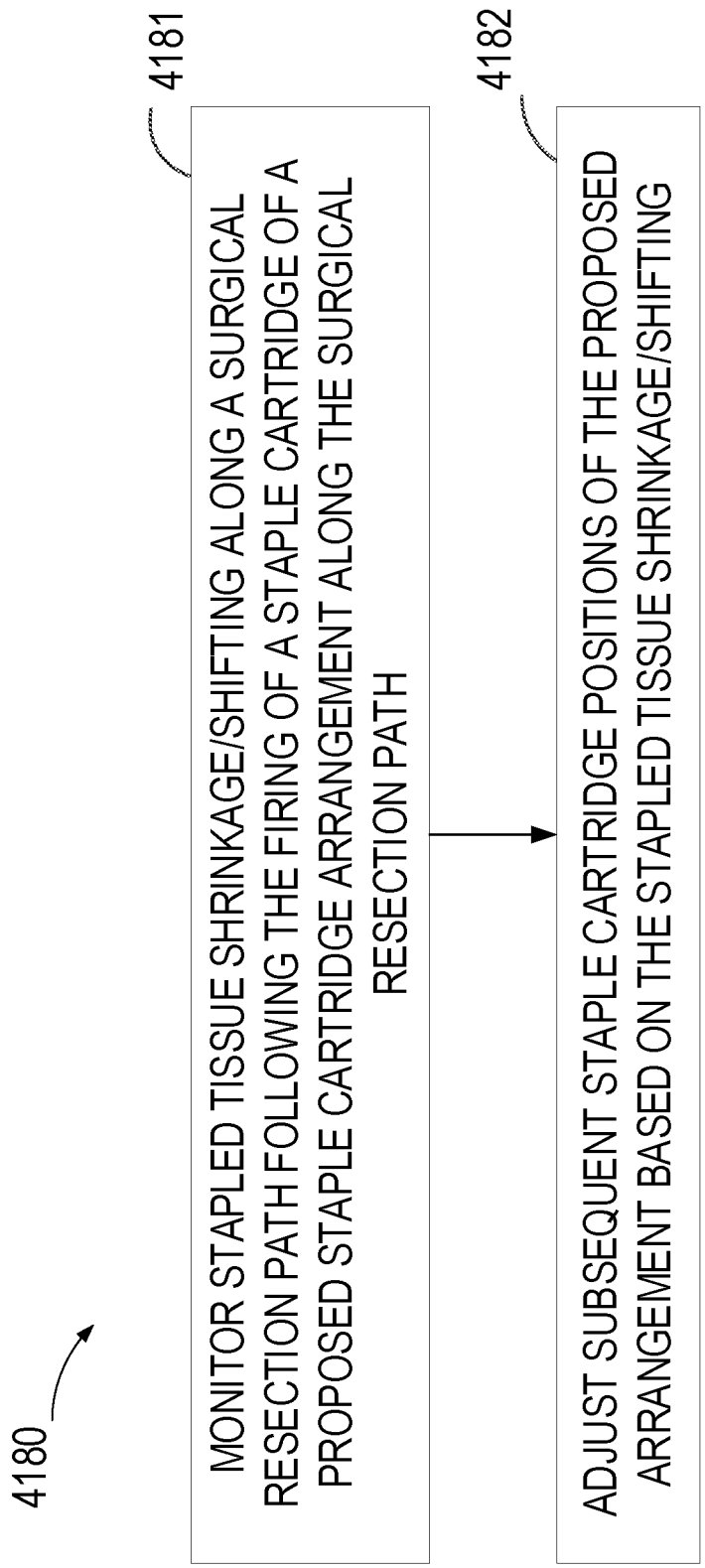

FIG. 38 is a logic flow diagram of a process depicting a control program or a logic configuration for a proposed staple cartridge arrangement along a proposed surgical resection path, in accordance with at least one aspect of the present disclosure.

Figure 39:
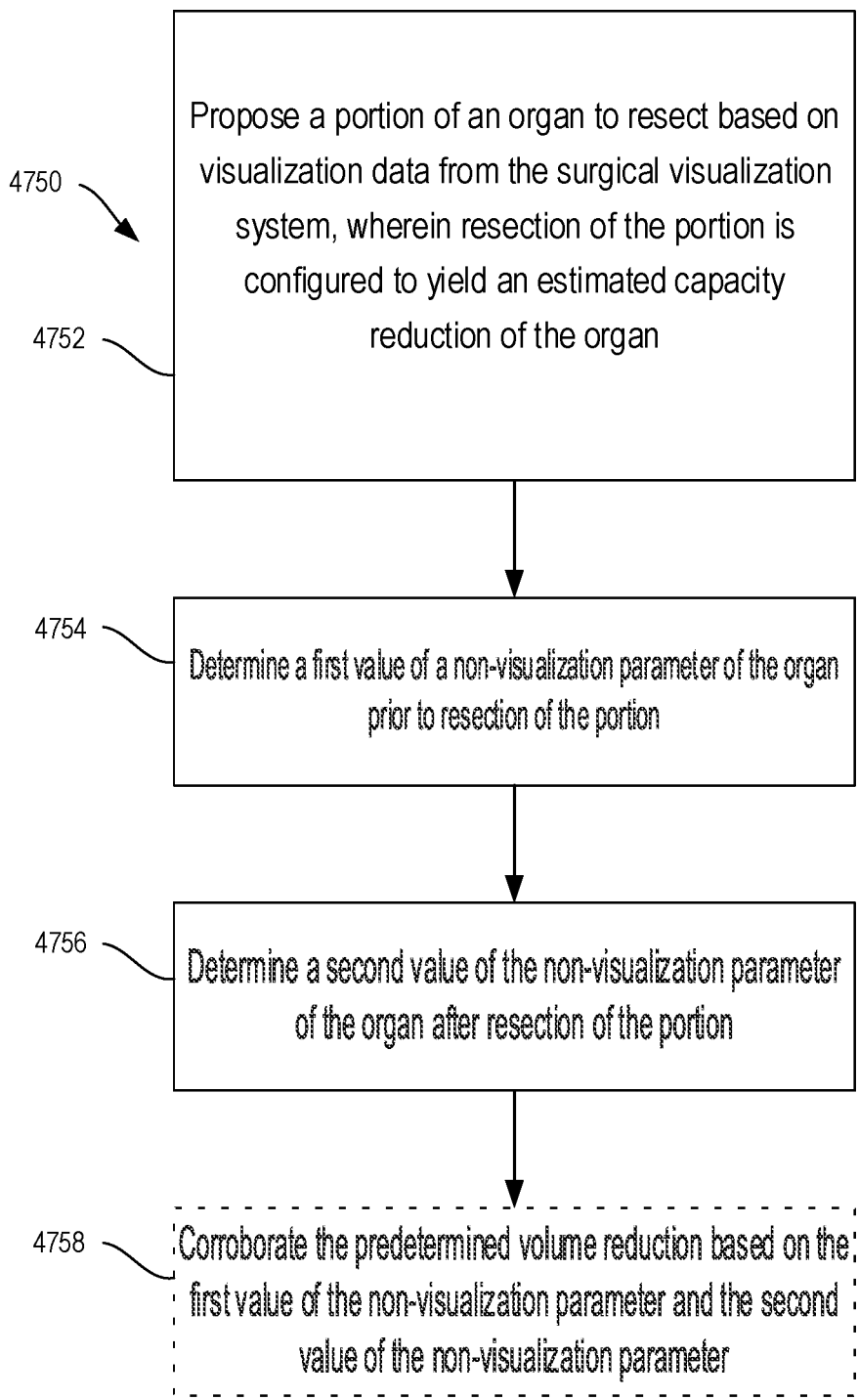

FIG. 39 is a logic flow diagram of a process depicting a control program or a logic configuration for proposing a surgical resection of an organ portion, in accordance with at least one aspect of the present disclosure.

Figure 40:
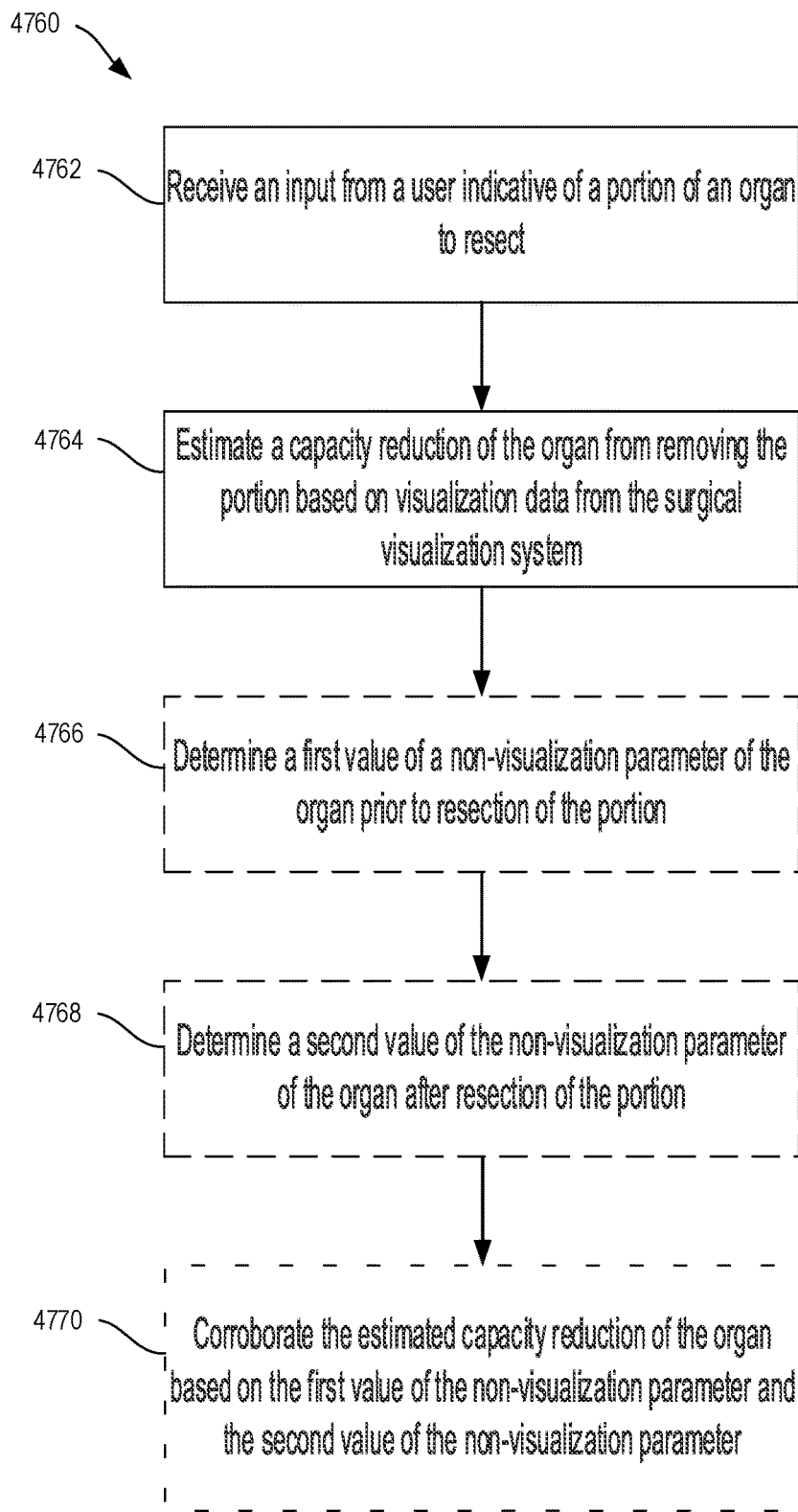

FIG. 40 is a logic flow diagram of a process depicting a control program or a logic configuration for estimating a capacity reduction of an organ resulting from the removal of a selected portion of the organ, in accordance with at least one aspect of the present disclosure.

FIG. 41A illustrates a patient's lungs exposed to structured light, which includes a portion to be resected during a surgical procedure, in accordance with at least one aspect of the present disclosure.

FIG. 41B illustrates the patient's lungs of FIG. 41A after resection of the portion, in accordance with at least one aspect of the present disclosure.

Figure 41C:
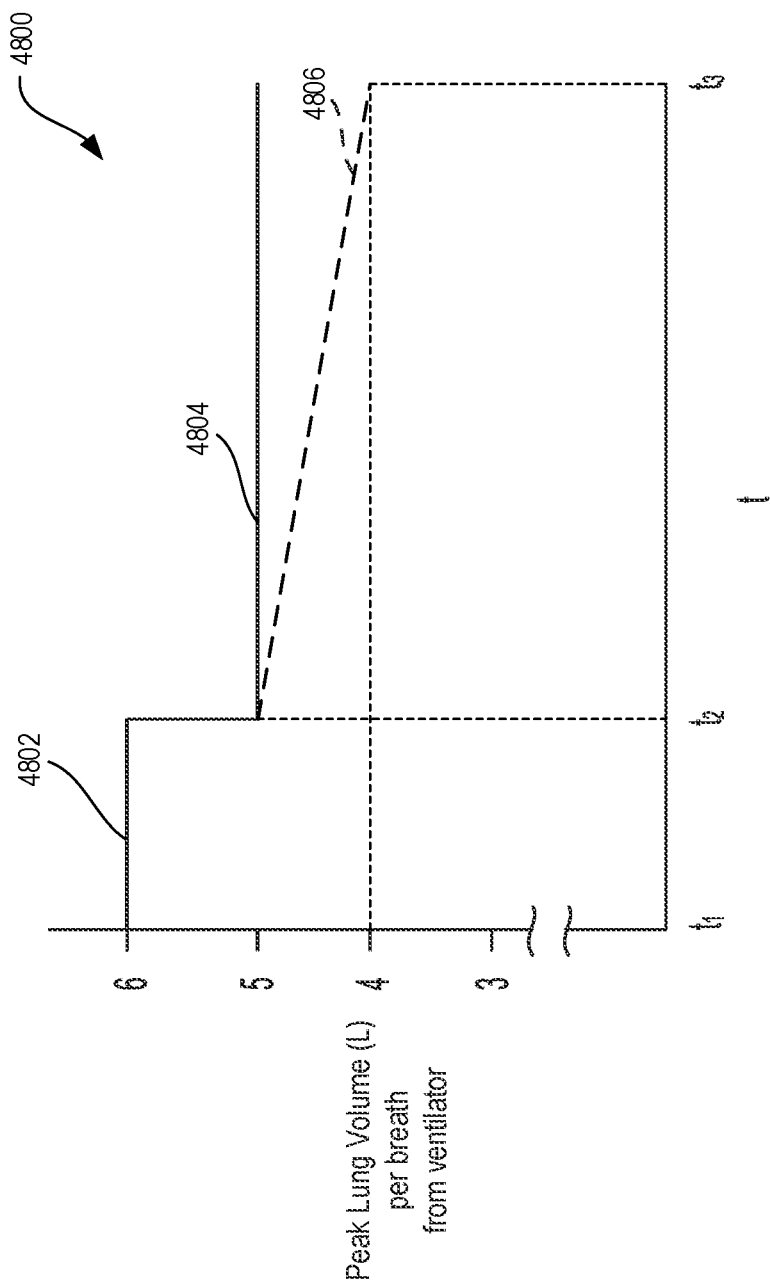

FIG. 41C illustrates a graph measuring peak lung volume of the patient's lungs from FIGS. 41A and 41B prior to and after the resection of the portion of the lung, in accordance with at least one aspect of the present disclosure.

Figure 42:
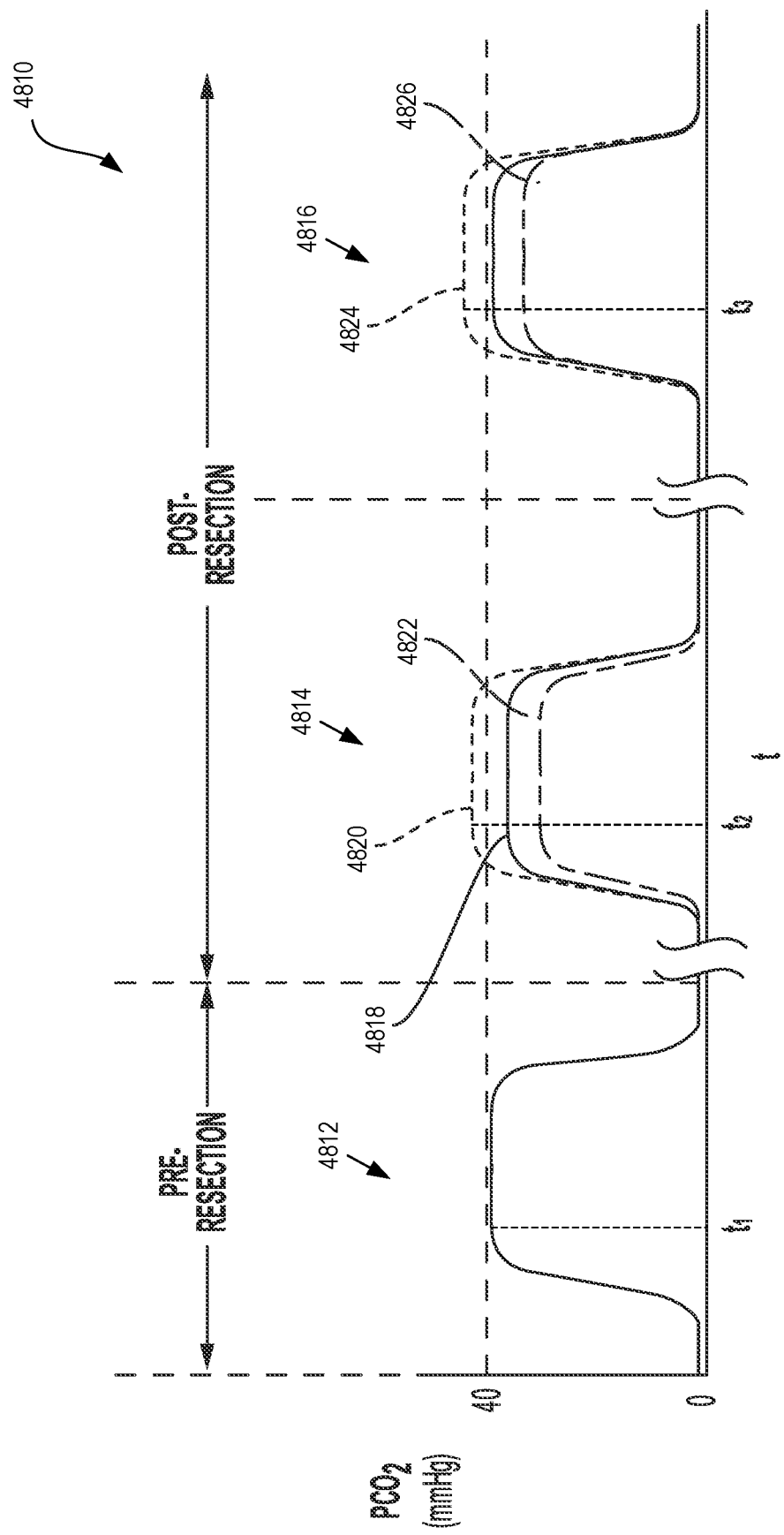

FIG. 42 illustrates a graph measuring partial pressure of carbon dioxide ("$PCO_2$") in a patient's lungs prior to, immediately after, and a minute after, resection of a portion of the lung, in accordance with at least one aspect of the present disclosure.

Figure 43:
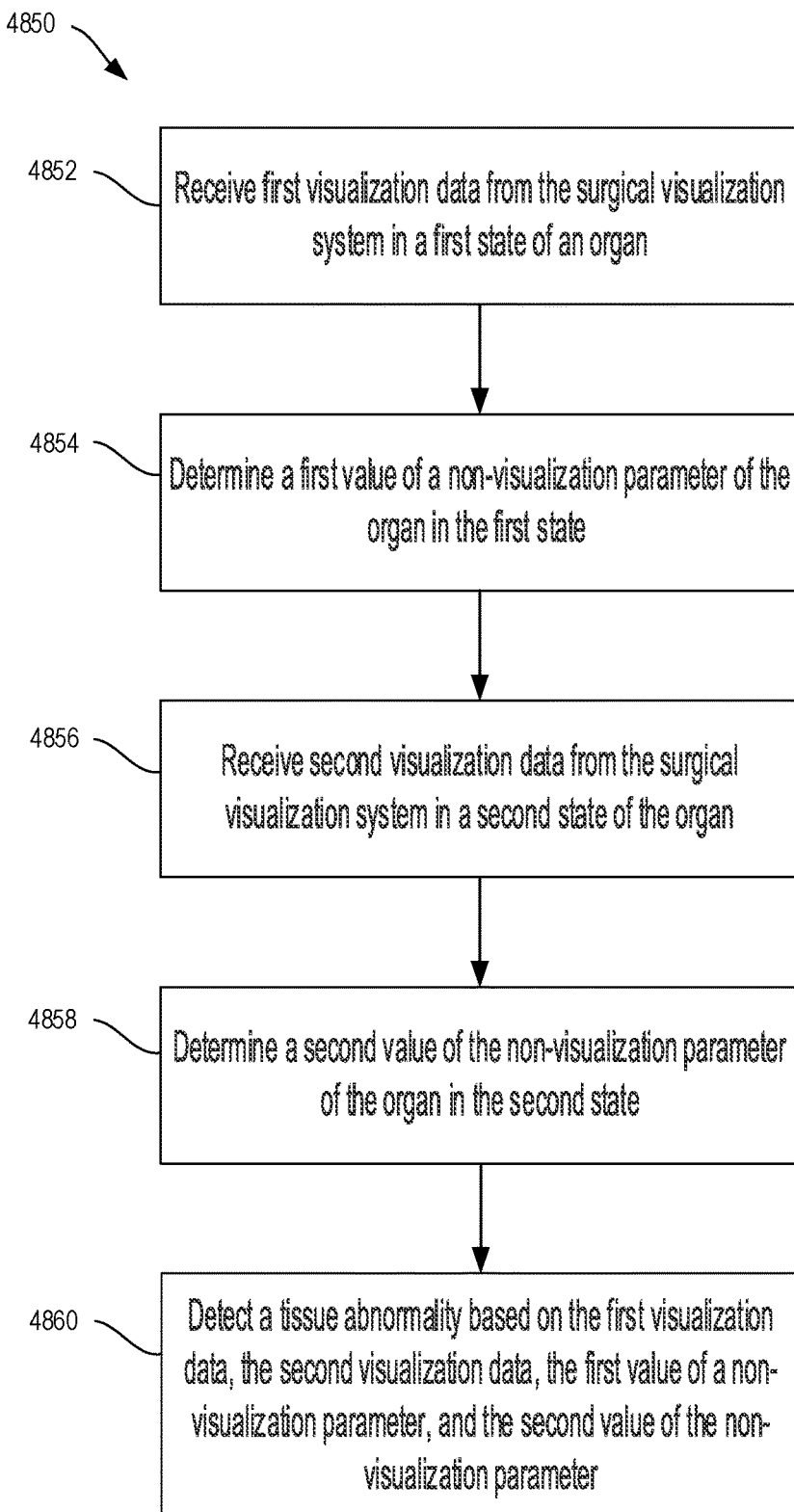

FIG. 43 is a logic flow diagram of a process depicting a control program or a logic configuration for detecting a tissue abnormality using visualization data and non-visualization data, in accordance with at least one aspect of the present disclosure.

Figure 44B:
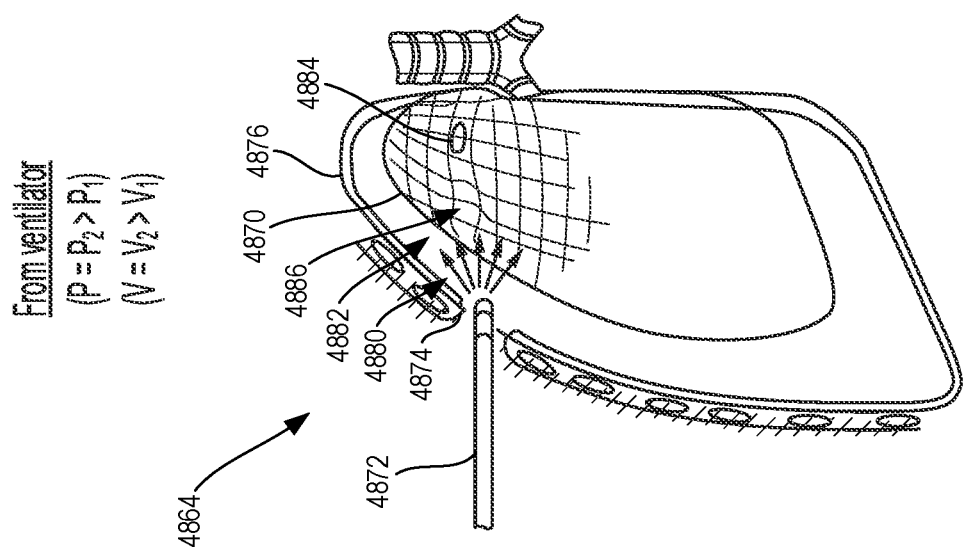
Figure 44A:
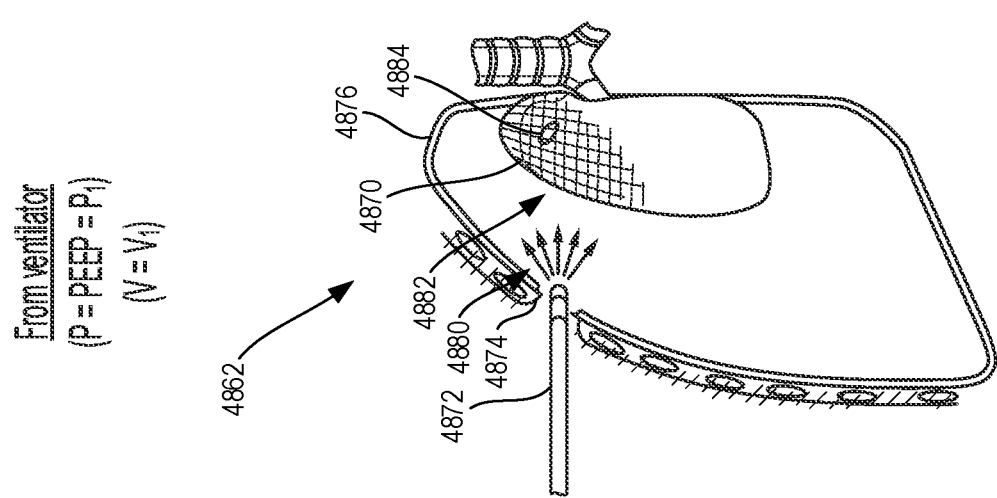

FIG. 44A illustrates a right lung in a first state with an imaging device emitting a pattern of light onto the surface thereof, in accordance with at least one aspect of the present disclosure.

FIG. 44B illustrates the right lung of FIG. 44A in a second state with the imaging device emitting a pattern of light onto the surface thereof, in accordance with at least one aspect of the present disclosure.

Figure 44D:
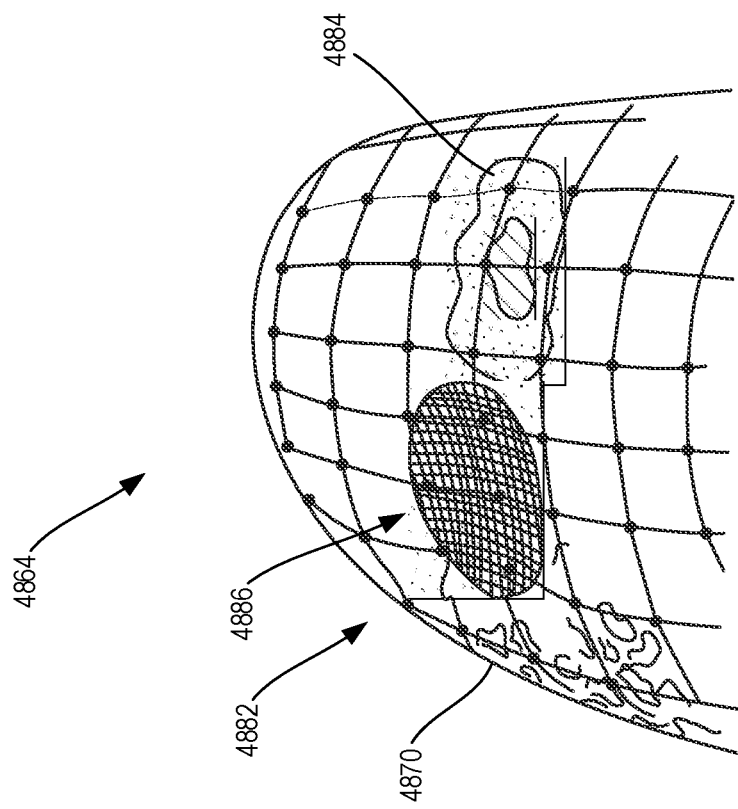
Figure 44C:
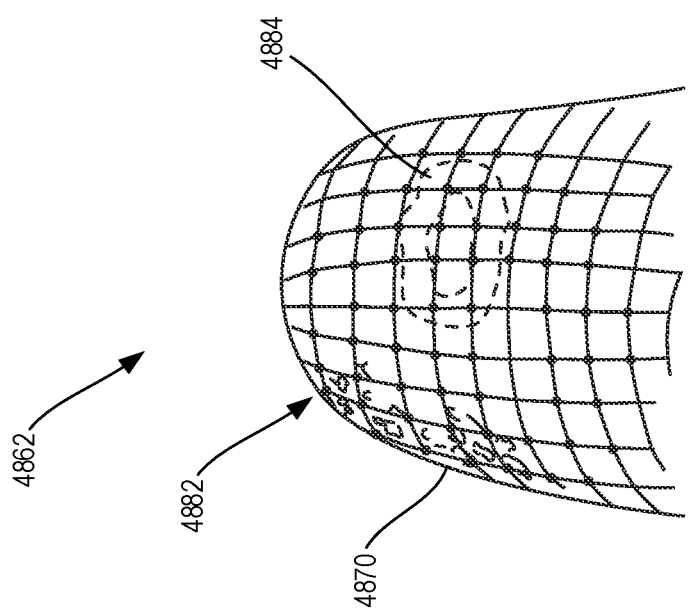

FIG. 44C illustrates a top portion of the right lung of FIG. 44A, in accordance with at least one aspect of the present disclosure.

FIG. 44D illustrates a top portion of the right lung of FIG. 44B, in accordance with at least one aspect of the present disclosure.

DESCRIPTION

Applicant of the present application owns the following U.S. Patent Applications, filed Dec. 30, 2019, each of which is herein incorporated by reference in its entirety:

U.S. patent application Ser. No. 16/729,807, titled METHOD OF USING IMAGING DEVICES IN SURGERY;

U.S. patent application Ser. No. 16/729,803, titled ADAPTIVE VISUALIZATION BY A SURGICAL SYSTEM;

U.S. patent application Ser. No. 16/729,790, titled SURGICAL SYSTEM CONTROL BASED ON MULTIPLE SENSED PARAMETERS;

U.S. patent application Ser. No. 16/729,796, titled ADAPTIVE SURGICAL SYSTEM CONTROL ACCORDING TO SURGICAL SMOKE PARTICLE CHARACTERISTICS;

U.S. patent application Ser. No. 16/729,737, titled ADAPTIVE SURGICAL SYSTEM CONTROL ACCORDING TO SURGICAL SMOKE CLOUD CHARACTERISTICS;

U.S. patent application Ser. No. 16/729,740, titled SURGICAL SYSTEMS CORRELATING VISUALIZATION DATA AND POWERED SURGICAL INSTRUMENT DATA;

U.S. patent application Ser. No. 16/729,735, titled SURGICAL SYSTEM FOR OVERLAYING SURGICAL INSTRUMENT DATA ONTO A VIRTUAL THREE DIMENSIONAL CONSTRUCT OF AN ORGAN;

U.S. patent application Ser. No. 16/729,729, titled SURGICAL SYSTEMS FOR PROPOSING AND CORROBORATING ORGAN PORTION REMOVALS;

U.S. patent application Ser. No. 16/729,778, titled SYSTEM AND METHOD FOR DETERMINING, ADJUSTING, AND MANAGING RESECTION MARGIN ABOUT A SUBJECT TISSUE;

U.S. patent application Ser. No. 16/729,744, titled VISUALIZATION SYSTEMS USING STRUCTURED LIGHT;

U.S. patent application Ser. No. 16/729,747, titled DYNAMIC SURGICAL VISUALIZATION SYSTEMS; and U.S. patent application Ser. No. 16/729,772, titled ANALYZING SURGICAL TRENDS BY A SURGICAL SYSTEM.

Applicant of the present application owns the following U.S. Patent Applications, filed on Mar. 15, 2019, each of which is herein incorporated by reference in its entirety:

U.S. patent application Ser. No. 16/354,417, titled INPUT CONTROLS FOR ROBOTIC SURGERY, now U.S. Patent Application Publication No. 2020/0289219;

U.S. patent application Ser. No. 16/354,420, titled DUAL MODE CONTROLS FOR ROBOTIC SURGERY, now U.S. Patent Application Publication No. 2020/0289228;

U.S. patent application Ser. No. 16/354,422, titled MOTION CAPTURE CONTROLS FOR ROBOTIC SURGERY, now U.S. Patent Application Publication No. 2020/0289216;

U.S. patent application Ser. No. 16/354,440, titled ROBOTIC SURGICAL SYSTEMS WITH MECHANISMS FOR SCALING SURGICAL TOOL MOTION ACCORDING TO TISSUE PROXIMITY, now U.S. Patent Application Publication No. 2020/0289220;

U.S. patent application Ser. No. 16/354,444, titled ROBOTIC SURGICAL SYSTEMS WITH MECHANISMS FOR SCALING CAMERA MAGNIFICATION ACCORDING TO PROXIMITY OF SURGICAL TOOL TO TISSUE, now U.S. Patent Application Publication No. 2020/0289205;

U.S. patent application Ser. No. 16/354,454, titled ROBOTIC SURGICAL SYSTEMS WITH SELECTIVELY LOCKABLE END EFFECTORS, now U.S. Patent Application Publication No. 2020/0289221;

U.S. patent application Ser. No. 16/354,461, titled SELECTABLE VARIABLE RESPONSE OF SHAFT MOTION OF SURGICAL ROBOTIC SYSTEMS, now U.S. Patent Application Publication No. 2020/0289222;

U.S. patent application Ser. No. 16/354,470, titled SEGMENTED CONTROL INPUTS FOR SURGICAL ROBOTIC SYSTEMS, now U.S. Patent Application Publication No. 2020/0289223;

U.S. patent application Ser. No. 16/354,474, titled ROBOTIC SURGICAL CONTROLS HAVING FEEDBACK CAPABILITIES, now U.S. Patent Application Publication No. 2020/0289229;

U.S. patent application Ser. No. 16/354,478, titled ROBOTIC SURGICAL CONTROLS WITH FORCE FEEDBACK, now U.S. Patent Application Publication No. 2020/0289230; and U.S. patent application Ser. No. 16/354,481, titled JAW COORDINATION OF ROBOTIC SURGICAL CONTROLS, now U.S. Patent Application Publication No. 2020/0289217.

Applicant of the present application also owns the following U.S. Patent Applications, filed on Sep. 11, 2018, each of which is herein incorporated by reference in its entirety:

U.S. patent application Ser. No. 16/128,179, titled SURGICAL VISUALIZATION PLATFORM, now U.S. Patent Application Publication No. 2020/0015923;

U.S. patent application Ser. No. 16/128,180, titled CONTROLLING AN EMITTER ASSEMBLY PULSE SEQUENCE, now U.S. Patent Application Publication No. 2020/0015900;

U.S. patent application Ser. No. 16/128,198, titled SINGULAR EMR SOURCE EMITTER ASSEMBLY, now U.S. Patent Application Publication No. 2020/0015668;

U.S. patent application Ser. No. 16/128,207, titled COMBINATION EMITTER AND CAMERA ASSEMBLY, now U.S. Patent Application Publication No. 2020/0015925;

U.S. patent application Ser. No. 16/128,176, titled SURGICAL VISUALIZATION WITH PROXIMITY TRACKING FEATURES, now U.S. Patent Application Publication No. 2020/0015899;

U.S. patent application Ser. No. 16/128,187, titled SURGICAL VISUALIZATION OF MULTIPLE TARGETS, now U.S. Patent Application Publication No. 2020/0015903;

U.S. patent application Ser. No. 16/128,192, titled VISUALIZATION OF SURGICAL DEVICES, now U.S. Pat. No. 10,792,034;

U.S. patent application Ser. No. 16/128,163, titled OPERATIVE COMMUNICATION OF LIGHT, now U.S. Patent Application Publication No. 2020/0015897;

U.S. patent application Ser. No. 16/128,197, titled ROBOTIC LIGHT PROJECTION TOOLS, now U.S. Patent Application Publication No. 2020/0015924;

U.S. patent application Ser. No. 16/128,164, titled SURGICAL VISUALIZATION FEEDBACK SYSTEM, now U.S. Patent Application Publication No. 2020/0015898;

U.S. patent application Ser. No. 16/128,193, titled SURGICAL VISUALIZATION AND MONITORING, now U.S. Patent Application Publication No. 2020/0015906;

U.S. patent application Ser. No. 16/128,195, titled INTEGRATION OF IMAGING DATA, now U.S. Patent Application Publication No. 2020/0015907;

U.S. patent application Ser. No. 16/128,170, titled ROBOTICALLY-ASSISTED SURGICAL SUTURING SYSTEMS, now U.S. Pat. No. 10,925,598;

U.S. patent application Ser. No. 16/128,183, titled SAFETY LOGIC FOR SURGICAL SUTURING SYSTEMS, now U.S. Patent Application Publication No. 2020/0015901;

U.S. patent application Ser. No. 16/128,172, titled ROBOTIC SYSTEM WITH SEPARATE PHOTOACOUSTIC RECEIVER, now U.S. Patent Application Publication No. 2020/0015914; and U.S. patent application Ser. No. 16/128,185, titled FORCE SENSOR THROUGH STRUCTURED LIGHT DEFLECTION, now U.S. Patent Application Publication No. 2020/0015902.

Applicant of the present application also owns the following U.S. Patent Applications, filed on Mar. 29, 2018, each of which is herein incorporated by reference in its entirety:

U.S. patent application Ser. No. 15/940,627, titled DRIVE ARRANGEMENTS FOR ROBOT-ASSISTED SURGICAL PLATFORMS, now U.S. Patent Application Publication No. 2019/0201111;

U.S. patent application Ser. No. 15/940,676, titled AUTOMATIC TOOL ADJUSTMENTS FOR ROBOT-ASSISTED SURGICAL PLATFORMS, now U.S. Patent Application Publication No. 2019/0201142;

U.S. patent application Ser. No. 15/940,711, titled SENSING ARRANGEMENTS FOR ROBOT-ASSISTED SURGICAL PLATFORMS, now U.S. Patent Application Publication No. 2019/0201120; and U.S. patent application Ser. No. 15/940,722, titled CHARACTERIZATION OF TISSUE IRREGULARITIES THROUGH THE USE OF MONO-CHROMATIC LIGHT REFRACTIVITY, now U.S. Patent Application Publication No. 2019/0200905.

Applicant of the present application owns the following U.S. Patent Applications, filed on Dec. 4, 2018, the disclosure of each of which is herein incorporated by reference in its entirety:

U.S. patent application Ser. No. 16/209,395, titled METHOD OF HUB COMMUNICATION, now U.S. Patent Application Publication No. 2019/0201136;

U.S. patent application Ser. No. 16/209,403, titled METHOD OF CLOUD BASED DATA ANALYTICS FOR USE WITH THE HUB, now U.S. Patent Application Publication No. 2019/0206569;

U.S. patent application Ser. No. 16/209,407, titled METHOD OF ROBOTIC HUB COMMUNICATION, DETECTION, AND CONTROL, now U.S. Patent Application Publication No. 2019/0201137;

U.S. patent application Ser. No. 16/209,416, titled METHOD OF HUB COMMUNICATION, PROCESS- ING, DISPLAY, AND CLOUD ANALYTICS, now U.S. Patent Application Publication No. 2019/0206562;

U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS, now U.S. Patent Application Publication No. 2019/0200981;

U.S. patent application Ser. No. 16/209,427, titled METHOD OF USING REINFORCED FLEXIBLE CIRCUITS WITH MULTIPLE SENSORS TO OPTIMIZE PERFORMANCE OF RADIO FREQUENCY DEVICES, now U.S. Patent Application Publication No. 2019/0208641;

U.S. patent application Ser. No. 16/209,433, titled METHOD OF SENSING PARTICULATE FROM SMOKE EVACUATED FROM A PATIENT, ADJUSTING THE PUMP SPEED BASED ON THE SENSED INFORMATION, AND COMMUNICATING THE FUNCTIONAL PARAMETERS OF THE SYSTEM TO THE HUB, now U.S. Patent Application Publication No. 2019/0201594;

U.S. patent application Ser. No. 16/209,447, titled METHOD FOR SMOKE EVACUATION FOR SURGICAL HUB, now U.S. Patent Application Publication No. 2019/0201045;

U.S. patent application Ser. No. 16/209,453, titled METHOD FOR CONTROLLING SMART ENERGY DEVICES, now U.S. Patent Application Publication No. 2019/0201046;

U.S. patent application Ser. No. 16/209,458, titled METHOD FOR SMART ENERGY DEVICE INFRASTRUCTURE, now U.S. Patent Application Publication No. 2019/0201047;

U.S. patent application Ser. No. 16/209,465, titled METHOD FOR ADAPTIVE CONTROL SCHEMES FOR SURGICAL NETWORK CONTROL AND INTERACTION, now U.S. Patent Application Publication No. 2019/0206563;

U.S. patent application Ser. No. 16/209,478, titled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE, now U.S. Patent Application Publication No. 2019/0104919;

U.S. patent application Ser. No. 16/209,490, titled METHOD FOR FACILITY DATA COLLECTION AND INTERPRETATION, now U.S. Patent Application Publication No. 2019/0206564; and U.S. patent application Ser. No. 16/209,491, titled METHOD FOR CIRCULAR STAPLER CONTROL ALGORITHM ADJUSTMENT BASED ON SITUATIONAL AWARENESS, now U.S. Patent Application Publication No. 2019/0200998.

Before explaining various aspects of a surgical visualization platform in detail, it should be noted that the illustrative examples are not limited in application or use to the details of construction and arrangement of parts illustrated in the accompanying drawings and description. The illustrative examples may be implemented or incorporated in other aspects, variations, and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects, and/or examples.

Surgical Visualization System

The present disclosure is directed to a surgical visualization platform that leverages "digital surgery" to obtain additional information about a patient's anatomy and/or a surgical procedure. The surgical visualization platform is further configured to convey data and/or information to one or more clinicians in a helpful manner. For example, various aspects of the present disclosure provide improved visualization of the patient's anatomy and/or the surgical procedure.

"Digital surgery" can embrace robotic systems, advanced imaging, advanced instrumentation, artificial intelligence, machine learning, data analytics for performance tracking and benchmarking, connectivity both inside and outside of the operating room (OR), and more. Although various surgical visualization platforms described herein can be used in combination with a robotic surgical system, surgical visualization platforms are not limited to use with a robotic surgical system. In certain instances, advanced surgical visualization can occur without robotics and/or with limited and/or optional robotic assistance. Similarly, digital surgery can occur without robotics and/or with limited and/or optional robotic assistance.

In certain instances, a surgical system that incorporates a surgical visualization platform may enable smart dissection in order to identify and avoid critical structures. Critical structures include anatomical structures such as a ureter, an artery such as a superior mesenteric artery, a vein such as a portal vein, a nerve such as a phrenic nerve, and/or a tumor, among other anatomical structures. In other instances, a critical structure can be a foreign structure in the anatomical field, such as a surgical device, surgical fastener, clip, tack, bougie, band, and/or plate, for example. Critical structures can be determined on a patient-by-patient and/or a procedure-by-procedure basis. Example critical structures are further described herein. Smart dissection technology may provide improved intraoperative guidance for dissection and/or can enable smarter decisions with critical anatomy detection and avoidance technology, for example.

A surgical system incorporating a surgical visualization platform may also enable smart anastomosis technologies that provide more consistent anastomoses at optimal location(s) with improved workflow. Cancer localization technologies may also be improved with the various surgical visualization platforms and procedures described herein. For example, cancer localization technologies can identify and track a cancer location, orientation, and its margins. In certain instances, the cancer localizations technologies may compensate for movement of a tool, a patient, and/or the patient's anatomy during a surgical procedure in order to provide guidance back to the point of interest for the clinician.

In certain aspects of the present disclosure, a surgical visualization platform may provide improved tissue characterization and/or lymph node diagnostics and mapping. For example, tissue characterization technologies may characterize tissue type and health without the need for physical haptics, especially when dissecting and/or placing stapling devices within the tissue. Certain tissue characterization technologies described herein may be utilized without ionizing radiation and/or contrast agents. With respect to lymph node diagnostics and mapping, a surgical visualization platform may preoperatively locate, map, and ideally diagnose the lymph system and/or lymph nodes involved in cancerous diagnosis and staging, for example.

During a surgical procedure, the information available to the clinician via the "naked eye" and/or an imaging system may provide an incomplete view of the surgical site. For example, certain structures, such as structures embedded or buried within an organ, can be at least partially concealed or hidden from view. Additionally, certain dimensions and/or relative distances can be difficult to ascertain with existing sensor systems and/or difficult for the "naked eye" to perceive. Moreover, certain structures can move preoperatively (e.g. before a surgical procedure but after a preoperative scan) and/or intraoperatively. In such instances, the clinician can be unable to accurately determine the location of a critical structure intraoperatively.

When the position of a critical structure is uncertain and/or when the proximity between the critical structure and a surgical tool is unknown, a clinician's decision-making process can be inhibited. For example, a clinician may avoid certain areas in order to avoid inadvertent dissection of a critical structure; however, the avoided area may be unnecessarily large and/or at least partially misplaced. Due to uncertainty and/or overly/excessive exercises in caution, the clinician may not access certain desired regions. For example, excess caution may cause a clinician to leave a portion of a tumor and/or other undesirable tissue in an effort to avoid a critical structure even if the critical structure is not in the particular area and/or would not be negatively impacted by the clinician working in that particular area. In certain instances, surgical results can be improved with increased knowledge and/or certainty, which can allow a surgeon to be more accurate and, in certain instances, less conservative/more aggressive with respect to particular anatomical areas.

In various aspects, the present disclosure provides a surgical visualization system for intraoperative identification and avoidance of critical structures. In one aspect, the present disclosure provides a surgical visualization system that enables enhanced intraoperative decision making and improved surgical outcomes. In various aspects, the disclosed surgical visualization system provides advanced visualization capabilities beyond what a clinician sees with the "naked eye" and/or beyond what an imaging system can recognize and/or convey to the clinician. The various surgical visualization systems can augment and enhance what a clinician is able to know prior to tissue treatment (e.g. dissection) and, thus, may improve outcomes in various instances.

For example, a visualization system can include a first light emitter configured to emit a plurality of spectral waves, a second light emitter configured to emit a light pattern, and one or more receivers, or sensors, configured to detect visible light, molecular responses to the spectral waves (spectral imaging), and/or the light pattern. It should be noted that throughout the following disclosure, any reference to "light," unless specifically in reference to visible light, can include electromagnetic radiation (EMR) or photons in the visible and/or non-visible portions of the EMR wavelength spectrum. The surgical visualization system can also include an imaging system and a control circuit in signal communication with the receiver(s) and the imaging system. Based on output from the receiver(s), the control circuit can determine a geometric surface map, i.e. three-dimensional surface topography, of the visible surfaces at the surgical site and one or more distances with respect to the surgical site.

In certain instances, the control circuit can determine one more distances to an at least partially concealed structure. Moreover, the imaging system can convey the geometric surface map and the one or more distances to a clinician. In such instances, an augmented view of the surgical site provided to the clinician can provide a representation of the concealed structure within the relevant context of the surgical site. For example, the imaging system can virtually augment the concealed structure on the geometric surface map of the concealing and/or obstructing tissue similar to a line drawn on the ground to indicate a utility line below the surface. Additionally or alternatively, the imaging system can convey the proximity of one or more surgical tools to the visible and obstructing tissue and/or to the at least partially concealed structure and/or the depth of the concealed structure below the visible surface of the obstructing tissue. For example, the visualization system can determine a distance with respect to the augmented line on the surface of the visible tissue and convey the distance to the imaging system.

In various aspects of the present disclosure, a surgical visualization system is disclosed for intraoperative identification and avoidance of critical structures. Such a surgical visualization system can provide valuable information to a clinician during a surgical procedure. As a result, the clinician can confidently maintain momentum throughout the surgical procedure knowing that the surgical visualization system is tracking a critical structure such as a ureter, specific nerves, and/or critical blood vessels, for example, which may be approached during dissection, for example. In one aspect, the surgical visualization system can provide an indication to the clinician in sufficient time for the clinician to pause and/or slow down the surgical procedure and evaluate the proximity to the critical structure to prevent inadvertent damage thereto. The surgical visualization system can provide an ideal, optimized, and/or customizable amount of information to the clinician to allow the clinician to move confidently and/or quickly through tissue while avoiding inadvertent damage to healthy tissue and/or critical structure(s) and, thus, to minimize the risk of harm resulting from the surgical procedure.

Figure 1:
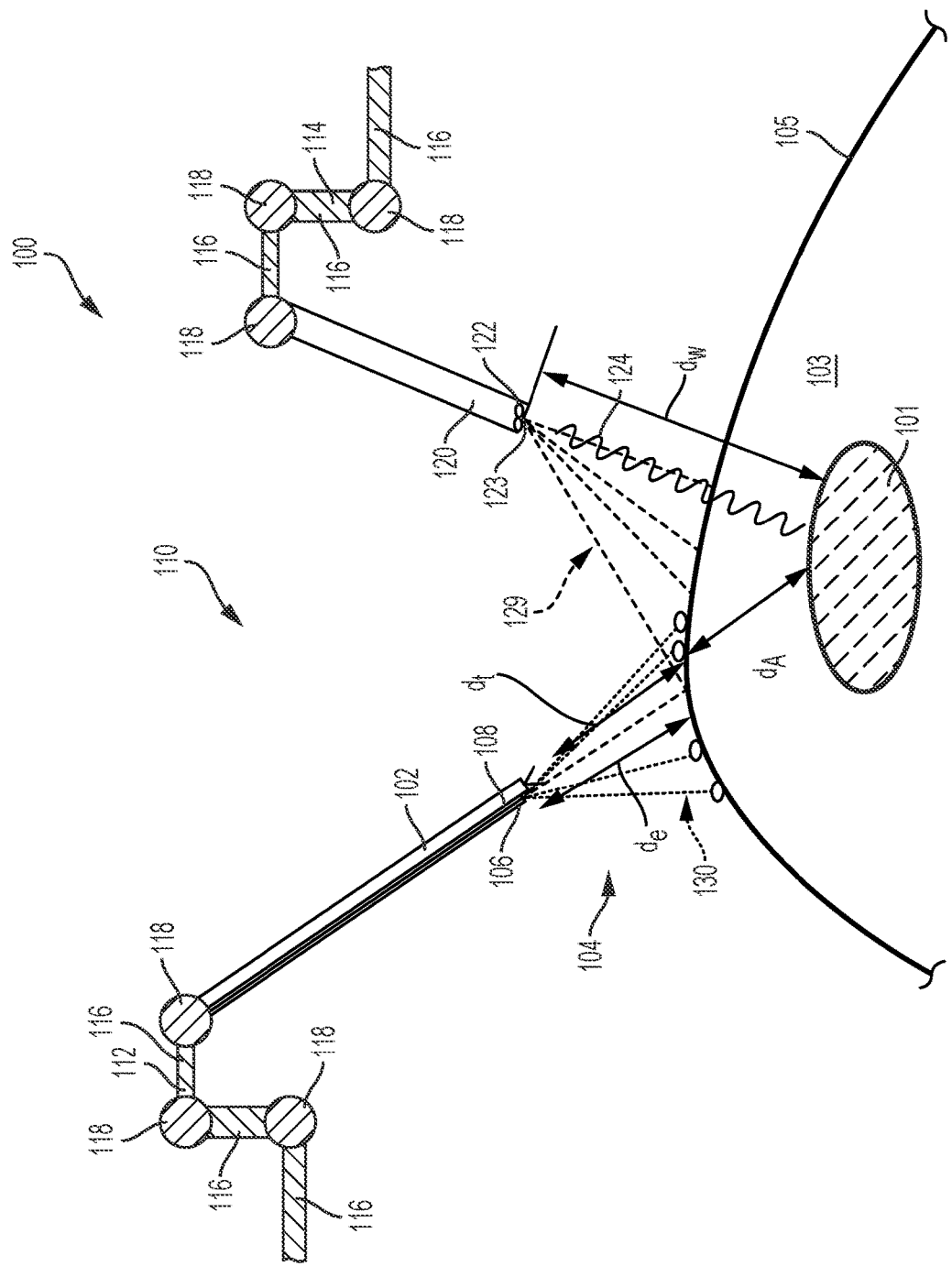
FIG. 1 is a schematic of a surgical visualization system including an imaging device and a surgical device, the surgical visualization system configured to identify a critical structure below a tissue surface, according to at least one aspect of the present disclosure.

FIG. 1 is a schematic of a surgical visualization system 100 according to at least one aspect of the present disclosure. The surgical visualization system 100 can create a visual representation of a critical structure 101 within an anatomical field. The surgical visualization system 100 can be used for clinical analysis and/or medical intervention, for example. In certain instances, the surgical visualization system 100 can be used intraoperatively to provide real-time, or near real-time, information to the clinician regarding proximity data, dimensions, and/or distances during a surgical procedure. The surgical visualization system 100 is configured for intraoperative identification of critical structure(s) and/or to facilitate the avoidance of the critical structure(s) 101 by a surgical device. For example, by identifying the critical structure 101, a clinician can avoid maneuvering a surgical device around the critical structure 101 and/or a region in a predefined proximity of the critical structure 101 during a surgical procedure. The clinician can avoid dissection of and/or near a vein, artery, nerve, and/or vessel, for example, identified as the critical structure 101, for example. In various instances, the critical structure 101 can be determined on a patient-by-patient and/or a procedure-by-procedure basis.

The surgical visualization system 100 incorporates tissue identification and geometric surface mapping in combination with a distance sensor system 104. In combination, these features of the surgical visualization system 100 can determine a position of a critical structure 101 within the anatomical field and/or the proximity of a surgical device 102 to the surface 105 of the visible tissue and/or to the critical structure 101. Moreover, the surgical visualization system 100 includes an imaging system that includes an imaging device 120, such as a camera, for example, configured to provide real-time views of the surgical site. In various instances, the imaging device 120 is a spectral camera (e.g. a hyperspectral camera, multispectral camera, or selective spectral camera), which is configured to detect reflected spectral waveforms and generate a spectral cube of images based on the molecular response to the different wavelengths. Views from the imaging device 120 can be provided to a clinician and, in various aspects of the present disclosure, can be augmented with additional information based on the tissue identification, landscape mapping, and the distance sensor system 104. In such instances, the surgical visualization system 100 includes a plurality of subsystems—an imaging subsystem, a surface mapping subsystem, a tissue identification subsystem, and/or a distance determining subsystem. These subsystems can cooperate to intra-operatively provide advanced data synthesis and integrated information to the clinician(s).

The imaging device can include a camera or imaging sensor that is configured to detect visible light, spectral light waves (visible or invisible), and a structured light pattern (visible or invisible), for example. In various aspects of the present disclosure, the imaging system can include an imaging device such as an endoscope, for example. Additionally or alternatively, the imaging system can include an imaging device such as an arthroscope, angioscope, bronchoscope, choledochoscope, colonoscope, cytoscope, duodenoscope, enteroscope, esophagogastro-duodenoscope (gastroscope), laryngoscope, nasopharyngo-neproscope, sigmoidoscope, thoracoscope, ureteroscope, or exoscope, for example. In other instances, such as in open surgery applications, the imaging system may not include a scope.

In various aspects of the present disclosure, the tissue identification subsystem can be achieved with a spectral imaging system. The spectral imaging system can rely on hyperspectral imaging, multispectral imaging, or selective spectral imaging, for example. Hyperspectral imaging of tissue is further described in U.S. Pat. No. 9,274,047, titled SYSTEM AND METHOD FOR GROSS ANATOMIC PATHOLOGY USING HYPERSPECTRAL IMAGING, issued Mar. 1, 2016, which is incorporated by reference herein in its entirety.

In various aspect of the present disclosure, the surface mapping subsystem can be achieved with a light pattern system, as further described herein. The use of a light pattern (or structured light) for surface mapping is known. Known surface mapping techniques can be utilized in the surgical visualization systems described herein.

Structured light is the process of projecting a known pattern (often a grid or horizontal bars) on to a surface. U.S. Patent Application Publication No. 2017/0055819, titled SET COMPRISING A SURGICAL INSTRUMENT, published Mar. 2, 2017, and U.S. Patent Application Publication No. 2017/0251900, titled DEPICTION SYSTEM, published Sep. 7, 2017, disclose a surgical system comprising a light source and a projector for projecting a light pattern. U.S. Patent Application Publication No. 2017/0055819, titled SET COMPRISING A SURGICAL INSTRUMENT, published Mar. 2, 2017, and U.S. Patent Application Publication No. 2017/0251900, titled DEPICTION SYSTEM, published Sep. 7, 2017, are incorporated by reference herein in their respective entireties.

In various aspects of the present disclosure, the distance determining system can be incorporated into the surface mapping system. For example, structured light can be utilized to generate a three-dimensional virtual model of the visible surface and determine various distances with respect to the visible surface. Additionally or alternatively, the distance determining system can rely on time-of-flight measurements to determine one or more distances to the identified tissue (or other structures) at the surgical site.

Figure 2:
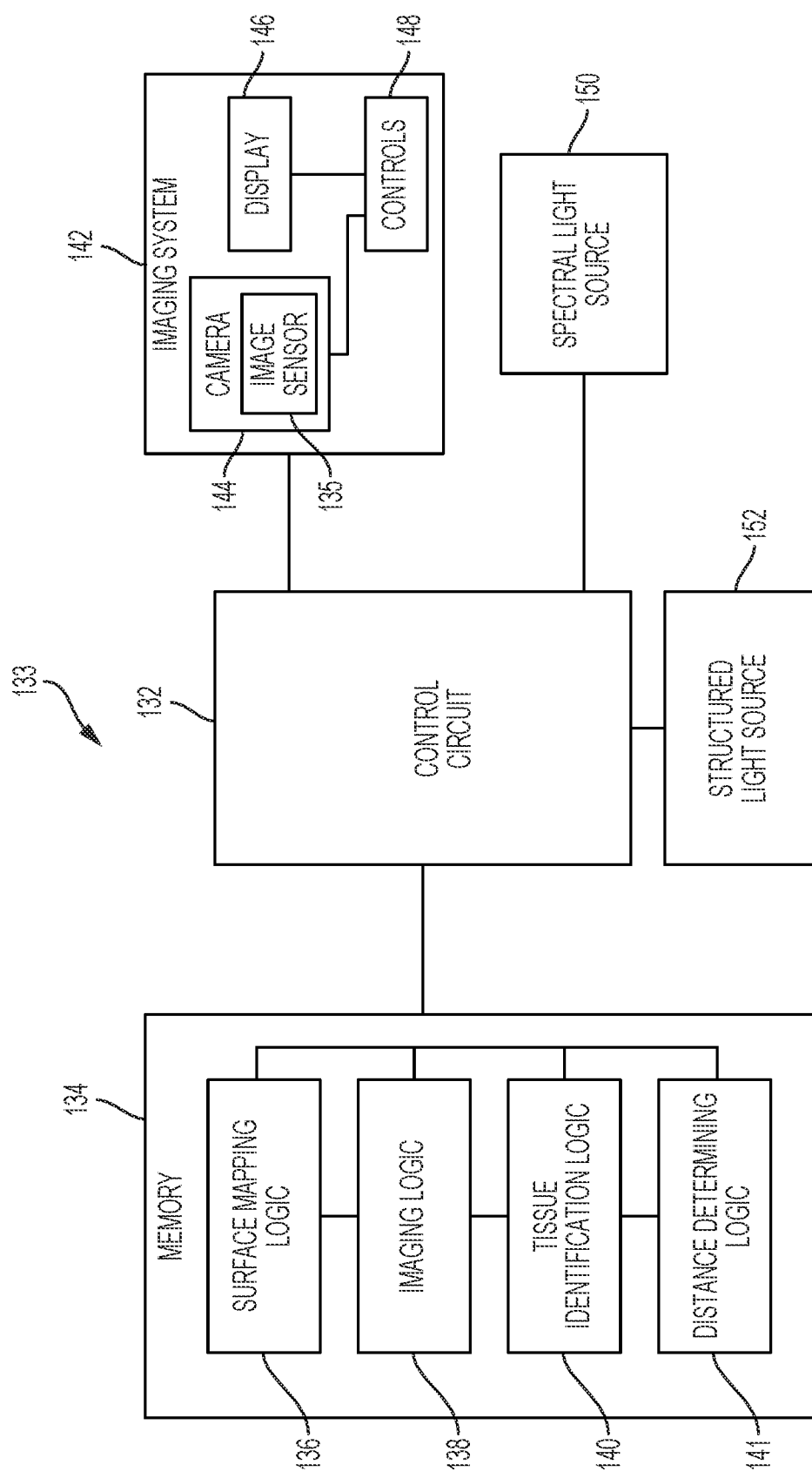
FIG. 2 is a schematic of a control system for a surgical visualization system, according to at least one aspect of the present disclosure.

FIG. 2 is a schematic diagram of a control system 133, which can be utilized with the surgical visualization system 100. The control system 133 includes a control circuit 132 in signal communication with a memory 134. The memory 134 stores instructions executable by the control circuit 132 to determine and/or recognize critical structures (e.g. the critical structure 101 in FIG. 1), determine and/or compute one or more distances and/or three-dimensional digital representations, and to communicate certain information to one or more clinicians. For example, the memory 134 stores surface mapping logic 136, imaging logic 138, tissue identification logic 140, or distance determining logic 141 or any combinations of the logic 136, 138, 140, and 141. The control system 133 also includes an imaging system 142 having one or more cameras 144 (like the imaging device 120 in FIG. 1), one or more displays 146, or one or more controls 148 or any combinations of these elements. The camera 144 can include one or more image sensors 135 to receive signals from various light sources emitting light at various visible and invisible spectra (e.g. visible light, spectral imagers, three-dimensional lens, among others). The display 146 can include one or more screens or monitors for depicting real, virtual, and/or virtually-augmented images and/or information to one or more clinicians.

In various aspects, the heart of the camera 144 is the image sensor 135. Generally, modern image sensors 135 are solid-state electronic devices containing up to millions of discrete photodetector sites called pixels. The image sensor 135 technology falls into one of two categories: Charge-Coupled Device (CCD) and Complementary Metal Oxide Semiconductor (CMOS) imagers and more recently, short-wave infrared (SWIR) is an emerging technology in imaging. Another type of image sensor 135 employs a hybrid CCD/CMOS architecture (sold under the name "sCMOS") and consists of CMOS readout integrated circuits (ROICs) that are bump bonded to a CCD imaging substrate. CCD and CMOS image sensors 135 are sensitive to wavelengths from approximately 350-1050 nm, although the range is usually given from 400-1000 nm. CMOS sensors are, in general, more sensitive to IR wavelengths than CCD sensors. Solid state image sensors 135 are based on the photoelectric effect and, as a result, cannot distinguish between colors. Accordingly, there are two types of color CCD cameras: single chip and three-chip. Single chip color CCD cameras offer a common, low-cost imaging solution and use a mosaic (e.g. Bayer) optical filter to separate incoming light into a series of colors and employ an interpolation algorithm to resolve full color images. Each color is, then, directed to a different set of pixels. Three-chip color CCD cameras provide higher resolution by employing a prism to direct each section of the incident spectrum to a different chip. More accurate color reproduction is possible, as each point in space of the object has separate RGB intensity values, rather than using an algorithm to determine the color. Three-chip cameras offer extremely high resolutions.

The control system 133 also includes a spectral light source 150 and a structured light source 152. In certain instances, a single source can be pulsed to emit wavelengths of light in the spectral light source 150 range and wavelengths of light in the structured light source 152 range. Alternatively, a single light source can be pulsed to provide light in the invisible spectrum (e.g. infrared spectral light) and wavelengths of light on the visible spectrum. The spectral light source 150 can be a hyperspectral light source, a multispectral light source, and/or a selective spectral light source, for example. In various instances, the tissue identification logic 140 can identify critical structure(s) via data from the spectral light source 150 received by the image sensor 135 portion of the camera 144. The surface mapping logic 136 can determine the surface contours of the visible tissue based on reflected structured light. With time-of-flight measurements, the distance determining logic 141 can determine one or more distance(s) to the visible tissue and/or the critical structure 101. One or more outputs from the surface mapping logic 136, the tissue identification logic 140, and the distance determining logic 141, can be provided to the imaging logic 138, and combined, blended, and/or overlaid to be conveyed to a clinician via the display 146 of the imaging system 142.

Figure 2A:
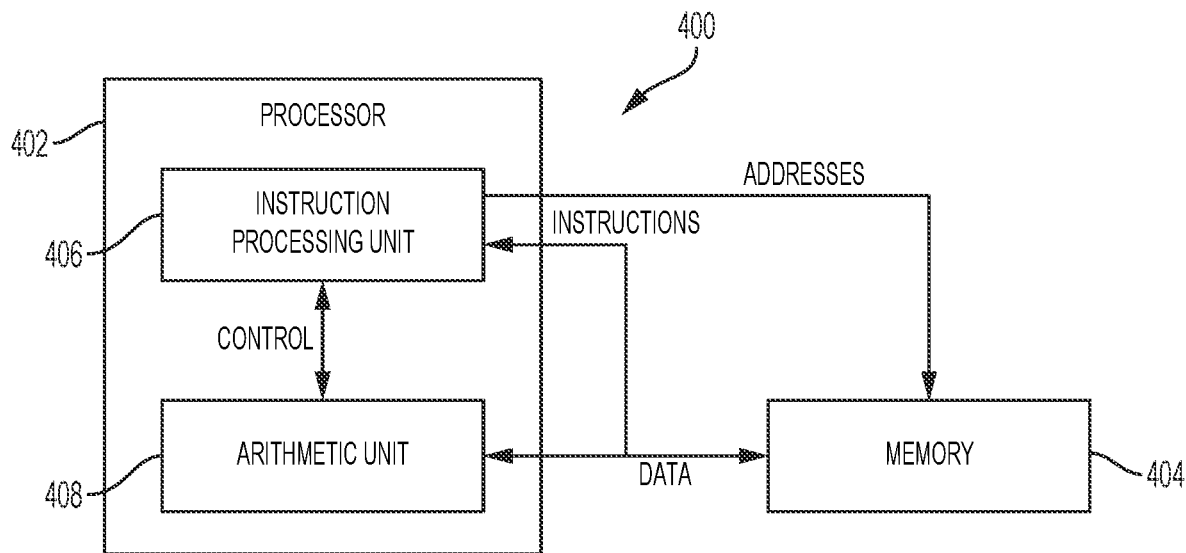
FIG. 2A illustrates a control circuit configured to control aspects of a surgical visualization system, according to at least one aspect of the present disclosure.
Figure 2B:
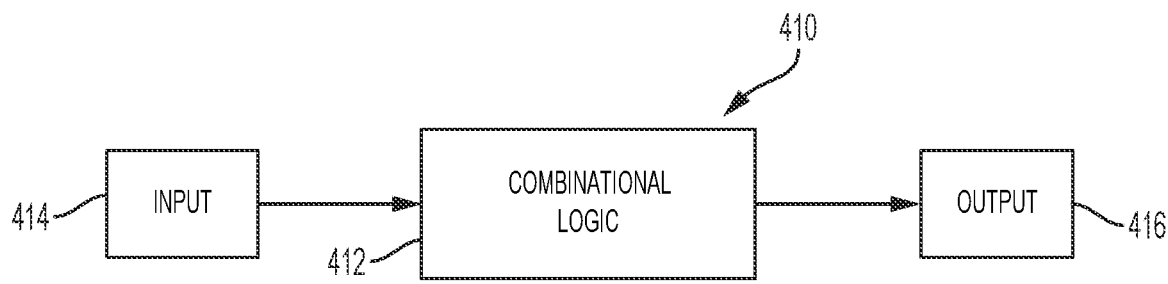
FIG. 2B illustrates a combinational logic circuit configured to control aspects of a surgical visualization system, according to at least one aspect of the present disclosure.
Figure 2C:
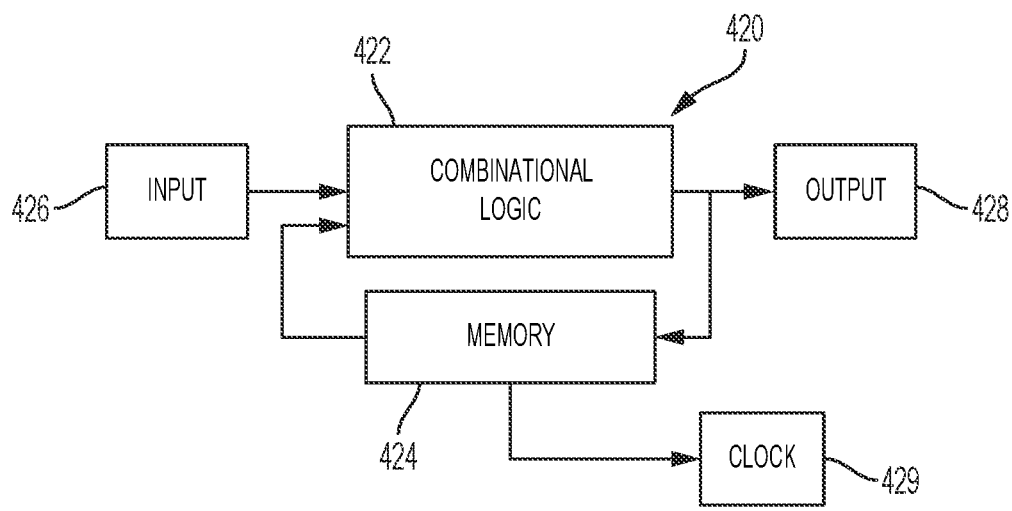
FIG. 2C illustrates a sequential logic circuit configured to control aspects of a surgical visualization system, according to at least one aspect of the present disclosure.

The description now turns briefly to FIGS. 2A-2C to describe various aspects of the control circuit 132 for controlling various aspects of the surgical visualization system 100. Turning to FIG. 2A, there is illustrated a control circuit 400 configured to control aspects of the surgical visualization system 100, according to at least one aspect of this disclosure. The control circuit 400 can be configured to implement various processes described herein. The control circuit 400 may comprise a microcontroller comprising one or more processors 402 (e.g., microprocessor, microcontroller) coupled to at least one memory circuit 404. The memory circuit 404 stores machine-executable instructions that, when executed by the processor 402, cause the processor 402 to execute machine instructions to implement various processes described herein. The processor 402 may be any one of a number of single-core or multicore processors known in the art. The memory circuit 404 may comprise volatile and non-volatile storage media. The processor 402 may include an instruction processing unit 406 and an arithmetic unit 408. The instruction processing unit may be configured to receive instructions from the memory circuit 404 of this disclosure.

FIG. 2B illustrates a combinational logic circuit 410 configured to control aspects of the surgical visualization system 100, according to at least one aspect of this disclosure. The combinational logic circuit 410 can be configured to implement various processes described herein. The combinational logic circuit 410 may comprise a finite state machine comprising a combinational logic 412 configured to receive data associated with the surgical instrument or tool at an input 414, process the data by the combinational logic 412, and provide an output 416.

FIG. 2C illustrates a sequential logic circuit 420 configured to control aspects of the surgical visualization system 100, according to at least one aspect of this disclosure. The sequential logic circuit 420 or the combinational logic 422 can be configured to implement various processes described herein. The sequential logic circuit 420 may comprise a finite state machine. The sequential logic circuit 420 may comprise a combinational logic 422, at least one memory circuit 424, and a clock 429, for example. The at least one memory circuit 424 can store a current state of the finite state machine. In certain instances, the sequential logic circuit 420 may be synchronous or asynchronous. The combinational logic 422 is configured to receive data associated with a surgical device or system from an input 426, process the data by the combinational logic 422, and provide an output 428. In other aspects, the circuit may comprise a combination of a processor (e.g., processor 402 in FIG. 2A) and a finite state machine to implement various processes herein. In other aspects, the finite state machine may comprise a combination of a combinational logic circuit (e.g., combinational logic circuit 410, FIG. 2B) and the sequential logic circuit 420.

Referring again to the surgical visualization system 100 in FIG. 1, the critical structure 101 can be an anatomical structure of interest. For example, the critical structure 101 can be a ureter, an artery such as a superior mesenteric artery, a vein such as a portal vein, a nerve such as a phrenic nerve, and/or a tumor, among other anatomical structures. In other instances, the critical structure 101 can be a foreign structure in the anatomical field, such as a surgical device, surgical fastener, clip, tack, bougie, band, and/or plate, for example. Example critical structures are further described herein and in the aforementioned U.S. Patent Applications, including U.S. patent application Ser. No. 16/128,192, titled VISUALIZATION OF SURGICAL DEVICES, filed Sep. 11, 2018, now U.S. Pat. No. 10,792,034, for example, which are incorporated by reference herein in their respective entireties.

In one aspect, the critical structure 101 may be embedded in tissue 103. Stated differently, the critical structure 101 may be positioned below the surface 105 of the tissue 103. In such instances, the tissue 103 conceals the critical structure 101 from the clinician's view. The critical structure 101 is also obscured from the view of the imaging device 120 by the tissue 103. The tissue 103 can be fat, connective tissue, adhesions, and/or organs, for example. In other instances, the critical structure 101 can be partially obscured from view.

FIG. 1 also depicts the surgical device 102. The surgical device 102 includes an end effector having opposing jaws extending from the distal end of the shaft of the surgical device 102. The surgical device 102 can be any suitable surgical device such as, for example, a dissector, a stapler, a grasper, a clip applier, and/or an energy device including mono-polar probes, bi-polar probes, ablation probes, and/or an ultrasonic end effector. Additionally or alternatively, the surgical device 102 can include another imaging or diagnostic modality, such as an ultrasound device, for example. In one aspect of the present disclosure, the surgical visualization system 100 can be configured to achieve identification of one or more critical structures 101 and the proximity of the surgical device 102 to the critical structure(s) 101.

The imaging device 120 of the surgical visualization system 100 is configured to detect light at various wavelengths, such as, for example, visible light, spectral light waves (visible or invisible), and a structured light pattern (visible or invisible). The imaging device 120 may include a plurality of lenses, sensors, and/or receivers for detecting the different signals. For example, the imaging device 120 can be a hyperspectral, multispectral, or selective spectral camera, as further described herein. The imaging device 120 can also include a waveform sensor 122 (such as a spectral image sensor, detector, and/or three-dimensional camera lens). For example, the imaging device 120 can include a right-side lens and a left-side lens used together to record two two-dimensional images at the same time and, thus, generate a three-dimensional image of the surgical site, render a three-dimensional image of the surgical site, and/or determine one or more distances at the surgical site. Additionally or alternatively, the imaging device 120 can be configured to receive images indicative of the topography of the visible tissue and the identification and position of hidden critical structures, as further described herein. For example, the field of view of the imaging device 120 can overlap with a pattern of light (structured light) on the surface 105 of the tissue, as shown in FIG. 1.

In one aspect, the surgical visualization system 100 may be incorporated into a robotic system 110. For example, the robotic system 110 may include a first robotic arm 112 and a second robotic arm 114. The robotic arms 112, 114 include rigid structural members 116 and joints 118, which can include servomotor controls. The first robotic arm 112 is configured to maneuver the surgical device 102, and the second robotic arm 114 is configured to maneuver the imaging device 120. A robotic control unit can be configured to issue control motions to the robotic arms 112, 114, which can affect the surgical device 102 and the imaging device 120, for example.

The surgical visualization system 100 also includes an emitter 106, which is configured to emit a pattern of light, such as stripes, grid lines, and/or dots, to enable the determination of the topography or landscape of the surface 105. For example, projected light arrays 130 can be used for three-dimensional scanning and registration on the surface 105. The projected light arrays 130 can be emitted from the emitter 106 located on the surgical device 102 and/or one of the robotic arms 112, 114 and/or the imaging device 120, for example. In one aspect, the projected light array 130 is employed to determine the shape defined by the surface 105 of the tissue 103 and/or the motion of the surface 105 intraoperatively. The imaging device 120 is configured to detect the projected light arrays 130 reflected from the surface 105 to determine the topography of the surface 105 and various distances with respect to the surface 105.

In one aspect, the imaging device 120 also may include an optical waveform emitter 123 that is configured to emit electromagnetic radiation 124 (NIR photons) that can penetrate the surface 105 of the tissue 103 and reach the critical structure 101. The imaging device 120 and the optical waveform emitter 123 thereon can be positionable by the robotic arm 114. A corresponding waveform sensor 122 (an image sensor, spectrometer, or vibrational sensor, for example) on the imaging device 120 is configured to detect the effect of the electromagnetic radiation received by the waveform sensor 122. The wavelengths of the electromagnetic radiation 124 emitted by the optical waveform emitter 123 can be configured to enable the identification of the type of anatomical and/or physical structure, such as the critical structure 101. The identification of the critical structure 101 can be accomplished through spectral analysis, photo-acoustics, and/or ultrasound, for example. In one aspect, the wavelengths of the electromagnetic radiation 124 may be variable. The waveform sensor 122 and optical waveform emitter 123 may be inclusive of a multispectral imaging system and/or a selective spectral imaging system, for example. In other instances, the waveform sensor 122 and optical waveform emitter 123 may be inclusive of a photoacoustic imaging system, for example. In other instances, the optical waveform emitter 123 can be positioned on a separate surgical device from the imaging device 120.

The surgical visualization system 100 also may include the distance sensor system 104 configured to determine one or more distances at the surgical site. In one aspect, the time-of-flight distance sensor system 104 may be a time-of-flight distance sensor system that includes an emitter, such as the emitter 106, and a receiver 108, which can be positioned on the surgical device 102. In other instances, the time-of-flight emitter can be separate from the structured light emitter. In one general aspect, the emitter 106 portion of the time-of-flight distance sensor system 104 may include a very tiny laser source and the receiver 108 portion of the time-of-flight distance sensor system 104 may include a matching sensor. The time-of-flight distance sensor system 104 can detect the "time of flight," or how long the laser light emitted by the emitter 106 has taken to bounce back to the sensor portion of the receiver 108. Use of a very narrow light source in the emitter 106 enables the distance sensor system 104 to determining the distance to the surface 105 of the tissue 103 directly in front of the distance sensor system 104. Referring still to FIG. 1, $d_e$ is the emitter-to-tissue distance from the emitter 106 to the surface 105 of the tissue 103 and $d_t$ is the device-to-tissue distance from the distal end of the surgical device 102 to the surface 105 of the tissue. The distance sensor system 104 can be employed to determine the emitter-to-tissue distance $d_e$. The device-to-tissue distance $d_t$ is obtainable from the known position of the emitter 106 on the shaft of the surgical device 102 relative to the distal end of the surgical device 102. In other words, when the distance between the emitter 106 and the distal end of the surgical device 102 is known, the device-to-tissue distance $d_t$ can be determined from the emitter-to-tissue distance $d_e$. In certain instances, the shaft of the surgical device 102 can include one or more articulation joints, and can be articulatable with respect to the emitter 106 and the jaws. The articulation configuration can include a multi-joint vertebrae-like structure, for example. In certain instances, a three-dimensional camera can be utilized to triangulate one or more distances to the surface 105.

In various instances, the receiver 108 for the time-of-flight distance sensor system 104 can be mounted on a separate surgical device instead of the surgical device 102. For example, the receiver 108 can be mounted on a cannula or trocar through which the surgical device 102 extends to reach the surgical site. In still other instances, the receiver 108 for the time-of-flight distance sensor system 104 can be mounted on a separate robotically-controlled arm (e.g. the robotic arm 114), on a movable arm that is operated by another robot, and/or to an operating room (OR) table or fixture. In certain instances, the imaging device 120 includes the time-of-flight receiver 108 to determine the distance from the emitter 106 to the surface 105 of the tissue 103 using a line between the emitter 106 on the surgical device 102 and the imaging device 120. For example, the distance $d_e$ can be triangulated based on known positions of the emitter 106 (on the surgical device 102) and the receiver 108 (on the imaging device 120) of the time-of-flight distance sensor system 104. The three-dimensional position of the receiver 108 can be known and/or registered to the robot coordinate plane intraoperatively.

In certain instances, the position of the emitter 106 of the time-of-flight distance sensor system 104 can be controlled by the first robotic arm 112 and the position of the receiver 108 of the time-of-flight distance sensor system 104 can be controlled by the second robotic arm 114. In other instances, the surgical visualization system 100 can be utilized apart from a robotic system. In such instances, the distance sensor system 104 can be independent of the robotic system.

In certain instances, one or more of the robotic arms 112, 114 may be separate from a main robotic system used in the surgical procedure. At least one of the robotic arms 112, 114 can be positioned and registered to a particular coordinate system without a servomotor control. For example, a closed-loop control system and/or a plurality of sensors for the robotic arms 110 can control and/or register the position of the robotic arm(s) 112, 114 relative to the particular coordinate system. Similarly, the position of the surgical device 102 and the imaging device 120 can be registered relative to a particular coordinate system.

Figure 3:
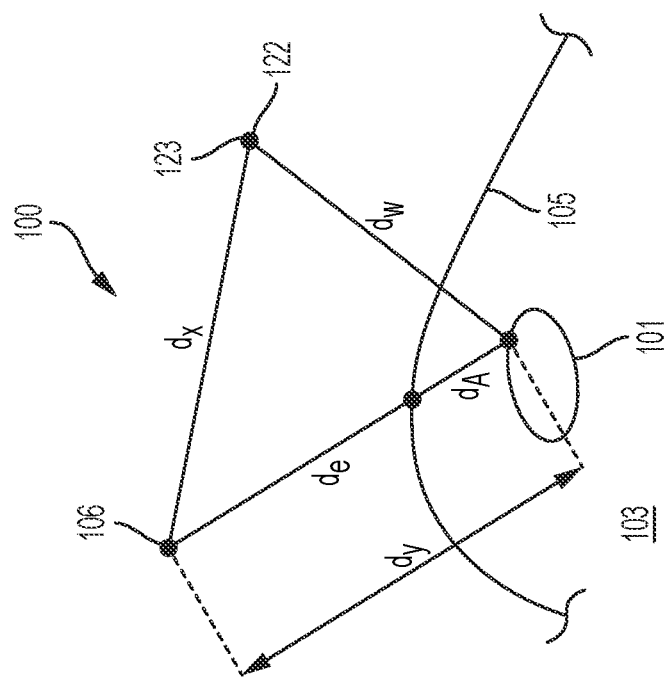
FIG. 3 is a schematic depicting triangularization between the surgical device, the imaging device, and the critical structure of FIG. 1 to determine a depth $d_A$ of the critical structure below the tissue surface, according to at least one aspect of the present disclosure.

Referring still to FIG. 1, $d_w$ is the camera-to-critical structure distance from the optical waveform emitter 123 located on the imaging device 120 to the surface of the critical structure 101, and $d_A$ is the depth of the critical structure 101 below the surface 105 of the tissue 103 (i.e., the distance between the portion of the surface 105 closest to the surgical device 102 and the critical structure 101). In various aspects, the time-of-flight of the optical waveforms emitted from the optical waveform emitter 123 located on the imaging device 120 can be configured to determine the camera-to-critical structure distance $d_w$. The use of spectral imaging in combination with time-of-flight sensors is further described herein. Moreover, referring now to FIG. 3, in various aspects of the present disclosure, the depth $d_A$ of the critical structure 101 relative to the surface 105 of the tissue 103 can be determined by triangulating from the distance $d_w$ and known positions of the emitter 106 on the surgical device 102 and the optical waveform emitter 123 on the imaging device 120 (and, thus, the known distance $d_x$ therebetween) to determine the distance $d_y$, which is the sum of the distances $d_e$ and $d_A$.

Additionally or alternatively, time-of-flight from the optical waveform emitter 123 can be configured to determine the distance from the optical waveform emitter 123 to the surface 105 of the tissue 103. For example, a first waveform (or range of waveforms) can be utilized to determine the camera-to-critical structure distance $d_w$ and a second waveform (or range of waveforms) can be utilized to determine the distance to the surface 105 of the tissue 103. In such instances, the different waveforms can be utilized to determine the depth of the critical structure 101 below the surface 105 of the tissue 103.

Additionally or alternatively, in certain instances, the distance $d_A$ can be determined from an ultrasound, a registered magnetic resonance imaging (MRI) or computerized tomography (CT) scan. In still other instances, the distance $d_A$ can be determined with spectral imaging because the detection signal received by the imaging device can vary based on the type of material. For example, fat can decrease the detection signal in a first way, or a first amount, and collagen can decrease the detection signal in a different, second way, or a second amount.

Figure 4:
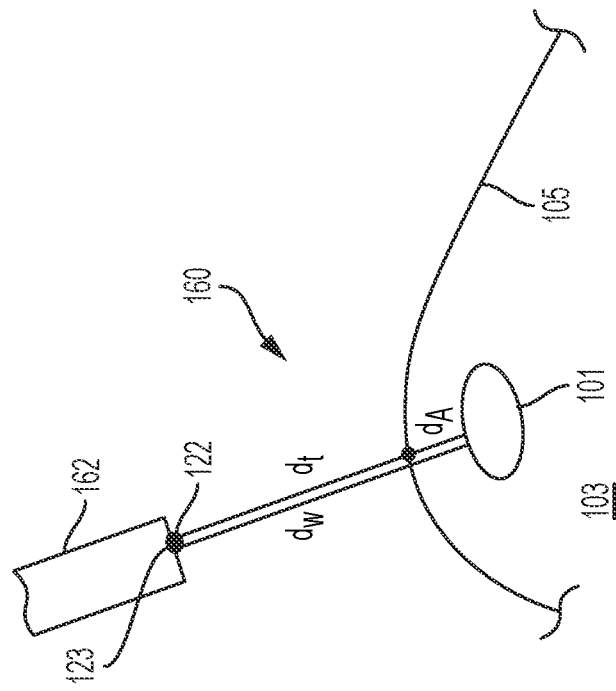
FIG. 4 is a schematic of a surgical visualization system configured to identify a critical structure below a tissue surface, wherein the surgical visualization system includes a pulsed light source for determining a depth $d_A$ of the critical structure below the tissue surface, according to at least one aspect of the present disclosure.

Referring now to a surgical visualization system 160 in FIG. 4, in which a surgical device 162 includes the optical waveform emitter 123 and the waveform sensor 122 that is configured to detect the reflected waveforms. The optical waveform emitter 123 can be configured to emit waveforms for determining the distances $d_t$ and $d_w$ from a common device, such as the surgical device 162, as further described herein. In such instances, the distance $d_A$ from the surface 105 of the tissue 103 to the surface of the critical structure 101 can be determined as follows:

$$d_A = d_w - d_t$$

As disclosed herein, various information regarding visible tissue, embedded critical structures, and surgical devices can be determined by utilizing a combination approach that incorporates one or more time-of-flight distance sensors, spectral imaging, and/or structured light arrays in combination with an image sensor configured to detect the spectral wavelengths and the structured light arrays. Moreover, the image sensor can be configured to receive visible light and, thus, provide images of the surgical site to an imaging system. Logic or algorithms are employed to discern the information received from the time-of-flight sensors, spectral wavelengths, structured light, and visible light and render three-dimensional images of the surface tissue and underlying anatomical structures. In various instances, the imaging device 120 can include multiple image sensors.

Figure 6:
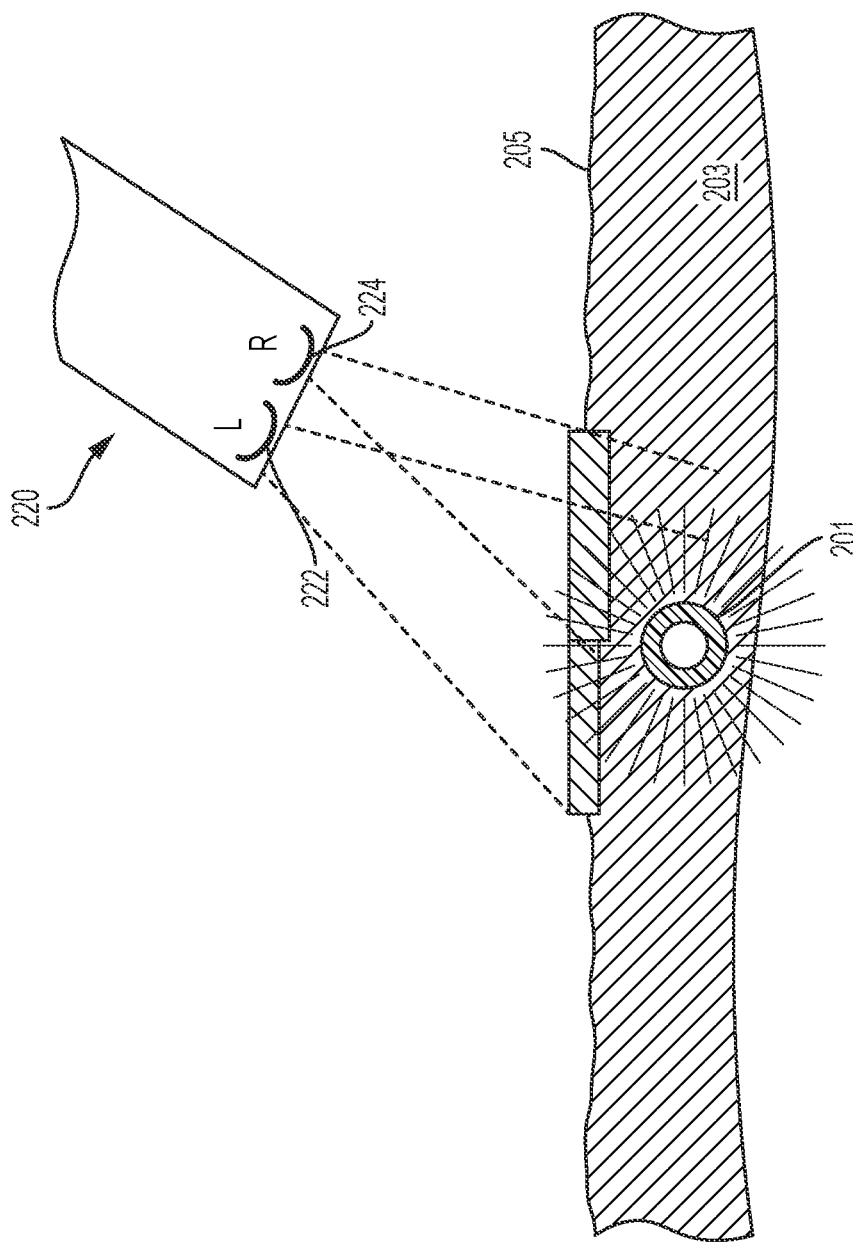
FIG. 6 is a schematic of a surgical visualization system including a three-dimensional camera, wherein the surgical visualization system is configured to identify a critical structure that is embedded within tissue, according to at least one aspect of the present disclosure.
Figures 7A, 7B:
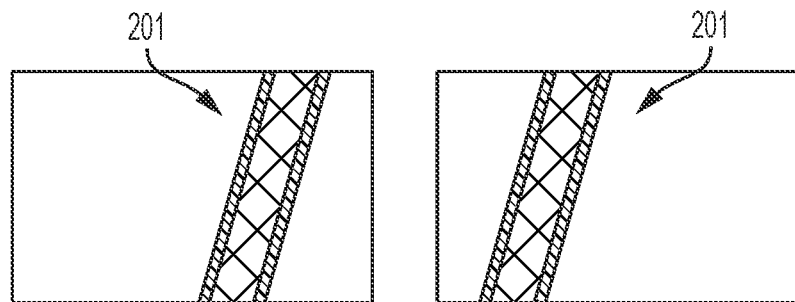
Figure 8:
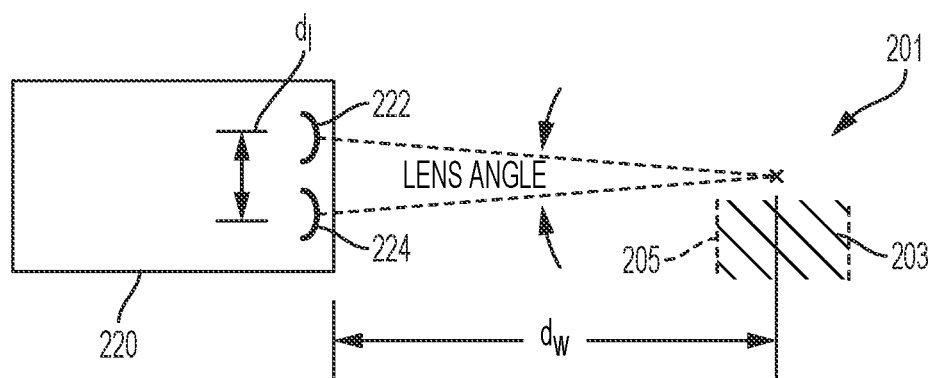
FIG. 8 is a schematic of the surgical visualization system of FIG. 6, in which a camera-to-critical structure distance $d_w$ from the three-dimensional camera to the critical structure can be determined, according to at least one aspect of the present disclosure.

The camera-to-critical structure distance $d_w$ can also be detected in one or more alternative ways. In one aspect, a fluoroscopy visualization technology, such as fluorescent indosciedine green (ICG), for example, can be utilized to illuminate a critical structure 201, as shown in FIGS. 6-8. A camera 220 can include two optical waveforms sensors 222, 224, which take simultaneous left-side and right-side images of the critical structure 201 (FIGS. 7A and 7B). In such instances, the camera 220 can depict a glow of the critical structure 201 below the surface 205 of the tissue 203, and the distance $d_w$ can be determined by the known distance between the sensors 222 and 224. In certain instances, distances can be determined more accurately by utilizing more than one camera or by moving a camera between multiple locations. In certain aspects, one camera can be controlled by a first robotic arm and a second camera by another robotic arm. In such a robotic system, one camera can be a follower camera on a follower arm, for example. The follower arm, and camera thereon, can be programmed to track the other camera and to maintain a particular distance and/or lens angle, for example.

Figure 9:
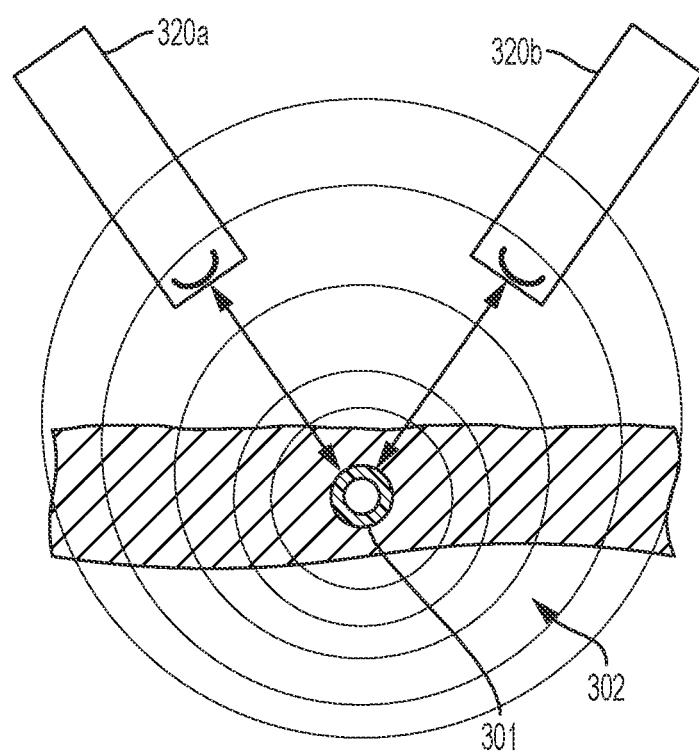
FIG. 9 is a schematic of a surgical visualization system utilizing two cameras to determine the position of an embedded critical structure, according to at least one aspect of the present disclosure.

In still other aspects, the surgical visualization system 100 may employ two separate waveform receivers (i.e. cameras/image sensors) to determine $d_w$. Referring now to FIG. 9, if a critical structure 301 or the contents thereof (e.g. a vessel or the contents of the vessel) can emit a signal 302, such as with fluoroscopy, then the actual location can be triangulated from two separate cameras 320a, 320b at known locations.

Figure 10B:
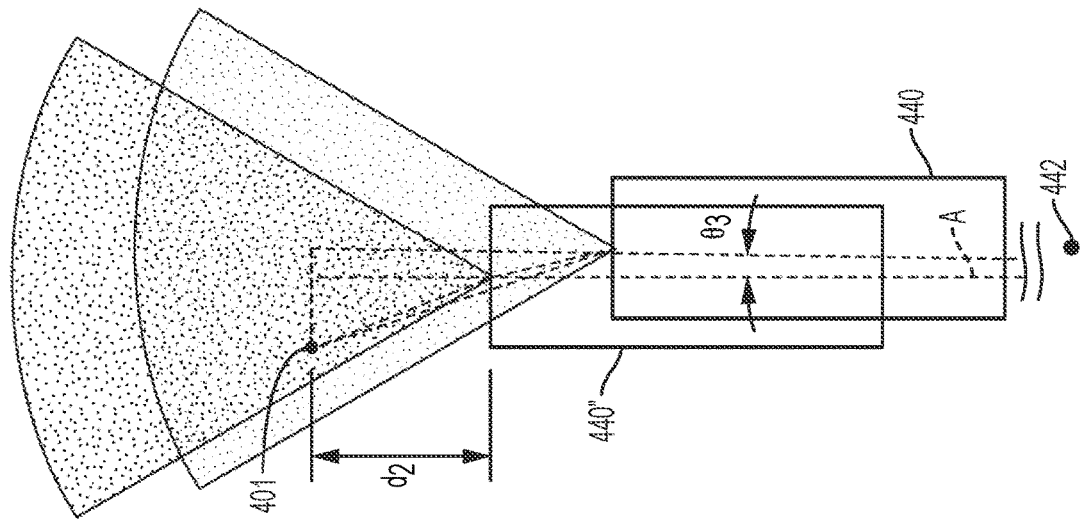
FIG. 10B is a schematic of the surgical visualization system of FIG. 10A, in which the camera is moved axially and rotationally between a plurality of known positions to determine a position of the embedded critical structure, according to at least one aspect of the present disclosure.
Figure 10A:
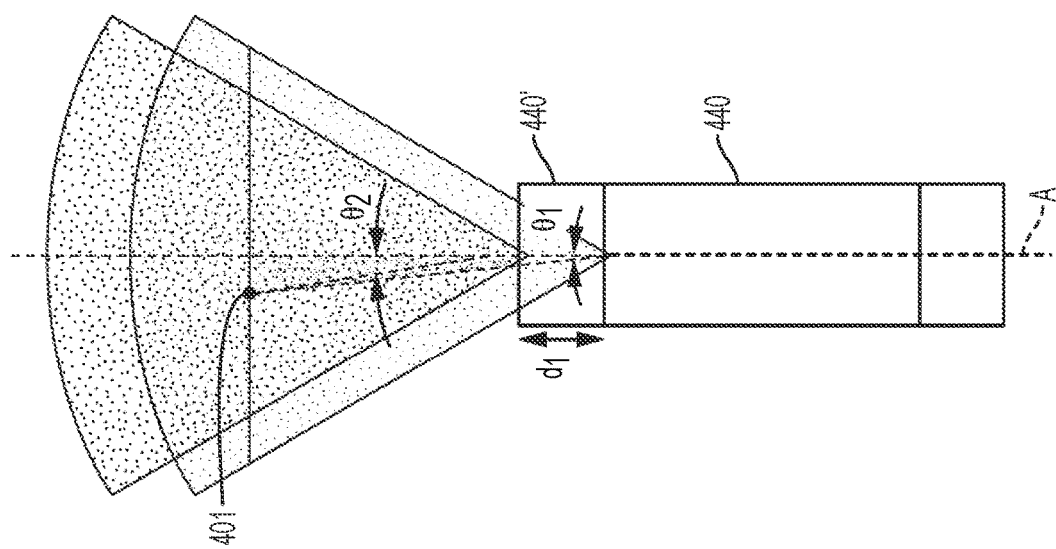
FIG. 10A is a schematic of a surgical visualization system utilizing a camera that is moved axially between a plurality of known positions to determine a position of an embedded critical structure, according to at least one aspect of the present disclosure.

In another aspect, referring now to FIGS. 10A and 10B, a surgical visualization system may employ a dithering or moving camera 440 to determine the distance $d_w$. The camera 440 is robotically-controlled such that the three-dimensional coordinates of the camera 440 at the different positions are known. In various instances, the camera 440 can pivot at a cannula or patient interface. For example, if a critical structure 401 or the contents thereof (e.g. a vessel or the contents of the vessel) can emit a signal, such as with fluoroscopy, for example, then the actual location can be triangulated from the camera 440 moved rapidly between two or more known locations. In FIG. 10A, the camera 440 is moved axially along an axis A. More specifically, the camera 440 translates a distance $d_1$ closer to the critical structure 401 along the axis A to the location indicated as a location 440', such as by moving in and out on a robotic arm. As the camera 440 moves the distance $d_1$ and the size of view change with respect to the critical structure 401, the distance to the critical structure 401 can be calculated. For example, a 4.28 mm axial translation (the distance $d_1$) can correspond to an angle $\theta_1$ of 6.28 degrees and an angle $\theta_2$ of 8.19 degrees. Additionally or alternatively, the camera 440 can rotate or sweep along an arc between different positions. Referring now to FIG. 10B, the camera 440 is moved axially along the axis A and is rotated an angle $\theta_3$ about the axis A. A pivot point 442 for rotation of the camera 440 is positioned at the cannula/patient interface. In FIG. 10B, the camera 440 is translated and rotated to a location 440". As the camera 440 moves and the edge of view changes with respect to the critical structure 401, the distance to the critical structure 401 can be calculated. In FIG. 10B, a distance $d_2$ can be 9.01 mm, for example, and the angle $\theta_3$ can be 0.9 degrees, for example.

Figure 5:
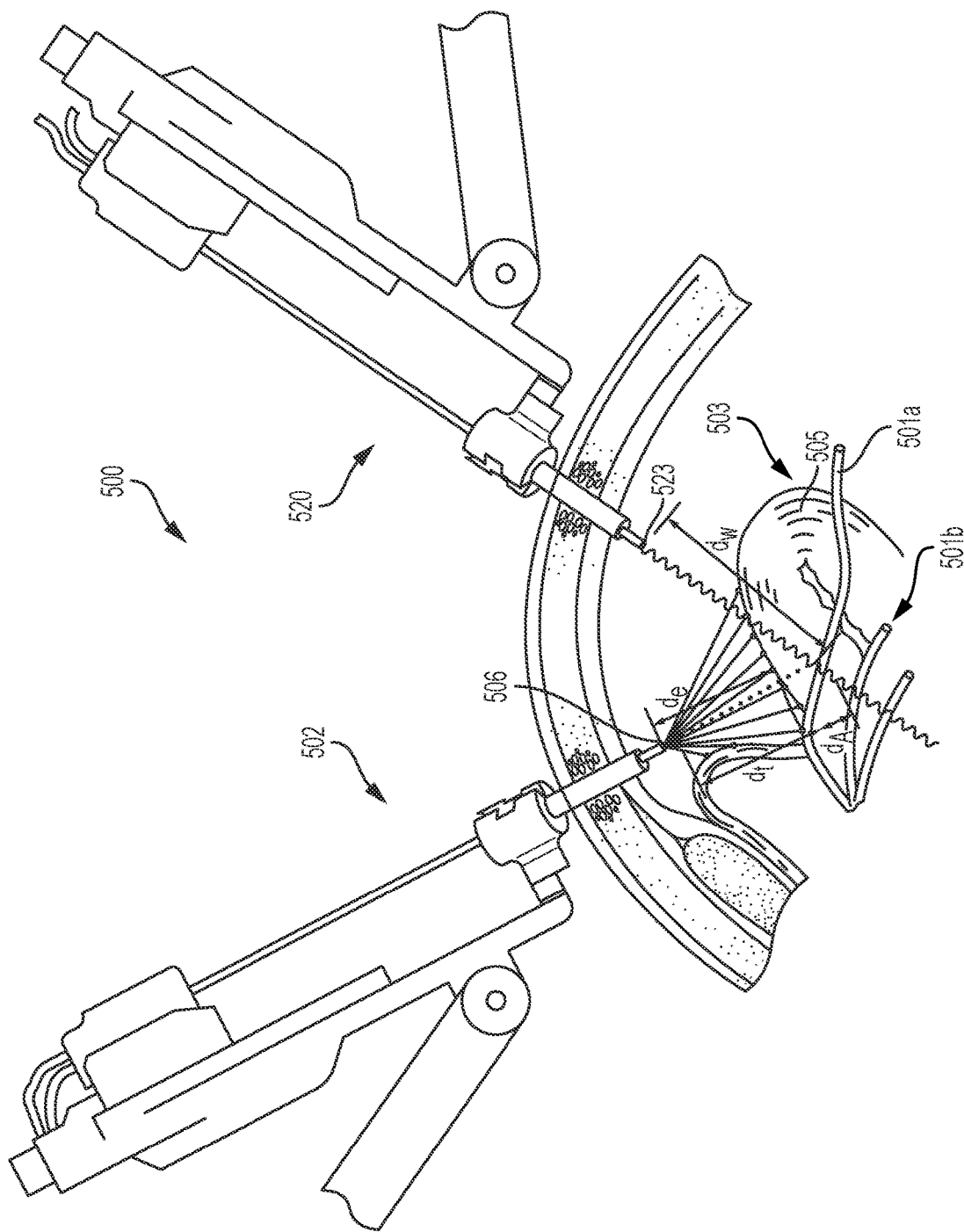
FIG. 5 is a schematic of a surgical visualization system including an imaging device and a surgical device, the surgical visualization system configured to identify a critical structure below a tissue surface, according to at least one aspect of the present disclosure.

FIG. 5 depicts a surgical visualization system 500, which is similar to the surgical visualization system 100 in many respects. In various instances, the surgical visualization system 500 can be a further exemplification of the surgical visualization system 100. Similar to the surgical visualization system 100, the surgical visualization system 500 includes a surgical device 502 and an imaging device 520. The imaging device 520 includes a spectral light emitter 523, which is configured to emit spectral light in a plurality of wavelengths to obtain a spectral image of hidden structures, for example. The imaging device 520 can also include a three-dimensional camera and associated electronic processing circuits in various instances. The surgical visualization system 500 is shown being utilized intraoperatively to identify and facilitate avoidance of certain critical structures, such as a ureter 501a and vessels 501b in an organ 503 (the uterus in this example), that are not visible on the surface.

The surgical visualization system 500 is configured to determine an emitter-to-tissue distance $d_e$ from an emitter 506 on the surgical device 502 to a surface 505 of the uterus 503 via structured light. The surgical visualization system 500 is configured to extrapolate a device-to-tissue distance $d_t$ from the surgical device 502 to the surface 505 of the uterus 503 based on the emitter-to-tissue distance $d_e$. The surgical visualization system 500 is also configured to determine a tissue-to-ureter distance $d_A$ from the ureter 501a to the surface 505 and a camera-to ureter distance $d_w$ from the imaging device 520 to the ureter 501a. As described herein with respect to FIG. 1, for example, the surgical visualization system 500 can determine the distance $d_w$ with spectral imaging and time-of-flight sensors, for example. In various instances, the surgical visualization system 500 can determine (e.g. triangulate) the tissue-to-ureter distance $d_A$ (or depth) based on other distances and/or the surface mapping logic described herein.

Figure 11:
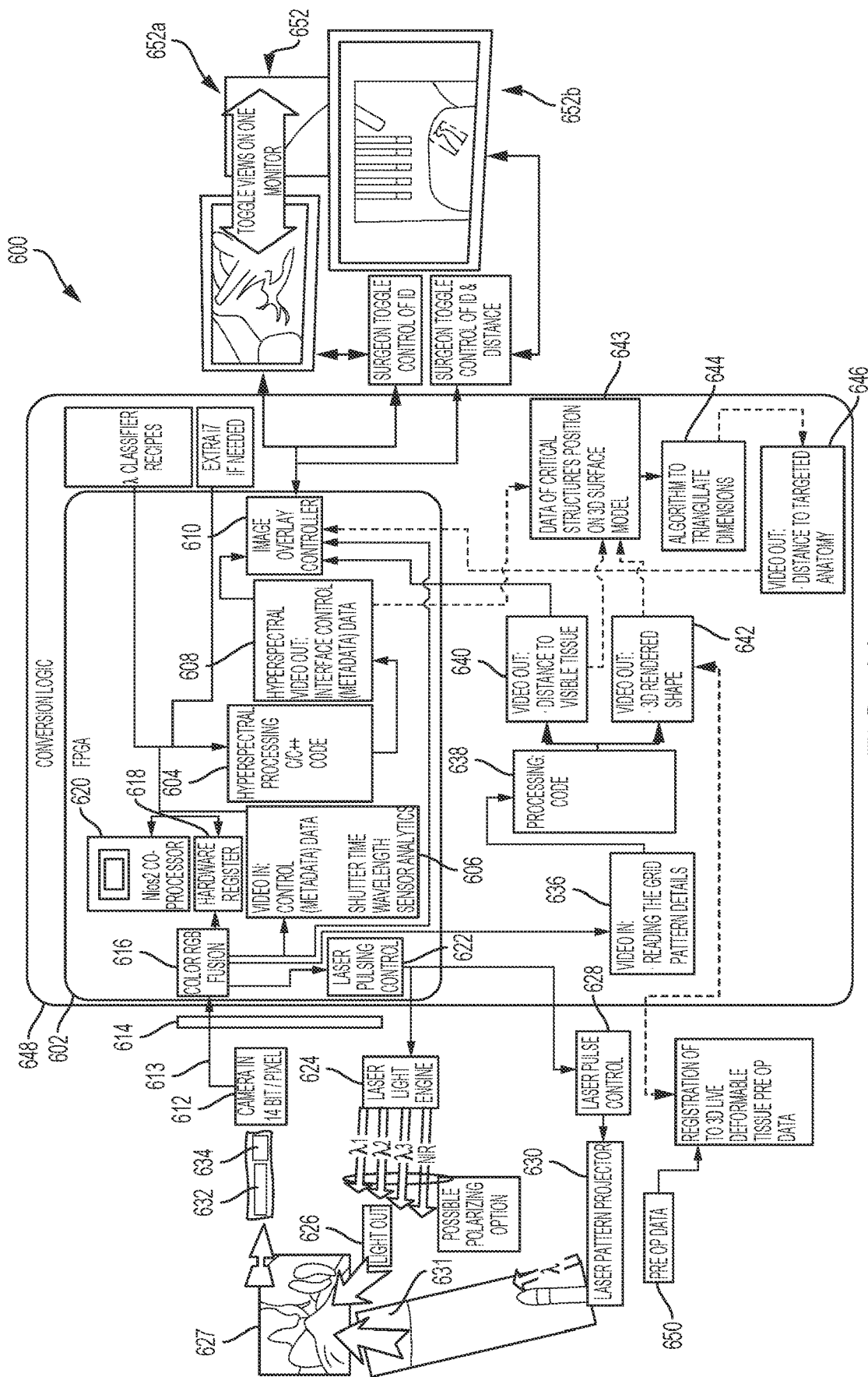
FIG. 11 is a schematic of a control system for a surgical visualization system, according to at least one aspect of the present disclosure.

Referring now to FIG. 11, where a schematic of a control system 600 for a surgical visualization system, such as the surgical visualization system 100, for example, is depicted. The control system 600 is a conversion system that integrates spectral signature tissue identification and structured light tissue positioning to identify critical structures, especially when those structures are obscured by other tissue, such as fat, connective tissue, blood, and/or other organs, for example. Such technology could also be useful for detecting tissue variability, such as differentiating tumors and/or non-healthy tissue from healthy tissue within an organ.

The control system 600 is configured for implementing a hyperspectral imaging and visualization system in which a molecular response is utilized to detect and identify anatomy in a surgical field of view. The control system 600 includes a conversion logic circuit 648 to convert tissue data to surgeon usable information. For example, the variable reflectance based on wavelengths with respect to obscuring material can be utilized to identify the critical structure in the anatomy. Moreover, the control system 600 combines the identified spectral signature and the structural light data in an image. For example, the control system 600 can be employed to create of three-dimensional data set for surgical use in a system with augmentation image overlays. Techniques can be employed both intraoperatively and preoperatively using additional visual information. In various instances, the control system 600 is configured to provide warnings to a clinician when in the proximity of one or more critical structures. Various algorithms can be employed to guide robotic automation and semi-automated approaches based on the surgical procedure and proximity to the critical structure(s).

A projected array of lights is employed to determine tissue shape and motion intraoperatively. Alternatively, flash Lidar may be utilized for surface mapping of the tissue.

The control system 600 is configured to detect the critical structure(s) and provide an image overlay of the critical structure and measure the distance to the surface of the visible tissue and the distance to the embedded/buried critical structure(s). In other instances, the control system 600 can measure the distance to the surface of the visible tissue or detect the critical structure(s) and provide an image overlay of the critical structure.

The control system 600 includes a spectral control circuit 602. The spectral control circuit 602 can be a field programmable gate array (FPGA) or another suitable circuit configuration as described herein in connection with FIGS. 2A-2C, for example. The spectral control circuit 602 includes a processor 604 to receive video input signals from a video input processor 606. The processor 604 can be configured for hyperspectral processing and can utilize C/C++ code, for example. The video input processor 606 receives video-in of control (metadata) data such as shutter time, wave length, and sensor analytics, for example. The processor 604 is configured to process the video input signal from the video input processor 606 and provide a video output signal to a video output processor 608, which includes a hyperspectral video-out of interface control (metadata) data, for example. The video output processor 608 provides the video output signal to an image overlay controller 610.

The video input processor 606 is coupled to a camera 612 at the patient side via a patient isolation circuit 614. As previously discussed, the camera 612 includes a solid state image sensor 634. The patient isolation circuit can include a plurality of transformers so that the patient is isolated from other circuits in the system. The camera 612 receives intraoperative images through optics 632 and the image sensor 634. The image sensor 634 can include a CMOS image sensor, for example, or may include any of the image sensor technologies discussed herein in connection with FIG. 2, for example. In one aspect, the camera 612 outputs images in 14 bit/pixel signals. It will be appreciated that higher or lower pixel resolutions may be employed without departing from the scope of the present disclosure. The isolated camera output signal 613 is provided to a color RGB fusion circuit 616, which employs a hardware register 618 and a Nios2 co-processor 620 to process the camera output signal 613. A color RGB fusion output signal is provided to the video input processor 606 and a laser pulsing control circuit 622.

The laser pulsing control circuit 622 controls a laser light engine 624. The laser light engine 624 outputs light in a plurality of wavelengths ($\lambda_1, \lambda_2, \lambda_3 \ldots \lambda_n$) including near infrared (NIR). The laser light engine 624 can operate in a plurality of modes. In one aspect, the laser light engine 624 can operate in two modes, for example. In a first mode, e.g. a normal operating mode, the laser light engine 624 outputs an illuminating signal. In a second mode, e.g. an identification mode, the laser light engine 624 outputs RGBG and NIR light. In various instances, the laser light engine 624 can operate in a polarizing mode.

Light output 626 from the laser light engine 624 illuminates targeted anatomy in an intraoperative surgical site 627. The laser pulsing control circuit 622 also controls a laser pulse controller 628 for a laser pattern projector 630 that projects a laser light pattern 631, such as a grid or pattern of lines and/or dots, at a predetermined wavelength ($\lambda_2$) on the operative tissue or organ at the surgical site 627. The camera 612 receives the patterned light as well as the reflected light output through the camera optics 632. The image sensor 634 converts the received light into a digital signal.

The color RGB fusion circuit 616 also outputs signals to the image overlay controller 610 and a video input module 636 for reading the laser light pattern 631 projected onto the targeted anatomy at the surgical site 627 by the laser pattern projector 630. A processing module 638 processes the laser light pattern 631 and outputs a first video output signal 640 representative of the distance to the visible tissue at the surgical site 627. The data is provided to the image overlay controller 610. The processing module 638 also outputs a second video signal 642 representative of a three-dimensional rendered shape of the tissue or organ of the targeted anatomy at the surgical site.

The first and second video output signals 640, 642 include data representative of the position of the critical structure on a three-dimensional surface model, which is provided to an integration module 643. In combination with data from the video out processor 608 of the spectral control circuit 602, the integration module 643 can determine the distance $d_A$ (FIG. 1) to a buried critical structure (e.g. via triangularization algorithms 644), and the distance $d_A$ can be provided to the image overlay controller 610 via a video out processor 646. The foregoing conversion logic can encompass the conversion logic circuit 648 intermediate video monitors 652 and the camera 624/laser pattern projector 630 positioned at the surgical site 627.

Preoperative data 650 from a CT or MRI scan can be employed to register or align certain three-dimensional deformable tissue in various instances. Such preoperative data 650 can be provided to the integration module 643 and ultimately to the image overlay controller 610 so that such information can be overlaid with the views from the camera 612 and provided to the video monitors 652. Registration of preoperative data is further described herein and in the aforementioned U.S. Patent Applications, including U.S. patent application Ser. No. 16/128,195, titled INTEGRATION OF IMAGING DATA, filed Sep. 11, 2018, now U.S. Patent Application Publication No. 2020/0015907, for example, which are incorporated by reference herein in their respective entireties.

The video monitors 652 can output the integrated/augmented views from the image overlay controller 610. A clinician can select and/or toggle between different views on one or more monitors. On a first monitor 652a, the clinician can toggle between (A) a view in which a three-dimensional rendering of the visible tissue is depicted and (B) an augmented view in which one or more hidden critical structures are depicted over the three-dimensional rendering of the visible tissue. On a second monitor 652b, the clinician can toggle on distance measurements to one or more hidden critical structures and/or the surface of visible tissue, for example.

The control system 600 and/or various control circuits thereof can be incorporated into various surgical visualization systems disclosed herein.

Figure 12:
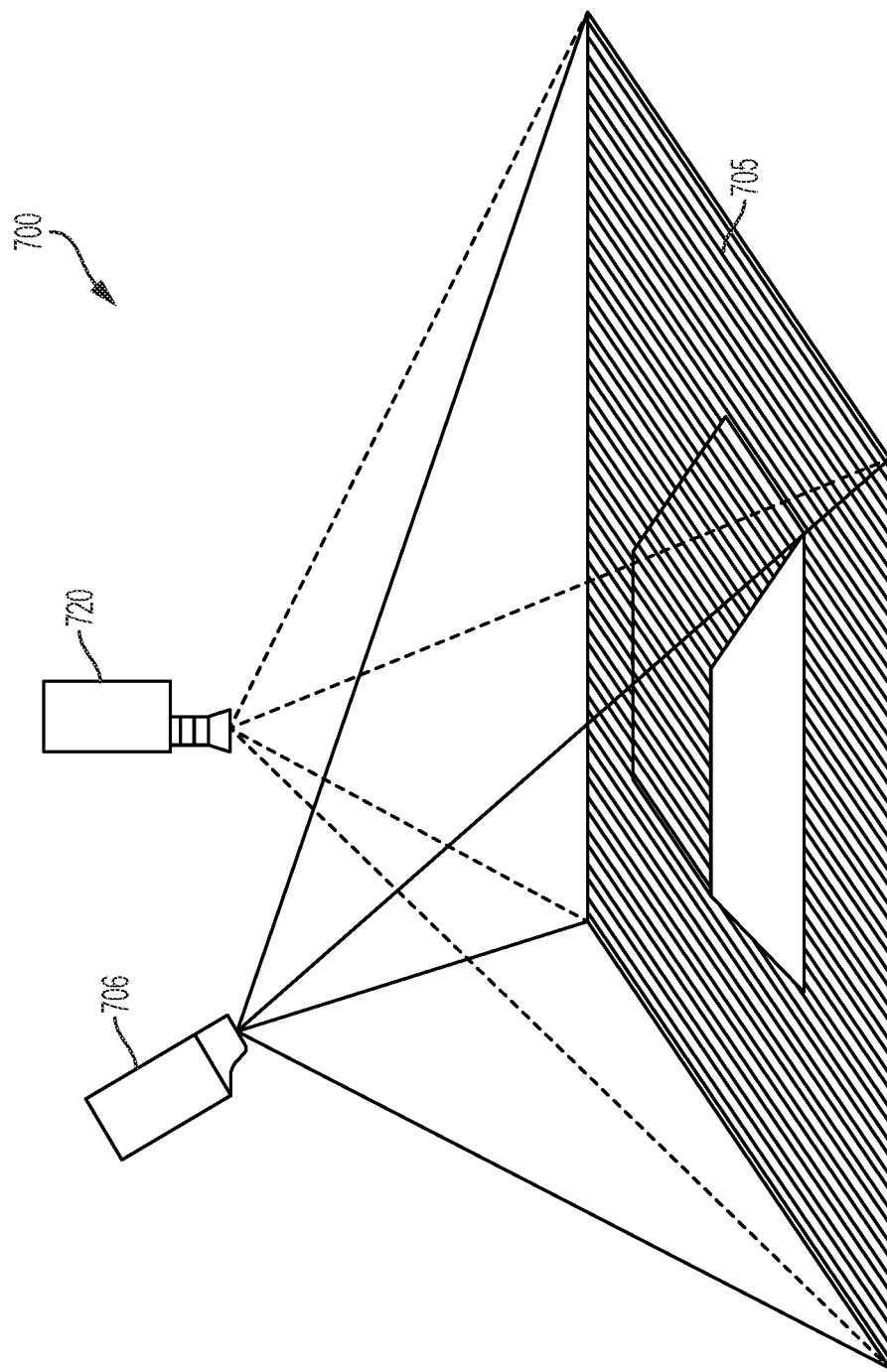
FIG. 12 is a schematic of a structured light source for a surgical visualization system, according to at least one aspect of the present disclosure.

FIG. 12 illustrates a structured (or patterned) light system 700, according to at least one aspect of the present disclosure. As described herein, structured light in the form of stripes or lines, for example, can be projected from a light source and/or projector 706 onto the surface 705 of targeted anatomy to identify the shape and contours of the surface 705. A camera 720, which can be similar in various respects to the imaging device 120 (FIG. 1), for example, can be configured to detect the projected pattern of light on the surface 705. The way that the projected pattern deforms upon striking the surface 705 allows vision systems to calculate the depth and surface information of the targeted anatomy.

In certain instances, invisible (or imperceptible) structured light can be utilized, in which the structured light is used without interfering with other computer vision tasks for which the projected pattern may be confusing. For example, infrared light or extremely fast frame rates of visible light that alternate between two exact opposite patterns can be utilized to prevent interference. Structured light is further described at en.wikipedia.org/wiki/Structured_light.

Figure 13A:
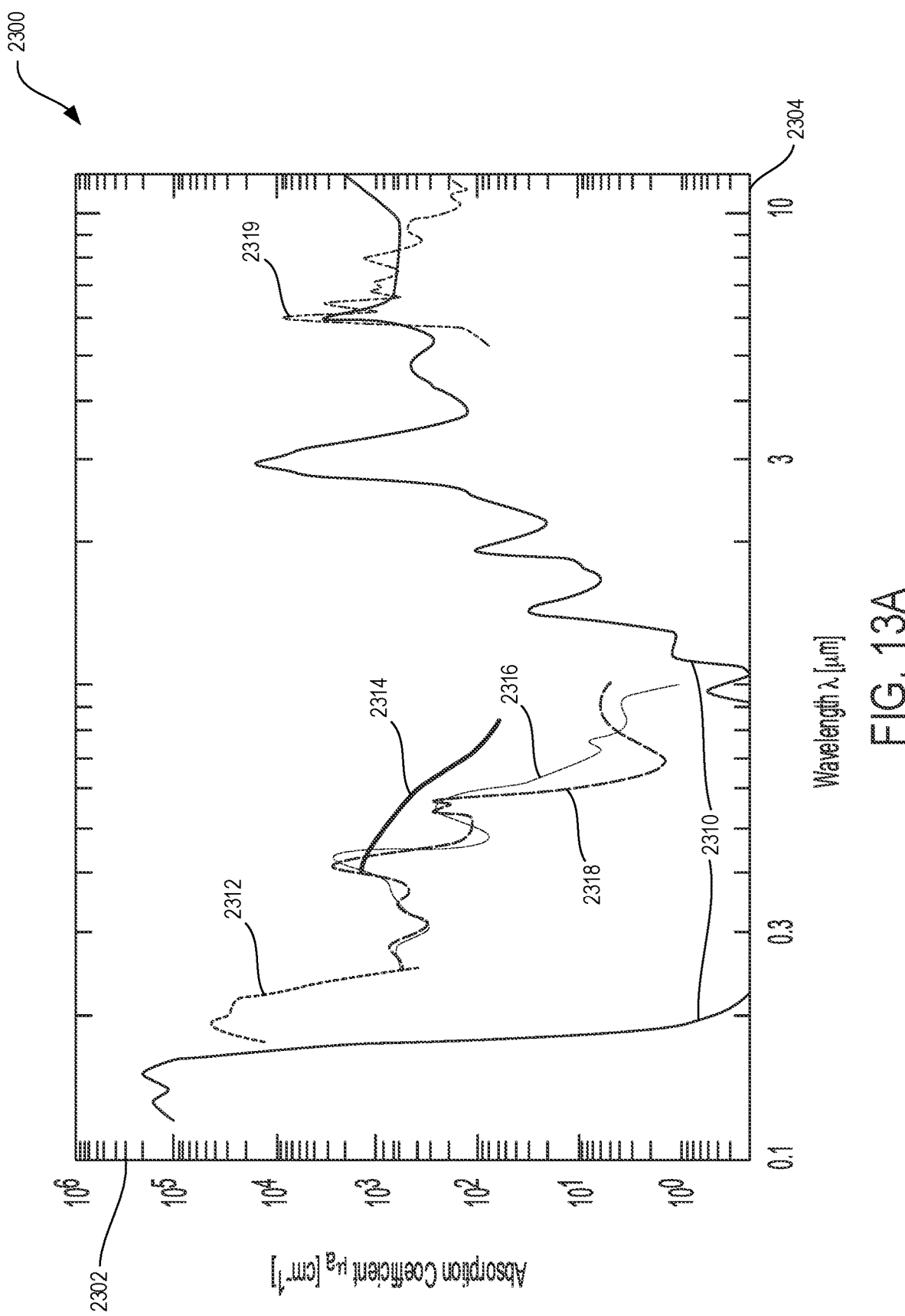
FIG. 13A is a graph of absorption coefficient verse wavelength for various biological materials, according to at least one aspect of the present disclosure.

As noted above, the various surgical visualization systems described herein can be utilized to visualize various different types of tissues and/or anatomical structures, including tissues and/or anatomical structures that may be obscured from being visualized by EMR in the visible portion of the spectrum. In one aspect, the surgical visualization systems can utilize a spectral imaging system to visualize different types of tissues based upon their varying combinations of constituent materials. In particular, a spectral imaging system can be configured to detect the presence of various constituent materials within a tissue being visualized based on the absorption coefficient of the tissue across various EMR wavelengths. The spectral imaging system can be further configured to characterize the tissue type of the tissue being visualized based upon the particular combination of constituent materials. To illustrate, FIG. 13A is a graph 2300 depicting how the absorption coefficient of various biological materials varies across the EMR wavelength spectrum. In the graph 2300, the vertical axis 2303 represents absorption coefficient of the biological material (e.g., in $cm^{-1}$) and the horizontal axis 2304 represents EMR wavelength (e.g., in μm). The graph 2300 further illustrates a first line 2310 representing the absorption coefficient of water at various EMR wavelengths, a second line 2312 representing the absorption coefficient of protein at various EMR wavelengths, a third line 2314 representing the absorption coefficient of melanin at various EMR wavelengths, a fourth line 2316 representing the absorption coefficient of deoxygenated hemoglobin at various EMR wavelengths, a fifth line 2318 representing the absorption coefficient of oxygenated hemoglobin at various EMR wavelengths, and a sixth line 2319 representing the absorption coefficient of collagen at various EMR wavelengths. Different tissue types have different combinations of constituent materials and, therefore, the tissue type(s) being visualized by a surgical visualization system can be identified and differentiated between according to the particular combination of detected constituent materials. Accordingly, a spectral imaging system can be configured to emit EMR at a number of different wavelengths, determine the constituent materials of the tissue based on the detected absorption EMR absorption response at the different wavelengths, and then characterize the tissue type based on the particular detected combination of constituent materials.

Figure 13B:
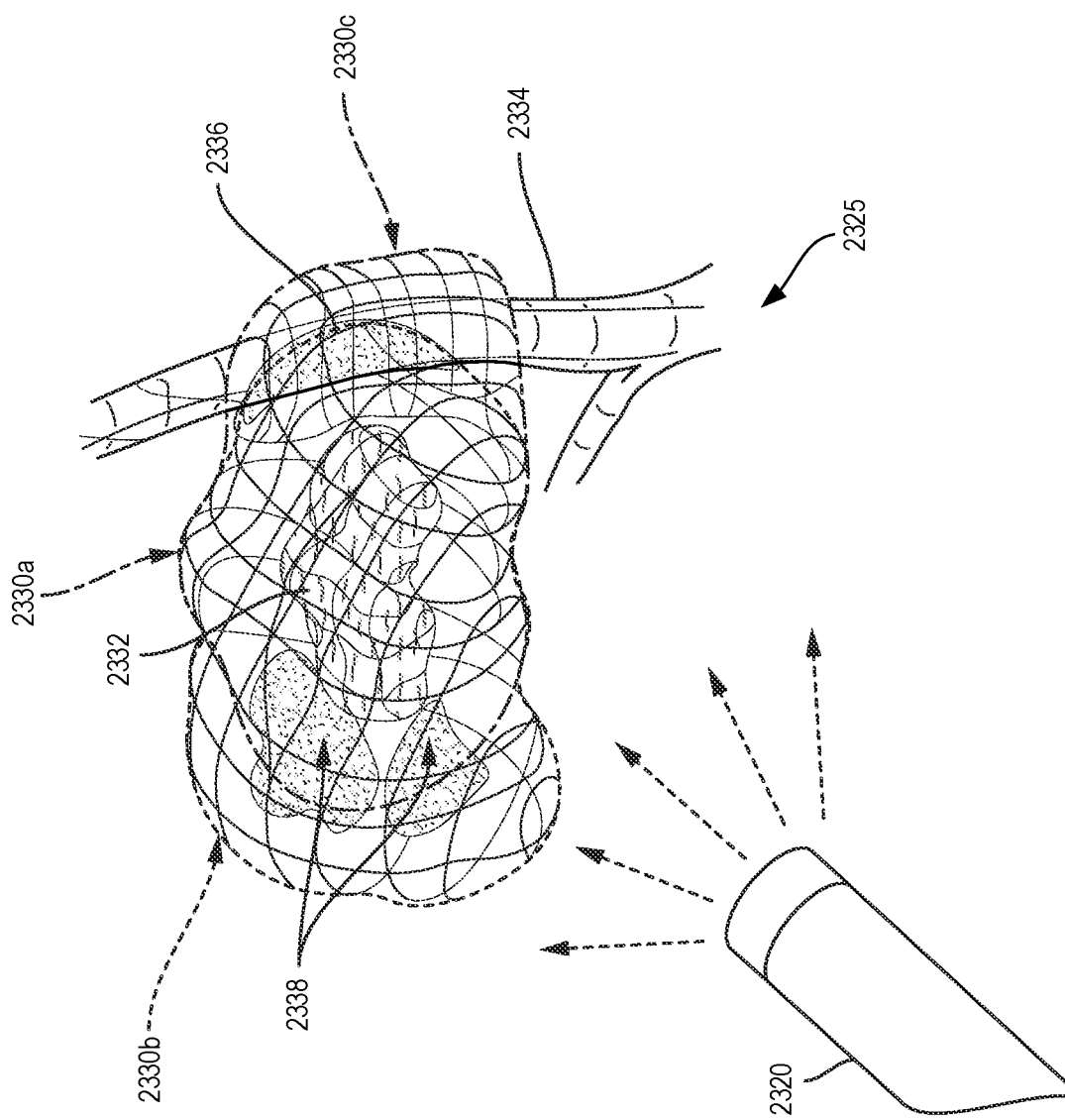
FIG. 13B is a schematic of the visualization of anatomical structures via a spectral surgical visualization system, according to at least one aspect of the present disclosure.

An illustration of the utilization of spectral imaging techniques to visualize different tissue types and/or anatomical structures is shown in FIG. 13B. In FIG. 13B, a spectral emitter 2320 (e.g., spectral light source 150) is being utilized by an imaging system to visualize a surgical site 2325. The EMR emitted by the spectral emitter 2320 and reflected from the tissues and/or structures at the surgical site 2325 can be received by an image sensor 135 (FIG. 2) to visualize the tissues and/or structures, which can be either visible (e.g., be located at the surface of the surgical site 2325) or obscured (e.g., underlay other tissue and/or structures at the surgical site 2325). In this example, an imaging system 142 (FIG. 2)

can visualize a tumor 2332, an artery 2334, and various abnormalities 2338 (i.e., tissues not confirming to known or expected spectral signatures) based upon the spectral signatures characterized by the differing absorptive characteristics (e.g., absorption coefficient) of the constituent materials for each of the different tissue/structure types. The visualized tissues and structures can be displayed on a display screen associated with or coupled to the imaging system 142, such as an imaging system display 146 (FIG. 2), a primary display 2119 (FIG. 18), a non-sterile display 2109 (FIG. 18), a hub display 2215 (FIG. 19), a device/instrument display 2237 (FIG. 19), and so on.

Further, the imaging system 142 can be configured to tailor or update the displayed surgical site visualization according to the identified tissue and/or structure types. For example, the imaging system 142 can display a margin 2330a associated with the tumor 2332 being visualized on a display screen (e.g., display 146). The margin 2330a can indicate the area or amount of tissue that should be excised to ensure complete removal of the tumor 2332. The control system 133 (FIG. 2) can be configured to control or update the dimensions of the margin 2330a based on the tissues and/or structures identified by the imaging system 142. In the illustrated example, the imaging system 142 has identified multiple abnormalities 2338 within the FOV. Accordingly, the control system 133 can adjust the displayed margin 2330a to a first updated margin 2330b having sufficient dimensions to encompass the abnormalities 2338. Further, the imaging system 142 has also identified an artery 2334 partially overlapping with the initially displayed margin 2330a (as indicated by the highlighted region 2336 of the artery 2334). Accordingly, the control system 133 can adjust the displayed margin 2330a to a second updated margin 2330c having sufficient dimensions to encompass the relevant portion of the artery 2334.

Tissues and/or structures can also be imaged or characterized according to their reflective characteristics, in addition to or in lieu of their absorptive characteristics described above with respect to FIGS. 13A and 13B, across the EMR wavelength spectrum. For example, FIGS. 13C-13E illustrate various graphs of reflectance of different types of tissues or structures across different EMR wavelengths. FIG. 13C is a graphical representation 1050 of an illustrative ureter signature versus obscurants. FIG. 13D is a graphical representation 1052 of an illustrative artery signature versus obscurants. FIG. 13E is a graphical representation 1054 of an illustrative nerve signature versus obscurants. The plots in FIGS. 13C-13E represent reflectance as a function of wavelength (nm) for the particular structures (ureter, artery, and nerve) relative to the corresponding reflectances of fat, lung tissue, and blood at the corresponding wavelengths. These graphs are simply for illustrative purposes and it should be understood that other tissues and/or structures could have corresponding detectable reflectance signatures that would allow the tissues and/or structures to be identified and visualized.

In various instances, select wavelengths for spectral imaging can be identified and utilized based on the anticipated critical structures and/or obscurants at a surgical site (i.e., "selective spectral" imaging). By utilizing selective spectral imaging, the amount of time required to obtain the spectral image can be minimized such that the information can be obtained in real-time, or near real-time, and utilized intraoperatively. In various instances, the wavelengths can be selected by a clinician or by a control circuit based on input by the clinician. In certain instances, the wavelengths can be selected based on machine learning and/or big data accessible to the control circuit via a cloud, for example.

The foregoing application of spectral imaging to tissue can be utilized intraoperatively to measure the distance between a waveform emitter and a critical structure that is obscured by tissue. In one aspect of the present disclosure, referring now to FIGS. 14 and 15, a time-of-flight sensor system 1104 utilizing waveforms 1124, 1125 is shown. The time-of-flight sensor system 1104 can be incorporated into the surgical visualization system 100 (FIG. 1) in certain instances. The time-of-flight sensor system 1104 includes a waveform emitter 1106 and a waveform receiver 1108 on the same surgical device 1102. The emitted wave 1124 extends to the critical structure 1101 from the emitter 1106 and the received wave 1125 is reflected back to by the receiver 1108 from the critical structure 1101. The surgical device 1102 is positioned through a trocar 1110 that extends into a cavity 1107 in a patient.

The waveforms 1124, 1125 are configured to penetrate obscuring tissue 1103. For example, the wavelengths of the waveforms 1124, 1125 can be in the NIR or SWIR spectrum of wavelengths. In one aspect, a spectral signal (e.g. hyperspectral, multispectral, or selective spectral) or a photoacoustic signal can be emitted from the emitter 1106 and can penetrate the tissue 1103 in which the critical structure 1101 is concealed. The emitted waveform 1124 can be reflected by the critical structure 1101. The received waveform 1125 can be delayed due to the distance d between the distal end of the surgical device 1102 and the critical structure 1101. In various instances, the waveforms 1124, 1125 can be selected to target the critical structure 1101 within the tissue 1103 based on the spectral signature of the critical structure 1101, as further described herein. In various instances, the emitter 1106 is configured to provide a binary signal on and off, as shown in FIG. 15, for example, which can be measured by the receiver 1108.

Based on the delay between the emitted wave 1124 and the received wave 1125, the time-of-flight sensor system 1104 is configured to determine the distance d (FIG. 14). A time-of-flight timing diagram 1130 for the emitter 1106 and the receiver 1108 of FIG. 14 is shown in FIG. 15. The delay is a function of the distance d and the distance d is given by:

$$d = \frac{ct}{2} \cdot \frac{q_2}{q_1 + q_2}$$

where:
c=the speed of light;
t=length of pulse;
$q_1$=accumulated charge while light is emitted; and
$q_2$=accumulated charge while light is not being emitted.

As provided herein, the time-of-flight of the waveforms 1124, 1125 corresponds to the distance d in FIG. 14. In various instances, additional emitters/receivers and/or pulsing signals from the emitter 1106 can be configured to emit a non-penetrating signal. The non-penetrating tissue can be configured to determine the distance from the emitter to the surface 1105 of the obscuring tissue 1103. In various instances, the depth of the critical structure 1101 can be determined by:

$$d_A = d_w - d_t$$

where:
$d_A$=the depth of the critical structure 1101;
$d_w$=the distance from the emitter 1106 to the critical structure 1101 (d in FIG. 14); and $d_t$=the distance from the emitter 1106 (on the distal end of the surgical device 1102) to the surface 1105 of the obscuring tissue 1103.

In one aspect of the present disclosure, referring now to FIG. 16, a time-of-flight sensor system 1204 utilizing waves 1224a, 1224b, 1224c, 1225a, 1225b, 1225c is shown. The time-of-flight sensor system 1204 can be incorporated into the surgical visualization system 100 (FIG. 1) in certain instances. The time-of-flight sensor system 1204 includes a waveform emitter 1206 and a waveform receiver 1208. The waveform emitter 1206 is positioned on a first surgical device 1202a, and the waveform receiver 1208 is positioned on a second surgical device 1202b. The surgical devices 1202a, 1202b are positioned through their respective trocars 1210a, 1210b, respectively, which extend into a cavity 1207 in a patient. The emitted waves 1224a, 1224b, 1224c extend toward a surgical site from the emitter 1206 and the received waves 1225a, 1225b, 1225c are reflected back to the –receiver 1208 from various structures and/or surfaces at the surgical site.

The different emitted waves 1224a, 1224b, 1224c are configured to target different types of material at the surgical site. For example, the wave 1224a targets the obscuring tissue 1203, the wave 1224b targets a first critical structure 1201a (e.g. a vessel), and the wave 1224c targets a second critical structure 1201b (e.g. a cancerous tumor). The wavelengths of the waves 1224a, 1224b, 1224c can be in the visible light, NIR, or SWIR spectrum of wavelengths. For example, visible light can be reflected off a surface 1205 of the tissue 1203 and NIR and/or SWIR waveforms can be configured to penetrate the surface 1205 of the tissue 1203. In various aspects, as described herein, a spectral signal (e.g. hyperspectral, multispectral, or selective spectral) or a photoacoustic signal can be emitted from the emitter 1206. In various instances, the waves 1224b, 1224c can be selected to target the critical structures 1201a, 1201b within the tissue 1203 based on the spectral signature of the critical structure 1201a, 1201b, as further described herein. Photoacoustic imaging is further described in various U.S. Patent Applications, which are incorporated by reference herein in the present disclosure.

The emitted waves 1224a, 1224b, 1224c can be reflected off the targeted material (i.e. the surface 1205, the first critical structure 1201a, and the second structure 1201b, respectively). The received waveforms 1225a, 1225b, 1225c can be delayed due to the distances $d_{1a}, d_{2a}, d_{3a}, d_{1b}, d_{2b}, d_{2c}$ indicated in FIG. 16.

In the time-of-flight sensor system 1204, in which the emitter 1206 and the receiver 1208 are independently positionable (e.g., on separate surgical devices 1202a, 1202b and/or controlled by separate robotic arms), the various distances $d_{1a}, d_{2a}, d_{3a}, d_{1b}, d_{2b}, d_{2c}$ can be calculated from the known position of the emitter 1206 and the receiver 1208. For example, the positions can be known when the surgical devices 1202a, 1202b are robotically-controlled. Knowledge of the positions of the emitter 1206 and the receiver 1208, as well as the time of the photon stream to target a certain tissue and the information received by the receiver 1208 of that particular response can allow a determination of the distances $d_{1a}, d_{2a}, d_{3a}, d_{1b}, d_{2b}, d_{2c}$. In one aspect, the distance to the obscured critical structures 1201a, 1201b can be triangulated using penetrating wavelengths. Because the speed of light is constant for any wavelength of visible or invisible light, the time-of-flight sensor system 1204 can determine the various distances.

Referring still to FIG. 16, in various instances, in the view provided to the clinician, the receiver 1208 can be rotated such that the center of mass of the target structure in the resulting images remains constant, i.e., in a plane perpendicular to the axis of a select target structures 1203, 1201a, or 1201b. Such an orientation can quickly communicate one or more relevant distances and/or perspectives with respect to the critical structure. For example, as shown in FIG. 16, the surgical site is displayed from a viewpoint in which the critical structure 1201a is perpendicular to the viewing plane (i.e. the vessel is oriented in/out of the page). In various instances, such an orientation can be default setting; however, the view can be rotated or otherwise adjusted by a clinician. In certain instances, the clinician can toggle between different surfaces and/or target structures that define the viewpoint of the surgical site provided by the imaging system.

In various instances, the receiver 1208 can be mounted on a trocar or cannula, such as the trocar 1210b, for example, through which the surgical device 1202b is positioned. In other instances, the receiver 1208 can be mounted on a separate robotic arm for which the three-dimensional position is known. In various instances, the receiver 1208 can be mounted on a movable arm that is separate from the robot that controls the surgical device 1202a or can be mounted to an operating room (OR) table that is intraoperatively registerable to the robot coordinate plane. In such instances, the position of the emitter 1206 and the receiver 1208 can be registerable to the same coordinate plane such that the distances can be triangulated from outputs from the time-of-flight sensor system 1204.

Combining time-of-flight sensor systems and near-infrared spectroscopy (NIRS), termed TOF-NIRS, which is capable of measuring the time-resolved profiles of NIR light with nanosecond resolution can be found in the article titled TIME-OF-FLIGHT NEAR-INFRARED SPECTROSCOPY FOR NONDESTRUCTIVE MEASUREMENT OF INTERNAL QUALITY IN GRAPEFRUIT, in the Journal of the American Society for Horticultural Science, May 2013, Vol. 138, No. 3, 225-228, which is incorporated by reference herein in its entirety, and is accessible at journal.ashspublications.org/content/138/3/225.full.

In various instances, time-of-flight spectral waveforms are configured to determine the depth of the critical structure and/or the proximity of a surgical device to the critical structure. Moreover, the various surgical visualization systems disclosed herein include surface mapping logic that is configured to create three-dimensional rendering of the surface of the visible tissue. In such instances, even when the visible tissue obstructs a critical structure, the clinician can be aware of the proximity (or lack thereof) of a surgical device to the critical structure. In one instances, the topography of the surgical site is provided on a monitor by the surface mapping logic. If the critical structure is close to the surface of the tissue, spectral imaging can convey the position of the critical structure to the clinician. For example, spectral imaging may detect structures within 5 or 10 mm of the surface. In other instances, spectral imaging may detect structures 10 or 20 mm below the surface of the tissue. Based on the known limits of the spectral imaging system, the system is configured to convey that a critical structure is out-of-range if it is simply not detected by the spectral imaging system. Therefore, the clinician can continue to move the surgical device and/or manipulate the tissue. When the critical structure moves into range of the spectral imaging system, the system can identify the structure and, thus, communicate that the structure is within range. In such instances, an alert can be provided when a structure is initially identified and/or moved further within a predefined proximity zone. In such instances, even non-identification of a critical structure by a spectral imaging system with known bounds/ranges can provide proximity information (i.e. the lack of proximity) to the clinician.

Various surgical visualization systems disclosed herein can be configured to identify intraoperatively the presence of and/or proximity to critical structure(s) and to alert a clinician prior to damaging the critical structure(s) by inadvertent dissection and/or transection. In various aspects, the surgical visualization systems are configured to identify one or more of the following critical structures: ureters, bowel, rectum, nerves (including the phrenic nerve, recurrent laryngeal nerve [RLN], promontory facial nerve, vagus nerve, and branches thereof), vessels (including the pulmonary and lobar arteries and veins, inferior mesenteric artery [IMA] and branches thereof, superior rectal artery, sigmoidal arteries, and left colic artery), superior mesenteric artery (SMA) and branches thereof (including middle colic artery, right colic artery, ilecolic artery), hepatic artery and branches thereof, portal vein and branches thereof, splenic artery/vein and branches thereof, external and internal (hypogastric) ileac vessels, short gastric arteries, uterine arteries, middle sacral vessels, and lymph nodes, for example. Moreover, the surgical visualization systems are configured to indicate proximity of surgical device(s) to the critical structure(s) and/or warn the clinician when surgical device(s) are getting close to the critical structure(s).

Various aspects of the present disclosure provide intraoperative critical structure identification (e.g., identification of ureters, nerves, and/or vessels) and instrument proximity monitoring. For example, various surgical visualization systems disclosed herein can include spectral imaging and surgical instrument tracking, which enable the visualization of critical structures below the surface of the tissue, such as 1.0-1.5 cm below the surface of the tissue, for example. In other instances, the surgical visualization system can identify structures less than 1.0 cm or more the 1.5 cm below the surface of the tissue. For example, even a surgical visualization system that can identify structures only within 0.2 mm of the surface, for example, can be valuable if the structure cannot otherwise be seen due to the depth. In various aspects, the surgical visualization system can augment the clinician's view with a virtual depiction of the critical structure as a visible white-light image overlay on the surface of visible tissue, for example. The surgical visualization system can provide real-time, three-dimensional spatial tracking of the distal tip of surgical instruments and can provide a proximity alert when the distal tip of a surgical instrument moves within a certain range of the critical structure, such as within 1.0 cm of the critical structure, for example.

Various surgical visualization systems disclosed herein can identify when dissection is too close to a critical structure. Dissection may be "too close" to a critical structure based on the temperature (i.e. too hot within a proximity of the critical structure that may risk damaging/heating/melting the critical structure) and/or based on tension (i.e. too much tension within a proximity of the critical structure that may risk damaging/tearing/pulling the critical structure). Such a surgical visualization system can facilitate dissection around vessels when skeletonizing the vessels prior to ligation, for example. In various instances, a thermal imaging camera can be utilized to read the heat at the surgical site and provide a warning to the clinician that is based on the detected heat and the distance from a tool to the structure. For example, if the temperature of the tool is over a predefined threshold (such as 120 degrees F., for example), an alert can be provided to the clinician at a first distance (such as 10 mm, for example), and if the temperature of the tool is less than or equal to the predefined threshold, the alert can be provided to the clinician at a second distance (such as 5 mm, for example). The predefined thresholds and/or warning distances can be default settings and/or programmable by the clinician. Additionally or alternatively, a proximity alert can be linked to thermal measurements made by the tool itself, such as a thermocouple that measures the heat in a distal jaw of a monopolar or bipolar dissector or vessel sealer, for example.

Various surgical visualization systems disclosed herein can provide adequate sensitivity with respect to a critical structure and specificity to enable a clinician to proceed with confidence in a quick but safe dissection based on the standard of care and/or device safety data. The system can function intraoperatively and in real-time during a surgical procedure with minimal ionizing radiation risk to a patient or a clinician and, in various instances, no risk of ionizing radiation risk to the patient or the clinician. Conversely, in a fluoroscopy procedure, the patient and clinician(s) may be exposed to ionizing radiation via an X-ray beam, for example, that is utilized to view the anatomical structures in real-time.

Various surgical visualization systems disclosed herein can be configured to detect and identify one or more desired types of critical structures in a forward path of a surgical device, such as when the path of the surgical device is robotically controlled, for example. Additionally or alternatively, the surgical visualization system can be configured to detect and identify one or more types of critical structures in a surrounding area of the surgical device and/or in multiple planes/dimensions, for example.

Various surgical visualization systems disclosed herein can be easy to operate and/or interpret. Moreover, various surgical visualization systems can incorporate an "override" feature that allows the clinician to override a default setting and/or operation. For example, a clinician can selectively turn off alerts from the surgical visualization system and/or get closer to a critical structure than suggested by the surgical visualization system such as when the risk to the critical structure is less than risk of avoiding the area (e.g. when removing cancer around a critical structure the risk of leaving the cancerous tissue can be greater than the risk of damage to the critical structure).

Various surgical visualization systems disclosed herein can be incorporated into a surgical system and/or used during a surgical procedure with limited impact to the workflow. In other words, implementation of the surgical visualization system may not change the way the surgical procedure is implemented. Moreover, the surgical visualization system can be economical in comparison to the costs of an inadvertent transection. Data indicates the reduction in inadvertent damage to a critical structure can drive incremental reimbursement.

Various surgical visualization systems disclosed herein can operate in real-time, or near real-time, and far enough in advance to enable a clinician to anticipate critical structure(s). For example, a surgical visualization system can provide enough time to "slow down, evaluate, and avoid" in order to maximize efficiency of the surgical procedure.

Various surgical visualization systems disclosed herein may not require a contrast agent, or dye, that is injected into tissue. For example, spectral imaging is configured to visualize hidden structures intraoperatively without the use of a contrast agent or dye. In other instances, the contrast agent can be easier to inject into the proper layer(s) of tissue than other visualization systems. The time between injection of the contrast agent and visualization of the critical structure can be less than two hours, for example.

Various surgical visualization systems disclosed herein can be linked with clinical data and/or device data. For example, data can provide boundaries for how close energy-enabled surgical devices (or other potentially damaging devices) should be from tissue that the surgeon does not want to damage. Any data modules that interface with the surgical visualization systems disclosed herein can be provided integrally or separately from a robot to enable use with stand-alone surgical devices in open or laparoscopic procedures, for example. The surgical visualization systems can be compatible with robotic surgical systems in various instances. For example, the visualization images/information can be displayed in a robotic console.

In various instances, clinicians may not know the location of a critical structure with respect to a surgical tool. For example, when a critical structure is embedded in tissue, the clinician may be unable to ascertain the location of the critical structure. In certain instances, a clinician may want to keep a surgical device outside a range of positions surrounding the critical structure and/or away from the visible tissue covering the hidden critical structure. When the location of a concealed critical structure is unknown, the clinician may risk moving too close to the critical structure, which can result in inadvertent trauma and/or dissection of the critical structure and/or too much energy, heat, and/or tension in proximity of the critical structure. Alternatively, the clinician may stay too far away from a suspected location of the critical structure and risk affecting tissue at a less desirable location in an effort to avoid the critical structure.

A surgical visualization system is provided that presents surgical device tracking with respect to one or more critical structures. For example, the surgical visualization system can track the proximity of a surgical device with respect to a critical structure. Such tracking can occur intraoperatively, in real-time, and/or in near real-time. In various instances, the tracking data can be provided to the clinicians via a display screen (e.g. a monitor) of an imaging system.

In one aspect of the present disclosure, a surgical visualization system includes a surgical device comprising an emitter configured to emit a structured light pattern onto a visible surface, an imaging system comprising a camera configured to detect an embedded structure and the structured light pattern on the visible surface, and a control circuit in signal communication with the camera and the imaging system, wherein the control circuit is configured to determine a distance from the surgical device to the embedded structure and provide a signal to the imaging system indicative of the distance. For example, the distance can be determined by computing a distance from the camera to the critical structure that is illuminated with fluoroscopy technology and based on a three-dimensional view of the illuminated structure provided by images from multiple lenses (e.g. a left-side lens and a right-side lens) of the camera. The distance from the surgical device to the critical structure can be triangulated based on the known positions of the surgical device and the camera, for example. Alternative means for determining the distance to an embedded critical structure are further described herein. For example, NIR time-of-flight distance sensors can be employed. Additionally or alternatively, the surgical visualization system can determine a distance to visible tissue overlying/covering an embedded critical structure. For example, the surgical visualization system can identify a hidden critical structure and augment a view of the hidden critical structure by depicting a schematic of the hidden critical structure on the visible structure, such as a line on the surface of the visible tissue. The surgical visualization system can further determine the distance to the augmented line on the visible tissue.

By providing the clinician with up-to-date information regarding the proximity of the surgical device to the concealed critical structure and/or visible structure, as provided by the various surgical visualization systems disclosed herein, the clinician can make more informed decisions regarding the placement of the surgical device relative to the concealed critical structure. For example, the clinician can view the distance between the surgical device and the critical structure in real-time/intraoperatively and, in certain instances, an alert and/or warning can be provided by the imaging system when the surgical device is moved within a predefined proximity and/or zone of the critical structure. In certain instances, the alert and/or warning can be provided when the trajectory of the surgical device indicates a likely collision with a "no-fly" zone in the proximity of the critical structure (e.g. within 1 mm, 2 mm, 5 mm, 10 mm, 20 mm or more of the critical structure). In such instances, the clinician can maintain momentum throughout the surgical procedure without requiring the clinician to monitor a suspected location of the critical structure and the surgical device's proximity thereto. As a result, certain surgical procedures can be performed more quickly, with fewer pauses/interruptions, and/or with improved accuracy and/or certainty, for example. In one aspect, the surgical visualization system can be utilized to detect tissue variability, such as the variability of tissue within an organ to differentiate tumors/cancerous tissue/unhealthy tissue from healthy tissue. Such a surgical visualization system can maximize the removal of the unhealthy tissue while minimizing the removal of the healthy tissue.

Surgical Hub System

The various visualization or imaging systems described herein can be incorporated into a surgical hub system, such as is illustrated in connection with FIGS. 17-19 and described in further detail below.

Referring to FIG. 17, a computer-implemented interactive surgical system 2100 includes one or more surgical systems 2102 and a cloud-based system (e.g., the cloud 2104 that may include a remote server 2113 coupled to a storage device 2105). Each surgical system 2102 includes at least one surgical hub 2106 in communication with the cloud 2104 that may include a remote server 2113. In one example, as illustrated in FIG. 17, the surgical system 2102 includes a visualization system 2108, a robotic system 2110, and a handheld intelligent surgical instrument 2112, which are configured to communicate with one another and/or the hub 2106. In some aspects, a surgical system 2102 may include an M number of hubs 2106, an N number of visualization systems 2108, an O number of robotic systems 2110, and a P number of handheld intelligent surgical instruments 2112, where M, N, O, and P are integers greater than or equal to one.

FIG. 18 depicts an example of a surgical system 2102 being used to perform a surgical procedure on a patient who is lying down on an operating table 2114 in a surgical operating room 2116. A robotic system 2110 is used in the surgical procedure as a part of the surgical system 2102. The robotic system 2110 includes a surgeon's console 2118, a patient side cart 2120 (surgical robot), and a surgical robotic hub 2122. The patient side cart 2120 can manipulate at least one removably coupled surgical tool 2117 through a minimally invasive incision in the body of the patient while the surgeon views the surgical site through the surgeon's console 2118. An image of the surgical site can be obtained by a medical imaging device 2124, which can be manipulated by the patient side cart 2120 to orient the imaging device 2124. The robotic hub 2122 can be used to process the images of the surgical site for subsequent display to the surgeon through the surgeon's console 2118.

Other types of robotic systems can be readily adapted for use with the surgical system 2102. Various examples of robotic systems and surgical tools that are suitable for use with the present disclosure are described in various U.S. Patent Applications, which are incorporated by reference herein in the present disclosure.

Various examples of cloud-based analytics that are performed by the cloud 2104, and are suitable for use with the present disclosure, are described in various U.S. Patent Applications, which are incorporated by reference herein in the present disclosure.

In various aspects, the imaging device 2124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 2124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 2124 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in various U.S. Patent Applications that are incorporated by reference herein in the present disclosure. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 2124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area. In various aspects, the visualization system 2108 includes one or more imaging sensors, one or more image-processing units, one or more storage arrays, and one or more displays that are strategically arranged with respect to the sterile field, as illustrated in FIG. 18. In one aspect, the visualization system 2108 includes an interface for HL7, PACS, and EMR. Various components of the visualization system 2108 are described in various U.S. Patent Applications that are incorporated by reference herein in the present disclosure.

As illustrated in FIG. 18, a primary display 2119 is positioned in the sterile field to be visible to an operator at the operating table 2114. In addition, a visualization tower 21121 is positioned outside the sterile field. The visualization tower 21121 includes a first non-sterile display 2107 and a second non-sterile display 2109, which face away from each other. The visualization system 2108, guided by the hub 2106, is configured to utilize the displays 2107, 2109, and 2119 to coordinate information flow to operators inside and outside the sterile field. For example, the hub 2106 may cause the visualization system 2108 to display a snapshot of a surgical site, as recorded by an imaging device 2124, on a non-sterile display 2107 or 2109, while maintaining a live feed of the surgical site on the primary display 2119. The snapshot on the non-sterile display 2107 or 2109 can permit a non-sterile operator to perform a diagnostic step relevant to the surgical procedure, for example.

In one aspect, the hub 2106 is also configured to route a diagnostic input or feedback entered by a non-sterile operator at the visualization tower 21121 to the primary display 2119 within the sterile field, where it can be viewed by a sterile operator at the operating table. In one example, the input can be in the form of a modification to the snapshot displayed on the non-sterile display 2107 or 2109, which can be routed to the primary display 2119 by the hub 2106.

Referring to FIG. 18, a surgical instrument 2112 is being used in the surgical procedure as part of the surgical system 2102. The hub 2106 is also configured to coordinate information flow to a display of the surgical instrument 2112, as is described in various U.S. Patent Applications that are incorporated by reference herein in the present disclosure. A diagnostic input or feedback entered by a non-sterile operator at the visualization tower 21121 can be routed by the hub 2106 to the surgical instrument display 2115 within the sterile field, where it can be viewed by the operator of the surgical instrument 2112. Example surgical instruments that are suitable for use with the surgical system 2102 are described in various U.S. Patent Applications that are incorporated by reference herein in the present disclosure.

FIG. 19 illustrates a computer-implemented interactive surgical system 2200. The computer-implemented interactive surgical system 2200 is similar in many respects to the computer-implemented interactive surgical system 2100. The surgical system 2200 includes at least one surgical hub 2236 in communication with a cloud 2204 that may include a remote server 2213. In one aspect, the computer-implemented interactive surgical system 2200 comprises a surgical hub 2236 connected to multiple operating theater devices such as, for example, intelligent surgical instruments, robots, and other computerized devices located in the operating theater. The surgical hub 2236 comprises a communications interface for communicably coupling the surgical hub 2236 to the cloud 2204 and/or remote server 2213. As illustrated in the example of FIG. 19, the surgical hub 2236 is coupled to an imaging module 2238 that is coupled to an endoscope 2239, a generator module 2240 that is coupled to an energy device 2421, a smoke evacuator module 2226, a suction/irrigation module 2228, a communication module 2230, a processor module 2232, a storage array 2234, a smart device/instrument 2235 optionally coupled to a display 2237, and a non-contact sensor module 2242. The operating theater devices are coupled to cloud computing resources and data storage via the surgical hub 2236. A robot hub 2222 also may be connected to the surgical hub 2236 and to the cloud computing resources. The devices/instruments 2235, visualization systems 2209, among others, may be coupled to the surgical hub 2236 via wired or wireless communication standards or protocols, as described herein. The surgical hub 2236 may be coupled to a hub display 2215 (e.g., monitor, screen) to display and overlay images received from the imaging module, device/instrument display, and/or other visualization systems 208. The hub display also may display data received from devices connected to the modular control tower in conjunction with images and overlaid images.

Situational Awareness

The various visualization systems or aspects of visualization systems described herein can be utilized as part of a situational awareness system that can be embodied or executed by a surgical hub 2106, 2236 (FIGS. 17-19). In particular, characterizing, identifying, and/or visualizing surgical instruments or other surgical devices (including their positions, orientations, and actions), tissues, structures, users, and other things located within the surgical field or the operating theater can provide contextual data that can be utilized by a situational awareness system to infer the type of surgical procedure or a step thereof being performed, the type of tissue(s) and/or structure(s) being manipulated by the surgeon, and so on. This contextual data can then be utilized by the situational awareness system to provide alerts to users, suggest subsequent steps or actions for the users to undertake, prepare surgical devices in anticipation for their use (e.g., activate an electrosurgical generator in anticipation of an electrosurgical instrument being utilized in a subsequent step of the surgical procedure), control surgical instruments intelligently (e.g., customize surgical instrument operational parameters based on each patient's particular health profile), and so on.

Although an "intelligent" device including control algorithms that respond to sensed data can be an improvement over a "dumb" device that operates without accounting for sensed data, some sensed data can be incomplete or inconclusive when considered in isolation, i.e., without the context of the type of surgical procedure being performed or the type of tissue that is being operated on. Without knowing the procedural context (e.g., knowing the type of tissue being operated on or the type of procedure being performed), the control algorithm may control modular device incorrectly or suboptimally given the particular context-free sensed data. Modular devices can include any surgical devices that is controllable by a situational awareness system, such as visualization system devices (e.g., a camera or display screen), surgical instruments (e.g., an ultrasonic surgical instrument, an electrosurgical instrument, or a surgical stapler), and other surgical devices (e.g., a smoke evacuator). For example, the optimal manner for a control algorithm to control a surgical instrument in response to a particular sensed parameter can vary according to the particular tissue type being operated on. This is due to the fact that different tissue types have different properties (e.g., resistance to tearing) and thus respond differently to actions taken by surgical instruments. Therefore, it may be desirable for a surgical instrument to take different actions even when the same measurement for a particular parameter is sensed. As one specific example, the optimal manner in which to control a surgical stapling and cutting instrument in response to the instrument sensing an unexpectedly high force to close its end effector will vary depending upon whether the tissue type is susceptible or resistant to tearing. For tissues that are susceptible to tearing, such as lung tissue, the instrument's control algorithm would optimally ramp down the motor in response to an unexpectedly high force to close to avoid tearing the tissue. For tissues that are resistant to tearing, such as stomach tissue, the instrument's control algorithm would optimally ramp up the motor in response to an unexpectedly high force to close to ensure that the end effector is clamped properly on the tissue. Without knowing whether lung or stomach tissue has been clamped, the control algorithm may make a suboptimal decision.

One solution utilizes a surgical hub including a system that is configured to derive information about the surgical procedure being performed based on data received from various data sources and then control the paired modular devices accordingly. In other words, the surgical hub is configured to infer information about the surgical procedure from received data and then control the modular devices paired to the surgical hub based upon the inferred context of the surgical procedure. FIG. 20 illustrates a diagram of a situationally aware surgical system 2400, in accordance with at least one aspect of the present disclosure. In some exemplifications, the data sources 2426 include, for example, the modular devices 2402 (which can include sensors configured to detect parameters associated with the patient and/or the modular device itself), databases 2422 (e.g., an EMR database containing patient records), and patient monitoring devices 2424 (e.g., a blood pressure (BP) monitor and an electrocardiography (EKG) monitor).

A surgical hub 2404, which may be similar to the hub 106 in many respects, can be configured to derive the contextual information pertaining to the surgical procedure from the data based upon, for example, the particular combination(s) of received data or the particular order in which the data is received from the data sources 2426. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 2404 to derive or infer information related to the surgical procedure from received data can be referred to as "situational awareness." In one exemplification, the surgical hub 2404 can incorporate a situational awareness system, which is the hardware and/or programming associated with the surgical hub 2404 that derives contextual information pertaining to the surgical procedure from the received data.

The situational awareness system of the surgical hub 2404 can be configured to derive the contextual information from the data received from the data sources 2426 in a variety of different ways. In one exemplification, the situational awareness system includes a pattern recognition system, or machine learning system (e.g., an artificial neural network), that has been trained on training data to correlate various inputs (e.g., data from databases 2422, patient monitoring devices 2424, and/or modular devices 2402) to corresponding contextual information regarding a surgical procedure. In other words, a machine learning system can be trained to accurately derive contextual information regarding a surgical procedure from the provided inputs. In another exemplification, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 2402. In one exemplification, the contextual information received by the situational awareness system of the surgical hub 2404 is associated with a particular control adjustment or set of control adjustments for one or more modular devices 2402. In another exemplification, the situational awareness system includes a further machine learning system, lookup table, or other such system, which generates or retrieves one or more control adjustments for one or more modular devices 2402 when provided the contextual information as input.

A surgical hub 2404 incorporating a situational awareness system provides a number of benefits for the surgical system 2400. One benefit includes improving the interpretation of sensed and collected data, which would in turn improve the processing accuracy and/or the usage of the data during the course of a surgical procedure. To return to a previous example, a situationally aware surgical hub 2404 could determine what type of tissue was being operated on; therefore, when an unexpectedly high force to close the surgical instrument's end effector is detected, the situationally aware surgical hub 2404 could correctly ramp up or ramp down the motor of the surgical instrument for the type of tissue.

As another example, the type of tissue being operated can affect the adjustments that are made to the compression rate and load thresholds of a surgical stapling and cutting instrument for a particular tissue gap measurement. A situationally aware surgical hub 2404 could infer whether a surgical procedure being performed is a thoracic or an abdominal procedure, allowing the surgical hub 2404 to determine whether the tissue clamped by an end effector of the surgical stapling and cutting instrument is lung (for a thoracic procedure) or stomach (for an abdominal procedure) tissue. The surgical hub 2404 could then adjust the compression rate and load thresholds of the surgical stapling and cutting instrument appropriately for the type of tissue.

As yet another example, the type of body cavity being operated in during an insufflation procedure can affect the function of a smoke evacuator. A situationally aware surgical hub 2404 could determine whether the surgical site is under pressure (by determining that the surgical procedure is utilizing insufflation) and determine the procedure type. As a procedure type is generally performed in a specific body cavity, the surgical hub 2404 could then control the motor rate of the smoke evacuator appropriately for the body cavity being operated in. Thus, a situationally aware surgical hub 2404 could provide a consistent amount of smoke evacuation for both thoracic and abdominal procedures.

As yet another example, the type of procedure being performed can affect the optimal energy level for an ultrasonic surgical instrument or radio frequency (RF) electrosurgical instrument to operate at. Arthroscopic procedures, for example, require higher energy levels because the end effector of the ultrasonic surgical instrument or RF electrosurgical instrument is immersed in fluid. A situationally aware surgical hub 2404 could determine whether the surgical procedure is an arthroscopic procedure. The surgical hub 2404 could then adjust the RF power level or the ultrasonic amplitude of the generator (i.e., "energy level") to compensate for the fluid filled environment. Relatedly, the type of tissue being operated on can affect the optimal energy level for an ultrasonic surgical instrument or RF electrosurgical instrument to operate at. A situationally aware surgical hub 2404 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 2404 can be configured to adjust the energy level for the ultrasonic surgical instrument or RF electrosurgical instrument throughout the course of a surgical procedure, rather than just on a procedure-by-procedure basis. A situationally aware surgical hub 2404 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

As yet another example, data can be drawn from additional data sources 2426 to improve the conclusions that the surgical hub 2404 draws from one data source 2426. A situationally aware surgical hub 2404 could augment data that it receives from the modular devices 2402 with contextual information that it has built up regarding the surgical procedure from other data sources 2426. For example, a situationally aware surgical hub 2404 can be configured to determine whether hemostasis has occurred (i.e., whether bleeding at a surgical site has stopped) according to video or image data received from a medical imaging device. However, in some cases the video or image data can be inconclusive. Therefore, in one exemplification, the surgical hub 2404 can be further configured to compare a physiologic measurement (e.g., blood pressure sensed by a BP monitor communicably connected to the surgical hub 2404) with the visual or image data of hemostasis (e.g., from a medical imaging device 124 (FIG. 2) communicably coupled to the surgical hub 2404) to make a determination on the integrity of the staple line or tissue weld. In other words, the situational awareness system of the surgical hub 2404 can consider the physiological measurement data to provide additional context in analyzing the visualization data. The additional context can be useful when the visualization data may be inconclusive or incomplete on its own.

Another benefit includes proactively and automatically controlling the paired modular devices 2402 according to the particular step of the surgical procedure that is being performed to reduce the number of times that medical personnel are required to interact with or control the surgical system 2400 during the course of a surgical procedure. For example, a situationally aware surgical hub 2404 could proactively activate the generator to which an RF electrosurgical instrument is connected if it determines that a subsequent step of the procedure requires the use of the instrument. Proactively activating the energy source allows the instrument to be ready for use a soon as the preceding step of the procedure is completed.

As another example, a situationally aware surgical hub 2404 could determine whether the current or subsequent step of the surgical procedure requires a different view or degree of magnification on the display according to the feature(s) at the surgical site that the surgeon is expected to need to view. The surgical hub 2404 could then proactively change the displayed view (supplied by, e.g., a medical imaging device for the visualization system 108) accordingly so that the display automatically adjusts throughout the surgical procedure.

As yet another example, a situationally aware surgical hub 2404 could determine which step of the surgical procedure is being performed or will subsequently be performed and whether particular data or comparisons between data will be required for that step of the surgical procedure. The surgical hub 2404 can be configured to automatically call up data screens based upon the step of the surgical procedure being performed, without waiting for the surgeon to ask for the particular information.

Another benefit includes checking for errors during the setup of the surgical procedure or during the course of the surgical procedure. For example, a situationally aware surgical hub 2404 could determine whether the operating theater is setup properly or optimally for the surgical procedure to be performed. The surgical hub 2404 can be configured to determine the type of surgical procedure being performed, retrieve the corresponding checklists, product location, or setup needs (e.g., from a memory), and then compare the current operating theater layout to the standard layout for the type of surgical procedure that the surgical hub 2404 determines is being performed. In one exemplification, the surgical hub 2404 can be configured to compare the list of items for the procedure scanned by a suitable scanner for example and/or a list of devices paired with the surgical hub 2404 to a recommended or anticipated manifest of items and/or devices for the given surgical procedure. If there are any discontinuities between the lists, the surgical hub 2404 can be configured to provide an alert indicating that a particular modular device 2402, patient monitoring device 2424, and/or other surgical item is missing. In one exemplification, the surgical hub 2404 can be configured to determine the relative distance or position of the modular devices 2402 and patient monitoring devices 2424 via proximity sensors, for example. The surgical hub 2404 can compare the relative positions of the devices to a recommended or anticipated layout for the particular surgical procedure. If there are any discontinuities between the layouts, the surgical hub 2404 can be configured to provide an alert indicating that the current layout for the surgical procedure deviates from the recommended layout.

As another example, a situationally aware surgical hub 2404 could determine whether the surgeon (or other medical personnel) was making an error or otherwise deviating from the expected course of action during the course of a surgical procedure. For example, the surgical hub 2404 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 2404 determined is being performed. In one exemplification, the surgical hub 2404 can be configured to provide an alert indicating that an unexpected action is being performed or an unexpected device is being utilized at the particular step in the surgical procedure.

Overall, the situational awareness system for the surgical hub 2404 improves surgical procedure outcomes by adjusting the surgical instruments (and other modular devices 2402) for the particular context of each surgical procedure (such as adjusting to different tissue types) and validating actions during a surgical procedure. The situational awareness system also improves surgeons' efficiency in performing surgical procedures by automatically suggesting next steps, providing data, and adjusting displays and other modular devices 2402 in the surgical theater according to the specific context of the procedure.

Referring now to FIG. 21, a timeline 2500 depicting situational awareness of a hub, such as the surgical hub 106 or 206 (FIGS. 1-11), for example, is depicted. The timeline 2500 is an illustrative surgical procedure and the contextual information that the surgical hub 106, 206 can derive from the data received from the data sources at each step in the surgical procedure. The timeline 2500 depicts the typical steps that would be taken by the nurses, surgeons, and other medical personnel during the course of a lung segmentectomy procedure, beginning with setting up the operating theater and ending with transferring the patient to a post-operative recovery room.

The situationally aware surgical hub 106, 206 receives data from the data sources throughout the course of the surgical procedure, including data generated each time medical personnel utilize a modular device that is paired with the surgical hub 106, 206. The surgical hub 106, 206 can receive this data from the paired modular devices and other data sources and continually derive inferences (i.e., contextual information) about the ongoing procedure as new data is received, such as which step of the procedure is being performed at any given time. The situational awareness system of the surgical hub 106, 206 is able to, for example, record data pertaining to the procedure for generating reports, verify the steps being taken by the medical personnel, provide data or prompts (e.g., via a display screen) that may be pertinent for the particular procedural step, adjust modular devices based on the context (e.g., activate monitors, adjust the field of view (FOV) of the medical imaging device, or change the energy level of an ultrasonic surgical instrument or RF electrosurgical instrument), and take any other such action described above.

As the first step 2502 in this illustrative procedure, the hospital staff members retrieve the patient's EMR from the hospital's EMR database. Based on select patient data in the EMR, the surgical hub 106, 206 determines that the procedure to be performed is a thoracic procedure.

Second step 2504, the staff members scan the incoming medical supplies for the procedure. The surgical hub 106, 206 cross-references the scanned supplies with a list of supplies that are utilized in various types of procedures and confirms that the mix of supplies corresponds to a thoracic procedure. Further, the surgical hub 106, 206 is also able to determine that the procedure is not a wedge procedure (because the incoming supplies either lack certain supplies that are necessary for a thoracic wedge procedure or do not otherwise correspond to a thoracic wedge procedure).

Third step 2506, the medical personnel scan the patient band via a scanner that is communicably connected to the surgical hub 106, 206. The surgical hub 106, 206 can then confirm the patient's identity based on the scanned data.

Fourth step 2508, the medical staff turns on the auxiliary equipment. The auxiliary equipment being utilized can vary according to the type of surgical procedure and the techniques to be used by the surgeon, but in this illustrative case they include a smoke evacuator, insufflator, and medical imaging device. When activated, the auxiliary equipment that are modular devices can automatically pair with the surgical hub 106, 206 that is located within a particular vicinity of the modular devices as part of their initialization process. The surgical hub 106, 206 can then derive contextual information about the surgical procedure by detecting the types of modular devices that pair with it during this pre-operative or initialization phase. In this particular example, the surgical hub 106, 206 determines that the surgical procedure is a VATS procedure based on this particular combination of paired modular devices. Based on the combination of the data from the patient's EMR, the list of medical supplies to be used in the procedure, and the type of modular devices that connect to the hub, the surgical hub 106, 206 can generally infer the specific procedure that the surgical team will be performing. Once the surgical hub 106, 206 knows what specific procedure is being performed, the surgical hub 106, 206 can then retrieve the steps of that procedure from a memory or from the cloud and then cross-reference the data it subsequently receives from the connected data sources (e.g., modular devices and patient monitoring devices) to infer what step of the surgical procedure the surgical team is performing.

Fifth step 2510, the staff members attach the EKG electrodes and other patient monitoring devices to the patient. The EKG electrodes and other patient monitoring devices are able to pair with the surgical hub 106, 206. As the surgical hub 106, 206 begins receiving data from the patient monitoring devices, the surgical hub 106, 206 thus confirms that the patient is in the operating theater.

Sixth step 2512, the medical personnel induce anesthesia in the patient. The surgical hub 106, 206 can infer that the patient is under anesthesia based on data from the modular devices and/or patient monitoring devices, including EKG data, blood pressure data, ventilator data, or combinations thereof, for example. Upon completion of the sixth step 2512, the pre-operative portion of the lung segmentectomy procedure is completed and the operative portion begins.

Seventh step 2514, the patient's lung that is being operated on is collapsed (while ventilation is switched to the contralateral lung). The surgical hub 106, 206 can infer from the ventilator data that the patient's lung has been collapsed, for example. The surgical hub 106, 206 can infer that the operative portion of the procedure has commenced as it can compare the detection of the patient's lung collapsing to the expected steps of the procedure (which can be accessed or retrieved previously) and thereby determine that collapsing the lung is the first operative step in this particular procedure.

Eighth step 2516, the medical imaging device (e.g., a scope) is inserted and video from the medical imaging device is initiated. The surgical hub 106, 206 receives the medical imaging device data (i.e., video or image data) through its connection to the medical imaging device. Upon receipt of the medical imaging device data, the surgical hub 106, 206 can determine that the laparoscopic portion of the surgical procedure has commenced. Further, the surgical hub 106, 206 can determine that the particular procedure being performed is a segmentectomy, as opposed to a lobectomy (note that a wedge procedure has already been discounted by the surgical hub 106, 206 based on data received at the second step 2504 of the procedure). The data from the medical imaging device 124 (FIG. 2) can be utilized to determine contextual information regarding the type of procedure being performed in a number of different ways, including by determining the angle at which the medical imaging device is oriented with respect to the visualization of the patient's anatomy, monitoring the number or medical imaging devices being utilized (i.e., that are activated and paired with the surgical hub 106, 206), and monitoring the types of visualization devices utilized. For example, one technique for performing a VATS lobectomy places the camera in the lower anterior corner of the patient's chest cavity above the diaphragm, whereas one technique for performing a VATS segmentectomy places the camera in an anterior intercostal position relative to the segmental fissure. Using pattern recognition or machine learning techniques, for example, the situational awareness system can be trained to recognize the positioning of the medical imaging device according to the visualization of the patient's anatomy. As another example, one technique for performing a VATS lobectomy utilizes a single medical imaging device, whereas another technique for performing a VATS segmentectomy utilizes multiple cameras. As yet another example, one technique for performing a VATS segmentectomy utilizes an infrared light source (which can be communicably coupled to the surgical hub as part of the visualization system) to visualize the segmental fissure, which is not utilized in a VATS lobectomy. By tracking any or all of this data from the medical imaging device, the surgical hub 106, 206 can thereby determine the specific type of surgical procedure being performed and/or the technique being used for a particular type of surgical procedure.

Ninth step 2518, the surgical team begins the dissection step of the procedure. The surgical hub 106, 206 can infer that the surgeon is in the process of dissecting to mobilize the patient's lung because it receives data from the RF or ultrasonic generator indicating that an energy instrument is being fired. The surgical hub 106, 206 can cross-reference the received data with the retrieved steps of the surgical procedure to determine that an energy instrument being fired at this point in the process (i.e., after the completion of the previously discussed steps of the procedure) corresponds to the dissection step. In certain instances, the energy instrument can be an energy tool mounted to a robotic arm of a robotic surgical system.

Tenth step 2520, the surgical team proceeds to the ligation step of the procedure. The surgical hub 106, 206 can infer that the surgeon is ligating arteries and veins because it receives data from the surgical stapling and cutting instrument indicating that the instrument is being fired. Similarly to the prior step, the surgical hub 106, 206 can derive this inference by cross-referencing the receipt of data from the surgical stapling and cutting instrument with the retrieved steps in the process. In certain instances, the surgical instrument can be a surgical tool mounted to a robotic arm of a robotic surgical system.

Eleventh step 2522, the segmentectomy portion of the procedure is performed. The surgical hub 106, 206 can infer that the surgeon is transecting the parenchyma based on data from the surgical stapling and cutting instrument, including data from its cartridge. The cartridge data can correspond to the size or type of staple being fired by the instrument, for example. As different types of staples are utilized for different types of tissues, the cartridge data can thus indicate the type of tissue being stapled and/or transected. In this case, the type of staple being fired is utilized for parenchyma (or other similar tissue types), which allows the surgical hub 106, 206 to infer that the segmentectomy portion of the procedure is being performed.

Twelfth step 2524, the node dissection step is then performed. The surgical hub 106, 206 can infer that the surgical team is dissecting the node and performing a leak test based on data received from the generator indicating that an RF or ultrasonic instrument is being fired. For this particular procedure, an RF or ultrasonic instrument being utilized after parenchyma was transected corresponds to the node dissection step, which allows the surgical hub 106, 206 to make this inference. It should be noted that surgeons regularly switch back and forth between surgical stapling/cutting instruments and surgical energy (i.e., RF or ultrasonic) instruments depending upon the particular step in the procedure because different instruments are better adapted for particular tasks. Therefore, the particular sequence in which the stapling/cutting instruments and surgical energy instruments are used can indicate what step of the procedure the surgeon is performing. Moreover, in certain instances, robotic tools can be utilized for one or more steps in a surgical procedure and/or handheld surgical instruments can be utilized for one or more steps in the surgical procedure. The surgeon(s) can alternate between robotic tools and handheld surgical instruments and/or can use the devices concurrently, for example. Upon completion of the twelfth step 2524, the incisions are closed up and the post-operative portion of the procedure begins.

Thirteenth step 2526, the patient's anesthesia is reversed. The surgical hub 106, 206 can infer that the patient is emerging from the anesthesia based on the ventilator data (i.e., the patient's breathing rate begins increasing), for example.

Lastly, the fourteenth step 2528 is that the medical personnel remove the various patient monitoring devices from the patient. The surgical hub 2106, 2236 can thus infer that the patient is being transferred to a recovery room when the hub loses EKG, BP, and other data from the patient monitoring devices. As can be seen from the description of this illustrative procedure, the surgical hub 2106, 2236 can determine or infer when each step of a given surgical procedure is taking place according to data received from the various data sources that are communicably coupled to the surgical hub 2106, 2236.

Situational awareness is further described in various U.S. Patent Applications that are incorporated by reference herein in the present disclosure, which is herein incorporated by reference in its entirety. In certain instances, operation of a robotic surgical system, including the various robotic surgical systems disclosed herein, for example, can be controlled by the hub 2106, 2236 based on its situational awareness and/or feedback from the components thereof and/or based on information from the cloud 2104 (FIG. 17).

FIG. 22 is a logic flow diagram of a process 4000 depicting a control program or a logic configuration for correlating visualization data with instrument data, in accordance with at least one aspect of the present disclosure. The process 4000 is generally executed during a surgical procedure and includes: receiving or deriving 4001 a first data set, visualization data, from a surgical visualization system indicative of a visual aspect of the surgical instrument relative to a surgical field, receiving or deriving 4002 a second data set, instrument data, from the surgical instrument indicative of a functional aspect of the surgical instrument, and correlating 4003 the first data set with the second data set.

In at least one example, correlating the visualization data with the instrument data is implemented by developing a composite data set from the visualization data and the instrument data. The process 4000 may further include comparing the composite data set to another composite data set, which can be received from an external source and/or can be derived from previously collected composite data sets. In at least one example, the process 4000 includes displaying a comparison of the two composite data sets, as described in greater detail below.

The visualization data of the process 4000 can be indicative of a visual aspect of the end effector of the surgical instrument relative to tissue in the surgical field. Additionally, or alternatively, the visualization data can be indicative of a visual aspect of the tissue being treated by the end effector of the surgical instrument. In at least one example, the visualization data represents one or more positions of the end effector, or a component thereof, relative to the tissue in the surgical field. Additionally, or alternatively, the visualization data may represent one or more movements of the end effector, or a component thereof, relative to the tissue in the surgical field. In at least one example, the visualization data represents one or more changes in shape, dimensions, and/or color of the tissue being treated by the end effector of the surgical instrument.

In various aspects, the visualization data is derived from a surgical visualization system (e.g. visualization system 100, 160, 500, 2108). The visualization data can be derived from various measurements, readings, and/or any other suitable parameters monitored and/or captured by a surgical visualization system, as described in greater detail in connection with FIGS. 1-18. In various examples, the visualization data is indicative of one or more visual aspects of tissue in a surgical field and/or one more visual aspects of a surgical instrument relative to the tissue in the surgical field. In certain examples, the visualization data represents or identifies position and/or movement of an end effector of the surgical instrument relative to a critical structure (e.g. the critical structure 101 in FIG. 1) in the surgical field. In certain examples, the visualization data is derived from surface mapping data, imaging data, tissue identification data, and/or distance data computed by surface mapping logic 136, imaging logic 138, tissue identification logic 140, or distance determining logic 141 or any combinations of the logic 136, 138, 140, and 141.

In at least one example, the visualization data is derived from tissue identification and geometric surface mapping performed by the visualization system 100 in combination with a distance sensor system 104, as described in greater detail in connection with FIG. 1. In at least one example, the visualization data is derived from measurements, readings, or any other sensor data captured by the imaging device 120. As described in connection with FIG. 1, the imaging device 120 is a spectral camera (e.g. a hyperspectral camera, multispectral camera, or selective spectral camera), which is configured to detect reflected spectral waveforms and generate a spectral cube of images based on the molecular response to the different wavelengths.

Additionally, or alternatively, the visualization data can be derived from measurements, readings, or any suitable sensor data captured by any suitable imaging device that includes a camera or imaging sensor that is configured to detect visible light, spectral light waves (visible or invisible), and a structured light pattern (visible or invisible), for example. In at least one example, the visualization data is derived from a visualization system 160 that includes an optical waveform emitter 123 and an waveform sensor 122 that is configured to detect the reflected waveforms, as described in greater detail in connection with FIGS. 3-4 and 13-16. In yet another example, the visualization data is derived from a visualization system that includes a three-dimensional (3D) camera and associated electronic processing circuits such as, for example, the visualization system 500. In yet another example, the visualization data is derived from a structured (or patterned) light system 700, which is described in greater detail in connection with FIG. 12. The foregoing examples can be used alone or in combination to derive the visualization data of the process 4000.

The instrument data of the process 4000 can be indicative of one or more operations of one or more internal components of the surgical instrument. In at least one example, the instrument data represents one or more operational parameters of an internal component of the surgical instrument. The instrument data may represent one or more positions and/or one or more movements of one or more internal components of the surgical instrument. In at least one example, the internal component is a cutting member configured to cut the tissue during a firing sequence of the surgical instrument. Additionally, or alternatively, the internal component can include one or more staples configured to be fired into the tissue during the firing sequence of the surgical instrument.

In at least one example, the instrument data represents one or more operations of one or more components of one or more drive assemblies of the surgical instrument such as, for example, an articulation drive assembly, a closure drive assembly, a rotation drive assembly, and/or a firing drive assembly. In at least one example, the instrument data set represents one or more operations of one or more drive members of the surgical instrument such as, for example, an articulation drive member, a closure drive member, a rotation drive member, and/or a firing drive member.

FIG. 23 is a schematic diagram of an example surgical instrument 4600 for use with the process 4000 that is similar in many respects to other surgical instruments or tools described by the present disclosure such as, for example, the surgical instrument 2112. For brevity, various aspects of the process 4000 are only described by the present disclosure using a handheld surgical instrument. However, this is not limiting. Such aspects of the process 4000 can be equally implemented using a robotic surgical tool such as, for example, the surgical tool 2117.

The surgical instrument 4600 includes a plurality of motors, which can be activated to perform various functions. The plurality of motors of surgical instrument 4600 can be activated to cause firing, closure, and/or articulation motions in the end effector. The firing, closure, and/or articulation motions can be transmitted to an end effector of the surgical instrument 4600 through a shaft assembly, for example. In other examples, however, a surgical instrument for use with the process 4000 can be configured to perform one or more of the firing, closure, and articulation motions manually. In at least one example, the surgical instrument 4600 includes an end effector that treats tissue by deploying staples into the tissue. In another example, the surgical instrument 4600 includes an end effector that treats tissue by applying therapeutic energy to the tissue.

In certain instances, the surgical instrument 4600 includes a firing motor 4602. The firing motor 4602 may be operably coupled to a firing motor drive assembly 4604, which can be configured to transmit firing motions, generated by the firing motor 4602 to the end effector, in particular to move a firing member in the form of an I-beam, for example, which may include a cutting member. In certain instances, the firing motions generated by the firing motor 4602 may cause the staples to be deployed from a staple cartridge into tissue captured by the end effector and, optionally, cause the cutting member of the I-beam to be advanced to cut the captured tissue, for example.

In certain instances, the surgical instrument or tool may include a closure motor 4603. The closure motor 4603 may be operably coupled to a closure motor drive assembly 4605 which can be configured to transmit closure motions, generated by the closure motor 4603 to the end effector, in particular to displace a closure tube to close the anvil and compress tissue between the anvil and the staple cartridge. The closure motions may cause the end effector to transition from an open configuration to an approximated configuration to capture tissue, for example.

In certain instances, the surgical instrument or tool may include one or more articulation motors 4606a, 4606b, for example. The articulation motors 4606a, 4606b may be operably coupled to respective articulation motor drive assemblies 4608a, 4608b, which can be configured to transmit articulation motions generated by the articulation motors 4606a, 4606b to the end effector. In certain instances, the articulation motions may cause the end effector to articulate relative to the shaft, for example.

In certain instances, the surgical instrument or tool may include a control module 4610 which can be employed with a plurality of motors of the surgical instrument 4600. Each of the motors 4602, 4603, 4606a, 4606b may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, as illustrated in FIG. 23, the control module 4610 may comprise a motor driver 4626 which may comprise one or more H-Bridge FETs. The motor driver 4626 may modulate the power transmitted from a power source 4628 to a motor coupled to the control module 4610 based on input from a microcontroller 4620 (the "controller"), for example. In certain instances, the controller 4620 can be employed to determine the current drawn by the motor, for example, while the motor is coupled to the control module 4610, as described above.

In certain instances, the controller 4620 may include a microprocessor 4622 (the "processor") and one or more non-transitory computer-readable mediums or memory units 4624 (the "memory"). In certain instances, the memory 4624 may store various program instructions, which when executed may cause the processor 4622 to perform a plurality of functions and/or calculations described herein. In certain instances, one or more of the memory units 4624 may be coupled to the processor 4622, for example. In various instances, the processor 4622 may control the motor driver 4626 to control the position, direction of rotation, and/or velocity of a motor that is coupled to the control module 4610.

In certain instances, one or more mechanisms and/or sensors such as, for example, sensors 4630 can be configured to detect forces (Force-to-Close "FTC") applied by the jaws of an end effector of the surgical instrument 4600 to tissue captured between the jaws. FTC can be transmitted to the jaws of the end effector through the closure motor drive assembly 4605. Additionally, or alternatively, the sensors 4630 can be configured to detect forces (Force-to-Fire "FTF") applied to the end effector through the firing motor drive assembly 4604. In various examples, the sensors 4630 can be configured to sense closure actuation (e.g., motor current and FTC), firing actuation (e.g., motor current and FTF), articulation (e.g., the angular position of the end effector), and rotation of the shaft or the end effector.

One or more aspects of the process 4000 can be executed by one or more of the control circuits (e.g. control circuit 132, 400, 410, 420, 602, 622, 2108, 4620) described by the present disclosure. In at least one example, one or more aspects of the process 4000 are executed by a control circuit (e.g. control circuit 400 of FIG. 2A) that includes a processor and a memory storing a set of computer-executable instructions that, when executed by the processor, cause the processor to perform the one or more aspects of the process 4000. Additionally, or alternatively, one or more aspects of the process 4000 can be executed by a combinational logic circuit (e.g. control circuit 410 of FIG. 2B) and/or a sequential logic circuit (e.g. control circuit 420 of FIG. 2C). Furthermore, the process 4000 can be executed by any suitable circuitry with any suitable hardware and/or software components that may be located in or associated with various suitable systems described by the present disclosure.

In various aspects, the process 4000 can be implemented by a computer-implemented interactive surgical system 2100 (FIG. 19) that includes one or more surgical systems 2102 and a cloud-based system (e.g., the cloud 2104 that may include a remote server 2113 coupled to a storage device 2105). Each surgical system 2102 includes at least one surgical hub 2106 in communication with the cloud 2104 that may include a remote server 2113. The control circuit executing one or more aspects of the process 4000 can be a component of a visualization system (e.g. visualization system 100, 160, 500, 2108), and can be in communication with a surgical instrument (e.g. surgical instrument 2112, 4600) to receive the instrument data therefrom. The communication between the surgical instrument and the control circuit of the visualization system can be a direct communication, or the instrument data can be routed to the visualization system through a surgical hub 2106, for example. In at least one example, the control circuit executing one or more aspects of the process 4000 can be a component of a surgical hub 2106.

Referring to FIG. 24, in various examples, visualization data 4010 is correlated with instrument data 4011 by developing a composite data set 4012 from the visualization data 4010 and the instrument data 4011. FIG. 24 displays a current user's composite data set 4012 in a Graph 4013, which is developed from the current user's visualization data 4010 and the current user's instrument data 4011. Graph 4013 illustrates visualization data 4010 that represents a first usage cycle of a surgical instrument 4600, which involves jaw positioning, clamping, and firing of the surgical instrument 4600. Graph 4013 also depicts visualization data 4010 that represents the beginning of a second usage cycle of the surgical instrument 4600 where the jaws are repositioned for a second clamping and firing of the surgical instrument 4600. Graph 4013 further depicts the current user's instrument data 4011 in the form of FTC data 4014, correlated to clamping visualization data, and FTF data 4015, correlated to firing visualization data.

As described above, the visualization data 4010 is derived from a visualization system (e.g. visualization system 100, 160, 500, 2108), and can represent, for example, the distance between the end effector of the surgical instrument 4600 and a critical structure in a surgical field during positioning, clamping, and/or firing of the end effector of the surgical instrument 4600. In at least one example, the visualization system identifies the end effector, or components thereof, in the surgical field, identifies a critical structure in the surgical field, and tracks the position of the end effector, or components thereof, with respect to the critical structure or with respect to tissue around the critical structure. In at least one example, the visualization system identifies jaws of the end effector in a surgical field, identifies a critical structure in the surgical field, and tracks the position of the jaws with respect to the critical structure or with respect to tissue around the critical structure within the surgical.

In at least one example, the critical structure is a tumor. To remove the tumor, surgeons generally prefer to cut tissue along a safety margin around the tumor to ensure that the entire tumor is removed. In such example, the visualization data 4010 can represent the distance between the jaws of the end effector and the safety margin of the tumor during positioning, clamping, and/or firing of the surgical instrument 4600.

The process 4000 may further include comparing a current user's composite data set 4012 to another composite data set 4012', which can be received from an external source and/or can be derived from previously collected composite data sets. Graph 4013 illustrates a comparison between the current user's composite data set 4012 and another composite data set 4012' that includes visualization data 4010' and instrument data 4011' including FTC data 4014' and FTF data 4015'. The comparison can be presented to a user of the surgical instrument 4600 in real time in the form of the graph 4013, or any other suitable format. The control circuit executing one or more aspects of the process 4000 may cause the comparison of two composite data sets to be displayed on any suitable screen within the operating room such as a screen of the visualization system, for example. In at least one example, the comparison can be displayed alongside the real-time video of the surgical field captured on any suitable screen within the operating room. In at least one example, the control circuit is configured to adjust an instrument parameter to address a detected deviation between the first composite data set and the second composite data set.

Furthermore, a control circuit (e.g. control circuit 132, 400, 410, 420, 602, 622, 2108, 4620) executing one or more aspects of the process 4000 may further cause current statuses of instrument data such as, for example, FTF data and/or FTC data to be displayed against best practice equivalents. In the example illustrated in FIG. 24, a current value of FTC—represented by a circle 4020—is depicted in real time against a gauge 4021 with an indicator 4022 representing a best practice FTC. Likewise, a current value of FTF—represented by a circle 4023—is depicted against a gauge 4024 with an indicator 4025 representing a best practice FTF. Such information can be overlaid onto the video feed of the surgical field in real time.

The example illustrated in FIG. 24 alerts the user that the current FTC is higher than the best practice FTC and that the current FTF is also higher than the best practice FTF. The control circuit executing one or more aspects of the process 4000 may further alert the current user of the surgical instrument 4600—using an audible, visual, and/or haptic alerting mechanism—if the current value of the FTF and/or FTC reaches and/or moves beyond a predetermined threshold.

In certain instances, a control circuit (e.g. control circuit 132, 400, 410, 420, 602, 622, 2108, 4620) executing one or more aspects of the process 4000 may further provide a current user of the surgical instrument 4600 with a projected instrument data based on current investment data. For example, as illustrated in FIG. 24, a projected FTF 4015" is determined based on a current value of the FTF, and is further displayed on the graph 4013 against current FTF 4015 and previously collected FTF'. Additionally, or alternatively, a projected FTF circle 4026 can be displayed against the gauge 4024, as illustrated in FIG. 24.

In various aspects, previously collected composite data sets and/or best practice FTF and/or FTC are determined from previous uses of the surgical instrument 4600 in the same surgical procedure and/or other surgical procedures performed by the user, other users within the hospitals, and/or users in other hospitals. Such data can be made available to a control circuit (e.g. control circuit 132, 400, 410, 420, 602, 622, 2108, 4620) executing one or more aspects of the process 4000 by importation from a cloud 104, for example.

In various aspects, a control circuit (e.g. control circuit 132, 400, 410, 420, 602, 622, 2108, 4620) executing one or more aspects of the process 4000 can cause feedback measurements of tissue thickness, compression, and stiffness to be visually overlaid onto a screen that displays a live feed of the surgical instrument 4600 in the surgical field as the jaws of the end effector begin to deform the tissue captured therebetween during the clamping phase. The visual overlay correlates the visualization data representing tissue deformation to changes in clamping force over time. The correlation helps a user confirm proper cartridge selection, determine the time to start firing, as well as determine a suitable firing speed. The correlation can further inform an adaptive clamping algorithm. Adaptive firing speed changes can be informed by measured forces as well as changes in tissue motions immediately adjacent the jaws of the surgical instrument 4600 (e.g. principal strains, tissue slippage, etc.) while a gauge or meter that communicates the results is overlaid on the screen that displays a live feed of the end effector in the surgical field.

Further to the above, the kinematics of the surgical instrument 4600 can also instruct instrument operation relative to another use or user. The kinematics can be ascertained via accelerometers, torque sensors, force sensors, motor encoders, or any other suitable sensors, and can yield various force, velocity, and/or acceleration data of the surgical instrument, or components thereof, for correlation with corresponding visualization data.

In various aspects, a control circuit (e.g. control circuit 132, 400, 410, 420, 602, 622, 2108, 4620) executing one or more aspects of the process 4000 may cause an alternate surgical technique to be presented, if a deviation from the best-practice surgical technique is detected from the visualization data and/or the instrument data. In at least one example, an adaptive display of instrument movement, force, tissue impendence, and results from proposed alternative techniques are presented. Where the visualization data indicates detection of a blood vessel and a clip applier in the surgical field, a control circuit (e.g. control circuit 132, 400, 410, 420, 602, 622, 2108, 4620) executing one or more aspects of the process 4000 may further ensure perpendicularity of the blood vessel with respect to the clip applier. The control circuit may suggest changing position, orientation, and/or roll angle to achieve the desired perpendicularity.

In various aspects, a control circuit (e.g. control circuit 132, 400, 410, 420, 602, 622, 2108, 4620) may execute the process 4000 by comparing real-time visualization data to pre-surgical planning simulations. The user can utilize pre-operative patient scans to simulate a surgical approach. The pre-surgical planning simulations can allow a user to follow a particular pre-surgical plan based on training runs. The control circuit can be configured to correlate fiducial landmarks of the pre-operative scans/simulations with current visualization data. In at least one example, the control circuit may employ boundary tracking of an object to establish the correlation.

As a surgical instrument interacts with tissue and deforms surface geometry, the change in surface geometry as a function of the surgical instrument's position can be computed. For a given change in the surgical instrument's position upon contact with the tissue, the corresponding change in tissue geometry can depend on the sub-surface structures in the tissue region contacted by the surgical instrument. For example, in thoracic procedures, the change in tissue geometry in regions with airway substructures is different than regions with parenchyma substructures. Generally, stiffer substructures yield a smaller change in surface tissue geometry in response to a given change in the surgical instrument's position. In various aspects, a control circuit (e.g. control circuit 132, 400, 410, 420, 602, 622, 2108, 4620) can be configured to compute a running average of the change in the surgical instrument position versus change in surface geometry for the given patient to give patient-specific differences. Additionally, or alternatively, the computed running average can be compared to a second set of previously collected data. In certain instances, a surface reference can be selected when no change in surface geometry is measured per change in tool position. In at least one example, a control circuit can be configured to determine the location of a substructure based on detected surface geometry changes in response to a given contact between a tissue region and a surgical instrument.

Furthermore, a control circuit (e.g. control circuit 132, 400, 410, 420, 602, 622, 2108, 4620) can be configured to maintain a set instrument-tissue contact throughout a tissue treatment based on the correlation between the set instrument-tissue contact and one or more tissue-surface geometry changes associated with the set instrument-tissue contact. For example, the end effector of a surgical instrument 4600 may clamp tissue between its jaws at a desired compression setting the instrument-tissue contact. A corresponding change in tissue-surface geometry can be detected by the visualization system. Furthermore, a control circuit (e.g. control circuit 132, 400, 410, 420, 602, 622, 2108, 4620) can derive visualization data indicative of the change in tissue-surface geometry associated with the desired compression. The control circuit can further cause a motor setting of the closure motor 4603 (FIG. 22) to be automatically adjusted to maintain the change in tissue-surface geometry associated with the desired compression. This arrangement requires a continuous interaction between the surgical instrument 4600 and visualization system to maintain the change in tissue-surface geometry associated with the desired compression by continuously adjusting the jaw compression against the tissue based on the visualization data.

In yet another example, where the surgical instrument 4600 is a robotic tool attached to a robotic arm of a robotic surgical system (e.g. robotic system 110), the robotic surgical system can be configured to automatically adjust one or more components of the robotic surgical system to maintain a set surface contact with tissue based on visualization data derived from a detected change in surface geometry of the tissue in response to the set surface contact with the tissue.

In various examples, the visualization data can be used in combination with measured instrument data to maintain contact between the tissue either in position or load control allowing the user to manipulate the tissue to apply a pre-defined load to the tissue while moving the instrument relative to the tissue. The user could specify that they wish to maintain contact or maintain a pressure and the visual tracking of the instrument along with the internal loading of the instrument could be used to enable repositioning without changing the fixed parameters.

Referring to FIGS. 25A and 25B, a screen 4601 of the visualization system (e.g. visualization system 100, 160, 500, 2108) displays a real-time video feed of a surgical field during a surgical procedure. An end effector 4642 of the surgical instrument 4600 includes jaws clamping tissue near a tumor identified in the surgical field via an overlaid MRI image, for example. The jaws of the end effector 4642 comprise an anvil 4643 and a channel housing a staple cartridge. At least one of the anvil 4643 and the channel is movable relative to the other to capture tissue between the anvil 4643 and the staple cartridge. The captured tissue is then stapled via staples 4644 deployable from the staple cartridge during a firing sequence of the surgical instrument 4600. In addition, the captured tissue is cut via a cutting member 4645 advanced distally during the firing sequence but slightly behind the staple deployment.

As apparent in FIG. 25A, during the firing sequence, the captured tissue, and positions and/or movements of certain internal components of the end effector 4642 such as staples 4644 and cutting member 4645, may not visible in a normal view 4640 of the live feed on the screen 4601. Certain end effectors include windows 4641, 4653 that permit a partial view of the cutting member 4645 in the beginning and the end of the firing sequence but not during the firing sequence. Accordingly, a user of the surgical instrument 4600 is unable to track the firing sequence progress on the screen 4601.

FIG. 26 is a logic flow diagram of a process 4030 depicting a control program or a logic configuration for synchronizing movement of a virtual representation of an end-effector component with actual movement of the end-effector component, in accordance with at least one aspect of the present disclosure. The process 4030 is generally executed during a surgical procedure and includes detecting 4031 a movement of an internal component of an end effector during the firing sequence, presenting, for example by overlaying 4032, a virtual representation of the internal component onto the end effector, and synchronizing 4033 a movement of the virtual representation on the screen 4601 with the detected movement of the internal component.

One or more aspects of the process 4030 can be executed by one or more of the control circuits (e.g. control circuit 132, 400, 410, 420, 602, 622, 2108, 4620) described by the present disclosure. In at least one example, one or more aspects of the process 4030 are executed by a control circuit (e.g. control circuit 400 of FIG. 2A) that includes a processor and a memory storing a set of computer-executable instructions that, when executed by the processor, cause the processor to perform the one or more aspects of the process 4030. Additionally, or alternatively, one or more aspects of the process 4030 can be executed by a combinational logic circuit (e.g. control circuit 410 of FIG. 2B) and/or a sequential logic circuit (e.g. control circuit 420 of FIG. 2C). Furthermore, the process 4030 can be executed by any suitable circuitry with any suitable hardware and/or software components that may be located in or associated with various suitable systems described by the present disclosure.

In various examples, a control circuit (e.g. control circuit 132, 400, 410, 420, 602, 622, 2108, 4620) executing one or more aspects of the process 4030 may receive instrument data indicative of the movement of an internal component of an end effector 4642 during a firing sequence thereof. The movement of the internal component can be tracked using conventional rotary encoders of the firing motor 4602, for example. In other examples, the movement of the internal component can be tracked by a tracking system that employs an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety. In certain examples, the movement of the internal component can be tracked using one or more position sensors that may comprise any number of magnetic sensing elements, such as, for example, magnetic sensors classified according to whether they measure the total magnetic field or the vector components of the magnetic field.

In various aspects, the process 4030 includes an overlay trigger. In at least one example, the overlay trigger can be detecting that a tissue is captured by the end effector 4642. If tissue captured by the end effector 4642 is detected, the process 4030 overlays, onto the end effector 4642, a virtual representation of the cutting member 4645 at a starting position. The process 4030 further includes projecting staple lines, outlining where staples will be deployed into the captured tissue. Furthermore, in response to an activation of the firing sequence by the user, the process 4030 causes the virtual representation of the cutting member 4645 to move distally mimicking actual movement of the cutting member 4645 within the end effector 4642. As the staples are deployed, the process 4030 converts unfired staples to fired staples, thereby allowing the user to visually track staple deployment and cutting member 4645 advancement in real-time.

In various examples, a control circuit (e.g. control circuit 132, 400, 410, 420, 602, 622, 2108, 4620) executing one or more aspects of the process 4030 may detect that a tissue is captured by the end effector 4642 from instrument data indicative of the force applied by the closure motor 4603 (FIG. 22) to the jaws of the end effector 4642 through the closure motor drive assembly 4605, for example. The control circuit may further determine the position of the end effector within the surgical field from visualization data derived from a visualization system (e.g. visualization system 100, 160, 500, 2108). In at least one example, the end effector position can be determined with respect to a reference point in the tissue such as, for example, a critical structure.

In any event, the control circuit causes a virtual representation of the internal component to be overlaid onto the end effector 4642 on the screen 4601 at a position commensurate with the position of the internal component within the end effector. The control circuit further causes the projected virtual representation of the internal component to move synchronously with the internal component during the firing sequence. In at least one example, the synchronization is improved by the integration of markings on the end effector 4642 that the control circuit can use as reference points for determining where to overlay the virtual representation.

FIG. 25B illustrates an augmented view 4651 of the live feed of the surgical field on the screen 4601. In the augmented view 4651 of the example of FIG. 25B, virtual representations of the staples 4644 and cutting member 4645 are overlaid onto the end effector 4642 during the firing sequence. The overlay distinguishes fired staples 4644a from unfired staples 4644b, and distinguishes a completed cutline 4646a from a projected cutline 4646b, which tracks the firing sequence progress. The overlay further shows the beginning of the staple lines 4647, and a projected end 4649 of the staple lines in the cutline that will not reach the end of the tissue. Furthermore, based on the overlay of the tumor MRI image, a safe margin distance "d" between the tumor and the projected cutline 4646b is measured and presented with the overlay. The overlaid safe margin distance "d" assures the user that all of the tumor will be removed.

As illustrated in FIG. 25B, the control circuit is configured to cause the visualization system to continuously reposition the virtual representation of the internal component to correlate with the actual movement of the internal component. In the example of FIG. 25B, the overlay shows the completed cutline 4646a slightly lagging behind the fired staple lines 4644a by a distance "d1", which assures the user that the firing sequence is progressing properly.

Referring now to FIG. 27, a visualization system (e.g. visualization system 100, 160, 500, 2108) can employ tool lighting 4058 and cameras 4059 to detect and/or define trocar locations. Based on determined trocar locations, a user can be directed to the most suitable trocar port for completing an intended function based on time efficiency, location of a critical structure, and/or avoidance or risk.

FIG. 27 illustrates three trocar positions (Trocar 1, Trocar 2, Trocar 3) extending through a body wall 4050 at different positions and orientations with respect to the body wall and with respect to a critical structure 4051 in a cavity 4052 inside the body wall 4050. The trocars are represented by arrows 4054, 4055, 4056. The lighting tool 4058 could be used to detect trocar locations by using cascading light or image on surrounding environment. Additionally, a light source of a lighting tool 4058 could be a rotatable light source. In at least one example, the light source of the lighting tool 4058 and the camera 4059 are utilized to detect distance of trocars relative to target location such as, for example, the critical structure 4051. In various examples, the visualization system could suggest a location change of an instrument if a more preferred instrument location is determined based on the visualization data derived from the camera 4059 recording of the light projected by the light source of the lighting tool 4058. A screen 4060 can display the distance between a trocar and a target tissue, whether a tool access through the trocar is acceptable, risk associated with utilizing the trocar, and/or expected operating time using the trocar, which can aid a user in selecting an optimal trocar for introducing a surgical tool into the cavity 4052.

In various aspects, a surgical hub (e.g. surgical hub 2106, 2122) may recommend an optimal trocar for insertion of a surgical tool into the cavity 4052 based on user characteristics, which can be received from a user database, for example. The user characteristics include user hand dominance, patient-side user preference, and/or user physical characteristics (e.g. height, arm length, range of motion). The surgical hub may utilize these characteristics, position and orientation data of the available trocars, and/or position data of a critical structure to select an optimal trocar for insertion of a surgical tool in an effort to reduce user fatigue and increase efficiency. In various aspects, the surgical hub may further cause a surgical instrument to invert its controls if the user inverts the end-effector orientation.

The surgical hub can reconfigure outputs of the surgical instrument based on visualization data. For example, the surgical hub may prohibit an activation of a therapeutic energy output of a surgical instrument if the visualization data indicates that the surgical instrument is being retracted, or is being utilized to perform a different task.

In various aspects, the visualization system can be configured to track blood surface or estimation of blood volume based reflective IR or red wavelength to delineate blood from non-blood surfaces and surface geometry measurements. This could be reported as an absolute static measure or as a rate of change to provide quantitative data on amount and degree of change of bleeding.

Referring to FIG. 28, various elements of a visualization system (e.g. visualization system 100, 160, 500, 2108) such as, for example, a structured light projector 706 and a camera 720 can be used to generate visualization data of an anatomical organ to generate a virtual 3D construct 4130 of the anatomical organ.

As described herein, structured light in the form of stripes or lines, for example, can be projected from a light source and/or projector 706 onto the surface 705 of targeted anatomy to identify the shape and contours of the surface 705. A camera 720, which can be similar in various respects to the imaging device 120 (FIG. 1), for example, can be configured to detect the projected pattern of light on the surface 705. The way that the projected pattern deforms upon striking the surface 705 allows vision systems to calculate the depth and surface information of the targeted anatomy.

FIG. 29 is a logic flow diagram of a process 4100 depicting a control program or a logic configuration, in accordance with at least one aspect of the present disclosure. In various instances, the process 4100 identifies 4101 a surgical procedure and identifies 4102 an anatomical organ targeted by the surgical procedure. The process 4100 further generates 4104 a virtual 3D construct 4130 of at least a portion of the anatomical organ, identifies 4105 anatomical structures of at least a portion of the anatomical organ which are relevant to the surgical procedure, couples 4106 the anatomical structures to the virtual 3D construct 4130, and overlays 4107 onto the virtual 3D construct 4130 a layout plan of the surgical procedure that is determined based on the anatomical structures.

One or more aspects of the process 4100 can be executed by one or more of the control circuits (e.g. control circuit 132, 400, 410, 420, 602, 622, 2108, 4620) described by the present disclosure. In at least one example, one or more aspects of the process 4100 are executed by a control circuit (e.g. control circuit 400 of FIG. 2A) that includes a processor and a memory storing a set of computer-executable instructions that, when executed by the processor, cause the processor to perform the one or more aspects of the process 4100. Additionally, or alternatively, one or more aspects of the process 4100 can be executed by a combinational logic circuit (e.g. control circuit 410 of FIG. 2B) and/or a sequential logic circuit (e.g. control circuit 420 of FIG. 2C). Furthermore, one or more aspects of the process 4100 can be executed by any suitable circuitry with any suitable hardware and/or software components that may be located in or associated with various suitable systems described by the present disclosure.

In various aspects, the process 4100 can be implemented by a computer-implemented interactive surgical system 2100 (FIG. 19) that includes one or more surgical systems 2102 and a cloud-based system (e.g., the cloud 2104 that may include a remote server 2113 coupled to a storage device 2105). Each surgical system 2102 includes at least one surgical hub 2106 in communication with the cloud 2104 that may include a remote server 2113. The control circuit executing one or more aspects of the process 4100 can be a component of a visualization system (e.g. visualization system 100, 160, 500, 2108).

A control circuit (e.g. control circuit 132, 400, 410, 420, 602, 622, 2108, 4620) executing one or more aspects of the process 4100 may identify 4101 a surgical procedure and/or identify 4102 an anatomical organ targeted by the surgical procedure by retrieving such information from a database storing the information, or obtaining the information directly from user input. In at least one example, the database is stored in a cloud-based system (e.g., the cloud 2104 that may include a remote server 2113 coupled to a storage device 2105). In at least one example, the database comprises hospital EMRs.

In one aspect, the surgical system 2200 comprises a surgical hub 2236 connected to multiple operating theater devices such as, for example, a visualization system (e.g. visualization system 100, 160, 500, 2108) located in the operating theater. In at least one example, the surgical hub 2236 comprises a communications interface for communicably coupling the surgical hub 2236 to the visualization system, the cloud 2204, and/or the remote server 2213. A control circuit of the surgical hub 2236 executing one or more aspects of the process 4100 may identify 4101 a surgical procedure and/or identify 4102 an anatomical organ targeted by the surgical procedure by retrieving such information from a database stored in the cloud 2204, and/or the remote server 2213.

The control circuit executing one or more aspects of the process 4100 may cause a visualization system (e.g. visualization system 100, 160, 500, 2108) to perform an initial scan of at least a portion of the anatomical organ to generate 4104 a three-dimensional ("3D") construct 4130 of at least a portion of the anatomical organ targeted by the surgical procedure. In the example illustrated in FIG. 28, the anatomical organ is a stomach 4110. The control circuit may cause one or more elements of the visualization system such as, for example, a structured light projector 706 and a camera 720 utilize structured light 4111 to generate visualization data by performing a scan of at least a portion of the anatomical organ when the camera(s) are introduced into the body. The current visualization data, pre-operative data (e.g. patient scans and other relevant clinical data), visualization data from previous similar surgical procedures performed on the same or other patients, and/or user input can be leveraged to generate a 3D construct of at least a portion of the anatomical organ.

Furthermore, a control circuit executing one or more aspects of the process 4100 identifies 4105 anatomical structures of at least a portion of the anatomical organ, which are relevant to the surgical procedure. In at least one example, a user may select the anatomical structures using any suitable input device. Additionally, or alternatively, the visualization system may include one or more imaging devices 120 with spectral cameras (e.g. a hyperspectral camera, multispectral camera, or selective spectral camera), which are configured to detect reflected spectral waveforms and generate images based on the molecular response to the different wavelengths. Optical absorption or refractive properties of the tissue can be utilized by the control circuit to distinguish different tissue types of the anatomical organ and, thereby, identify the relevant anatomical structures. In addition, current visualization data, pre-operative data (e.g. patient scans and other relevant clinical data), stored visualization data from previous similar surgical procedures performed on the same or other patients, and/or user input can be leveraged by the control circuit to identify the relevant anatomical structures.

The identified anatomical structures can be anatomical structures in a surgical field and/or anatomical structures are selected by a user. In various examples, position tracking of the relevant anatomical structures can be expanded beyond a current visibility view of a camera directed at the surgical field. In one example, this is achieved by using common visible coupled landmarks or through the use of secondary coupled movement tracking. The secondary tracking could be accomplished through a secondary imaging source, calculation of scope movement, and/or through pre-established beacons that are measures by a second visualization system, for example.

As described above in greater detail in connection with FIG. 14, a visualization system can utilize a structured light projector 706 to cast an array of patterns or lines in which the camera 720 could determine a distance to a target location. The visualization system can then emit a known size pattern or line at a set distance equal to the determined distance. In addition, a spectral camera can determine a size of the pattern, which can vary depending on the optical absorption or refractive properties of the tissue at the target location. The difference between the known size and the determined size is indicative of tissue density at the target location, which is indicative of tissue type at the target location. A control circuit executing one or more aspects of the process 4100 may identify the relevant anatomical structures based, at least in part, on determined tissue densities at target locations.

In at least one example, a detected abnormality in the tissue density can be associated with a disease state. Furthermore, the control circuit select, update, or modify one or more settings of a surgical instrument treating the tissue based on the tissue density detected via visualization data. For example, the control circuit may change various clamping and/or firing parameters of a surgical stapler utilized to staple and cut the tissue. In at least one example, the control circuit may slow down the firing sequence and/or allow more clamping time based on the tissue density detected by the visualization data. In various examples, the control circuit may alert a user of the surgical instrument to the abnormal tissue density by, for example, displaying over a screen, instructions to reduce bite size, increase or decrease the energy delivery output for an electrosurgical instrument, and adjust the amount the jaw closure. In another example, if the visualization data indicate that the tissue is a fatty tissue, the instructions could be to increase power to reduce energy application time.

Furthermore, identification of the surgical procedure type can facilitate target organ identification by the control circuit. For example, if the procedure is a left upper lobectomy, it is highly likely that the lung is the target organ. Accordingly, the control circuit will only consider visualization data and non-visualization data relevant to the lung and/or tools that are generally used in such procedure. In addition, knowledge of the procedure type better enables other image fusion algorithms that inform tumor location and staple line placement, for example.

In various aspects, knowledge of surgical table position and/or insufflation pressure can be used by a control circuit executing one or more aspects of the process 4100 to establish a baseline position of a target anatomical organ and/or relevant anatomical structures identified from visualization data. Motion of the surgical table (e.g., moving the patient from a flat position to a reverse Trendelenburg position) can cause deformation of anatomical structures, which can be tracked, and compared to a baseline, to continuously inform target organ and/or relevant anatomical structures locations and states. Likewise, changes in insufflation pressure within a body cavity can interfere with baseline visualization data of a target organ and/or relevant anatomical structures within the body cavity.

A control circuit (e.g. control circuit 132, 400, 410, 420, 602, 622, 2108, 4620) may execute one or more aspects of a process that derives baseline visualization data of a target organ and/or relevant anatomical structures of a patient on a surgical table during a surgical procedure, determines a change in the surgical table position, and re-derives the baseline visualization data of the target organ and/or the relevant anatomical structures of the patient in the new position.

Likewise, a control circuit (e.g. control circuit 132, 400, 410, 420, 602, 622, 2108, 4620) may execute one or more aspects of a process that derives baseline visualization data of a target organ and/or relevant anatomical structures of a patient on a surgical table during a surgical procedure, determines a change in insufflation pressure in the patient's body cavity, and re-derives the baseline visualization data of the target organ and/or the relevant anatomical structures of the patient under the new insufflation pressure.

In various instances, the control circuit executing one or more aspects of the process 4100 may couple identified anatomical structures to the virtual 3D construct by overlaying landmarks or signs onto the virtual 3D construct of the organ to indicate positions of the anatomical structures, as illustrated in FIG. 28. The control circuit may also cause user defined structures and tissue planes to be overlaid onto the virtual 3D construct. In various aspects, a hierarchy of tissue types can be established to organize the anatomical structures identified on the virtual 3D construct. Table 1, which is provided below, sets forth example hierarchies for the lung and the stomach.

| ORGAN | TIER 1 | TIER 2 | TIER 3 |
|---|---|---|---|
| Lung | Left Lung | Left upper lobe | Segments in the left upper lobe, major vessels/airways |
| Stomach | Stomach | Fundus, antrum, pylorus | Angle of His, Angularis Incisura, Greater/Lesser Curvature |

In various aspects, relevant anatomical structures that are identified on a virtual 3D construct can be renamed and/or repositioned by a user to correct errors or for preference. In at least one example, corrections can be voice activated. In at least one example, corrections are recorded for future machine learning.

Further to the above, a control circuit (e.g. control circuit 132, 400, 410, 420, 602, 622, 2108, 4620) executing one or more aspects of the process 4100 may overlay 4107 a surgical procedure layout plan (e.g. layout plan 4120) onto the virtual 3D construct of the target organ (e.g. stomach 4110). In at least one example, the virtual 3D construct is displayed on a separate screen of the visualization system from the screen displaying the live feed/view of the surgical field. In another example, one screen may alternate displaying the live feed of the surgical field and the 3D construct. In such example, a user can use any suitable input device to alternate between the two views.

In the example illustrated in FIG. 28, the control circuit has determined that the surgical procedure is a sleeve gastrectomy procedure, and that the target organ is the stomach. In an initial scan of the abdominal cavity, the control circuit identifies the stomach, liver, spleen, greater curvature of the stomach, and pylorus using visualization data such as, for example, structured light data and/or spectral data. This is informed by knowledge of the procedure and the structures of interest.

Visualization data such as, for example, structured light data and/or spectral data can be utilized by the control circuit to identify the stomach 4110, liver, and/or the spleen by comparing current structured light data with stored structured light data previously associated with such organs. In at least one example, a control circuit (e.g. control circuit 132, 400, 410, 420, 602, 622, 2108, 4620) can utilize structured light data that represent signature anatomical contours of an organ and/or spectral data that represent signature subsurface tissue characteristics to identify anatomical structures relevant to a surgical procedure layout plan (e.g. layout plan 4120).

In at least one example, visualization data could be utilized to identify the pyloric vein 4112, which indicates the position 4113 of the pylorus 4131, identify the gastricomental vessel 4114, which indicates the position 4115 of the greater curvature of the stomach 4110, identify the bend 4116 in the right gastric vein, which indicates the position 4117 of the angle of incisura 4132, and/or identify a position 4119 of the Angle of His 4121. The control circuit may assign landmarks to one or more of the identified position. In at least one example, as illustrated in FIG. 28 the control circuit causes the visualization system to overlay landmarks onto the positions 4113, 4117, 4119 on a virtual 3D construct of stomach 4110 generated using visualization data, as described above. In various aspects, the landmarks can be synchronously overlaid onto the virtual 3D construct and the surgical field views to allow the user to switch between the views without losing sight of the landmarks. The user may zoom out in the view of the screen displaying the virtual 3D construct to show the overall layout plan or may zoom in to show a portion analogous to the surgical field view. The control circuit may continuously track and update the landmarks.

In a sleeve gastrectomy, the surgeon typically staples stomach tissue at, or about, 4 cm from the pylorus. Prior to stapling, an energy device is introduced into the abdominal cavity of the patient in the beginning of the sleeve gastrectomy procedure to dissect the gastroepiploic artery and omentum away from the greater curvature at, or about, 4 cm from the pylorus. A control circuit that has identified the position 4113, as described above, may automatically cause an overlay of an end effector of the energy device at, or about, 4 cm from the position 4113. The overlay of the end effector of the energy device, or any suitable landmark, at, or about, 4 cm from the pylorus identifies a starting position of the sleeve gastrectomy.

As the surgeon dissects along the greater curvature of the stomach, the control circuit causes the landmark at position 4113 and/or the overlaid end effector of the energy device to be removed. As the surgeon approaches the spleen, a distance indicator is automatically overlaid onto the virtual 3D construct view and/or the surgical field view. The control circuit may cause the distance indicator to identify a 2 cm distance from the spleen. The control circuit may cause the distance indicator to flash and/or change colors when the dissection path reaches, or is about to reach, 2 cm from the spleen, for example. The distance indicator overlay remains until the user reaches to the position 4119 at the Angle of His 4121.

Referring to FIG. 30, once a surgical stapler is introduced into the abdominal cavity, the control circuit may utilize visualization data to identify the pylorus 4131, Angular Incisura 4132, greater curvature 4133 of the stomach 4110, lesser curvature 4134 of the stomach 4110, and/or other anatomical structure relevant to the sleeve gastrectomy procedure. An overlay of a bougie can be shown as well. Introduction of a surgical instrument into a body cavity (e.g. introduction of the surgical stapler into the abdominal cavity), can be detected by a control circuit from visualization data indicative of visual cues on the end effector, such as distinctive colors, signs, and/or shapes. The control circuit can identify the surgical instrument in a database storing such visual cues and corresponding visual cues. Alternatively, the control circuit may prompt a user to identify the surgical instrument inserted into the body cavity. Alternatively, a surgical trocar facilitating access to the body cavity may include one or more sensors for detecting a surgical instrument inserted therethrough. In at least one example, the sensors comprise an RFID reader configured to identify the surgical instrument from an RFID chip on the surgical instrument.

In addition to the landmarks identifying relevant anatomical structures, the visualization system may also overlay a procedure layout plan 4135, which can be in the form a recommended treatment path, onto the 3D critical structure and/or onto the surgical field view. In the example of FIG. 30, the surgical procedure is a sleeve gastrectomy, and the procedure layout plan 4135 is in the form of three resection paths 4136, 4137, 4138 and corresponding outcome volumes of the resulting sleeves.

As illustrated in FIG. 30, distances (a, $a_1$, $a_2$) from the pylorus 4131 to starting points for making the sleeves. Each starting point yields a different sleeve size (e.g. 400 cc, 425 cc, 450 cc for the starting points 4146, 4147, 4148, at distances a, $a_1$, $a_2$ from pylorus 4131, respectively). In one example, the control circuit prompts the user to enter a size selection and, in response, present a procedure layout plan, which can be in the form of a resection path, which yields the selected sleeve size. In another example, as illustrated in FIG. 30, the control circuit presents a plurality of resection paths 4136, 4137, 4138 and corresponding sleeve sizes. The user may then select one of the proposed resection paths 4136, 4137, 4138 and, in response, the control circuit removes the unselected resection paths.

In yet another example, the control circuit allows the user to make adjustments to a proposed resection path on a screen showing the resection path overlaid onto the virtual 3D construct and/or the surgical field. The control circuit may calculate a sleeve size based on the adjustments. Alternatively, in another example, the user is permitted to select a starting point, for forming the sleeve, at a desired distance from the pylorus 4131. In response, the control circuit calculates a sleeve size based on the selected starting point.

Presenting resection paths can be achieved by causing the visualization system to overlay the resection paths onto the virtual 3D construct view and/or the surgical field view, for example. Conversely, removing proposed resection paths can be achieved by causing the visualization system to remove the overlay of such resection paths from the virtual 3D construct view and/or the surgical field view.

Referring still to FIG. 30, in certain examples, once an end effector of a surgical stapler clamps the stomach tissue between a starting point, selected from proposed starting points 4146, 4147, 4147, and an end position 4140, at a predefined distance from the Angle of incisura 4132, the control circuit presents information about the clamping and/or firing the surgical stapler. In at least one example, as illustrated in FIG. 24, a composite data set 4012 from the visualization data 4010 and the instrument data 4011 can be displayed. Additionally, or alternatively, FTC and/or FTF values can be displayed. For example, a current value of FTC—represented by a circle 4020—can be depicted in real time against a gauge 4021 with an indicator 4022 representing a best practice FTC. Likewise, a current value of FTF—represented by a circle 4023—can be depicted against a gauge 4024 with an indicator 4025 representing a best practice FTF.

After the surgical stapler is fired, recommendations for new cartridge selections can be presented onto the screen of the surgical stapler or any of the screens of the visualization system, as described below in greater detail. When the surgical stapler is removed from the abdominal cavity, reloaded with a selected staple cartridge, and reintroduced into the abdominal cavity, distance indicators—identifying a constant distance (d) from a plurality of points along the lesser curvature 4134 of the stomach 4110 to the selected resection path—are overlaid onto the virtual 3D construct view and/or the surgical field view. To ensure a proper orientation of the end effector of the surgical stapler, the distance from the target of the distal end of the end effector of the surgical stapler, as well as the distance from the proximal end to the previously fired staple lines are overlaid onto the virtual 3D construct view and/or the surgical field view. This process is repeated until the resection is complete.

One or more of the distances proposed and/or calculated by the control circuit can be determined based on stored data. In at least one example, the stored data includes preoperative data, user preference data, and/or data from previously performed surgical procedures by the user or other users.

Referring to FIG. 31, a process 4150 depicting a control program or a logic configuration for proposing resection paths for removing a portion of an anatomical organ, in accordance with at least one aspect of the present disclosure. The process 4150 identifies 4151 an anatomical organ targeted by the surgical procedure, identifies 4152 anatomical structures of the anatomical organ which are relevant to the surgical procedure, and proposes 4153 surgical resection paths for removing a portion of the anatomical organ by the surgical instrument, as described in greater detail elsewhere herein in connection with the process 4100. The surgical resection paths are determined based on the anatomical structures. In at least one example, the surgical resection path comprise different starting points.

One or more aspects of the process 4150 can be executed by one or more of the control circuits (e.g. control circuit 132, 400, 410, 420, 602, 622, 2108, 4620) described by the present disclosure. In at least one example, one or more aspects of the process 4150 are executed by a control circuit (e.g. control circuit 400 of FIG. 2A) that includes a processor and a memory storing a set of computer-executable instructions that, when executed by the processor, cause the processor to perform the one or more aspects of the process 4150. Additionally, or alternatively, one or more aspects of the process 4150 can be executed by a combinational logic circuit (e.g. control circuit 410 of FIG. 2B) and/or a sequential logic circuit (e.g. control circuit 420 of FIG. 2C).

Furthermore, the process 4150 can be executed by any suitable circuitry with any suitable hardware and/or software components that may be located in or associated with various suitable systems described by the present disclosure.

Referring to FIGS. 32A-32D, a control circuit (e.g. control circuit 132, 400, 410, 420, 602, 622, 2108, 4620) executing on or more aspects of the process 4100 or the process 4150 may utilize dynamic visualization data to update or modify a surgical procedure layout plan in real time during implementation. In at least one example, the control circuit modifies a set resection path (FIG. 32B) for removing a portion of an organ or an abnormality (e.g. a tumor or region) by a surgical instrument to an alternative resection path (FIG. 32D) based on the dynamic visualization data from one or more imaging devices of a visualization system (e.g. visualization system 100, 160, 500, 2108) tracking progress of the tissue being resected and surrounding tissue. The resection path modification can be triggered by a shift in the position of a critical structure (e.g. a blood vessel) into the resection path. For instance, the tissue resection process can sometimes lead to tissue inflammation that changes the tissue shape and/or volume, which can cause a critical structure (e.g. a blood vessel) to shift position. Dynamic visualization data enable the control circuit to detect position and/or volume changes of critical structures and/or relevant anatomical structure near a set resection path. If the changes in position and/or volume cause the critical structures to shift into, or within a safe margin from, the resection path, the control circuit modifies the set resection path by selecting, or at least recommending, an alternative resection path of the surgical instrument.

FIG. 32A illustrates a live view 4201 of a surgical field on a screen 4230 of the visualization system. A surgical instrument 4200 is introduced into the surgical field to remove a target region 4203. An initial plan layout 4209 for removing the region is overlaid onto the live view 4201, as illustrated in the expanded view of the region 4203 in FIG. 32B. The region 4203 is surrounded by critical structures 4205, 4206, 4207, 4208. The initial plan layout 4209, as illustrated in FIG. 32B, extends a resection path around the region 4203 at a predefined safe margin from the region 4203. The resection path avoids crossing over or passing through a critical structure by extending either on the outside (e.g. critical structure 4208) or on the inside (e.g. critical structure 4206) of the critical structure. As described above, the initial plan layout 4209 is determined by the control circuit based on visualization data from visualization system.

FIG. 32C illustrates a live view 4201' of the surgical field on the screen 4230 of the visualization system at a later time (00:43). An end effector 4202 of the surgical instrument 4200 resects tissue along the predefined resection path defined by the layout plan 4209. A volume change of tissue including the region 4203 due tissue inflammation, for example, causes critical structures 4206 and 4208 to be shifted into the predefined resection path. In response, the control circuit proposes an alternative resection path 4210 that navigates around the critical structures 4206, 4208, which protects the critical structures 4206, 4208 from being damaged, as illustrated in FIG. 32D. In various examples, alternative resection paths can be proposed to optimize the amount of healthy tissue that would remain and provide user with guidance to ensure they did not hit critical structures which would minimize bleeding and, therefore, reducing surgery time and pressure of dealing with unintended situations, while balancing that against the impacts on remaining organ volume.

In various aspects, a control circuit executing one or more aspects of one or more of the processes described by the present disclosure may receive and/or derive visualization data from multiple imaging devices of a visualization system. The visualization data facilitates tracking of critical structures that are outside the live view of the surgical field. Common landmarks can allow the control circuit to consolidate the visualization data from multiple imaging devices of the visualization system. In at least one example, secondary tracking of critical structures outside a live view of the surgical filed, for example, could be achieved through a secondary imaging source, calculation of scope movement, or through pre-established beacons/landmarks that are measure by a second system.

Referring generally to FIGS. 33-35, a logic flow diagram of a process 4300 depicts a control program or a logic configuration for presenting, or overlaying, parameters of a surgical instrument onto, or near, a proposed surgical resection path, in accordance with at least one aspect of the present disclosure. The process 4300 is generally executed during a surgical procedure and includes identifying 4301 an anatomical organ targeted by the surgical procedure, identifying 4302 anatomical structures relevant to the surgical procedure from visualization data from at least one imaging device, and proposing 4303 a surgical resection path for removing a portion of the anatomical organ by a surgical instrument. In at least one example, the surgical resection path is determined based on the anatomical structures. The process 4300 further includes presenting 4304 parameters of the surgical instrument in accordance with the surgical resection path. Additionally, or alternatively, the process 4300 further includes adjusting 4305 parameters of the surgical instrument in accordance with the surgical resection path.

One or more aspects of the process 4300 can be executed by one or more of the control circuits (e.g. control circuit 132, 400, 410, 420, 602, 622, 2108, 4620) described by the present disclosure. In at least one example, one or more aspects of the process 4300 are executed by a control circuit (e.g. control circuit 400 of FIG. 2A) that includes a processor and a memory storing a set of computer-executable instructions that, when executed by the processor, cause the processor to perform the one or more aspects of the process 4030. Additionally, or alternatively, one or more aspects of the process 4300 can be executed by a combinational logic circuit (e.g. control circuit 410 of FIG. 2B) and/or a sequential logic circuit (e.g. control circuit 420 of FIG. 2C). Furthermore, the process 4300 can be executed by any suitable circuitry with any suitable hardware and/or software components that may be located in or associated with various suitable systems described by the present disclosure.

In various examples, a control circuit (e.g. control circuit 132, 400, 410, 420, 602, 622, 2108, 4620) executing one or more aspects of the process 4300 may identify 4301 an anatomical organ targeted by the surgical procedure, identify 4302 anatomical structures relevant to the surgical procedure from visualization data from at least one imaging device of a visualization system (e.g. visualization system 100, 160, 500, 2108), and/or propose 4303 a surgical resection path for removing a portion of the anatomical organ by a surgical instrument (e.g. surgical instrument 4600), as described elsewhere herein in connection with the processes 4150 (FIG. 31), 4100 (FIG. 29). Furthermore, the control circuit executing one or more aspects of the process 4300 may propose or recommend one or more parameters of the surgical instrument in accordance with the proposed 4303 surgical resection path. In at least one example, the control circuit presents 4304 the recommended parameters of the surgical instrument by overlaying such parameters onto, or near, the proposed surgical path, as illustrated in FIGS. 34 and 35.

FIG. 34 illustrates a virtual 3D construct 4130 of a stomach of a patient undergoing a sleeve gastrectomy performed using a surgical instrument 4600, in accordance with at least one aspect of the present disclosure. As described in greater detail in connection with FIG. 28, for example, various elements of a visualization system (e.g. visualization system 100, 160, 500, 2108) such as, for example, a structured light projector 706 and a camera 720 can be used to generate visualization data to create the virtual 3D construct 4130. Relevant anatomical structures (e.g. pylorus 4131, Angular Incisura 4132, Angle of His 4121) are identified from visualization data from one or more imaging devices of the visualization system. In at least one example, landmarks are assigned to positions 4113, 4117, 4119 of such anatomical structures by overlaying the landmarks onto the virtual 3D construct 4130.

In addition, a surgical resection path 4312 is proposed 4303 based on the identified anatomical structures. In at least one example, the control circuit overlays the surgical resection path 4312 onto the virtual 3D construct 4130, as illustrated in FIG. 34. As described in greater detail elsewhere herein, adjustments can be automatically made to proposed surgical paths based on desired volume outputs. In addition, adjustments can be automatically made to projected margins based on critical structures and/or tissue abnormalities automatically identified by the control circuit from the visualization data.

In various aspects, the control circuit executing at least one aspect of the process 4300 presents parameters 4314 of the surgical instrument that are selected in accordance with the proposed 4303 surgical resection path 4312. In the example illustrated in FIG. 34, the parameters 4314 are indicative of staple cartridges automatically selected for use with the surgical instrument 4600 in performing the sleeve gastrectomy based on the proposed 4303 surgical resection path. In at least one example, the parameters 4314 comprise at least one of a staple cartridge size, a staple cartridge color, a staple cartridge type, and a staple cartridge length. In at least one example, the control circuit presents 4304 the parameters 4314 of the surgical instrument 4600 by overlaying such parameters onto, or near, the proposed 4303 surgical resection path 4312, as illustrated in FIGS. 34 and 35.

In various aspects, the control circuit executing at least one aspect of the process 4300 presents tissue parameters 4315 along one or more portions of the surgical resection path 4312. In the example illustrated in FIG. 34, the tissue parameters 4315 are tissue thicknesses presented by displaying a cross-section taken along the line A-A, which represents tissue thicknesses along at least a portion of the surgical resection path 4312. In various aspects, the staple cartridges utilized by the surgical instrument 4600 can be selected in accordance with the tissue parameters 4315. For example, as illustrated in FIG. 34, a black cartridge, which comprises a larger staple size, is selected for use with the thicker muscle tissue of the Antrum, and a green cartridge, which comprises a smaller staple size, is selected for use with the heart muscle tissue of the body and fundus portions of the stomach.

The tissue parameters 4315 include at least one of a tissue thickness, a tissue type, and a volume outcome of the sleeve resulting from the proposed surgical resection path 4312. Tissue parameters 4315 can be derived from previously captured CT, ultrasound, and/or MRI images of the organ of the patient and/or from previously known average tissue thicknesses. In at least one example, the surgical instrument 4600 is an intelligent instrument (similar to the intelligent instrument 2112), and the tissue thicknesses and/or the selected staple cartridge information are transmitted to the surgical instrument 4600 for optimization of closure setting, firing settings, and/or any other suitable surgical instrument settings. In one example, the tissue thickness and/or the selected staple cartridge information can be transmitted to the surgical instrument 4600 from a surgical hub (e.g. surgical hub 2106, 2122) in communication with a visualization system (e.g. visualization system 100, 160, 500, 2108) and the surgical instrument 4600, as described in connection with FIGS. 17-19.

In various examples, the control circuit executing at least one aspect of the process 4300 proposes an arrangement 4317 of two or more staple cartridge sizes (e.g. 45 mm and 60 mm) in accordance with determined tissue thicknesses along at least a portion of the surgical resection path 4312. Furthermore, as illustrated in FIG. 35, the control circuit may further present the arrangement 4317 along the proposed 4303 surgical resection path 4312. Alternatively, the control circuit can present a suitable arrangement 4317 along a user-selected surgical resection path. The control circuit can determine tissue thicknesses along the user-selected resection path, as described above, and propose a staple cartridge arrangement in accordance with the tissue thicknesses.

In various aspects, the control circuit executing one or more aspects of the process 4300 may propose a surgical resection path, or optimize a selected surgical resection path, to minimize the number of staple cartridges in the staple cartridge arrangement 4317 without compromising the size of the resulting sleeve beyond a predetermined threshold. Reducing the number of spent cartridges reduces procedure time and cost, and reduces patient trauma.

Still referring to FIG. 35, the arrangement 4317 comprises a first staple cartridge 4352 and a last staple cartridge 4353 defining the beginning and end of the surgical resection path 4312. Where only a small portion of a last staple cartridge 4353 of a proposed staple cartridge arrangement 4317 is needed, the control circuit may adjust the surgical resection path 4312 to eliminate the need for the last staple cartridge 4353 without compromising the size of the resulting sleeve beyond a predetermined threshold.

In various examples, the control circuit executing at least one aspect of the process 4300 presents a virtual firing of the proposed staple cartridge arrangement 4317, which virtually separates the virtual 3D construct 4130 into a retained portion 4318 and a removed portion 4319, as illustrated in FIG. 35. The retained portion 4318 is a virtual representation of a sleeve that would result from implementation of the proposed surgical resection path 4312 by firing the staple cartridge arrangement 4317. The control circuit may further determine an estimate volume of the retained portion 4318 and/or the removed portion 4319. The volume of the retained portion 4318 represents the volume of the resulting sleeve. In at least one example, the volume of the retained portion 4318 and/or the removed portion 4319 is derived from the visualization data. In another example, the volume of the retained portion 4318 and/or the removed portion 4319 is determined from a database storing retained volumes, removed portion volumes, and corresponding surgical resection paths. The database can be constructed from surgical procedures previously performed on organs with the same, or at least similar, dimensions, which have been resected using the same, or at least similar, resection paths.

In various examples, a combination of predetermined average tissue thickness data based on the situational awareness of the organ, as described above in greater detail, in combination with volumetric analysis from the visualization source and CT, MRI, and/or ultrasound secondary imaging, if available for the patient, can be utilized to select a first staple cartridge for the arrangement 4317. Firings of subsequent staple cartridges in the arrangement 4317 can use instrument data from pervious firings, in addition to the visualization data, to optimize the firing parameters. The instrument data that could be used to supplement volume measurements include FTF, FTC, current draw by motors driving the firing and/or closure, end-effector closure gap, rate of firing, tissue impendence measurements across the jaws, and/or wait or pause time during use of the surgical instrument, for example.

In various examples, visualization data such as, for example, structured light data can be used to track surface geometry changes in tissue being treated by a surgical instrument (e.g. surgical instrument 4600). Additionally, visualization data such as, for example, spectral data can be used to track critical structures below the tissue surface. The structured data and/or the spectral data can be used to maintain a set instrument-tissue contact throughout the tissue treatment.

In at least one example, the end effector 4642 of the surgical instrument 4600 can be used to grasp tissue between its jaws. Once a desired tissue-instrument contact is confirmed by a user input, for example, the visualization data for the end effector and surrounding tissue, which are associated with the desired tissue-instrument contact, can be used to automatically maintain the desired tissue-surface contact throughout at least a portion of the tissue treatment. The desired tissue-surface contact can be automatically maintained by, for example, slight manipulations to position, orientation, and/or FTC parameters of the end effector 4642.

In the event the surgical instrument 4600 is a hand-held surgical instrument, position and/or orientation manipulations could be provided to a user in the form of instructions that could be presented on a display 4625 (FIG. 22) of the surgical instrument 4600, for example. An alert could also be issued by the surgical instrument 4600 when user manipulations are needed to reestablish the desired tissue-surface contact. Meanwhile, non-user manipulations such as, for example, manipulations to the FTC parameters and/or articulation angle can be communicated to the controller 4620 of the surgical instrument 4600 from the surgical hub 2106 or the visualization system 2108, for example. The controller 4620 could then cause the motor driver 4626 to implement the desired manipulations. In the event the surgical instrument 4600 is a surgical tool coupled to a robotic arm of a robotic system 2110, position and/or orientation manipulations could be communicated to the robotic system 2110 from the surgical hub 2106 or the visualization system 2108, for example.

Referring primarily to FIGS. 36A-36C, a firing of a surgical instrument 4600 loaded with a first staple cartridge 4652 in the staple cartridge arrangement 4317 is illustrated. In a first stage, as illustrated in FIG. 36A, a first landmark 4361 and a second landmark 4362 are overlaid onto the surgical resection path 4312. The landmarks 4361, 4362 are spaced apart a distance (d1) defined by the size (e.g. 45) of the staple cartridge 4652 which represents the length of a staple line 4363 to be deployed by the staple cartridge 4652 onto the surgical resection path 4312. The control circuit executing one or more aspects of the process 4300 can employ visualization data, as described in greater detail elsewhere herein, to overlay the landmarks 4361, 4362 onto the surgical resection path 4312, and continuously track and update their positions with respect to predetermined critical structures such as, for example, anatomical structures 4364, 4365, 4366, 4367.

During firing, as illustrated in FIG. 36B, staples of the staple line 4363 are deployed into tissue and the cutting member 4645 is advanced to cut the tissue along the surgical resection path 4312 between the landmarks 4361, 4362. In various instances, the advancement of the cutting member 4645 causes the tissue being treated to stretch and/or shift. Tissue stretching and/or shifting beyond a predetermined threshold indicates that the cutting member 4645 is moving too fast through the tissue being treated.

FIG. 37 is a logic flow diagram of a process 4170 depicting a control program or a logic configuration for adjusting a firing speed of a surgical instrument to address tissue stretching/shifting during firing. The process 4170 includes monitoring 4171 a tissue stretch/shift during firing of the surgical instrument and adjusting 4173 firing parameters if 4172 the tissue stretch/shift is greater than or equal to a predetermined threshold.

One or more aspects of the process 4170 can be executed by one or more of the control circuits (e.g. control circuit 132, 400, 410, 420, 602, 622, 2108, 4620) described by the present disclosure. In at least one example, one or more aspects of the process 4170 are executed by a control circuit (e.g. control circuit 400 of FIG. 2A) that includes a processor and a memory storing a set of computer-executable instructions that, when executed by the processor, cause the processor to perform the one or more aspects of the process 4170. Additionally, or alternatively, one or more aspects of the process 4170 can be executed by a combinational logic circuit (e.g. control circuit 410 of FIG. 2B) and/or a sequential logic circuit (e.g. control circuit 420 of FIG. 2C). Furthermore, the process 4170 can be executed by any suitable circuitry with any suitable hardware and/or software components that may be located in or associated with various suitable systems described by the present disclosure.

In various examples, a control circuit (e.g. control circuit 132, 400, 410, 420, 602, 622, 2108, 4620) executing one or more aspects of the process 4170 monitors 4171 tissue stretch/shift during firing of the surgical instrument 4600 using visualization data from a visualization system (e.g. visualization system 100, 160, 500, 2108). In the example illustrated in FIG. 36B, a tissue stretch/shift (d) is monitored 4171 by tracking distortions in a structured light grid projected onto the tissue during firing and/or tracking the landmarks 4364, 4365, 4366, 4367, which represent positions of adjacent anatomical structure, using visualization data. Additionally, or alternatively, the tissue stretch (d) can be monitored 4171 by tracking the position of the landmark 4362 during firing. In the example of FIG. 36B, tissue stretch/shift (d) is the difference between the distance (d1) between the landmarks 4361, 4362 during firing and a distance (d2) between the landmarks 4361, 4362 during the firing. In any event, if 4172 the tissue stretch/shift (d) is greater than or equal to a predetermined threshold, the control circuit adjusts 4173 the firing parameters of the surgical instrument 4600 to reduce the tissue stretch/shift (d). For example, the control circuit may cause the controller 4620 to reduce the speed of the firing motor drive assembly 4604 by reducing current draw of the firing motor 4602, for example, which reduces the speed of advancement of the cutting member 4645. Additionally, or alternatively, the control circuit may cause the controller 4620 to pause the firing motor 4602 for a predetermined period of time to reduce the tissue stretch/shift (d).

Post firing, as illustrated in FIG. 36C, the jaws of the end effector 4642 are unclamped, and the stapled tissue shrinks due to the fired staples of the staple line 4363. FIG. 36C illustrates the projected staple line length defined by the distance (d1) and an actual staple line defined by a distance (d3) less than the distance (d1). The difference between the distances d1, d2 represents the shrinkage/shifting distance (d').

FIG. 38 is a logic flow diagram of a process 4180 depicting a control program or a logic configuration for adjusting a proposed staple cartridge arrangement along a proposed surgical resection path. The process 4180 includes monitoring 4081 stapled tissue shrinkage/shifting along a proposed surgical resection path following the firing of a staple cartridge of the proposed arrangement, and adjusting subsequent staple cartridge positions of the proposed arrangement along the proposed surgical resection path.

One or more aspects of the process 4180 can be executed by one or more of the control circuits (e.g. control circuit 132, 400, 410, 420, 602, 622, 2108, 4620) described by the present disclosure. In at least one example, one or more aspects of the process 4180 are executed by a control circuit (e.g. control circuit 400 of FIG. 2A) that includes a processor and a memory storing a set of computer-executable instructions that, when executed by the processor, cause the processor to perform the one or more aspects of the process 4180. Additionally, or alternatively, one or more aspects of the process 4180 can be executed by a combinational logic circuit (e.g. control circuit 410 of FIG. 2B) and/or a sequential logic circuit (e.g. control circuit 420 of FIG. 2C). Furthermore, the process 4180 can be executed by any suitable circuitry with any suitable hardware and/or software components that may be located in or associated with various suitable systems described by the present disclosure.

In various examples, a control circuit (e.g. control circuit 132, 400, 410, 420, 602, 622, 2108, 4620) executing one or more aspects of the process 4180 monitors 4181 shrinkage/shifting of a stapled tissue along a proposed resection path 4312. In the example illustrated in FIG. 36C, a staple line 4363 is deployed into the tissue between the landmarks 4361, 4362 from a staple cartridge of the staple cartridge arrangement 4317. When the jaws of the end effector 4642 are unclamped, the stapled tissue shrinks/shifts a distance (d'). The distance (d') is the difference between the distance (d1) between the landmarks 4361, 4362 pre-firing, which represents a length of the staple line 4361 proposed by the arrangement 4317, and a distance (d3) representing the actual length of the staple line 4363.

To avoid gaps between consecutive staple lines, the control circuit adjusts subsequent staple cartridge positions of the proposed arrangement 4317 along the proposed surgical resection path 4312. For example, as illustrated in FIG. 36C an originally proposed staple line 4368 is removed and replaced by an updated staple line 4369 that extends through, or covers, the gap defined by the distance (d'). In various aspects, a tissue shrinkage/shift (d') is monitored 4181 by tracking distortions in a structured light grid projected onto the tissue after the jaws of the end effector 4642 are unclamped and/or tracking the landmarks 4364, 4365, 4366, 4367, which represent positions of adjacent anatomical structure, using visualization data. Additionally, or alternatively, the tissue shrinkage distance (d') can be monitored 4181 by tracking the position of the landmark 4362.

In various aspects, it may be desirable to corroborate visualization data derived from a surgical visualization system (e.g. visualization system 100, 160, 500, 2108) using non-visualization data from non-visualization systems and vice versa. In one example, a non-visualization system can include a ventilator, which can be configured to measure non-visualization data, such as volume, pressure, partial pressure of carbon dioxide ($PCO_2$), partial pressure of oxygen ($PO_2$), etc., of a patient's lungs. Corroborating visualization data with non-visualization data provides a clinician with greater confidence that the visualization data derived from the visualization system is accurate. In addition, corroborating the visualization data with the non-visualization data allows a clinician to better identify post-operative complications, as well as determine the overall efficiency of the organ, as will described in greater detail below. The corroboration may also be helpful in segmentectomy or complicated lobectomies without fissures.

In various aspects, a clinician may need to resect a portion of a patient's organ to remove a critical structure, such as a tumor, and/or other tissue. In one example, the patient's organ can be the right lung. A clinician may need to resect a portion of the patient's right lung in order to remove unhealthy tissue. However, the clinician may not want to remove too much of the patient's lung during the surgical procedure in order to ensure the lung's functionality is not too compromised. The lung's functionality can be assessed based on peak lung volume per breath, which represents peak lung capacity. In determining how much of the lung can be safely removed, the clinician is limited by a predetermined peak lung-capacity reduction beyond which the lung loses its viability, necessitating a full organ resection.

In at least one example, the surface area and/or volume of the lung is estimated from visualization data from surgical visualization system (e.g. visualization system 100, 160, 500, 2108). The lung surface area and/or volume can be estimated at peak lung capacity, or peak lung volume per breath. In at least one example, the lung surface area and/or volume can be estimated at multiple points throughout the inhalation/exhalation cycle. In at least one aspect, prior to resection of a portion of the lung, visualization data and non-visualization data can be utilized to correlate the surface area and/or volume of the lung determined by the visualization system with lung capacity as determined by a ventilator. Correlation data can be employed in developing a mathematical relation between the surface area and/or volume of the lung, as derived from visualization data, and the lung capacity, as determined by a ventilator, for example. The relation can be employed in estimating the size of a lung portion that could be removed while maintaining the peak lung-capacity reduction at a value less than or equal to a predetermined threshold that sustains the viability of the lung.

FIG. 39 illustrates a logic flow diagram of a process 4750 for proposing a surgical resection of an organ portion, in accordance with at least one aspect of the present disclosure. The process 4750 is generally executed during a surgical procedure. The process 4750 may include proposing 4752 a portion of an organ to resect based on visualization data from the surgical visualization system, wherein resection of the portion is configured to yield an estimated capacity reduction of the organ. The process 4750 may further include determining 4754 a first value of a non-visualization parameter of the organ prior to resection of the portion and determining 4756 a second value of the non-visualization parameter of the organ after resection of the portion. Additionally, in certain examples, the process 4750 may further include corroborating 4758 the predetermined capacity reduction based on the first value of the non-visualization parameter and the second value of the non-visualization parameter.

One or more aspects of the process 4750 can be executed by one or more of the control circuits (e.g. control circuit 132, 400, 410, 420, 602, 622, 2108, 4620) described by the present disclosure. In at least one example, one or more aspects of the process 4750 are executed by a control circuit (e.g. control circuit 400 of FIG. 2A) that includes a processor and a memory storing a set of computer-executable instructions that, when executed by the processor, cause the processor to perform the one or more aspects of the process 4750. Additionally, or alternatively, one or more aspects of the process 4750 can be executed by a combinational logic circuit (e.g. control circuit 410 of FIG. 2B) and/or a sequential logic circuit (e.g. control circuit 420 of FIG. 2C). Furthermore, one or more aspects of the process 4750 can be executed by any suitable circuitry with any suitable hardware and/or software components that may be located in or associated with various suitable systems described by the present disclosure.

In various aspects, the process 4750 can be implemented by a computer-implemented interactive surgical system 2100 (FIG. 19) that includes one or more surgical systems 2102 and a cloud-based system (e.g., the cloud 2104 that may include a remote server 2113 coupled to a storage device 2105). Each surgical system 2102 includes at least one surgical hub 2106 in communication with the cloud 2104 that may include a remote server 2113. The control circuit executing one or more aspects of the process 4750 can be a component of a visualization system (e.g. visualization system 100, 160, 500, 2108).

FIG. 41A illustrates a set of patient's lungs 4780. In one embodiment, a clinician can utilize an imaging device 4782 to emit 4784 a pattern 4785 of light onto the surface of the patient's right lung 4786, such as stripes, grid lines, and/or dots, to enable the determination of the topography or landscape of the surface of the patient's right lung 4786. The imaging device can be similar in various respects to imaging device 120 (FIG. 1). As described elsewhere herein, projected light arrays can be employed to determine the shape defined by the surface of the patient's right lung 4786, and/or motion of the patient's right lung 4786 intraoperatively. In one embodiment, the imaging device 4782 can be coupled to the structured light source 152 of control system 133. In one embodiment, a surgical visualization system, such as surgical visualization system 100, could utilize the surface mapping logic 136 of control circuit 133, described elsewhere herein, to determine the topography or landscape of the surface of the patient's right lung 4786.

A clinician may provide a type of procedure that is to be performed, such as an upper right lobectomy, to a surgical system, such as surgical system 2100. In addition to providing the surgical procedure to be performed, the clinician may provide the surgical system with a maximum desired capacity of the organ to be removed during the surgical procedure. Based on the visualization data obtained from the imaging device 4782, the type of surgical procedure to be performed, and the maximum desired capacity to be removed, the surgical system can propose a resection path 4788 to remove a portion of the right lung 4790 that satisfies all of the clinician's inputs. Other methods of proposing surgical resection paths are described elsewhere herein. Any number of additional parameters can be considered by the surgical system in order to propose the resection path 4788.

In various instances, it may be desirable to ensure that the volume of the organ resected yields the desired capacity reduction from the patient's organ. In order to corroborate that the volume resected yields the desired capacity reduction, non-visualization data from non-visualization systems can be utilized. In one embodiment, a ventilator can be utilized to measure peak lung capacity in a patient over time.

In at least one example, a clinician may utilize the surgical system 2100 in a surgical procedure to remove a lung tumor. The control circuit may identify the tumor from visualization data, as described above in connection with FIGS. 13A-13E and may propose a surgical resection path that provides a safe margin around the tumor, as described above in connection with FIGS. 29-38. The control circuit may further estimate a volume of the lung at peak lung capacity. A ventilator can be utilized to measure the peak lung capacity prior to the surgical procedure. Using a predetermined mathematical correlation between visually estimated lung volume and lung capacity as detected by the ventilator, the control circuit is able to estimate a peak lung-capacity reduction associated with removing a portion of the lung, which includes the tumor and a safe margin of tissue around it. If the estimated lung capacity reduction is beyond a predetermined safety threshold, the control circuit can alert the clinician and/or propose a different surgical resection path that yields a lesser reduction in the lung capacity.

FIG. 41C illustrates a graph 4800 measuring a patient's peak lung capacity over time. Prior to resection of the portion of organ ($t_1$), a ventilator can measure peak lung capacity. In FIG. 41C, at time $t_1$ prior to resection of the portion 4790, the peak lung capacity is measured as being 6 L. In the example described above where the surgical procedure to be performed is an upper right lobectomy, a clinician may desire to only remove a volume of the patient's lung that yields a predetermined capacity reduction such that the patient's ability to breath is not compromised. In one embodiment, a clinician may desire to remove a portion yielding up to about 17% reduction of the patient's peak lung capacity, for example. Based on the surgical procedure and the desired capacity reduction, the surgical system can propose a surgical resection path 4788 that achieves removal of the lung portion while maintain peak lung capacity at a value greater than or equal to 83% of the un-resected peak lung capacity.

Utilizing ventilator data, as shown in FIG. 41C, the clinician can monitor the patient's peak lung capacity over time, such as prior to section 4802 and after resection 4804 of the portion of the lung 4790. At time $t_2$, the portion of the lung 4790 is resected along the proposed resection path 4788. As a result, the peak lung capacity measured by the ventilator drops. A clinician can corroborate with the ventilator data (pre-resection peak lung volume 4802 and post resection peak lung volume 4804) to ensure that the volume of the lung resected yields the desired capacity reduction from the lungs. As shown in FIG. 41C, after resection, the peak lung capacity has dropped to 5 L, which is approximately a 17% drop in peak lung capacity, which is approximately the same as the desired reduction in capacity. Using the ventilator data, the clinician has greater confidence that the actual reduction in capacity is aligned with the desired reduction in capacity achieved by the proposed surgical resection path 4788. In other embodiments, where there is a discrepancy between the non-visualization data and the visualization data, such as a larger drop in peak lung capacity than expected (too much lung resected) or a smaller drop in peak lung capacity than expected (not enough lung resected), the clinician can determine if appropriate action should be taken.

Referring now to FIG. 41B, the patient's right lung 4792 is shown after resection of the portion 4790. After resection of the portion 4790, the clinician may have inadvertently caused an air leak 4794, which results in air leaking into the space between the lung 4794 and chest wall, resulting in a pneumothorax 4796. As a result of the aft leak 4794, the patient's peak lung volume per breath will steadily diminish over time as the right lung 4792 collapses, Dynamic surface area/volumetric analysis of the lung can be performed using the visualization data derived from a visualization system (e.g. visualization system 100, 160, 500, 2108) to detect an aft leak by visually tracking a change in the volume of the lung. The volume and/or surface area of the lung can be tracked visually at one or more points during the inhalation/exhalation cycle to detect a volume change indicative of the air leak 4794. In one embodiment, as discussed above, projected light arrays from the imaging device 4782 can be employed to monitor motion of the patient's right lung 4786 over time, such as monitoring a decrease in size. In another embodiment, the surgical visualization system could utilize surface mapping logic, such as surface mapping logic 136, to determine the topography or landscape of the surface of the patient's right lung 4786 and monitor changes in the topography or landscape over time.

In one aspect, the clinician can utilize the non-visualization system, such as the ventilator, to corroborate the reduction in volume detected by the visualization system. Referring again to FIG. 41C, as described above, a patient's peak lung capacity can be measured prior to resection of the portion of the lung 4802 and after resection of the portion to corroborate the desired reduction in capacity aligns with the actual reduction in capacity of the lung. In the example described above where an air leak inadvertently occurred, peak lung capacity may steadily decline over time 4806, In one instance, at time $t_2$ immediately after resection of the portion, a clinician may note the peak lung capacity has dropped from 6 L to 5 L, which is approximately aligned with the desired reduction in lung capacity. After resection of the portion, the surgical visualization system can monitor the patient's lung volume over time. If the surgical visualization system determines that there is a change in volume, the clinician can measure peak lung capacity again, such as at time $t_3$. At time $t_3$, the clinician may note that the peak lung capacity has dropped from 5 L to 4 L, which corroborates the data determined from the visualization system, which indicates that there may be an air leak in the right lung 4792.

In addition, the control circuit can be configured measure organ efficiency based on the visualization data and the non-visualization data. In one aspect, the organ efficiency can be determined by comparing visualization data to a difference in the non-visualization data before and after resection of the portion. In one example, the visualization system can generate the resection path to cause a 17% reduction in peak lung capacity. The ventilator can be configured to measure peak lung capacity before resection of the portion and after the resection of the portion. In the instance illustrated in FIG. 41C, there is approximately a 17% drop in peak lung capacity (6 L to 5 L). As there is a near 1:1 drop in actual lung capacity (17%) against desired lung capacity (17%), the clinician can determine that the lung is functionally efficient. In another example, the visualization system can generate the resection path to cause a 17% reduction in peak lung capacity. However, the ventilator may measure a drop in peak lung capacity that is greater than 17%, such as 25%, as an example. In this instance, the clinician can determine that the lung is not functionally efficient as resecting the portion of the lung resulted in a larger drop in peak lung capacity than would be expected.

FIG. 40 illustrates a logic flow diagram of a process 4760 for estimating a capacity reduction of an organ resulting from the removal of a selected portion of the organ, in accordance with at least one aspect of the present disclosure. The process 4760 is similar in many respects to the process 4750. Unlike the process 4750, however, the process 4760 relies on the clinician to select or propose a surgical resection path for removing a portion of an organ during a surgical procedure. The process 4760 includes receiving 4762 an input from a user indicative of a portion of an organ to resect. The process 4760 further includes estimating 4764 a capacity reduction of the organ that would result from removing the portion. In at least one example, the organ is a patient's lung, and the estimated 4762 capacity reduction is a reduction in the peak lung volume per breath of the patient's lung. Visualization data from a surgical visualization system (e.g. visualization system 100, 160, 500, 2108) can be employed to estimate the capacity reduction corresponding to removal of the portion. The process 4760 may further include determining 4766 a first value of a non-visualization parameter of the organ prior to resection of the portion and determining 4768 a second value of the non-visualization parameter of the organ after resection of the portion. Finally, the process 4760 may further include corroborating 4768 the estimated capacity reduction of the organ based on the first value of the non-visualization parameter and the second value of the non-visualization parameter.

One or more aspects of the process 4760 can be executed by one or more of the control circuits (e.g. control circuit 132, 400, 410, 420, 602, 622, 2108, 4620) described by the present disclosure. In at least one example, one or more aspects of the process 4760 are executed by a control circuit (e.g. control circuit 400 of FIG. 2A) that includes a processor and a memory storing a set of computer-executable instructions that, when executed by the processor, cause the processor to perform the one or more aspects of the process 4760. Additionally, or alternatively, one or more aspects of the process 4760 can be executed by a combinational logic circuit (e.g. control circuit 410 of FIG. 2B) and/or a sequential logic circuit (e.g. control circuit 420 of FIG. 2C). Furthermore, one or more aspects of the process 4760 can be executed by any suitable circuitry with any suitable hardware and/or software components that may be located in or associated with various suitable systems described by the present disclosure.

In various aspects, the process 4760 can be implemented by a computer-implemented interactive surgical system 2100 (FIG. 19) that includes one or more surgical systems 2102 and a cloud-based system (e.g., the cloud 2104 that may include a remote server 2113 coupled to a storage device 2105). Each surgical system 2102 includes at least one surgical hub 2106 in communication with the cloud 2104 that may include a remote server 2113. The control circuit executing one or more aspects of the process 4760 can be a component of a visualization system (e.g. visualization system 100, 160, 500, 2108).

In one instance, a clinician may provide an input to the surgical visualization system, such as surgical visualization system 2100, indicative of a portion of an organ to resect. In one instance, a clinician may draw a resection path on a virtual 3D construct of the organ, such as the virtual 3D construct generated 4104 during process 4100. In other instances, the visualization system can overlay a procedure layout plan, described in greater detail elsewhere herein, which can be in the form of a recommended treatment path. The recommended treatment path can based on a type of surgical procedure being performed. In one embodiment, the recommended treatment path can propose different starting points and propose different resection paths that the clinician can select between, similar to the resection paths 4146, 4147, 4148 described elsewhere herein. The proposed resection paths can be determined by the visualization system such that certain critical structures, such as arteries, are avoided. The clinician can select the proposed resection paths until a desired resection path to remove the portion of the organ is complete.

In one instance, the surgical visualization system can determine an estimated capacity reduction of the organ based on the selected resection path. After resecting the predetermined portion along the resection path, the clinician may desire to use non-visualization data to corroborate that the actual reduction in capacity corresponds to the estimated capacity reduction based on the visualization data. In one embodiment, this corroboration can be done using a similar procedure as described above in regard to process 4750 where the organ is a lung. The clinician can measure peak lung capacity before 4802 and after 4804 resection of the lung and compare the change in peak lung capacity to determine an actual drop in peak lung capacity. In one example, the surgical visualization system may estimate a 17% reduction in peak lung capacity based on the clinician's proposed resection path. Prior to resection, the clinician may note a peak lung capacity of 6 L (time $t_1$). After resection, the clinician may note a peak lung capacity of 5 L (time $t_2$), which is approximately a 17% drop in peak lung capacity. Using this non-visualization/ventilator data, the clinician has greater confidence that the actual reduction in capacity is aligned with the estimated reduction in capacity. In other instances, where there is a discrepancy between the non-visualization data and the visualization data, such as a larger drop in peak lung capacity than expected (too much lung resected) or a smaller drop in peak lung capacity than expected (not enough lung resected), the clinician can determine if appropriate action should be taken.

In addition, the control circuit can be configured to measure organ efficiency based on the visualization data and the non-visualization data. In one aspect, the organ efficiency can be determined by comparing visualization data to a difference in the non-visualization data before and after resection of the portion. In one example, the visualization system may estimate a 17% reduction in peak lung capacity based on the clinician's desired resection path. The ventilator can be configured to measure peak lung capacity before resection of the portion and after the resection of the portion. In the instance illustrated in FIG. 41C, there is approximately a 17% drop in peak lung capacity (6 L to 5 L). As there is a near 1:1 drop in actual lung capacity (17%) against the estimated lung capacity (17%), the clinician can determine that the lung is functionally efficient. In another example, the visualization system may estimate a 17% reduction in peak lung capacity based on the clinician's desired resection path. However, the ventilator may measure a drop in peak lung capacity that is greater than 17%, such as 25%, as an example. In this instance, the clinician can determine that the lung is not functionally efficient as resecting the portion of the lung resulted in a larger drop in peak lung capacity than would be expected.

As described above in regard to processes 4750, 4760, a clinician can corroborate visualization data with non-visualization data, such as by using a ventilator to measure peak lung volume before and after resection of a portion of the lung. Another example of corroborating visualization data with non-visualization data is through capnography.

FIG. 42 illustrates a graph 4810 measuring partial pressure of carbon dioxide ($PCO_2$) exhaled by a patient over time. In other instances, partial pressure of oxygen ($PO_2$) exhaled by a patient can be measured over time. The graph 4810 illustrates $PCO_2$ measured prior to resection 4812, immediately following resection 4814, and a minute after resection 4816. In FIG. 42, prior to resection 4812, $PCO_2$ is measured to be ~40 mmHg (at time $t_1$). In the examples described above where the surgical procedure to be performed is an upper right lobectomy, a visualization system may desire or estimate a 17% decrease in lung capacity. The $PCO_2$ levels measured by the ventilator can be used to corroborate this desired or estimated reduction in capacity.

Utilizing the ventilator data, as shown in FIG. 42, the clinician can monitor the patient's $PCO_2$ over time, such as prior to section 4812 and immediately after resection 4814 of the portion of the lung 4790. At time $t_2$, the portion of the lung 4790 has been resected, and as a result, the $PCO_2$ measured by the ventilator can drop 4818. A clinician can corroborate with the ventilator data (pre-resection 4812 $PCO_2$ (at $t_1$) and post resection 4814 $PCO_2$ (at $t_2$)) to ensure that the actual reduction in capacity of the lung aligns with the estimated or desired reduction in capacity of the lungs. As shown in FIG. 42, immediately after resection 4814 of the portion 4790, the $PCO_2$ drops 4812, which can be measured as an approximate 17% drop in $PCO_2$ (~33.2 mmHg). Using this non-visualization/ventilator data, the clinician has greater confidence that the actual reduction in capacity of the lung aligns with the desired or estimated reduction in capacity of the lung.

In other instances, the clinician can utilize the non-visualization/$PCO_2$ data to determine discrepancies when compared to the visualization data. In one instance, immediately after resection 4814 of the portion 4790, at time $t_2$, the $PCO_2$ may be measured at 4820, which is higher than the $PCO_2$ measured prior to resection 4812. The increase in $PCO_2$ may be the result of a bronchus being inadvertently occluded during the surgical procedure, causing $CO_2$ to build up within the patient. In another instance, immediately after resection 4814 of the portion 4790, at time $t_2$, the $PCO_2$ may be measured at 4822, which is lower than the $PCO_2$ measured prior to resection 4812 and lower than expected. The decrease in $PCO_2$ may be a result of a vessel being inadvertently occluded during the surgical procedure, causing less $O_2$ being delivered to the body, and thus, less $CO_2$ being produced. In either case, the clinician can take appropriate action to remedy the situation.

The changes in $PCO_2$ can also be measured at a time other than immediately resection 4814, such as a minute after resection 4816 (such as at time $t_3$). At time $t_3$, other body functions (such as kidneys) compensate for the changes in $PCO_2$ as a result of the resection. In this situation, $PCO_2$ can be measured to be ~40 mm Hg, or approximately the same that was measured prior to resection 4812. At time $t_3$, differences measured between the $PCO_2$ prior to resection 4812 can indicate the inadvertent occlusions discussed above. For example, at time $t_3$, $PCO_2$ may be measured 4824 as being higher than prior to resection 4812, indicating a possible inadvertently occluded bronchus, or $PCO_2$ may be measured 4826 as being lower than prior to resection 4812, indicating a possible inadvertently occluded vessel.

In addition, the control circuit can be configured measure organ efficiency based on the visualization data and the non-visualization data. In one aspect, the organ efficiency can be determined by comparing visualization data to a difference in the non-visualization data before and after resection of the portion. In one example, the visualization system may estimate a 17% reduction in capacity of the lung based on a clinician's desired resection path. The ventilator can be configured to measure $PCO_2$ before resection of the portion and after the resection of the portion. In the embodiment illustrated in FIG. 42, there is approximately a 17% drop in $PCO_2$ immediately after resection 4814. As there is a near 1:1 drop in $PCO_2$ (17%) against estimated reduction in capacity of the lung (17%), the clinician can determine that the lung is functionally efficient. In another example, the visualization system may estimate a 17% reduction in capacity of the lung based on the clinician's desired resection path. However, the ventilator may measure a drop in $PCO_2$ that is greater than 17%, such as 25%, as an example. In this instance, the clinician can determine that the lung is not functionally efficient as resecting the portion of the lung resulted in a larger drop in $PCO_2$ than would be expected.

In addition to peak lung volume and $PCO_2$ measurements described above, other non-visualization parameters that could be utilized including blood pressure or EKG data. EKG data would provide approximate frequency data on deformation of arteries. This frequency data with surface geometry changes within a similar frequency range could help identify critical vascular structures.

As described above, it may be desirable to utilize non-visualization data from non-visualization systems to corroborate visualization data derived from a surgical visualization system (e.g. visualization system 100, 160, 500, 2108). In the examples described above, the non-visualization data provides a means for corroborating visualization data after a portion of an organ has already been resected. In some instances, it may be desirable to supplement visualization data with non-visualization data prior to a portion of an organ being resected. In one example, non-visualization data could be used with visualization data to help determine characteristics of an organ that is going to be operated on. In one aspect, the characteristic could be an abnormality of the organ tissue that may not be suitable for cutting. The non-visualization data and the visualization data could help inform the surgical visualization system and the clinician about areas to avoid when planning out a resection path for the organ. This may be helpful in segmentectomy or complicated lobectomies without fissures.

FIG. 43 illustrates a logic flow diagram of a process 4850 for detecting a tissue abnormality based on visualization data and non-visualization data, in accordance with at least one aspect of the present disclosure. The process 4850 is generally executed during a surgical procedure. The process 4850 may include receiving 4852 first visualization data from the surgical visualization system in a first state of an organ and determining 4854 a first value of a non-visualization parameter of the organ in the first state. The process 4850 may further include receiving 4856 second visualization data from the surgical visualization system in a second state of the organ and determining 4858 a second value of the non-visualization parameter of the organ in the second state. The process may also include detecting 4860 a tissue abnormality based on the first visualization data, the second visualization data, the first value of a non-visualization parameter, and the second value of the non-visualization parameter.

One or more aspects of the process 4850 can be executed by one or more of the control circuits (e.g. control circuit 132, 400, 410, 420, 602, 622, 2108, 4620) described by the present disclosure. In at least one example, one or more aspects of the process 4850 are executed by a control circuit (e.g. control circuit 400 of FIG. 2A) that includes a processor and a memory storing a set of computer-executable instructions that, when executed by the processor, cause the processor to perform the one or more aspects of the process 4850. Additionally, or alternatively, one or more aspects of the process 4850 can be executed by a combinational logic circuit (e.g. control circuit 410 of FIG. 2B) and/or a sequential logic circuit (e.g. control circuit 420 of FIG. 2C). Furthermore, one or more aspects of the process 4850 can be executed by any suitable circuitry with any suitable hardware and/or software components that may be located in or associated with various suitable systems described by the present disclosure.

In various aspects, the process 4850 can be implemented by a computer-implemented interactive surgical system 2100 (FIG. 19) that includes one or more surgical systems 2102 and a cloud-based system (e.g., the cloud 2104 that may include a remote server 2113 coupled to a storage device 2105). Each surgical system 2102 includes at least one surgical hub 2106 in communication with the cloud 2104 that may include a remote server 2113. The control circuit executing one or more aspects of the process 4850 can be a component of a visualization system (e.g. visualization system 100, 160, 500, 2108).

FIG. 44A illustrates a right lung 4870 of a patient in a first state 4862. In one example, the first state 4862 could be a deflated state. In another example, the first state 4862 could be a collapsed state. An imaging device 4872 is shown inserted through a cavity 4874 in the patient's chest wall 4876. A clinician can utilize the imaging device 4872 to emit 4880 a pattern of light 4882 onto the surface of the right lung 4870, such as stripes, grid lines, and/or dots, to enable the determination of the topography or landscape of the surface of a patient's right lung 4870. The imaging device can be similar in various respects to imaging device 120 (FIG. 1). As described elsewhere herein, projected light arrays are employed to determine the shape defined by the surface of the patient's right lung 4870, and/or motion of the patient's right lung 4870 intraoperatively. In one embodiment, the imaging device 4782 can be coupled to the structured light source 152 of control system 133. In one embodiment, a surgical visualization system, such as surgical visualization system 100, could utilize the surface mapping logic 136 of control circuit 133, described elsewhere herein, to determine the topography or landscape of the surface of the patient's right lung 4786. In the first state 4862 of the right lung 4870, a ventilator can be used to measure parameters of the right lung 4870, such as a first state pressure ($P_1$ or positive end-expiratory pressure (PEEP)) or a first state volume ($V_1$).

FIG. 44B illustrates the right lung 4870 of the patient in a second state 4864. In one example, the second state 4864 could be a partially inflated state. In another example, the second state 4864 could be a completed inflated state. The imaging device 4872 can be configured to continue emitting 4880 the pattern of light 4882 onto the surface of the lung 4870 to enable the determination of the topography or landscape of the surface of the patient's right lung 4870 in the second state 4864. In the second state 4864 of the right lung 4870, the ventilator can be used to measure parameters of the right lung 4870, such as second state pressure ($P_2$)

which is larger than the first state 4862 pressure $P_1$ and a second state volume ($V_2$) which is larger than the first state 4862 volume $V_1$.

Based on the surface topography determined from the surgical visualization system and imagine device 4872, along with the non-visualization data determined from the ventilator (pressure/volume), the surgical visualization system can be configured to determine abnormalities of the tissue of the right lung 4870. In one example, in the first state 4862, the imaging device 4872 can determine the first state 4662 topography of the right lung 4870 (shown in FIG. 44A and in greater detail in FIG. 44C) and the ventilator could determine a first state pressure/volume. In the second state 4864, the imaging device 4872 can determine the second state 4864 topography of the right lung 4870 (shown in FIG. 44B and in greater detail in FIG. 44D) and the ventilator could determine a second state pressure/volume, which are greater than the first state pressure/volume due to the lung being partially or completed inflated. Based on the known increase in pressure/volume, the visualization system can be configured to monitor changes in the topography of the right lung 4870 that are in accordance with the known increases in pressure/volume. In one aspect, this pressure/volume measurement from the ventilator can be correlated with surface deformation of the right lung 4870 to identify regions of disease within the lung to help inform stapler placement.

In one aspect, referring to FIGS. 44B and 44D, where pressure has increased from $P_1$ to $P_2$ (and volume has increased from $V_1$ to $V_2$), the surface topography determined from the structured light 4880 has changed compared to the first state 4862. In one example, the pattern of light 4882 can be dots and the dots have been spaced apart by distances from each other as the lung size increases. In another example, the pattern of light 4882 can be grid lines and the grid lines have been spaced apart or contoured as the lung size increases. Based on the known pressure increase, the imaging device can determine regions 4886 that did not change in accordance with the known pressure and volume increases. For example, where the imaging device 4872 emits a pattern 4882 of grid lines and dots onto the surface of the right lung 4870 (shown in FIGS. 6A-6D), the visualization system can be configured to monitor the contours of the grid lines and the positioning of the dots relative to one another for known pressure/volume increases. Where the visualization systems notices irregularities in the spacing of the dots or the positioning and curvature of the gridlines, the visualization system can determine that those regions correspond to potential abnormalities of the tissue, such as subsurface voids 4886 or regions where a critical structure 4884, such as a tumor, may be positioned. In one embodiment, referring to process 4100 where the process 4100 identifies 4105 anatomical structures of at least a portion of the anatomical organ, which are relevant to the surgical procedure, the process 4100 could identify abnormalities as described hereinabove and overlay these abnormalities onto the 3D construct.

In one example, a patient may have emphysema, which is a lung condition that causes shortness of breath. In people with emphysema, the air sacs in the lungs (alveoli) are damaged and, over time, the inner walls of the air sacs weaken and rupture, creating larger air spaces instead of many small ones. This reduces the internal surface area for of the lungs, used for $O_2/CO_2$ exchange, which therefore, reduces the amount of oxygen that reaches the bloodstream. In addition, the damaged alveoli do not function properly and old air becomes trapped, leaving no room for fresh, oxygen-rich air to enter. The voids within the lung in emphysema patients represent regions with less tissue thickness and can therefore influence stapling outcomes in the region. The tissue is also weakened, which results in the alveoli rupturing, and is less able to hold staples that pass through them.

As the lung with emphysema inflates and deflates, the regions with subsurface voids will have different amounts of deformation as the pressure changes compared to healthy tissue. Utilizing the above-described process 4850, these weak tissue regions with subsurface voids can be detected to inform the clinician that they should avoid stapling through these regions, which can decrease the likelihood of post-operative air leaks. The tissue deformation capabilities of this process 4850 would permit the detection of these differences allowing the surgeon to be guided in the placement of the stapler.

In a second example, a patient may have cancer. Prior to the procedure, the tumor may have been irradiated, which damages the tissue as well as the surrounding tissue. Irradiation changes the properties of the tissue, often making it much stiffer and less compressible. If the surgeon needs to staple across this tissue, the change in tissue stiffness should be considered when selecting a staple reload type (e.g. stiffer tissue will require a taller formed staple).

As the lung inflates and deflates, the regions with stiffer tissues will have different amounts of deformation compared to healthy tissue as the lung is less compliant in these regions. The tissue deformation capabilities of this process 4850 would permit the detection of these differences allowing the surgeon to be guided in the placement of the stapler, as well as and the selection of the cartridge/reload color.

In another aspect, a memory, such as memory 134, may be configured to store surface topographies of lungs for known pressures and volumes. In this instance, an imaging device, such as imaging device 4872, can emit a pattern of light to determine the topography of the surface of the patient's lung at a first known pressure or volume. The surgical system, such as surgical system 2100, can be configured to compare the first determined topography at the known first pressure or volume to topographies stored in the memory 134 for the given first pressure or volume. Based on the comparison, the visualization system can be configured to indicate potential abnormalities of the tissue in only a single state. The visualization system can note these potential areas of abnormalities and proceed with determining the topography of the surface of the patient's lung at a second known pressure or volume. The visualization system can compare the second determined surface topography to topographies stored in the memory for the second given pressure or volume, as well as the topography determined at the first known pressure or volume. If the visualization system determines potential areas of abnormalities that overlap with first determined potential areas of abnormalities, the visualization system can be configured to indicate the overlapping areas as potential abnormalities with greater confidence based on the comparisons at the first and second known pressure or volumes.

In addition to the above, a $PO_2$ measurement from a ventilator could be compared with the inflation lung volume, such as $V_2$ versus the deflated lung volume, such as $V_1$. The volume comparison could utilize EKG data to compare inhalation and exhalation that could be compared with blood oxygenation. This could also be compared with anesthesia gas exchange measurement to determine breathing volume versus oxygen intake versus sedation. In addition, EKG data could provide approximate frequency data on deformation of arteries. This frequency data with surface geometry changes within a similar frequency range could help identify critical vascular structures.

In another embodiment, current tracking/procedure information can be compared with a pre-surgical planning simulation. In challenging or high-risk procedures, the clinician can utilize pre-operative patient scans to simulate a surgical approach. This dataset could be compared in the display, such as display 146, against real time measurements to help enable a surgeon to follow a particular pre-surgical plan based on training runs. This would require the ability to match fiducial landmarks between pre-operative scans/simulations and current visualization. One method may simply use boundary tracking of an object. Insights into how current device-tissue interaction compares against previous interactions (per patient) or anticipated interaction (database or past patients) for tissue type discernment, relative tissue deformation assessment, or sub-surface structural differences can be stored in memory, such as memory 134.

In one embodiment, surface geometry could be a function of a tool position. A surface reference can be selected when no change in surface geometry is measured per change in tool position. As the tool interacts with tissue and deforms the surface geometry, the change in surface geometry as a function in tool position can be computed by the surgical system. For a given change in tool position upon contact with the tissue, the change in tissue geometry may be different in regions with sub-surface structures, such as critical structure 4884, than in regions without such structures, such as sub-surface voids 4886. In one example, such as thoracic procedures, this could be above an airway versus being in parenchyma only. A running average of the change in tool position versus change in surface geometry can be computed by the surgical system using the surgical visualization system for the given patient to given patient-specific differences, or the value can be compared to a second set of previously collected data.

Example Clinical Applications

Various surgical visualization systems disclosed herein may be employed in one or more of the following clinical applications. The following clinical applications are non-exhaustive and merely illustrative applications for one or more of the various surgical visualization systems disclosed herein.

A surgical visualization system, as disclosed herein, can be employed in a number of different types of procedures for different medical specialties, such as urology, gynecology, oncology, colorectal, thoracic, bariatric/gastric, and hepato-pancreato-biliary (HPB), for example. In urological procedures, such as a prostatectomy, for example, the ureter may be detected in fat or connective tissue and/or nerves may be detected in fat, for example. In gynecological oncology procedures, such as a hysterectomy, for example, and in colorectal procedures, such as a low anterior resection (LAR) procedure, for example, the ureter may be detected in fat and/or in connective tissue, for example. In thoracic procedures, such as a lobectomy, for example, a vessel may be detected in the lung or in connective tissue and/or a nerve may be detected in connective tissue (e.g., an esophagostomy). In bariatric procedures, a vessel may be detected in fat. In HPB procedures, such as a hepatectomy or pancreatectomy, for example, a vessel may be detected in fat (extrahepatic), in connective tissue (extrahepatic), and the bile duct may be detected in parenchyma (liver or pancreas) tissue.

In one example, a clinician may want to remove an endometrial myoma. From a preoperative magnetic resonance imaging (MRI) scan, the clinician may know that the endometrial myoma is located on the surface of the bowel. Therefore, the clinician may want to know, intraoperatively, what tissue constitute a portion of the bowel and what tissue constitutes a portion of the rectum. In such instances, a surgical visualization system, as disclosed herein, can indicate the different types of tissue (bowel versus rectum) and convey that information to a clinician via an imaging system. Moreover, the imaging system can determine and communicate the proximity of a surgical device to the select tissue. In such instances, the surgical visualization system can provide increased procedural efficiency without critical complications.

In another example, a clinician (e.g. a gynecologist) may stay away from certain anatomic regions to avoid getting too close to critical structures and, thus, the clinician may not remove all of the endometriosis, for example. A surgical visualization system, as disclosed herein, can enable the gynecologist to mitigate the risk of getting too close to the critical structure such that the gynecologist can get close enough with the surgical device to remove all the endometriosis, which can improve the patient outcomes (democratizing surgery). Such a system can enable the surgeon to "keep moving" during the surgical procedure instead of repeatedly stopping and restarting in order to identify areas to avoid, especially during the application of therapeutic energy such as ultrasonic or electrosurgical energy, for example. In gynecological applications, uterine arteries and ureters are important critical structures and the system may be particularly useful for hysterectomy and endometriosis procedures given the presentation and/or thickness of tissue involved.

In another example, a clinician may risk dissection of a vessel at a location that is too proximal and, thus, which can affect blood supply to a lobe other than the target lobe. Moreover, anatomic differences from patient to patient may lead to dissection of a vessel (e.g. a branch) that affects a different lobe based on the particular patient. A surgical visualization system, as disclosed herein, can enable the identification of the correct vessel at the desired location, which enables the clinician to dissect with appropriate anatomic certainty. For example, the system can confirm that the correct vessel is in the correct place and then the clinician can safely divide the vessel.

In another example, a clinician may make multiple dissections before dissecting at the best location due to uncertainty about the anatomy of the vessel. However, it is desirable to dissect in the best location in the first instance because more dissection can increase the risk of bleeding. A surgical visualization system, as disclosed herein, can minimize the number of dissections by indicating the correct vessel and the best location for dissection. Ureters and cardinal ligaments, for example, are dense and provide unique challenges during dissection. In such instances, it can be especially desirable to minimize the number of dissections.

In another example, a clinician (e.g. a surgical oncologist) removing cancerous tissue may want to know the identification of critical structures, localization of the cancer, staging of the cancer, and/or an evaluation of tissue health. Such information is beyond what a clinician sees with the "naked eye". A surgical visualization system, as disclosed herein, can determine and/or convey such information to the clinician intraoperatively to enhance intraoperative decision making and improve surgical outcomes. In certain instances, the surgical visualization system can be compatible with minimally invasive surgery (MIS), open surgery, and/or robotic approaches using either an endoscope or exoscope, for example.

In another example, a clinician (e.g. a surgical oncologist) may want to turn off one or more alerts regarding the proximity of a surgical tool to one or more critical structure to avoid being overly conservative during a surgical procedure. In other instances, the clinician may want to receive certain types of alerts, such as haptic feedback (e.g. vibrations/buzzing) to indicate proximity and/or or "no fly zones" to stay sufficiently far away from one or more critical structures. A surgical visualization system, as disclosed herein, can provide flexibility based on the experience of the clinician and/or desired aggressiveness of the procedure, for example. In such instances, the system provides a balance between "knowing too much" and "knowing enough" to anticipate and avoid critical structures. The surgical visualization system can assist in planning the next step(s) during a surgical procedure.

Various aspects of the subject matter described herein are set out in the following numbered examples.

Example 1. A surgical system for use in a surgical procedure, the surgical system comprising at least one imaging device and a control circuit configured to identify an anatomical organ targeted by the surgical procedure, generate a virtual three-dimensional (3D) construct of at least a portion of the anatomical organ based on visualization data from the at least one imaging device, identify anatomical structures relevant to the surgical procedure from the visualization data from the at least one imaging device, couple the anatomical structures to the virtual 3D construct, and overlay onto the virtual 3D construct a layout plan of the surgical procedure determined based on the anatomical structures.

Example 2. The surgical system of Example 1, wherein the visualization data comprises at least one of structured light data and spectral data.

Example 3. The surgical system of Examples 1 or 2, wherein the layout plan comprises a starting position determined based on the anatomical structures.

Example 4. The surgical system of Examples 1 or 2, wherein the layout plan comprises a surgical resection path for removing a portion of the anatomical organ, and wherein the surgical resection path is determined based on the anatomical structures.

Example 5. The surgical system of Example 4, wherein the control circuit is configured to predict a resulting volume of the anatomical organ based on the surgical resection path.

Example 6. The surgical system of any one of Examples 1-5, wherein identifying anatomical structures of the anatomical organ comprises distinguishing tissue types of the anatomical organ.

Example 7. The surgical system of any one of Examples 1-6, wherein identifying at least one of the surgical procedure, the anatomical organ type, and the anatomical structures is based on stored data.

Example 8. The surgical system of Example 7, wherein the stored data comprises at least one of preoperative data, user preference data, and data from previously performed surgical procedures.

Example 9. A surgical system for use with a surgical instrument in a surgical procedure, the surgical system comprising at least one imaging device and a control circuit configured to identify an anatomical organ targeted by the surgical procedure, identify anatomical structures relevant to the surgical procedure from visualization data from the at least one imaging device, and propose surgical resection paths for removing a portion of the anatomical organ by the surgical instrument, wherein the surgical resection paths are determined based on the anatomical structures.

Example 10. The surgical system of Example 9, wherein the surgical resection paths comprise different starting points.

Example 11. The surgical system of Examples 9 or 10, wherein the surgical resection paths yield different organ volumes.

Example 12. The surgical system of any one of Examples 9-11, wherein the surgical resection paths are overlaid onto a virtual 3D construct of at least a portion of the anatomical organ.

Example 13. The surgical system of any one of Examples 9-12, wherein the visualization data comprises at least one of structured light data and spectral data.

Example 14. The surgical system of any one of Examples 9-13, wherein identifying anatomical structures of the anatomical organ comprises distinguishing tissue types of the anatomical organ.

Example 15. The surgical system of any one of Examples 9-14, wherein identifying at least one of the surgical procedure, the anatomical organ type, and the anatomical structures is based on stored data.

Example 16. The surgical system of Example 15, wherein the stored data comprises at least one of preoperative data, user preference data, and data from previously performed surgical procedures.

Example 17. A surgical system for use with a surgical instrument in a surgical procedure, the surgical system comprising at least one imaging device and a control circuit configured to identify an anatomical organ targeted by the surgical procedure, identify anatomical structures relevant to the surgical procedure from visualization data from the at least one imaging device, propose a surgical resection path for removing a portion of the anatomical organ by the surgical instrument, wherein the surgical resection path is determined based on the anatomical structures, and modify the surgical resection path during the surgical procedure.

Example 18. The surgical system of Example 17, wherein the surgical resection path is overlaid onto a virtual 3D construct of at least a portion of the anatomical organ.

Example 19. The surgical system of Examples 17 or 18, wherein the visualization data comprise at least one of structured light data and spectral data.

Example 20. The surgical system of any one of Examples 17-19, wherein identifying anatomical structures of the anatomical organ comprises distinguishing tissue types of the anatomical organ.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A surgical visualization system comprising:
   a plurality of light sources;
   at least one optical sensor;
   at least one display device; and
   a controller comprising a processor and a memory unit, wherein the memory unit is configured to store instructions that, when executed by the processer, cause the controller to:
      control at least one of the plurality of light sources to illuminate a tissue in a first manner by projecting a pattern of light onto a surface of the tissue;
      control the at least one optical sensor to receive first light reflected by the surface of the tissue when illuminated in the first manner;
      calculate first imaging data of a three-dimensional image of one or more surface features of the tissue based on the first light reflected by the surface of the tissue when illuminated in the first manner;
      control at least one of the plurality of light sources to illuminate the tissue in a second manner by illuminating the tissue with a plurality of emitted light waves, wherein each of the plurality of emitted light waves has a unique light spectrum, and wherein at least one of the plurality of emitted light waves has a light spectrum configured based on a spectral signature of one or more subsurface critical anatomic structures of the tissue;
      control the at least one optical sensor to receive second light from the tissue when illuminated in the second manner;
      calculate second imaging data of the one or more subsurface critical anatomic structures of the tissue based on the second light received by the at least one optical sensor; and
      display a combination of the first imaging data and the second imaging data on the at least one display device.

2. The surgical visualization system of claim 1, wherein the instructions that, when executed by the processor, cause the controller to control at least one of the plurality of light sources to illuminate a tissue in a first manner by projecting a pattern of light onto the surface of the tissue comprise instructions that, when executed by the processor, cause the controller to control at least one of the plurality of light sources to project at least one of a pattern of grid lines, stripes, or dots onto the surface of the tissue.

3. The surgical visualization system of claim 1, wherein the unique light spectrum of each of the plurality of emitted light waves comprises a visible light spectrum, a near infra red light spectrum, or a short wave infra red light spectrum.

4. The surgical visualization system of claim 1, wherein the unique light spectrum of each of the plurality of emitted light waves comprises a red light spectrum, a green light spectrum, or a blue light spectrum.

5. The surgical visualization system of claim 1, wherein the second imaging data comprise hyperspectral data.

6. The surgical visualization system of claim 1, wherein the second imaging data comprise critical anatomic structure subsurface location data.

7. The surgical visualization system of claim 1, wherein the second imaging data comprise critical anatomic structure compositional data.

8. The surgical visualization system of claim 1, wherein the second imaging data comprise critical anatomic structure identification data.

9. The surgical visualization system of claim 1, wherein the combination of the first imaging data and the second imaging data comprise data of an image combining the three-dimensional image of the one or more surface features of the tissue and the critical anatomic structure.

10. A method of visualizing a tissue, comprising:
    illuminating, by at least one of a plurality of light sources, a tissue in a first manner by projecting a pattern of light onto a surface of the tissue;
    receiving, by at least one optical sensor, light reflected from the surface of the tissue illuminated in the first manner;
    calculating, by a processor, first imaging data based on the light reflected from the surface of the tissue illuminated in the first manner, wherein the first imaging data comprise a three-dimensional image of one or more surface features of the tissue illuminated in the first manner;
    illuminating, by at least one of the plurality of light sources, the tissue in a second manner by illuminating the tissue with a plurality of emitted light waves, wherein each of the plurality of emitted light waves has a unique light spectrum, and wherein at least one of the plurality of emitted light waves has a light spectrum configured based on a spectral signature of one or more subsurface critical anatomic structures of the tissue;
    receiving, by at least one optical sensor, light reflected from the tissue illuminated in the second manner;
    calculating, by the processor, second imaging data based on the light reflected from the tissue illuminated in the second manner, wherein the second imaging data comprise an image of the one or more subsurface critical anatomic structures of the tissue illuminated in the second manner; and
    displaying, on at least one display device, a combination of the first imaging data and the second imaging data.

11. The method of claim 10, wherein illuminating, by at least one of a plurality of light sources, a tissue in a first manner by projecting a pattern of light onto the surface of the tissue comprises illuminating, by at least one of the plurality of light sources, the tissue by projecting at least one of a pattern of grid lines, stripe, or dots onto the surface of the tissue.

12. The method of claim 10, wherein illuminating the tissue with a plurality of emitted light waves comprises illuminating the tissue with a plurality of emitted light waves, each emitted light wave having a visible light spectrum, a near infra red light spectrum, or a short wave infra red light spectrum.

13. The method of claim 10, wherein illuminating the tissue with a plurality of emitted light waves comprises illuminating the tissue with a plurality of emitted light waves, each emitted light wave having a red light spectrum, a green light spectrum, or a blue light spectrum.

14. The method of claim 10, wherein calculating, by the processor, second imaging data based on the light reflected from the tissue illuminated in the second manner comprises calculating, by the processor, hyperspectral data.

15. The method of claim 10, wherein calculating, by the processor, second imaging data based on the light reflected from the tissue illuminated in the second manner comprises calculating, by the processor, critical anatomic structure subsurface location data.

16. The method of claim 10, wherein calculating, by the processor, second imaging data based on the light reflected from the tissue illuminated in the second manner comprises calculating, by the processor, critical anatomic structure compositional data.

17. The method of claim 10, wherein calculating, by the processor, second imaging data based on the light reflected from the tissue illuminated in the second manner comprises calculating, by the processor, critical anatomic structure identification data.

18. The method of claim 10, displaying, on at least one display device, a combination of the first imaging data and the second imaging data comprises displaying, on the at least one display device, an image combining the three-dimensional image of the one or more surface features of the tissue and the image of the one or more subsurface critical anatomic structures.

\* \* \* \* \*